(12) United States Patent
Marshall et al.

(10) Patent No.: US 11,674,132 B2
(45) Date of Patent: Jun. 13, 2023

(54) ISOTACHOPHORESIS FOR PURIFICATION OF NUCLEIC ACIDS

(71) Applicant: Purigen Biosystems, Inc., Pleasanton, CA (US)

(72) Inventors: Lewis A. Marshall, Oakland, CA (US); Amy L. Hiddessen, Pleasanton, CA (US); Nathan P. Hoverter, Pleasanton, CA (US); Klint A. Rose, Pleasanton, CA (US); Juan G. Santiago, Stanford, CA (US)

(73) Assignee: Purigen Biosystems, Inc., Pleasanton, CA (US)

( * ) Notice: Subject to any disclaimer, the term of this patent is extended or adjusted under 35 U.S.C. 154(b) by 190 days.

(21) Appl. No.: 16/997,614

(22) Filed: Aug. 19, 2020

(65) Prior Publication Data
US 2021/0054361 A1 Feb. 25, 2021

Related U.S. Application Data

(63) Continuation of application No. 16/046,560, filed on Jul. 26, 2018, now Pat. No. 10,822,603, which is a
(Continued)

(51) Int. Cl.
*G01N 27/453* (2006.01)
*C12N 15/10* (2006.01)
(Continued)

(52) U.S. Cl.
CPC ...... *C12N 15/101* (2013.01); *B01L 3/502753* (2013.01); *C12N 15/10* (2013.01);
(Continued)

(58) Field of Classification Search
CPC ............................................. G01N 27/447–453
See application file for complete search history.

(56) References Cited

U.S. PATENT DOCUMENTS

| 863,583 A | 8/1907 | Blankmeister |
| 3,799,742 A | 3/1974 | Coleman |
| (Continued) | | |

FOREIGN PATENT DOCUMENTS

| CA | 2304641 A1 | 4/1999 |
| CN | 1326549 A | 12/2001 |
| (Continued) | | |

OTHER PUBLICATIONS

Marshall et al., "An injection molded microchip for nucleic acid purification from 25 microliter samples using isotachophoresis," Journal of Chromatography A, 1331 (2014) 139-142 with Supporting information (Year: 2014).*
(Continued)

*Primary Examiner* — Alexander S Noguerola
(74) *Attorney, Agent, or Firm* — Bret. E. Field; Bozicevic, Field & Francis LLP

(57) ABSTRACT

The present disclosure relates to fluidic systems and devices for processing, extracting, or purifying one or more analytes. These systems and devices can be used for processing samples and extracting nucleic acids, for example by isotachophoresis. In particular, the systems and related methods can allow for extraction of nucleic acids, including non-crosslinked nucleic acids, from samples such as tissue or cells. The systems and devices can also be used for multiplex parallel sample processing.

14 Claims, 56 Drawing Sheets

Related U.S. Application Data continuation of application No. PCT/US2017/015519, filed on Jan. 28, 2017.

(60) Provisional application No. 62/288,930, filed on Jan. 29, 2016.

(51) Int. Cl.

| | | |
|---|---|---|
| *G01N 27/447* | (2006.01) | |
| *B01L 3/00* | (2006.01) | |
| *C12Q 1/6806* | (2018.01) | |
| *B81B 1/00* | (2006.01) | |
| *B81B 7/00* | (2006.01) | |

(52) U.S. Cl.
CPC ....... *C12Q 1/6806* (2013.01); *G01N 27/4473* (2013.01); *G01N 27/44739* (2013.01); *G01N 27/44791* (2013.01); *G01N 27/44795* (2013.01); *B01L 3/502738* (2013.01); *B01L 2300/0627* (2013.01); *B01L 2300/0867* (2013.01); *B81B 1/004* (2013.01); *B81B 7/0087* (2013.01); *B81B 2201/0278* (2013.01); *B81B 2201/05* (2013.01); *B81B 2203/0338* (2013.01); *G01N 27/44704* (2013.01)

(56) References Cited

U.S. PATENT DOCUMENTS

| | | |
|---|---|---|
| 3,811,326 A | 5/1974 | Sokol |
| 3,869,365 A | 3/1975 | Sunden |
| 3,912,609 A | 10/1975 | Arlinger |
| 3,948,753 A | 4/1976 | Arlinger |
| 3,992,150 A | 11/1976 | Retzer |
| 4,061,560 A | 12/1977 | Hannig et al. |
| 4,233,029 A | 11/1980 | Columbus |
| 4,416,762 A | 11/1983 | Akiyama et al. |
| 4,426,451 A | 1/1984 | Columbus |
| 4,454,235 A | 6/1984 | Johnson |
| 4,537,747 A | 8/1985 | Castaneda |
| 4,596,780 A | 6/1986 | Castaneda |
| 4,618,476 A | 10/1986 | Columbus |
| 4,790,919 A | 12/1988 | Baylor, Jr. et al. |
| 4,868,129 A | 9/1989 | Gibbons et al. |
| 4,897,169 A | 1/1990 | Bier et al. |
| 4,900,677 A | 2/1990 | Hewitt et al. |
| 5,322,608 A | 6/1994 | Karger et al. |
| 5,447,612 A | 9/1995 | Bier et al. |
| 5,464,515 A | 11/1995 | Bellon et al. |
| 5,580,523 A | 12/1996 | Bard |
| 5,629,414 A | 5/1997 | Boothroyd et al. |
| 5,631,128 A | 5/1997 | Kozal et al. |
| 5,650,268 A | 7/1997 | Kozal et al. |
| 5,800,692 A | 9/1998 | Naylor et al. |
| 5,817,225 A | 10/1998 | Hinton et al. |
| 5,827,415 A | 10/1998 | Guer et al. |
| 5,856,086 A | 1/1999 | Kozal et al. |
| 5,859,196 A | 1/1999 | Boothroyd et al. |
| 5,939,291 A | 8/1999 | Loewy et al. |
| 5,981,235 A | 11/1999 | Shultz et al. |
| 5,992,820 A | 11/1999 | Fare et al. |
| 6,090,251 A | 7/2000 | Sundberg et al. |
| 6,107,038 A | 8/2000 | Choudhary et al. |
| 6,130,098 A | 10/2000 | Handique et al. |
| 6,132,579 A | 10/2000 | Edwards et al. |
| 6,143,248 A | 11/2000 | Kellogg et al. |
| 6,296,020 B1 | 10/2001 | McNeely et al. |
| 6,352,838 B1 | 3/2002 | Krulevitch et al. |
| 6,561,224 B1 | 5/2003 | Cho |
| 6,581,899 B2 | 6/2003 | Williams |
| 6,626,417 B2 | 9/2003 | Winger et al. |
| RE38,352 E | 12/2003 | Kozal et al. |
| 6,669,831 B2 | 12/2003 | Chow et al. |
| 6,685,813 B2 | 2/2004 | Williams et al. |
| 6,695,009 B2 | 2/2004 | Chien et al. |
| 6,730,204 B2 | 5/2004 | Mariella, Jr. et al. |
| 6,761,811 B2 | 7/2004 | Mariella, Jr. et al. |
| 6,770,182 B1 | 8/2004 | Griffiths et al. |
| 6,780,584 B1 | 8/2004 | Edman et al. |
| 6,818,113 B2 | 11/2004 | Williams et al. |
| 6,905,583 B2 | 6/2005 | Wainright et al. |
| 6,908,593 B1 | 6/2005 | Shartle et al. |
| 6,934,836 B2 | 8/2005 | Strand et al. |
| 6,935,772 B2 | 8/2005 | Karp et al. |
| 6,939,454 B2 | 9/2005 | Kaji |
| 7,005,050 B2 | 2/2006 | Burns et al. |
| 7,204,263 B2 | 4/2007 | Tsukita et al. |
| 7,214,299 B2 | 5/2007 | Armstrong et al. |
| 7,223,325 B2 | 5/2007 | Landers et al. |
| 7,316,771 B2 | 1/2008 | Weber et al. |
| 7,364,916 B2 | 4/2008 | Sundberg et al. |
| 7,371,533 B2 | 5/2008 | Slater et al. |
| 7,399,394 B2 | 7/2008 | Weber et al. |
| 7,429,354 B2 | 9/2008 | Andersson et al. |
| 7,473,551 B2 | 1/2009 | Warthoe et al. |
| 7,494,577 B2 | 2/2009 | Williams et al. |
| 7,517,442 B1 | 4/2009 | Champagne et al. |
| 7,591,936 B2 | 9/2009 | Sarrut et al. |
| 7,635,563 B2 | 12/2009 | Horvitz et al. |
| 7,694,694 B2 | 4/2010 | Welle et al. |
| 7,875,160 B2 | 1/2011 | Jary et al. |
| 7,926,514 B2 | 4/2011 | Park et al. |
| 7,951,278 B2 | 5/2011 | Santiago et al. |
| 8,017,408 B2 | 9/2011 | Meinhart et al. |
| 8,021,531 B2 | 9/2011 | Park et al. |
| 8,037,903 B2 | 10/2011 | Wang et al. |
| 8,105,471 B1 | 1/2012 | Han et al. |
| 8,133,371 B2 | 3/2012 | Marziali et al. |
| 8,277,628 B2 | 10/2012 | Ronaghi et al. |
| 8,394,251 B2 | 3/2013 | Santiago et al. |
| 8,414,754 B1 | 4/2013 | Santiago et al. |
| 8,524,061 B2 | 9/2013 | Utz et al. |
| 8,562,804 B2 | 10/2013 | Santiago et al. |
| 8,580,097 B2 | 11/2013 | Kurosawa et al. |
| 8,585,883 B2 | 11/2013 | Schoch |
| 8,597,590 B2 | 12/2013 | Yue et al. |
| 8,721,858 B2 | 5/2014 | Chambers et al. |
| 8,821,704 B2 | 9/2014 | Santiago et al. |
| 8,846,314 B2 | 9/2014 | Chambers et al. |
| 8,894,946 B2 | 11/2014 | Nielsen et al. |
| 8,986,529 B2 | 3/2015 | Santiago et al. |
| 8,999,129 B2 | 4/2015 | Jung et al. |
| 9,057,673 B2 | 6/2015 | Rogacs et al. |
| 9,144,799 B2 | 9/2015 | Rose et al. |
| 9,151,732 B2 | 10/2015 | Santiago et al. |
| 9,285,340 B2 | 3/2016 | Jung et al. |
| 9,297,039 B2 | 3/2016 | Santiago et al. |
| 9,599,590 B2 * | 3/2017 | Sabin ............... G01N 27/44739 |
| 9,753,007 B1 | 9/2017 | Chambers et al. |
| 10,073,054 B2 | 9/2018 | Santiago et al. |
| 10,132,775 B2 | 11/2018 | Santiago et al. |
| 10,233,441 B2 | 3/2019 | Santiago et al. |
| 10,415,030 B2 | 9/2019 | Marshall et al. |
| 10,787,660 B2 | 9/2020 | Santiago et al. |
| 10,822,603 B2 * | 11/2020 | Marshall ................ C12N 15/10 |
| 2001/0055812 A1 | 12/2001 | Mian et al. |
| 2002/0008029 A1 | 1/2002 | Williams et al. |
| 2002/0036018 A1 | 3/2002 | McNeely et al. |
| 2002/0079223 A1 | 6/2002 | Williams et al. |
| 2002/0139674 A1 | 10/2002 | Mariella et al. |
| 2002/0189946 A1 * | 12/2002 | Wainright ........ G01N 27/44743 |
| | | 204/453 |
| 2003/0224436 A1 | 12/2003 | Nelson et al. |
| 2003/0230486 A1 | 12/2003 | Chien et al. |
| 2004/0031683 A1 | 2/2004 | Eipel et al. |
| 2004/0050698 A1 | 3/2004 | Eckerskorn et al. |
| 2004/0058349 A1 | 3/2004 | Van Ness et al. |
| 2004/0063217 A1 | 4/2004 | Webster et al. |
| 2004/0108207 A1 | 6/2004 | Kurnik et al. |
| 2004/0120856 A1 | 6/2004 | Andersson et al. |
| 2004/0241656 A1 | 12/2004 | Jan et al. |
| 2004/0256230 A1 | 12/2004 | Yager et al. |
| 2004/0265172 A1 | 12/2004 | Pugia et al. |
| 2005/0014134 A1 | 1/2005 | West et al. |

(56) References Cited

U.S. PATENT DOCUMENTS

| | | |
|---|---|---|
| 2005/0079519 A1 | 4/2005 | Boles et al. |
| 2005/0115837 A1 | 6/2005 | Burgi et al. |
| 2005/0121324 A1 | 6/2005 | Park et al. |
| 2005/0133370 A1 | 6/2005 | Park et al. |
| 2005/0142570 A1 | 6/2005 | Parthasarathy et al. |
| 2005/0167269 A1 | 8/2005 | Updyke et al. |
| 2005/0170362 A1 | 8/2005 | Wada et al. |
| 2006/0002817 A1 | 1/2006 | Bohm et al. |
| 2006/0019286 A1 | 1/2006 | Horvitz et al. |
| 2006/0042948 A1 | 3/2006 | Santiago et al. |
| 2006/0065528 A1 | 3/2006 | Lopez et al. |
| 2006/0078998 A1 | 4/2006 | Puskas et al. |
| 2006/0094119 A1 | 5/2006 | Ismagilov et al. |
| 2006/0254915 A1 | 11/2006 | Hirokawa et al. |
| 2007/0026439 A1 | 2/2007 | Faulstich et al. |
| 2007/0229631 A1 | 10/2007 | Yano |
| 2007/0284250 A1 | 12/2007 | Magnant et al. |
| 2008/0000774 A1 | 1/2008 | Park et al. |
| 2008/0020386 A1 | 1/2008 | Chen et al. |
| 2008/0021674 A1 | 1/2008 | Puskas et al. |
| 2008/0156080 A1 | 7/2008 | Balgley et al. |
| 2008/0166770 A1 | 7/2008 | Morita et al. |
| 2008/0197019 A1 | 8/2008 | Santiago et al. |
| 2008/0227185 A1 | 9/2008 | Schonfeld et al. |
| 2008/0233402 A1 | 9/2008 | Carlson et al. |
| 2009/0134031 A1 | 5/2009 | Ogle et al. |
| 2009/0178929 A1 | 7/2009 | Broer et al. |
| 2009/0194420 A1 | 8/2009 | Mariella, Jr. et al. |
| 2009/0220948 A1 | 9/2009 | Oviso et al. |
| 2009/0250345 A1 | 10/2009 | Powell et al. |
| 2009/0269745 A1 | 10/2009 | Tonoike et al. |
| 2009/0282978 A1 | 11/2009 | Jensen et al. |
| 2009/0317894 A1 | 12/2009 | Diges et al. |
| 2010/0084271 A1 | 4/2010 | Santiago et al. |
| 2010/0089529 A1 | 4/2010 | Barholm-Hansen et al. |
| 2010/0116657 A1 | 5/2010 | Fiering et al. |
| 2010/0120130 A1 | 5/2010 | Srinivasan et al. |
| 2010/0209927 A1 | 8/2010 | Menon et al. |
| 2010/0224494 A1 | 9/2010 | Chambers et al. |
| 2010/0261612 A1 | 10/2010 | Young et al. |
| 2010/0270157 A1 | 10/2010 | Kurosawa et al. |
| 2010/0294663 A1 | 11/2010 | Weber |
| 2010/0323913 A1 | 12/2010 | Young et al. |
| 2011/0024296 A1 | 2/2011 | Park et al. |
| 2011/0036718 A1 | 2/2011 | Jung et al. |
| 2011/0104816 A1 | 5/2011 | Pollack et al. |
| 2011/0174624 A1 | 7/2011 | Weber et al. |
| 2011/0220499 A1 | 9/2011 | Chambers et al. |
| 2011/0290648 A1 | 12/2011 | Majlof et al. |
| 2011/0297546 A1 | 12/2011 | Schoch et al. |
| 2012/0061242 A1 | 3/2012 | Santiago et al. |
| 2012/0097272 A1 | 4/2012 | Vulto et al. |
| 2012/0152746 A1 | 6/2012 | Santiago et al. |
| 2012/0160689 A1 | 6/2012 | Utz et al. |
| 2012/0175258 A1 | 7/2012 | Mariella, Jr. et al. |
| 2013/0175173 A1 | 7/2013 | Ivory et al. |
| 2014/0014515 A1 | 1/2014 | Santiago et al. |
| 2014/0332389 A1 | 11/2014 | Young et al. |
| 2015/0037784 A1 | 2/2015 | Rogacs et al. |
| 2015/0191717 A1 | 7/2015 | Santiago et al. |
| 2015/0219594 A1 | 8/2015 | Vulto et al. |
| 2016/0139078 A1 | 5/2016 | Henry et al. |
| 2016/0153934 A1 | 6/2016 | Santiago et al. |
| 2016/0160208 A1 | 6/2016 | Santiago et al. |
| 2016/0209360 A1 | 7/2016 | Santiago et al. |
| 2016/0320286 A1 | 11/2016 | Miki et al. |
| 2017/0021350 A1 | 1/2017 | Goodwin, Jr. |
| 2017/0153202 A1 | 6/2017 | Dolnik |
| 2018/0237767 A1 | 8/2018 | Santiago et al. |
| 2019/0039069 A1 | 2/2019 | Marshall et al. |
| 2019/0071661 A1 | 3/2019 | Marshall et al. |

FOREIGN PATENT DOCUMENTS

| | | |
|---|---|---|
| CN | 1422180 A | 6/2003 |
| CN | 1548957 A | 11/2004 |
| CN | 1715929 A | 1/2006 |
| CN | 102395421 A | 3/2012 |
| CN | 103402641 A | 11/2013 |
| CN | 104419764 A | 3/2015 |
| CN | 105190280 A | 12/2015 |
| DE | 3328964 C1 | 2/1985 |
| DE | 102012219156 A1 | 4/2014 |
| EP | 0305210 A2 | 3/1989 |
| EP | 1742057 A1 | 1/2007 |
| EP | 1932593 A1 | 6/2008 |
| EP | 2213364 A1 | 8/2010 |
| EP | 2340122 A1 | 7/2011 |
| EP | 2541239 A2 | 1/2013 |
| EP | 2972185 A1 | 1/2016 |
| JP | H0387648 A | 4/1991 |
| JP | 2002527250 A | 8/2002 |
| JP | 2004521315 A | 7/2004 |
| JP | 2008539443 A | 11/2008 |
| JP | 2012516414 A | 7/2012 |
| JP | 2015530240 A | 10/2015 |
| JP | 2016024021 A | 2/2016 |
| JP | 2016512886 A | 5/2016 |
| JP | 2016212090 A | 12/2016 |
| WO | WO-0022436 A1 | 4/2000 |
| WO | WO-03015901 A1 | 2/2003 |
| WO | WO-2005033283 A2 | 4/2005 |
| WO | WO-2008053047 A2 | 5/2008 |
| WO | WO-2008105308 A1 | 9/2008 |
| WO | WO-2008124064 A1 | 10/2008 |
| WO | WO-2009079028 A1 | 6/2009 |
| WO | WO-2009137415 A2 | 11/2009 |
| WO | WO-2010026222 A1 | 3/2010 |
| WO | WO-2012120101 A1 | 9/2012 |
| WO | WO-2014060998 A1 | 4/2014 |
| WO | WO-2014153092 A1 | 9/2014 |
| WO | WO-2017132630 A1 | 8/2017 |
| WO | WO-2019028197 A1 | 2/2019 |

OTHER PUBLICATIONS

Bahga, et al., Coupled Isotachophoretic Preconcentration and Electrophoretic Separation Using Bidirectional Isotachophoresis, Anal. Chem. 2011, 83, 6154-6162.

Bahga, et al., Integration of rapid DNA hybridization and capillary zone electrophoresis using bidirectional isotachophoresis†. Analyst, 2013;138:87-90.

Beard N.R. et al., In-Column Field-Amplified Sample Stacking of Biogenic Amines on Microfabricated Electrophoresis Devices. Electrophoresis, 24.4 (2003): 732-739.

Bercovici, et al., Rapid Detection of Urinary Tract Infections Using Isotachophoresis and Molecular Beacons. Anal. Chem. 2011, 83, 4110-4117.

Birnboim et al. A rapid alkaline extraction procedure for screening recombinant plasmid DNA. Nucl. Acids Res 7:1513-1526 (1979).

Blidner, R. et al., "Choice of FFPE DNA isolation method affects both yield and functional quality and impacts variant calling by targeted NGS", published online Nov. 5, 2015 [retrieved from Internet Apr. 13, 2017]<url: http:="" asuragen.com="" wp-content= "" uploads="" 2016="" 06="" blidner_choice-of-ffpe-dna-isolation-method-affects-both-yield-and-functional-quality...pdf=""></url:>.

Bocek, Petr, et al., "Effect of a Concentration Cascade of the Leading Electrolyte on the Separation Capacity in isotachophresis", Journal of Chromatography, 1978, pp. 323-326, vol. 156, Publisher: Elsevier Scientific Publishing Company, Published in: Amsterdam, Netherlands.

Breadmore, M.C., Unlimited-volume stacking of ions in capillary electrophoresis. Part 1: Stationary isotachophoretic stacking of anions. Electrophoresis 2008, 29, 1082-1091.

Chambers R.D. et al., Imaging and Quantification of Isotachophoresis Zones Using Nonfocusing Fluorescent Tracers. Analytical Chemistry, 81.8 (2009): 3022-3028.

(56) References Cited

OTHER PUBLICATIONS

Chen, et al., Determination of Binding Constants by Affinity Capillary Electrophoresis, Electrospray Ionization Mass Spectrometry and Phase-distribution Methods, Trends Analyt Chem., Oct. 2008, 27(9); 738-748 D.
CIPO. Search Report for related Chinese Patent Application No. 201480021876.2 dated Jun. 2, 2017, 15 Pages.
Co-pending U.S. Appl. No. 15/668,557, filed Aug. 3, 2017.
Desjardin et al. (1996) Alkaline decontamination of sputum specimens adversely affects stability of mycobacterial mRNA. J. Clin. Microbial. 34(10):2435-2439.
Devolder et al., "Pneumatic and hydraulic microactuators: a review", 2010, pp. 1-18, J.Micromech. Microeng. v20.
Dossil., et al., Microchip Free-Flow Electrophoresis on Glass Substrate Using Laser-Printing Toner as Structural Material. Electrophoresis, 27 (2006): 4935-4942.
Eddington et al., "Flow control with hydrogels", 2004, pp. 199-210, Advanced Drug DeliveryReviews v56.
Eisenbarth G.S., Application of Monoclonal Antibody Techniques to Biochemical Research. Analytical Biochemistry, 111.1 (1981): 1-16.
EP17745057.4 Extended European Search Report dated May 15, 2019.
Erlich, et al. Recent advances in the polymerase chain reaction. Science. Jun. 21, 1991;252(5013):1643-51.
European search report dated Jan. 25, 2017 for EP Application No. 14769958.1.
Foret et al., Indirect Photometric Detection in Capillary Zone Electrophoresis. Journal of Chromatography, 470 (1989): 299-308.
Friend, J. et al. Fabrication of microfluidic devices using polydimethylsiloxane, 2010, Biomicrofluidics, vol. 4, pp. 026502 (1-5).
Fu J. et al., A Patterned Anisotropic Nanofluidic Sieving Structure for Continuous-flow Separation of DNA and Proteins. Nature, 2.2 (2007): 121-128.
Fung, et al., Application of Capillary electrophoresis fortrace ion analysis in rain water, J, Microcolumn separations, 2000; 12(6):337-344.
Garcia-Schwarz, G., et al. On-chip Isotachophoresis for Separation of Ions and Purification of Nucleic Acids, Journal of VisualizedExperiments, vol. 61, pp. 1-8 (Year: 2012).
Goet et al., Micro Contact Based on Isotachophoretic Sample Transport. Lab Chip, 9 (2009): 3586-3593.
Gohring, et al. The scaffold/matrix attachment region binding protein hnRNP-U (SAF-A) is directly bound to chromosomal DNA in vivo: a chemical cross-linking study. Biochemistry. Jul. 8, 1997;36(27):8276-83.
Gross L. et al., Indirect Fluorometric Detection of Cations in Capillary Zone Electrophoresis. American Chemical Society, (1990): 427-431.
Hilber, W., Stimulus-active polymer actuators for next-generation microfluidic devices. Applied Physics A, Aug. 2016; 122:75, 39 Pages.
Hinckley, J. 0. N., Transphoresis and Isotachophoresis—Automatable Fast Analysis of Electrolytes, Proteins, and Cells, with Supression of Gravitational Effects, Clinical Chemistry, vol. 20, No. 8, 1974, 973-991 D.
Hosokawa et al.. "Power-free poly(dimethylsiloxane) microfluidic devices for gold nanoparticle-based DNA analysis", Lab Chip, vol. 4, pp. 181-185, May 12, 2004. http://pubs.rsc.org/en/Content/Articlelanding/2004/LC/b403930k#! divAbstract.entire document.
International Search Report dated Jul. 29, 2014 for International PCT Patent Application No. PCT/US2014/029017.
Jacob et al., Micro Free-Flow IEF Enhanced by Active Cooling and Functionalized Gels. Electrophoresis, 27 (2006): 4960-4969.
Jacobson S. et al., Microchip Electrophoresis With Sample Stacking. Electrophoresis, 16.4 (1995): 481-486.
Janasek D. et al., Isotachophoresis in Free-Flow Using a Miniaturized Device. Analytical Chemistry, 78.11 (2006): 3815-3819.
Juan S.G. et al., Stanford Microfluidics Laboratory. Stanford University, May 2016, http://microfluidics.stanford.edu.
Jung, et al., On-Chip Millionfold Sample Stacking Using Transient Isotachophoresis, Anal. Chem., Apr. 2006, 78:2319-27.
Karsenty, et al., Current Monitoring in a Microchannel with Repeated Constrictions for Accurate Detection of Sample Location in Isotachophoresis. Anal. Chem. 2015, 87, 388-393.
Khurana, et al., Effects of Carbon Dioxide on Peak Mode Isotachophoresis: Simultaneous Preconcentration and Separation, Lab Chip, 2009, 9, 1377-1384.
Khurana, et al., Preconcentration, Separation, and Indirect Detection of Nonftuorescent Analytes Using Fluorescent Mobility Markers, Analytical Chemistry, vol. 80, No. 1, Jan. 1, 2008, 279-286 D.
Khurana, et al., Sample Zone Dynamics in Peak Mode Isotachophoresis, Analytical Chemistry, Published on Web, Jul. 22, 2008, pp. A-H.
Kitagawa. et al., High-speed Analysis of Proteins by Microchip Isoelectric Focusing with Linear-imaging UV Detection, Analytical Sciences, Aug. 2009, vol. 25, 979-984.
Křivánková L., et al., Synergism of Capillary Isotachophoresis and Capillary Zone Electrophoresis. Journal of Chromatography B: Biomedical Sciences and Applications, 689 (1997): 13-34.
Kondratova, et al., Concentration and isolation of DNA from biological fluids by agarose gel isotachophoresis. BioTechniques, Nov. 2005; 39:695-699.
Krivankova et al., Isotachophoresis 17. Methods in Enzymology, 270 (1996): 375-401.
Lee, G-8, et al. Microfluidic Chips for DNA Amplification, Electrophoresis Separation and On-Line Optical Detection, 2003, IEEE pp. 423-426.
Liao et al. (2007) Development of an advanced electrochemical DNA biosensor for bacterial pathogen detection. J. Mol. Diagn. 9 (2):158-168.
Liu, et al., Isotachophoresis preconcentration integrated microfluidic chip for highly sensitive genotyping of the hepatitis B virus. Journal of Chromatography B, 844 (2006) 32-38.
Mariella R. Jr., Sample Preparation: The Weak Link in Microfluidics-Based Biodetection. Biomed Microdevices, 10 (2008): 777-784.
Marshall, et al., An injection molded microchip for nucleic acid purification from 25 microliter samples using isotachophoresis. Journal of Chromatography A, 1331 (2014) 139-142.
Marshall, et al. An Injection Molded Microchip for Nucleic Acid Purification from 25 Microliter Samples Using Isotachophoresis, Supporting Information, 2014. 5 pages.
Marshall, et al., Integrated Printed Circuit Board Device for Cell Lysis and Nucleic Acid Extraction. | Anal. Chem. 2012, 84, 9640-9645.
Marshall L. A. et al. "An Injection-Molded Device for Purification of Nucleic Acids From Whole Blood Using Isotachophoresis." 2013 Annual Meeting of the AES, 8 pgs. (Nov. 2013).
Marshall L.A. and Santiago, J. G. "A Novel Device for Highly-Efficient Extraction of Nucleic Acids from 100 Microliter Whole Blood Samples." 2012 Annual Meeting of the AES, 4 pgs. (Oct. 31, 2012).
Morio, et al. Quantitative analysis of trifluoroacetate in the urine and blood by isotachophoresis. Anesthesiology. Jul. 1980;53(I ):56-9.
Mowio., "Mowio—History/Manufacture/Structure, p. A 1—no date available."
Nagoyova I. et al., Discrete Spacers for Photometric Characterization of Humic Acids Separated by Capillary Isotachophoresis. Journal of Chromatography A, (2001): 191-200.
Notice of Allowance dated May 29, 2014 for U.S. Appl. No. 12/716,142.
Notice of Allowance dated May 30, 2017 for U.S. Appl. No. 14/497,050.
Notice of Allowance dated Jun. 6, 2014 for U.S. Appl. No. 12/716,142.
Oerlemans, F. et al., Isotachophoresis of Urinary Purines and Pyrimidines: The Use of Spacers and Enzymes for Identification. Journal of Chromatography, 225 (1981): 369-379.
Office Action dated Mar. 10, 2017 for U.S. Appl. No. 14/213,832.
Office Action dated Mar. 17, 2016 for U.S. Appl. No. 14/497,050.
Office Action dated May 16, 2012 for U.S. Appl. No. 12/716,142.
Office Action dated Aug. 24, 2017 for U.S. Appl. No. 14/213,832.
Office Action dated Sep. 16, 2016 for U.S. Appl. No. 14/497,050.

(56) References Cited

OTHER PUBLICATIONS

Office Action dated Oct. 19, 2011 for U.S. Appl. No. 12/716,142.
Oh et al., "A review of microvalves", 2006, pp. R13-R39, J. Micromech. Microeng. v16.
Oshurkova et al., Coulophoretic Titration. Translated from Doklady Akademii Nauk SSSR v227n6, (1975): 316-319.
Oshurkova et al., Russian Chemical Reviews, 62.8 (1993): 729-742.
Oshurkova et al., Russian Journal of Electrochemistry, 40.5 (2004): 583-587.
Park et al., Controlling Data Quality and Reproducibility of a High-Sensitivity Immuniassay Using Isotachophoresis in a Microchip. Analytical Chemistry, 80 (2008): 808-814.
PCT/US2017/015519 International Search Report and Written Opinion dated Apr. 27, 2017.
PCT/US2018/044898 International Search Report and Written Opinion dated Dec. 11, 2018.
Pei, et al., Isotachophoretic detemincaoint of Urea-Ammonium in Plasma: A candidate reference method, J. Clin. Chem. Clin. Biochem, 1990; 28:447-451.
Persat, A. and Santiago, J.G., Electrokinetic control of sample splitting at a channel bifurcation using isotachophoresis. New Journal of Physics, 2009: 15 Pages.
Persat, A. and Santiago, J.G., On-Chip Isothermal Polymerase Chain Reaction. IMECE 2007; 2 Pages.
Persat et al., MicroRNA Profiling by Simultaneous Selective Isotachophoresis and Hybridization With Molecular Beacons. Analytical Chemistry, 83 (2011): 2310-2316.
Persat, et al., Purification of Nucleic Acids from Whole Blood Using Isotachophoresis, Analytical Chemistry, 81.22 (Nov. 15, 2009): 9507-9511, supporting materials.
Persat, et al., Purification of Nucleic Acids from Whole Blood Using Isotachophoresis, Analytical Chemistry, vol. 81, No. 22, Nov. 15, 2009,9507-9511 D.
Persat, et al., Supporting information: Quantification of global microRNA abundance by selective isotachophoresis. Department of mechanical engineering, 2010.
Petr et al., Capillary Isotachophoresis From the Student Point of View—Images and the Reality. Journal of Separation Science, 29 (2006): 2705-2715.
Prest et al., Bidirectional Isotachophoresis on a Planar Chip With Integrated Conductivity Detection. Analyst, 127 (2002): 1413-1419.
Prest et al "Miniaturised isotachophoresis of DNA" J. of Chromatography A, 2007, 1156: 154-159.
Prest J.E. et al., Miniaturised isotachophoresis of DNA. Journal of Chromatography A, 1156 (2007): 154-159.
Quirino J.P. et al., Sample Stacking of Fast-Moving Anions in Capillary Zone Electrophoresis With pH-Suppressed Electroosmotic Flow. Journal of Chromatography, 850.1-2 (1999): 339-344.
Rogacs, A. et al., "Purification of nucleic acids using isotachophoresis", Journal of Chromatography A, 2014, vol. 1335, pp. 105-120.
Ross, et al., Microfluidic Temperature Gradient Focusing, Anal. Chem., Jun. 2002, 74:2556-64.
Ryan et al., Micro Free-Flow Electrophoresis: Theory and Applications. Anal Bioanal Chem, 394 (2009): 187-198.
Schafer-Neilsen et al., Separation of Macromolecules in Isotachophoresis Systems Involving Single or Multiple Counterions. Journal of Biochemical and Biophysical Methods, 3 (1980): 97-128.
Schoch, et al., Rapid and Selective Extraction, Isolation, Preconcentration, and Quantitation of Small RNAs from Cell Lysate Using On-chip Isotachophoresis, Lab Chip, 2009, 9, 2145-2152 D.
Singh et al. (2006) An alkaline solution simplifies nucleic acid preparation for RT-PCR and infectivity assays of viroids from crude sap and spotted membrane. J. Viral. Methods 132(1-2):204-211.
Stover, Fredericks., "Enhancing Isotachophoresis Sensitivity by Low-Concentration Electrolyte Cascading", Journal of Chromatography, 1985, pp. 45-48, vol. 320, Publisher: Elsevier Science Publishers BV., Published in: Amsterdam, Netherlands.
Thormann, et al., Impact of electoosmosis on isotachophoresis in open-tubular fused-silica capillaries: Analysis of the evolution of a stationary steady-state zone structure by computer simulation and experimental validation. Electrophoresis, 1995; 16:2016-2026.
U.S. Appl. No. 14/828,487 Notice of Allowance dated Jul. 17, 2018.
U.S. Appl. No. 15/081,415 Notice of Allowance dated May 10, 2018.
U.S. Pat. No. 7,247,224, Jul. 2007, Weber (withdrawn).
U.S. Appl. No. 11/755,449 Notice of Allowance dated Dec. 3, 2012.
U.S. Appl. No. 11/755,449 Office Action dated Apr. 23, 2012.
U.S. Appl. No. 11/755,449 Office Action dated Dec. 30, 2011.
U.S. Appl. No. 11/755,449 Office Action dated Jan. 5, 2011.
U.S. Appl. No. 11/755,449 Office Action dated Jul. 26, 2011.
U.S. Appl. No. 11/755,449 Office Action dated Jul. 7, 2010.
U.S. Appl. No. 11/880,479 Notice of Allowance dated Aug. 4, 2010.
U.S. Appl. No. 11/880,479 Notice of Allowance dated Mar. 23, 2011.
U.S. Appl. No. 12/542,215 Notice of Allowance dated Dec. 18, 2015.
U.S. Appl. No. 12/542,215 Office Action dated Aug. 27, 2014.
U.S. Appl. No. 12/542,215 Office Action dated Jul. 9, 2015.
U.S. Appl. No. 12/542,215 Office Action dated May 29, 2012.
U.S. Appl. No. 12/542,215 Office Action dated Sep. 28, 2011.
U.S. Appl. No. 12/587,537 Notice of Allowance dated Nov. 13, 2012.
U.S. Appl. No. 12/587,537 Office Action dated Feb. 23, 2012.
U.S. Appl. No. 12/943,677 Notice of Allowance dated Jun. 10, 2015.
U.S. Appl. No. 12/943,677 Office Action dated Mar. 26, 2015.
U.S. Appl. No. 12/943,677 Office Action dated May 6, 2013.
U.S. Appl. No. 12/943,677 Office Action dated Oct. 19, 2012.
U.S. Appl. No. 13/065,168 Notice of Allowance dated Mar. 6, 2014.
U.S. Appl. No. 13/065,168 Office Action dated Apr. 26, 2013.
U.S. Appl. No. 13/065,168 Office Action dated Aug. 22, 2013.
U.S. Appl. No. 13/134,165 Notice of Allowance dated Jun. 12, 2013.
U.S. Appl. No. 13/134,165 Office Action dated Feb. 21, 2013.
U.S. Appl. No. 13/199,895 Notice of Allowance dated Dec. 17, 2014.
U.S. Appl. No. 13/199,895 Office Action dated Jul. 30, 2013.
U.S. Appl. No. 13/199,895 Office Action dated May 8, 2014.
U.S. Appl. No. 13/199,895 Office Action dated Nov. 6, 2012.
U.S. Appl. No. 13/252,138 Notice of Allowance dated May 18, 2015.
U.S. Appl. No. 13/252,138 Office Action dated Feb. 5, 2014.
U.S. Appl. No. 13/252,138 Office Action dated Jun. 18, 2014.
U.S. Appl. No. 13/252,138 Office Action dated Oct. 22, 2014.
U.S. Appl. No. 13/373,773 Notice of Allowance dated Jul. 18, 2013.
U.S. Appl. No. 13/413,161 Notice of Allowance dated Dec. 19, 2014.
U.S. Appl. No. 13/413,161 Office Action dated May 8, 2014.
U.S. Appl. No. 13/764,376 Notice of Allowance dated Apr. 25, 2014.
U.S. Appl. No. 13/764,376 Office Action dated Oct. 15, 2013.
U.S. Appl. No. 13/972,655 Notice of Allowance dated May 6, 2015.
U.S. Appl. No. 13/972,655 Office Action dated Feb. 20, 2015.
U.S. Appl. No. 13/972,655 Office Action dated Jul. 29, 2014.
U.S. Appl. No. 13/972,655 Office Action dated Oct. 29, 2014.
U.S. Appl. No. 14/450,069 Office Action dated Dec. 6, 2017.
U.S. Appl. No. 14/450,069 Office Action dated Oct. 1, 2018.
U.S. Appl. No. 14/450,069 Office Action dated Jun. 14, 2019.
U.S. Appl. No. 14/465,138 Notice of Allowance dated Nov. 19, 2015.
U.S. Appl. No. 14/465,138 Office Action dated Apr. 30, 2015.
U.S. Appl. No. 14/828,487 Office Action dated Apr. 9, 2018.
U.S. Appl. No. 14/828,487 Office Action dated Nov. 1, 2017.
U.S. Appl. No. 15/081,415 Office Action dated Jan. 16, 2018.
U.S. Appl. No. 15/668,557 Office Action dated Apr. 1, 2019.
U.S. Appl. No. 15/668,557 Office Action dated May 1, 2020.
U.S. Appl. No. 15/668,557 Office Action dated Nov. 19, 2019.
U.S. Appl. No. 15/668,557 Office Action dated Oct. 19, 2018.
U.S. Appl. No. 16/046,560 Notice of Allowance dated Jul. 29, 2020.
U.S. Appl. No. 16/046,560 Office Action dated Apr. 24, 2020.
U.S. Appl. No. 16/121,219 Office Action dated Mar. 20, 2020.

(56) References Cited

OTHER PUBLICATIONS

U.S. Appl. No. 16/175,500 Notice of Allowance dated Jun. 17, 2019.
U.S. Appl. No. 16/175,500 Office Action dated Feb. 4, 2019.
U.S. Appl. No. 16/192,034 Notice of Allowance dated Jul. 20, 2020.
U.S. Appl. No. 16/192,034 Office Action dated Feb. 7, 2020.
U.S. Appl. No. 16/192,034 Office Action dated Jan. 18, 2019.
U.S. Appl. No. 16/192,034 Office Action dated May 13, 2019.
U.S. Appl. No. 16/192,034 Office Action dated May 14, 2020.
U.S. Appl. No. 15/853,370 Notice of Allowance dated Nov. 9, 2018.
Wagner H., Free-Flow Electrophoresis. Nature, 341 (1989): 669-670.
Wainright A. et al., Preconcentration and Separation of Double-stranded DNA Fragments by Electrophoresis in Plastic Microfluidic Devices. Electrophoresis, 24.21 (2003): 3784-3792.
Wainright A. et al., Sample Pre-Concentration by Isotachophoresis in Microfluidic Devices. Journal of Chromatography, 979.1-2 (2002): 69-80.
Wanget al., Million-fold Preconcentration of Proteins and Peptides by Nanofluidic Filter, Anal. Chem., Jul. 15, 2005, 77:4293-99.
Woolley et al., Ultra-High-Speed DNA Fragment Separations Using Microfabricated Capillary Array Electrophoresis Chips. Proceedings of the National Academy of Sciences of the United States of America, 99 (1994): 11348-11352.
Xu et al., Electrokinetic Supercharging Preconcentration and Microchip Gel Electrophoretic Separation of Sodium Dodecyl Sulfate-Protein Complexes. Electrophoresis, 24 (2003): 3821-3827.
Xu et al., High-Sensitivity Capillary Gel Electrophoretic Analysis of DNA Fragments on an Electrophoresis Microchip Using Electrokinetic Injection With Transient Isotachophoretic Preconcentration. Journal of Chromatography A, 990 (2003): 53-61.
Xu et al., Optimization of the Electrokinetic Supercharging Preconcentration for High-Sensitivity Microchip Gel Electrophoresis on a Cross-Geometry Microchip. Electrophoresis, 25 (2004): 2357-2362.
Xu et al., Performance of Electrokinetic Supercharging for High-sensitivity Detection of DNA Fragments in Chip Gel Electrophoresis. Electrophoresis, 24 (2004): 3875-3881.
Yang, et al., Sample Stacking in Laboratory-on-a-Chip Devices, J. Chromatogr., A, Jul. 2001, 924:155-63.
Zhang C.X. et al., Head-Column-Field-Amplified Sample Stacking in Binary System Capillary Electrophoresis: A Robust Approach Providing Over 1000-Fold Sensitivity Enhancement. Analytical Chemistry, 68.15 (1996): 2523-2532.
Zhang, W., B.A. Direct PCT sequencing with denaturants in:Rapley R. (eds.) PCR sequencing protocols methods in molecular biology, 1996; 65.
Zhong, et al., Automatic Extraction and Processing of Small RNAs on a Multi-well/Multi-channel (M&M) Chip. Analyst. Dec. 7, 2012;137(23):5546-52. doi: 10.1039/c2an35883b. Epub Sep. 21, 2012.
EP18841854.5 Extended European Search Report dated Mar. 18, 2021.
Persat, A. et al., "Quantification of Global MicroRNA Abundance by Selective Isotachophoresis", Analytical Chemistry, 2010, vol. 82, pp. 9631-9635.
U.S. Appl. No. 14/450,069 Office Action dated Jan. 10, 2020.
U.S. Appl. No. 14/450,069 Office Action dated Oct. 6, 2020.
U.S. Appl. No. 15/668,557 Office Action dated Jan. 11, 2021.
U.S. Appl. No. 16/052,565 Notice of Allowance dated Apr. 1, 2021.
U.S. Appl. No. 16/052,565 Office Action dated Nov. 16, 2020.
U.S. Appl. No. 16/121,219 Notice of Allowance dated Sep. 17, 2020.
U.S. Appl. No. 16/121,219 Office Action dated Jun. 2, 2020.
U.S. Appl. No. 16/121,219 Office Action dated Sep. 11, 2019.
U.S. Appl. No. 16/998,839 Office Action dated Sep. 16, 2022.
U.S. Appl. No. 16/998,839 Final Office Action dated Jan. 6, 2023.
U.S. Appl. No. 17/230,582 Non-Final Office Action dated Dec. 30, 2022.

\* cited by examiner

ISOTACHOPHORESIS FOR PURIFICATION OF NUCLEIC ACIDS

CROSS-REFERENCE

This is a continuation application of U.S. patent application Ser. No. 16/046,560, filed on Jul. 26, 2018, entitled "Isotachophoresis for Purification of Nucleic Acids", which is a continuation application of PCT/US2017/015519, filed on Jan. 28, 2017, entitled "Isotachophoresis for Purification of Nucleic Acids", which claims the benefit of U.S. Provisional Application No. 62/288,930, filed Jan. 29, 2016, entitled "Isotachophoresis for Purification of Nucleic Acids", the entire contents of which are herein incorporated by reference.

STATEMENT AS TO FEDERALLY SPONSORED RESEARCH

This invention was made with the support of the United States government under contract number 1R43HG007620-01 awarded by the National Institutes of Health. The government has certain rights in the invention.

BACKGROUND

Formalin-fixed paraffin-embedded (FFPE) samples have been collected, prepared, stored, and archived in large tissue banks for more than a century. As of 2008, there were over 400 million FFPE samples stored in biobanks worldwide, and this number is growing. These samples are often accompanied by clinical information such as primary diagnosis, therapeutic regimen, and follow-up data, making them an important resource for the development of therapeutics and the discovery of genome and transcriptome biomarkers.

Sample preparation methods to extract and purify nucleic acids from FFPE samples remain manually intensive and laborious. Approaches for FFPE extraction and purification vary widely but often include difficult-to-automate and difficult-to-accelerate steps of wax removal, centrifugation, buffer exchanges, temperature control, cross-link reduction and enzyme treatment. FFPE generally refers to cross-linking proteins in a sample using formalin and embedding the sample in paraffin (wax). FFPE treatment of a sample often enables the sample to be preserved over time and can be especially useful for long-term storage. The cross-linked proteins may bind up the DNA and RNA in the sample, thereby generally making it unusable for downstream applications such as amplification, library preparation, or sequencing.

Removal of paraffin and protein crosslinks in FFPE samples may be a challenging process. Deparaffinization is traditionally performed using highly flammable xylenes. Alternately or in series, the sample can be treated with other solvents, mineral oil and alkaline chemistry and/or elevated temperature. After deparaffinization, proteins in the sample can be treated with different agents or subjected to conditions that may require additional time and effort.

At the end of digestion and denaturation, a mix of crosslinked and non-crosslinked nucleic acids may remain. Removal of the non-crosslinked material may be important for high quality results from assays such as amplification or sequencing; in some cases, if the fraction of non-crosslinked material is too low, the downstream assay may fail to perform resulting in a loss of not only the sample itself, but also labor, time and resources.

SUMMARY

Isotachophoresis (ITP) is an electrophoretic technique which can use a discontinuous buffer containing a leading electrolyte (LE) with a higher effective mobility magnitude and a trailing electrolyte (TE) with a lower effective mobility magnitude (e.g., relative to the LE) to focus sample species that have a greater effective mobility magnitude than the trailing electrolyte but a lower effective mobility magnitude than the leading electrolyte. ITP can selectively focus nucleic acids from samples by more than 10,000-fold in less than five minutes. The present disclosure provides methods and devices employing and automating ITP for sample preparation, including extraction, purification, enrichment, and highly sensitive quantitation, and is particularly useful for preparing and purifying nucleic acids from FFPE samples and other biological samples.

Sample preparation is important to genomic analysis, yet it remains a primary source of analysis variability and can require significant manual labor. The present disclosure includes techniques and devices to address this challenge, such as by using on-chip isotachophoresis (ITP) for extraction and purification of nucleic acids. These techniques include methods to enrich (concentrate) non-crosslinked nucleic acids to enable higher yield and higher quality nucleic acid sample preparation and produce more useable samples (e.g., fewer quality-check rejections) from FFPE and other preserved or fresh samples.

The present disclosure includes techniques and devices for automation of nucleic acid sample preparation from samples, including solid tissue, lysed solid tissue, preserved or fixed tissue samples (e.g., FFPE), whole blood, plasma and serum, buccal swabs, dried blood spots and other forensic samples, fresh or fresh frozen (FF) tissues, biopsy tissue, organ tissue, solid organ tissue, samples comprising connections (e.g. gap junctions, tight junctions, adherent junctions) between cells, cultured or harvested cells from blood or tissues, stool, and bodily fluids (e.g., saliva, urine), or any combination thereof. Samples can include cellular and cell-free nucleic acids, for both eukaryotic and prokaryotic organisms, or any combination thereof. The techniques of the present disclosure, compared to existing approaches, can be faster, less manually intensive, more suited for both small and large starting amounts of tissue, and can achieve higher yield from samples and higher quality analyses of samples.

An aspect of the present disclosure provides a method for sample purification, comprising: (a) loading into a fluidic device (i) a tissue sample comprising lysed solid tissue, wherein said lysed solid tissue comprises nucleic acids and a contaminant, (ii) a trailing electrolyte buffer comprising first trailing electrolyte ions with an effective mobility having a magnitude lower than a magnitude of an effective mobility of said nucleic acids, and (iii) a leading electrolyte buffer comprising first leading electrolyte ions, with a second effective mobility, wherein said second effective mobility has a magnitude greater than said magnitude of said effective mobility of said nucleic acids; and (b) applying an electric field within said fluidic device to conduct isotachophoresis with said first trailing electrolyte ions, said nucleic acids, and said first leading electrolyte ions, thereby purifying said nucleic acids from said contaminant in said tissue sample.

In some embodiments of aspects provided herein, said effective mobility of said first trailing electrolyte ions has a magnitude greater than a magnitude of an effective mobility of said contaminant. In some embodiments of aspects provided herein, said fluidic device is a microfluidic chip and said tissue sample, said trailing electrolyte buffer and said leading electrolyte buffer are loaded into a first zone of said microfluidic chip. Some embodiments of aspects provided herein may further comprise, in said first zone of said microfluidic chip, conducting on said tissue sample at least one sample preparation procedure selected from the group consisting of (1) removing embedding material, (2) disrupting tissue, (3) lysing cells, (4) de-crosslinking said nucleic acids, (5) digesting proteins, and (6) digesting said nucleic acids. In some embodiments of aspects provided herein, said isotachophoresis is conducted in a second zone of said microfluidic chip, wherein said second zone is separate from and fluidically connected to said first zone. In some embodiments of aspects provided herein, said solid tissue is derived from a solid organ. In some embodiments of aspects provided herein, said lysed solid tissue comprises a chemical fixative. In some embodiments of aspects provided herein, said chemical fixative is formalin. In some embodiments of aspects provided herein, said solid tissue is formalin fixed paraffin embedded tissue (FFPE). In some embodiments of aspects provided herein, said lysed solid tissue comprises urea or thiourea. Some embodiments of aspects provided herein further comprise disrupting cell-cell junctions, extracellular matrix, or connective tissue in order to obtain said lysed solid tissue. In some embodiments of aspects provided herein, said lysed solid tissue comprises solid particles. In some embodiments of aspects provided herein, said nucleic acids comprise dispersed or solvated nucleic acids. In some embodiments of aspects provided herein, said contaminant is selected from the group consisting of crosslinked nucleic acids, embedding material, tissue debris, fixation chemicals, proteins, inhibitors, and combinations thereof. In some embodiments of aspects provided herein, said contaminant comprises crosslinked nucleic acids. In some embodiments of aspects provided herein, said tissue sample is combined with said trailing electrolyte buffer prior to said loading. In some embodiments of aspects provided herein, said tissue sample is combined with said leading electrolyte buffer prior to said loading. In some embodiments of aspects provided herein, said loading of said leading electrolyte buffer is conducted prior to said loading of said tissue sample. In some embodiments of aspects provided herein, said solid tissue is lysed in said leading electrolyte buffer prior to said loading of said tissue sample. In some embodiments of aspects provided herein, said solid tissue is lysed in said trailing electrolyte buffer prior to said loading of said tissue sample. In some embodiments of aspects provided herein, said sample preparation procedure comprises, prior to said applying of said electric field, removing embedding material by incubating said tissue sample in said fluidic device at a temperature of at least about 37° C. for a duration of at least about 1 minute. In some embodiments of aspects provided herein, said temperature is from about 40° C. to about 80° C. In some embodiments of aspects provided herein, said duration is from about 1 minute to about 120 minutes. In some embodiments of aspects provided herein, said sample preparation procedure comprises disrupting tissue or lysing cells by applying mechanical stress to said tissue sample. In some embodiments of aspects provided herein, said sample preparation procedure comprises disrupting tissue or lysing cells by applying heat to said tissue sample. In some embodiments of aspects provided herein, said applying heat results in a temperature of said tissue sample from about 30° C. to about 80° C. In some embodiments of aspects provided herein, said sample preparation procedure comprises disrupting tissue or lysing cells by contacting said tissue sample with a solution with pH of at least 10 or by proteolytically digesting said tissue sample. In some embodiments of aspects provided herein, said proteolytic digestion is conducted at a temperature greater than about 25° C. In some embodiments of aspects provided herein, said sample preparation procedure comprises disrupting tissue or lysing cells by applying at least one surfactant to said tissue sample. In some embodiments of aspects provided herein, said sample preparation procedure comprises disrupting tissue or lysing cells by applying a solution comprising urea to said tissue or cell sample. In some embodiments of aspects provided herein, said solution further comprises thiourea. In some embodiments of aspects provided herein, a concentration of said urea in said solution is within a range of from about 4 M to about 9 M and a concentration of said thiourea in said solution is in a range of from about 0.5 M to about 3.5 M. In some embodiments of aspects provided herein, a concentration of said urea in said solution is from about 6.5 M to about 7.5 M and a concentration of said thiourea in said solution is from about 1.5 M to about 2.5 M. In some embodiments of aspects provided herein, said sample preparation procedure comprises de-crosslinking said nucleic acids by digesting crosslinking proteins with proteinase K. In some embodiments of aspects provided herein, said sample preparation procedure comprises digesting said nucleic acids with DNase or RNase. Some embodiments of aspects provided herein further comprise eluting an output solution comprising said purified nucleic acids from an outlet reservoir of said fluidic device. In some embodiments of aspects provided herein, a concentration of said purified nucleic acids in said output solution is at least about two-fold higher than a concentration of said nucleic acids in said tissue sample. In some embodiments of aspects provided herein, said tissue sample and said purified nucleic acids in said output solution comprise crosslinked nucleic acids and a concentration of said crosslinked nucleic acids in said output solution is at least about two-fold lower than a concentration of said crosslinked nucleic acids in said tissue sample. In some embodiments of aspects provided herein, said contaminant is present in said output solution at a concentration that is at least two-fold less than a concentration of said contaminant in said tissue sample. In some embodiments of aspects provided herein, said first trailing electrolyte ions comprise caproic acid. In some embodiments of aspects provided herein, said first leading electrolyte ions comprise chloride. In some embodiments of aspects provided herein, said trailing electrolyte buffer comprises second trailing electrolyte ions having a different effective mobility than said first trailing electrolyte ions. In some embodiments of aspects provided herein, said second trailing electrolyte ions comprise HEPES (4-(2-hydroxyethyl)-1-piperazineethanesulfonic acid) or MOPS (3-(N-morpholino)propanesulfonic acid). In some embodiments of aspects provided herein, said second trailing electrolyte ions comprise HEPES (4-(2-hydroxyethyl)-1-piperazineethanesulfonic acid) and said first trailing electrolyte ions comprise caproic acid. In some embodiments of aspects provided herein, said second trailing electrolyte ions comprise MOPS (3-(N-morpholino)propanesulfonic acid) and said first trailing electrolyte ions comprise caproic acid. In some embodiments of aspects provided herein, said second trailing electrolyte ions comprise HEPES (4-(2-hydroxyethyl)-1-piperazineethanesulfonic acid) and said first trailing electrolyte ions comprise MOPS. In some embodiments of aspects provided herein, said trailing electrolyte buffer comprises second trailing electrolyte ions with a second effective mobility, wherein said second effective mobility has a magnitude about the same as or lower than said magnitude of said effective mobility of said contaminant. In some embodiments of aspects provided herein, said tissue sample loaded into said fluidic device has a volume of at least 50 µl. Some embodiments of aspects provided herein further comprise, in said first zone of said microfluidic chip, conducting on said tissue sample a first sample processing procedure, and in a second zone of said microfluidic chip, conducting on said tissue sample an enzymatic reaction. In some embodiments of aspects provided herein, said first sample processing procedure comprises removal of embedding material, disruption of tissue, or cell lysis, and said enzymatic reaction comprises de-crosslinking said nucleic acids, digesting proteins, or digesting nucleic acids. In some embodiments of aspects provided herein, said first zone and said second zone each are each heated to a temperature above 37° C. In some embodiments of aspects provided herein, said first zone is heated to a temperature of about 60° C. to 100° C. during said first sample processing procedure and wherein said second zone is heated to a temperature of 40° C. to 60° C.

An aspect of the present disclosure provides a method for simultaneously purifying nucleic acids from at least two different samples comprising: (a) loading into a first channel of a microfluidic chip (i) a first sample comprising first nucleic acids and a first contaminant, (ii) a first trailing electrolyte buffer comprising first trailing ions, wherein a magnitude of an effective mobility of said first trailing ions is less than a magnitude of an effective mobility of said first nucleic acids, and (iii) a first leading electrolyte buffer comprising first leading ions, wherein a magnitude of an effective mobility of said first leading ions is greater than said magnitude of said effective mobility of said first nucleic acids; (b) loading into a second channel of said microfluidic chip (i) a second sample comprising second nucleic acids and a second contaminant, (ii) a second trailing electrolyte buffer comprising second trailing ions, wherein a magnitude of said second trailing ions is less than a magnitude of an effective mobility of said second nucleic acids, and (iii) a second leading electrolyte buffer comprising second leading ions, wherein a magnitude of an effective mobility of said second leading ions is greater than said magnitude of said effective mobility of said second nucleic acids; and (c) applying a first electric field within said microfluidic chip to conduct isotachophoresis in said first channel with said first trailing ions, said first nucleic acids, and said first leading ions, and applying a second electric field to conduct isotachophoresis in said second channel with said second trailing ions, said second nucleic acids, and said second leading ions, thereby simultaneously purifying said first nucleic acids from said first contaminant and said second nucleic acids from said second contaminant.

In some embodiments of aspects provided herein, said first sample and said second sample are different sample types. In some embodiments of aspects provided herein, said first nucleic acids and said second nucleic acids are different types or lengths of nucleic acids. In some embodiments of aspects provided herein, said first trailing electrolyte buffer or said first leading electrolyte buffer further comprises a lysis agent or a tissue disruption agent. In some embodiments of aspects provided herein, said lysis agent or said tissue disruption agent comprises one or more agents selected from the group consisting of a solution with pH greater than about 12, a proteinase, urea, thiourea, and a surfactant. In some embodiments of aspects provided herein, said first sample comprises lysed solid tissue. In some embodiments of aspects provided herein, said second sample comprises lysed cells. In some embodiments of aspects provided herein, said first sample does not contact said second sample during said conducting of isotachophoresis. Some embodiments of aspects provided herein further comprise loading into a third channel of said microfluidic chip (i) a third sample comprising third nucleic acids and a third contaminant, (ii) a third trailing electrolyte buffer comprising third trailing ions, wherein a magnitude of an effective mobility of said third trailing ions is less than a magnitude of an effective mobility of said third nucleic acids, and (iii) a third leading electrolyte buffer comprising third leading ions, wherein a magnitude of an effective mobility of said third leading ions is greater than said magnitude of said effective mobility of said third nucleic acids, wherein said electric field is applied within said microfluidic chip to conduct said isotachophoresis in said third channel with said third trailing ions, said third nucleic acids, and said third leading ions, thereby simultaneously purifying said first nucleic acids from said first contaminant, said second nucleic acids from said second contaminant and said third nucleic acids from said third contaminant. In some embodiments of aspects provided herein, said first and second electric fields are generated from a single electrode pair. In some embodiments of aspects provided herein, said first and second electric fields are generated from different electrode pairs. In some embodiments of aspects provided herein, said first and second channels are coupled to independent sensors. In some embodiments of aspects provided herein, feedback from said independent sensors is used to independently control said first and second electric fields. In some embodiments of aspects provided herein, said independent sensors sense voltage and said feedback is used to control current (or resistance) within said first and second channels. In some embodiments of aspects provided herein, said nucleic acids comprise DNA. In some embodiments of aspects provided herein, said nucleic acids comprise RNA.

As aspect of the present disclosure provides a method for sample purification, comprising: (a) loading onto a fluidic device (i) a sample comprising fixed cells, fixed tissue, or embedded tissue, wherein said sample comprise nucleic acids, (ii) a trailing electrolyte buffer comprising trailing electrolytes, wherein said trailing electrolytes have a lower effective mobility than said nucleic acids, and (iii) a leading electrolyte buffer comprising leading electrolytes, wherein said leading electrolytes have a higher effective mobility than said nucleic acids; and (b) applying an electric field on said fluidic device to conduct isotachophoresis with said trailing electrolytes, said nucleic acids, and said leading electrolytes, thereby purifying said nucleic acids from a contaminant in said sample.

In some embodiments of aspects provided herein, said contaminant is selected from the group consisting of cross-linked nucleic acids, embedding material, fixation chemicals, enzymes, and inhibitors. In some embodiments of aspects provided herein, said sample comprises said fixed cells, said fixed tissue, or both said fixed cells and said fixed tissue. In some embodiments of aspects provided herein, said sample is formalin-fixed. In some embodiments of aspects provided herein, said sample comprises said embedded tissue. In some embodiments of aspects provided herein, said sample comprises said tissue embedded in paraffin. In some embodiments of aspects provided herein, said sample is a formalin-fixed paraffin-embedded (FFPE) tissue sample. In some embodiments of aspects provided herein, said sample comprises a tissue biopsy. In some embodiments of aspects provided herein, said sample is a dissected formalin-fixed paraffin-embedded (FFPE) sample. Some embodiments of aspects provided herein further comprise comparing a characteristic of said nucleic acids to nucleic acids from other samples, wherein said characteristic is an expression level, a nucleic acid sequence, a molecular weight, nucleic acid integrity, nucleic-acid stranded-ness (e.g. double-versus single-stranded), or nucleic acid purity. In some embodiments of aspects provided herein, said sample is a tumor sample. In some embodiments of aspects provided herein, said trailing electrolyte buffer has a pH of greater than about 7. Some embodiments of aspects provided herein further comprises, prior to said applying said electric field, incubating said tissue sample in said fluidic device at a temperature of at least about 37° C. for a duration of at least about 1 minute. In some embodiments of aspects provided herein, said temperature is from about 40° C. to about 80° C. In some embodiments of aspects provided herein, said duration is from about 1 minute to about 120 minutes. In some embodiments of aspects provided herein, said leading electrolyte buffer comprises proteinase K. Some embodiments of aspects provided herein further comprise removing protein crosslinks from said nucleic acids using said proteinase K. Some embodiments of aspects provided herein further comprise, after said applying said electric field, removing protein crosslinks from said nucleic acids using heat. Some embodiments of aspects provided herein further comprise eluting an output solution comprising said purified nucleic acids from an outlet reservoir of said fluidic device. In some embodiments of aspects provided herein, a concentration of said purified nucleic acids in said output solution is at least about two-fold higher than a concentration of said nucleic acids in said tissue sample. In some embodiments of aspects provided herein, a concentration of said crosslinked nucleic acids in said output solution is at least about two-fold lower than a concentration of said crosslinked nucleic acids in said tissue sample. In some embodiments of aspects provided herein, said output solution has a volume equal to or less than about 50 µL. In some embodiments of aspects provided herein, said tissue sample has a mass of at least about 1 ng. In some embodiments of aspects provided herein, said tissue sample has a volume greater than 25 µL. In some embodiments of aspects provided herein, said trailing electrolytes have a higher effective mobility than said contaminant. In some embodiments of aspects provided herein, said trailing electrolytes comprise (i) first ions, wherein said first ions have a higher effective mobility magnitude than said contaminant, and (ii) second ions, wherein said second ions have an effective mobility magnitude about the same as or lower than said contaminant. In some embodiments of aspects provided herein, said conducting isotachophoresis quenches a pH of said tissue sample to about 7.5. Some embodiments of aspects provided herein further comprise, prior to said loading, conducting de-paraffinization on said sample. Some embodiments of aspects provided herein further comprise detecting a concentration of said nucleic acids. In some embodiments of aspects provided herein, said concentration is less than or equal to about 1 picogram per microliter (pg/µL).

An aspect of the present disclosure provides a method for sample purification, comprising: (a) loading into a fluidic device (i) a tissue sample comprising lysed solid tissue and nucleic acids, (ii) a trailing electrolyte buffer, said trailing electrolyte buffer comprising trailing electrolyte ions with a first effective mobility, wherein said first effective mobility has a magnitude lower than a magnitude of an effective mobility of said nucleic acids, (iii) a first leading electrolyte buffer in a first leading electrolyte reservoir, said first leading electrolyte buffer comprising first leading electrolyte ions with a second effective mobility, wherein said second effective mobility has a magnitude greater than said magnitude of said effective mobility of said nucleic acids, and (iv) a second leading electrolyte buffer in a second leading electrolyte reservoir, said second leading electrolyte buffer comprising second leading electrolyte ions with a third effective mobility, wherein said third effective mobility has a magnitude greater than said magnitude of said effective mobility of said nucleic acids, wherein said first leading electrolyte buffer is different from said second leading electrolyte buffer; (b) first conducting isotachophoresis with said trailing electrolyte ions, said nucleic acids, and said first leading electrolyte ions, thereby purifying said nucleic acids from said contaminant in said tissue sample; and (c) second conducting isotachophoresis with said trailing electrolyte ions, said nucleic acids, and said second leading electrolyte ions.

In some embodiments of aspects provided herein, said second conducting isotachophoresis comprises changing an applied current from a first channel to a second channel. In some embodiments of aspects provided herein, said first leading electrolyte ions are the same as said second leading electrolyte ions, and wherein a concentration of said first leading electrolyte ions in said first leading electrolyte buffer is different from a concentration of said second leading electrolyte ions in said second leading electrolyte buffer. In some embodiments of aspects provided herein, said second effective mobility has a magnitude greater than said magnitude of said third effective mobility. In some embodiments of aspects provided herein, said first leading electrolyte ions are different from said second leading electrolyte ions. In some embodiments of aspects provided herein, said first leading electrolyte ions are the same as said second leading electrolyte ions, and wherein a concentration of said first leading electrolyte ions in said first leading electrolyte buffer is the same as a concentration of said second leading electrolyte ions in said second leading electrolyte buffer, and wherein said first leading electrolyte buffer comprises third leading electrolyte ions. In some embodiments of aspects provided herein, said first leading electrolyte ions are the same as said second leading electrolyte ions, and wherein a concentration of said first leading electrolyte ions in said first leading electrolyte buffer is the same as a concentration of said second leading electrolyte ions in said second leading electrolyte buffer, and wherein said second leading electrolyte buffer comprises third leading electrolyte ions. Some embodiments of aspects provided herein further comprise collecting said nucleic acids in said second leading electrolyte reservoir and removing said nucleic acids from said second leading electrolyte reservoir. In some embodiments of aspects provided herein, said first conducting isotachophoresis and said second conducting isotachophoresis are performed by applying a single electric field. In some embodiments of aspects provided herein, said first conducting isotachophoresis and said second conducting isotachophoresis are performed by applying more than one electric field. In some embodiments of aspects provided herein, the concentration of said second leading electrolyte ions in said second leading electrolyte buffer is less than 50 mM. In some embodiments of aspects provided herein, said second leading electrolyte buffer comprises 50 mM Tris HCl.

An aspect of the present disclosure provides a microfluidic device comprising: (a) a first isotachophoresis region in a microfluidic chip comprising: (i) a first sample reservoir in fluid communication with a first fluidic channel, (ii) a first buffer reservoir in fluid communication with said first fluidic channel, and (iii) a second buffer reservoir in fluid communication with said first channel; and (b) a second isotachophoresis region in said microfluidic chip comprising: (i) a second sample reservoir in fluid communication with a second fluidic channel, (ii) a third buffer reservoir in fluid communication with said second fluidic channel, and (iii) a fourth buffer reservoir in fluid communication with said second channel, wherein said first isotachophoresis region is not in fluid communication with said second isotachophoresis region and wherein said microfluidic device is configured to independently control a first electric circuit that applies current to said first isotachophoresis region and a second electric circuit that applies current to said second isotachophoresis region.

In some embodiments of aspects provided herein, a leakage rate between said first and second isotachophoresis regions is less than 1 µl per hour. In some embodiments of aspects provided herein, current leakage between said first and second isotachophoresis regions is less than 1 µA. In some embodiments of aspects provided herein, an impedance is greater than 1 megaOhm. In some embodiments of aspects provided herein, said first fluidic channel holds a liquid volume greater than 100 µl. In some embodiments of aspects provided herein, said first fluidic channel is separated from said second fluidic channel by a distance that is at least 5-fold less than a width of said first channel. In some embodiments of aspects provided herein, said microfluidic device is configured to control said first electric circuit simultaneously with said second electric circuit. Some embodiments of aspects provided herein further comprise an elution reservoir in fluid communication to said first channel, wherein a temperature sensor is situated within 5 mm of said elution reservoir.

An aspect of the present disclosure provides a method, comprising: (a) providing an electrokinetic fluidic device comprising a sample input reservoir in fluid communication with a channel; (b) loading a sample volume into said sample input reservoir; (c) moving at least 50% of said sample volume from said sample input reservoir to said channel, without adding additional volume to said sample input reservoir; and (d) applying an ionic current through said channel.

In some embodiments of aspects provided herein, said moving is conducted with aid of gravity. In some embodiments of aspects provided herein, said ionic current does not substantially pass through said channel. In some embodiments of aspects provided herein, said at least 50% of said sample volume comprises at least 80% of said sample volume. In some embodiments of aspects provided herein, said sample volume comprises nucleic acids. In some embodiments of aspects provided herein, said sample volume comprises a tissue sample or a formalin-fixed paraffin-embedded (FFPE) sample. In some embodiments of aspects provided herein, said applying an ionic current comprises conducting isotachophoresis. In some embodiments of aspects provided herein, a total sample volume loaded into said sample input reservoir is less than or equal to an internal volume of said input reservoir. In some embodiments of aspects provided herein, said sample input reservoir comprises a top region connected to a bottom region via a tapered region, wherein said top region has a first diameter and said bottom region has a second diameter, wherein said first diameter is at least two-fold longer than said second diameter in order to facilitate said moving at least 50% of said sample volume from said sample input reservoir to said channel. In some embodiments of aspects provided herein, said sample volume is at least 25 µl. In some embodiments of aspects provided herein, said sample volume is at least 50 µl. In some embodiments of aspects provided herein, said sample volume is at least 100 µl.

An aspect of the present disclosure provides a microfluidic chip comprising: a first sample input reservoir, wherein said first sample input reservoir comprises a top region connected to a bottom region via a tapered region, wherein said top region has a first inner hydraulic diameter and said bottom region has a second inner hydraulic diameter, wherein said first inner hydraulic diameter is at least 2-fold longer than said second inner hydraulic diameter and wherein said first sample input reservoir is in fluid communication with a first channel; a first buffer reservoir in fluid communication with said first channel, wherein said first sample reservoir is configured so that a free surface of a liquid in said first sample reservoir has a negligible buffer head height difference relative to a liquid in said first buffer reservoir; and a second buffer reservoir in fluid communication with said first channel.

In some embodiments of aspects provided herein, said first inner hydraulic diameter is a range of about 1 mm to about 15 mm. In some embodiments of aspects provided herein, said second inner hydraulic diameter is a range of about 0.5 mm to about 5 mm. In some embodiments of aspects provided herein, said first sample reservoir is configured to hold a sample volume of at least 100 µl. In some embodiments of aspects provided herein, said microfluidic chip is configured to move at least 50% of said sample volume from said first sample reservoir to said first channel when a vacuum is applied thereto. In some embodiments of aspects provided herein, said microfluidic chip is configured to conduct isotachophoresis on a sample that enters said first channel.

An aspect of the present disclosure provides a method of extracting nucleic acids, comprising: (a) exposing a biological sample comprising cells or tissue to a solution comprising urea or thiourea, thereby lysing said cells or tissue within said biological sample and producing a cellular lysate; (b) introducing said cellular lysate into a device; and (c) performing isotachophoresis with said device in order to isolate nucleic acids from said cellular lysate.

Some embodiments of aspects provided herein further comprise digesting said sample with proteinase K. In some embodiments of aspects provided herein, said solution comprises urea and thiourea. In some embodiments of aspects provided herein, said solution comprises a ratio of urea to thiourea of about 2 to 1. In some embodiments of aspects provided herein, a concentration of said urea in said solution is from about 4 M to about 9 M and a concentration of said thiourea in said solution is from about 0.5 M to about 3.5 M. In some embodiments of aspects provided herein, a concentration of said urea in said solution is from about 6.5 M to about 7.5 M and a concentration of said thiourea in said solution is from about 1.5 M to about 2.5 M. In some embodiments of aspects provided herein, said solution comprises trailing electrolyte ions or leading electrolyte ions or both trailing electrolyte ions and leading electrolyte ions.

An aspect of the present disclosure provides a method of purifying high molecular weight nucleic acids from a tissue sample, comprising: (a) loading into a fluidic device: (i) a cellular sample comprising genomic DNA and a contaminant, wherein said cellular sample is contacted with a lysis buffer prior to or after said loading of said cellular sample into said fluidic device, (ii) a trailing electrolyte buffer, said trailing electrolyte buffer comprising trailing electrolyte ions with a first effective mobility, wherein said first effective mobility has a magnitude lower than a magnitude of an effective mobility of said high molecular weight nucleic acids and a magnitude greater than a magnitude of said contaminant, and (iii) a first leading electrolyte buffer, said first leading electrolyte buffer comprising first leading electrolyte ions with a second effective mobility, wherein said second effective mobility has a magnitude greater than said magnitude of said effective mobility of said high molecular weight nucleic acids; (b) conducting isotachophoresis with said trailing electrolyte ions, said high molecular weight nucleic acids, and said first leading electrolyte ions, thereby separating said high molecular weight nucleic acids from said contaminant and enriching said high molecular weight nucleic acids in an isotachophoresis zone; and (c) eluting said genomic DNA into a solution in an output reservoir, wherein greater than 50% of the mass of nucleic acids within said solution are greater than 30 kilobases.

In some embodiments of aspects provided herein, said lysis buffer does not comprise an alkaline buffer. In some embodiments of aspects provided herein, said lysis buffer comprises octylphenol ethoxylate. In some embodiments of aspects provided herein, greater than 50% of the mass of nucleic acids within said solution are greater than 50 kilobases.

An aspect of the present disclosure provides a method of conducting isotachophoresis, comprising: (a) providing a fluidic device comprising a first channel in fluid communication with a sample input reservoir comprising a tissue sample comprising lysed solid tissue, a first buffer reservoir comprising a first leading electrolyte buffer, and a second buffer reservoir comprising a trailing electrolyte buffer; (b) contacting a first electrode to said first leading electrolyte buffer in said first buffer reservoir; (c) contacting a second electrode to said trailing electrolyte buffer in said second buffer reservoir; and (d) applying an electric field within said fluidic device to conduct isotachophoresis, wherein said isotachophoresis occurs without direct contact between said tissue sample and said first and second electrodes.

In some embodiments of aspects provided herein, said fluidic device further comprises a third buffer reservoir in fluid communication with said first channel and said first buffer reservoir, said third buffer reservoir comprising a lower concentration of said first leading electrolyte buffer than said first buffer reservoir. In some embodiments of aspects provided herein, said third buffer reservoir and said first buffer reservoir are connected by a second channel comprising one or more capillary barriers to limit pressure-driven flow within said second channel and between said third buffer reservoir and said first buffer reservoir. In some embodiments of aspects provided herein, said fluidic device further comprises an elution reservoir. In some embodiments of aspects provided herein, said elution reservoir is in fluid communication with a fourth buffer reservoir.

An aspect of the present disclosure provides a microfluidic system, said microfluidic system comprising: (a) a microfluidic chip comprising a first channel and a first reservoir in fluid communication with said first channel, wherein said first channel and said first reservoir meet at a first junction; and (b) a mechanical member comprising a first tooth, wherein said mechanical member is configured to apply mechanical pressure to said first channel via said first tooth in order to at least partially close said first channel by plastic deformation of at least one wall of said first channel and increase fluid resistance between said first channel and said first reservoir.

In some embodiments of aspects provided herein, said microfluidic chip further comprises a second reservoir in fluid communication with said first reservoir and a second channel connecting said first reservoir and second reservoir, and wherein said mechanical member further comprises a second tooth configured to apply mechanical pressure to said second channel in order to plastically close said second channel and prevent fluid communication between said first reservoir and said second reservoir. In some embodiments of aspects provided herein, said first tooth is configured to deliver mechanical pressure to said first junction in order to close said first channel by plastic deformation of at least one wall of said first channel. In some embodiments of aspects provided herein, said first tooth is configured to heat said first channel. In some embodiments of aspects provided herein, said mechanical member comprises a material with a Young's modulus of elasticity greater than a Young's modulus of elasticity of said first channel. In some embodiments of aspects provided herein, said microfluidic system is configured to perform isotachophoresis. In some embodiments of aspects provided herein, said first tooth is thermally coupled to a heating element. In some embodiments of aspects provided herein, said first tooth is heated to a temperature greater than the glass transition temperature of said at least one wall of said first channel. Some embodiments of aspects provided herein comprise a method of completing a process in a fluidic system comprising using said microfluidic system to at least partially close said first channel by plastic deformation, thereby increasing resistance to fluid flow between said first channel and said first reservoir. In some embodiments of aspects provided herein, said first tooth of said mechanical member applies a force of at least 0.25 lbs to said first channel. In some embodiments of aspects provided herein, said process in said fluidic system is isotachophoresis.

An aspect of the present disclosure provides a method of performing isotachophoresis on a sample comprising nucleic acids comprising: (a) loading said sample comprising nucleic acids into a first reservoir of a microfluidic chip; (b) loading a trailing electrolyte buffer into a second reservoir of said microfluidic chip, wherein said trailing electrolyte buffer comprises first trailing electrolyte ions with an effective mobility having a magnitude lower than a magnitude of an effective mobility of said nucleic acids; (c) loading a leading electrolyte buffer into a third reservoir of said microfluidic chip, wherein said third reservoir comprises first leading electrolyte ions with a second effective mobility, wherein said second effective mobility has a magnitude greater than said magnitude of said effective mobility of said nucleic acids; (d) applying an electric field within said microfluidic chip to conduct isotachophoresis with said first trailing electrolyte ions, said nucleic acids, and said first leading electrolyte ions, thereby confining said nucleic acids, or a portion thereof, to an isotachophoresis zone; and (e) using a temperature sensor to sense a temperature change in or near said isotachophoresis zone, wherein feedback from said temperature sensor is used to control said electric field.

In some embodiments of aspects provided herein, said control of said electric field results in positioning of said nucleic acids, or portion thereof, in an elution reservoir or region of said microfluidic chip. In some embodiments of aspects provided herein, said temperature sensor is located within at most 8 mm of said elution reservoir. In some embodiments of aspects provided herein, said temperature change is within a range of about 0.2° C. to 5° C. In some embodiments of aspects provided herein, said applied electric field causes said leading electrolyte and said trailing electrolyte to meet at an isotachophoresis interface and said temperature sensor senses said isotachophoresis interface.

An aspect of the present disclosure provides a microfluidic device comprising: (a) a first isotachophoresis region in a microfluidic chip comprising: (i) a first sample reservoir in fluid communication with a first fluidic channel; (ii) a first, a second, and a third buffer reservoir in fluid communication with said first fluidic channel, wherein said first and second buffer reservoirs are separated by a capillary barrier; and (iii) an elution reservoir in fluid communication with said first fluidic channel; (b) a sensor configured to detect a temperature change in said first fluidic channel within said first isotachophoresis region; and (c) an apparatus positioned to supply electrical current within said first channel within said first isotachophoresis region.

Some embodiments of aspects provided herein further comprise a controller configured to trigger a reduction or elimination of said electrical current when said sensor receives a thermal signal. In some embodiments of aspects provided herein, said temperature change is an increase in temperature within a range of about 0.2° C. to 5° C. In some embodiments of aspects provided herein, said microfluidic device is further configured to isolate a sample of nucleic acids in said elution reservoir after said sensor detects a change in temperature. In some embodiments of aspects provided herein, said sensing of said nucleic acids is performed with a sensor located within at most 8 mm of said elution reservoir. In some embodiments of aspects provided herein, said first channel comprises a single sensor.

An aspect of the present disclosure provides a kit comprising: (a) said microfluidic device of claim 111, said microfluidic device of claim 165, or said microfluidic chip of claim 128; (b) a trailing electrolyte buffer comprising trailing electrolytes; and (c) a leading electrolyte buffer comprising leading electrolytes.

In some embodiments of aspects provided herein, said trailing electrolyte buffer comprises a mixture of at least two electrolytes with different effective mobilities. In some embodiments of aspects provided herein, said mixture comprises (i) a first electrolyte that has a lower effective mobility magnitude than a nucleic acid and a higher effective mobility magnitude than a contaminant, and (ii) a second electrolyte which has a lower effective mobility magnitude than said contaminant. In some embodiments of aspects provided herein, said first electrolyte comprises caproic acid. In some embodiments of aspects provided herein, said second electrolyte comprises HEPES (4-(2-hydroxyethyl)-1-piperazineethanesulfonic add). In some embodiments of aspects provided herein, said kit further comprises sample buffer, wherein said sample buffer comprises leading electrolyte buffer, trailing electrolyte buffer, or urea in any combination. In some embodiments of aspects provided herein, said kit further comprises a sample buffer comprising urea and thiourea.

An aspect of the present disclosure provides a method for sample purification, comprising: (a) loading into a fluidic device (i) a tissue sample comprising nucleic acids and a contaminant, wherein said tissue sample is not an unlysed whole blood sample, (ii) a trailing electrolyte buffer comprising trailing electrolyte ions with an effective mobility having a magnitude greater than a magnitude of an effective mobility of said contaminant and lower than a magnitude of an effective mobility of said nucleic acids, and (iii) a leading electrolyte buffer comprising leading electrolyte ions, with a second effective mobility, wherein said second effective mobility has a magnitude greater than said magnitude of said effective mobility of said nucleic acids; and (b) applying an electrical field within said fluidic device to conduct isotachophoresis with said trailing electrolyte ions, said nucleic acids, and said leading electrolyte ions, thereby purifying said nucleic acids from said contaminant in said tissue sample.

In some embodiments of aspects provided herein, said tissue sample is not a whole blood sample. In some embodiments of aspects provided herein, said trailing electrolyte ions comprise caproic acid. In some embodiments of aspects provided herein, said leading electrolyte ions comprise chloride. In some embodiments of aspects provided herein, said trailing electrolyte buffer comprises second trailing electrolyte ions having a different effective mobility than said first trailing electrolyte ions. In some embodiments of aspects provided herein, said second trailing electrolyte ions comprise HEPES (4-(2-hydroxyethyl)-1-piperazineethanesulfonic acid). In some embodiments of aspects provided herein, said second trailing electrolyte ions comprise MOPS (3-(N-morpholino)propanesulfonic acid). In some embodiments of aspects provided herein, said second trailing electrolyte ions comprise HEPES (4-(2-hydroxyethyl)-1-piperazineethanesulfonic acid) and first trailing electrolyte ions are comprised of caproic acid. In some embodiments of aspects provided herein, said second trailing electrolyte ions comprise MOPS (3-(N-morpholino)propanesulfonic acid) and first trailing electrolyte ions are comprised of caproic acid. In some embodiments of aspects provided herein, said second trailing electrolyte ions comprise HEPES and first trailing electrolyte ions comprise MOPS. In some embodiments of aspects provided herein, said trailing electrolyte buffer comprises second trailing electrolyte ions with a second effective mobility, wherein said second effective mobility has a magnitude about the same as or lower than said magnitude of said effective mobility of said contaminant. In some embodiments of aspects provided herein, said contaminant is selected from the group consisting of crosslinked nucleic acids, embedding material, fixation chemicals, proteins, inhibitors, and combinations thereof. In some embodiments of aspects provided herein, said contaminant comprises crosslinked nucleic acids. In some embodiments of aspects provided herein, said tissue sample is combined with said trailing electrolyte buffer prior to said loading. In some embodiments of aspects provided herein, said tissue sample is combined with said leading electrolyte buffer prior to said loading. In some embodiments of aspects provided herein, said loading of said leading electrolyte buffer is conducted prior to said loading of said tissue sample. In some embodiments of aspects provided herein, the method further comprises eluting an output solution comprising said purified nucleic acids from an outlet reservoir of said fluidic device. In some embodiments of aspects provided herein, a concentration of said purified nucleic acids in said output solution is at least about two-fold higher than a concentration of said nucleic acids in said tissue sample. In some embodiments of aspects provided herein, a concentration of said crosslinked nucleic acids in said output solution is at least about two-fold lower than a concentration of said crosslinked nucleic acids in said tissue sample. In some embodiments of aspects provided herein, said output solution does not comprise said contaminant. In some embodiments of aspects provided herein, said tissue sample is fresh tissue. In some embodiments of aspects provided herein, said tissue sample is fresh frozen (FF) tissue. In some embodiments of aspects provided herein, said tissue sample is formalin fixed paraffin embedded tissue (FFPE). In some embodiments of aspects provided herein, the method further comprises, prior to said loading, lysing or disrupting said tissue sample. In some embodiments of aspects provided herein, said lysing or disrupting is conducted using urea or thiourea.

An aspect of the present disclosure provides a method for sample purification, comprising: (a) loading into a first channel on a fluidic device (i) a first tissue sample comprising first nucleic acids and a first contaminant, (ii) a first trailing electrolyte buffer comprising first trailing ions, wherein a magnitude of an effective mobility of said first trailing ions is less than a magnitude of an effective mobility of said first nucleic acids, and (iii) a first leading electrolyte buffer comprising first leading ions, wherein a magnitude of an effective mobility of said first leading ions is greater than said magnitude of said effective mobility of said first nucleic acids; (b) loading into a second channel on said fluidic device (iv) a second tissue sample comprising second nucleic acids and a second contaminant, (v) a second trailing electrolyte buffer comprising second trailing ions, wherein a magnitude of said second trailing ions is less than a magnitude of an effective mobility of said second nucleic acids, and (vi) a second leading electrolyte buffer comprising second leading ions, wherein a magnitude of an effective mobility of said second leading ions is greater than said magnitude of said effective mobility of said second nucleic acids; and (c) applying an electrical field within said fluidic device to conduct isotachophoresis in said first channel with said first trailing ions, said first nucleic acids, and said first leading ions, and to conduct isotachophoresis in said second channel with said second trailing ions, said second nucleic acids, and said second leading ions, thereby purifying said first nucleic acids from said first contaminant and purifying said second nucleic acids from said second contaminant.

In some embodiments of aspects provided herein, said first trailing electrolyte buffer or said first leading electrolyte buffer further comprises a lysis agent or a tissue disruption agent. In some embodiments of aspects provided herein, said second trailing electrolyte buffer or said second leading electrolyte buffer further comprises a lysis agent or a tissue disruption agent. In some embodiments of aspects provided herein, said lysis agent or said tissue disruption agent comprises one or more agents selected from the group consisting of a solution with pH greater than about 12, a proteinase, urea, thiourea, and a surfactant.

An aspect of the present disclosure provides a method for sample purification, comprising: (a) loading into a first zone of a fluidic device (i) a tissue sample comprising nucleic acids and a contaminant, (ii) a trailing electrolyte buffer comprising trailing ions, wherein a magnitude of an effective mobility of said trailing ions is lower than a magnitude of an effective mobility of said nucleic acids, and (iii) a leading electrolyte buffer comprising leading ions, wherein a magnitude of an effective mobility of said leading ions is greater than said magnitude of said effective mobility of said nucleic acids; and (b) applying an electrical field on said fluidic device to conduct isotachophoresis in a second zone of said fluidic device with said trailing ions, said nucleic acids, and said leading ions, thereby purifying said nucleic acids from said contaminant, wherein during said applying, said first zone is maintained at a first temperature and said second zone is maintained at a second temperature different from said first temperature.

In some embodiments of aspects provided herein, said trailing electrolyte buffer or said leading electrolyte buffer further comprises a lysis agent or a tissue disruption agent. In some embodiments of aspects provided herein, said lysis agent or said tissue disruption agent comprises one or more agents selected from the group consisting of a solution with pH greater than about 12, a proteinase, urea, thiourea, and a surfactant. In some embodiments of aspects provided herein, said first temperature is between about 4° C. and about 40° C. In some embodiments of aspects provided herein, said first temperature is between about 40° C. and about 80° C.

An aspect of the present disclosure provides a method for sample purification, comprising: (a) loading into a first zone of a fluidic device (i) a tissue sample comprising nucleic acids, (ii) a trailing electrolyte buffer comprising trailing ions, wherein a magnitude of an effective mobility of said trailing ions is lower than a magnitude of an effective mobility of said nucleic acids, and (iii) a leading electrolyte buffer comprising leading ions, wherein a magnitude of an effective mobility of said leading ions is greater than said magnitude of said effective mobility of said nucleic acids; (b) in said first zone, conducting on said tissue sample at least one sample preparation selected from the group consisting of (1) removing embedding material, (2) disrupting tissue, (3) lysing cells, (4) de-crosslinking nucleic acids, (5) digesting proteins and (6) digesting nucleic acids; and (c) applying an electrical field within said fluidic device to conduct isotachophoresis in a second zone of said fluidic device with said trailing ions, said nucleic acids, and said leading ions, thereby purifying said nucleic acids from a contaminant in said tissue sample.

In some embodiments of aspects provided herein, said removing embedding material or said lysing cells comprises, prior to said applying said electric field, incubating said tissue sample in said fluidic device at a temperature of at least about 37° C. for duration of at least about 1 minute. In some embodiments of aspects provided herein, said temperature is from about 40° C. to about 80° C. In some embodiments of aspects provided herein, said duration is from about 1 minute to about 60 minutes. In some embodiments of aspects provided herein, said disrupting tissue or said lysing cells comprises applying mechanical stress to said sample. In some embodiments of aspects provided herein, said disrupting tissue or said lysing cells comprises applying heat to said sample. In some embodiments of aspects provided herein, said applying heat results in a temperature of said tissue sample from about 30° C. to about 65° C. In some embodiments of aspects provided herein, said disrupting tissue or said lysing cells comprises a solution pH of at least 12. In some embodiments of aspects provided herein, said disrupting tissue or said lysing cells comprises proteolytic digestion. In some embodiments of aspects provided herein, said proteolytic digestion is conducted at a temperature greater than about 25° C. In some embodiments of aspects provided herein, said temperature is from about 30° C. to about 65° C. In some embodiments of aspects provided herein, said disrupting tissue or said lysing cells comprises applying at least one surfactant to said tissue or said cells. In some embodiments of aspects provided herein, said disrupting tissue or said lysing cells comprises applying a solution comprising urea to said tissue or said cells. In some embodiments of aspects provided herein, said solution further comprises thiourea. In some embodiments of aspects provided herein, a concentration of said urea in said solution is from about 4 M to about 9 M and a concentration of said thiourea in said solution is from about 0.5 M to about 3.5 M. In some embodiments of aspects provided herein, a concentration of said urea in said solution is from about 6.5 M to about 7.5 M and a concentration of said thiourea in said solution is from about 1.5 M to about 2.5 M. In some embodiments of aspects provided herein, said de-crosslinking nucleic acids comprises digesting crosslinking proteins with proteinase K. In some embodiments of aspects provided herein, said digesting nucleic acids is performed with DNase or RNase.

An aspect of the present disclosure provides a method for sample purification, comprising: (a) loading onto a fluidic device (i) a tissue sample comprising nucleic acids, wherein said tissue sample is embedded or fixed, (ii) a trailing electrolyte buffer comprising trailing electrolytes, wherein said trailing electrolytes have a lower effective mobility than said nucleic acids, and (iii) a leading electrolyte buffer comprising leading electrolytes, wherein said leading electrolytes have a higher effective mobility than said nucleic acids; and (b) applying an electrical field on said fluidic device to conduct isotachophoresis with said trailing electrolytes, said nucleic acids, and said leading electrolytes, thereby purifying said nucleic acids from a contaminant in said tissue sample.

In some embodiments of aspects provided herein, said contaminant is selected from the group consisting of crosslinked nucleic acids, embedding material, fixation chemicals, enzymes, and inhibitors. In some embodiments of aspects provided herein, said embedding material comprises paraffin. In some embodiments of aspects provided herein, said tissue sample is formalin-fixed. In some embodiments of aspects provided herein, said tissue sample is embedded and fixed. In some embodiments of aspects provided herein, said tissue sample is a formalin-fixed paraffin-embedded (FFPE) tissue sample. In some embodiments of aspects provided herein, said tissue sample is a dissected tissue sample. In some embodiments of aspects provided herein, said dissected tissue sample is dissected FFPE sample. In some embodiments of aspects provided herein, the method further comprises the step of comparing a characteristic of said nucleic acids to nucleic acids from other samples. In some embodiments of aspects provided herein, said characteristic is an expression level. In some embodiments of aspects provided herein, said characteristic is a nucleic acid sequence. In some embodiments of aspects provided herein, said characteristic is a molecular weight. In some embodiments of aspects provided herein, said characteristic is a nucleic acid integrity. In some embodiments of aspects provided herein, said characteristic is a nucleic acid purity. In some embodiments of aspects provided herein, the method further comprises a step of administering a drug based on said characteristic of said nucleic acids. In some embodiments of aspects provided herein, said tissue sample is a tumor sample. In some embodiments of aspects provided herein, said trailing electrolyte buffer has a pH of about 7. In some embodiments of aspects provided herein, said trailing electrolyte buffer has a pH of greater than about 7. In some embodiments of aspects provided herein, the method further comprises, prior to said applying said electric field, incubating said tissue sample in said fluidic device at a temperature of at least about 37° C. for duration of at least about 1 minute. In some embodiments of aspects provided herein, said temperature is from about 40° C. to about 80° C. In some embodiments of aspects provided herein, said duration is from about 1 minute to about 60 minutes. In some embodiments of aspects provided herein, said leading electrolyte buffer comprises proteinase K. In some embodiments of aspects provided herein, the method further comprises removing protein crosslinks from said nucleic acids using said proteinase K. In some embodiments of aspects provided herein, the method further comprises, after said applying said electric field, removing protein crosslinks from said nucleic acids using heat. In some embodiments of aspects provided herein, the method further comprises eluting an output solution comprising said purified nucleic acids from an outlet reservoir of said fluidic device. In some embodiments of aspects provided herein, a concentration of said purified nucleic acids in said output solution is at least about two-fold higher than a concentration of said nucleic acids in said tissue sample. In some embodiments of aspects provided herein, a concentration of said crosslinked nucleic acids in said output solution is at least about two-fold lower than a concentration of said crosslinked nucleic acids in said tissue sample. In some embodiments of aspects provided herein, said output solution does not comprise said contaminant. In some embodiments of aspects provided herein, said output solution has a volume equal to or less than about 50 µL. In some embodiments of aspects provided herein, said tissue sample has a mass of at least about 1 ng. In some embodiments of aspects provided herein, said tissue sample has a volume of less than about 500 µL. In some embodiments of aspects provided herein, said trailing electrolytes have a higher effective mobility than said contaminant. In some embodiments of aspects provided herein, said trailing electrolytes comprise (i) first ions, wherein said first ions have a higher effective mobility magnitude than said contaminant, and (ii) second ions, wherein said second ions have an effective mobility magnitude about the same as or lower than said contaminant. In some embodiments of aspects provided herein, said conducting isotachophoresis quenches a pH of said tissue sample to about 7. In some embodiments of aspects provided herein, the method further comprises, prior to said loading, conducting de-paraffinization on said tissue sample. In some embodiments of aspects provided herein, said tissue sample is a historical formalin-fixed paraffin-embedded (FFPE) sample, further comprising comparing a characteristic of said nucleic acids to a characteristic of different nucleic acids from a different tissue sample. In some embodiments of aspects provided herein, the method further comprises a step of detecting a concentration of said nucleic acids. In some embodiments of aspects provided herein, said concentration is less than or equal to about 1 picogram per microliter (pg/µL). In some embodiments of aspects provided herein, said concentration is less than or equal to about 0.5 pg/µL. In some embodiments of aspects provided herein, said concentration is at least about 1 picogram per microliter (pg/µL).

An aspect of the present disclosure provides a fluidic device, comprising: a sample purification region, comprising: (a) a first zone; (b) a sample inlet located in said first zone; (c) a trailing electrolyte reservoir in fluid communication with said first zone; (d) a second zone in fluid communication with said first zone; (e) a leading electrolyte reservoir in fluid communication with said second zone; (f) a sample outlet in fluid communication with said second zone; (g) a first heater in thermal communication with said first zone; and (h) a second heater configured to transfer heat to said second zone, wherein said first zone is substantially thermally isolated from said second zone.

An aspect of the present disclosure provides a fluidic device, comprising: a sample purification region, comprising: (a) a first zone; (b) a sample inlet located in said first zone; (c) a trailing electrolyte reservoir in fluid communication with said first zone; (d) a second zone in fluid communication with said first zone; (e) a leading electrolyte reservoir in fluid communication with said second zone; (f) a sample outlet in fluid communication with said second zone; and (g) a heater in thermal communication with said first zone and said second zone.

In some embodiments of aspects provided herein, the device further comprises a second sample purification region. In some embodiments of aspects provided herein, said first zone is a de-paraffinization zone. In some embodiments of aspects provided herein, said first zone is a disruption zone. In some embodiments of aspects provided herein, said second zone is an isotachophoresis zone. In some embodiments of aspects provided herein, said first zone or said second zone has a width of less than about 1 mm. In some embodiments of aspects provided herein, said first zone or said second zone has a width of less than about 0.5 mm.

An aspect of the present disclosure provides a kit, comprising a device provided herein, a trailing electrolyte buffer comprising trailing electrolytes, and a leading electrolyte buffer comprising leading electrolytes.

In some embodiments of aspects provided herein, said trailing electrolyte buffer contains a mixture of at least two electrolytes with different effective mobilities. In some embodiments of aspects provided herein, said mixture comprises (i) a first electrolyte that has a lower effective mobility magnitude than a nucleic acid and a higher effective mobility magnitude than a contaminant, and (ii) a second electrolyte which has a lower effective mobility magnitude than said contaminant. In some embodiments of aspects provided herein, said contaminant comprises crosslinked nucleic acids. In some embodiments of aspects provided herein, said first electrolyte comprises caproic acid. In some embodiments of aspects provided herein, said second electrolyte comprises HEPES.

An aspect of the present disclosure provides a method for sample purification, comprising: (a) loading into a fluidic device (i) a tissue sample comprising nucleic acids, (ii) a trailing electrolyte buffer, said trailing electrolyte buffer comprising trailing electrolyte ions with a first effective mobility, wherein said first effective mobility has a magnitude lower than a magnitude of an effective mobility of said nucleic acids, (iii) a first leading electrolyte buffer in a first leading electrolyte reservoir, said first leading electrolyte buffer comprising first leading electrolyte ions with a second effective mobility, wherein said second effective mobility has a magnitude greater than said magnitude of said effective mobility of said nucleic acids, and (iv) a second leading electrolyte buffer in a second leading electrolyte reservoir, said second leading electrolyte buffer comprising second leading electrolyte ions with a third effective mobility, wherein said third effective mobility has a magnitude greater than said magnitude of said effective mobility of said nucleic acids, wherein said first leading electrolyte buffer is different from said second leading electrolyte buffer; (b) first conducting isotachophoresis with said trailing electrolyte ions, said nucleic acids, and said first leading electrolyte ions, thereby purifying said nucleic acids from said contaminant in said tissue sample; and (c) second conducting isotachophoresis with said trailing electrolyte ions, said nucleic acids, and said second leading electrolyte ions.

In some embodiments of aspects provided herein, said second conducting isotachophoresis comprises changing an applied current from a first channel to a second channel. In some embodiments of aspects provided herein, said first leading electrolyte ions are the same as said second leading electrolyte ions, and wherein a concentration of said first leading electrolyte ions in said first leading electrolyte buffer is different from a concentration of said second leading electrolyte ions in said second leading electrolyte buffer. In some embodiments of aspects provided herein, said concentration of said first leading electrolyte ions in said first leading electrolyte buffer is different from said concentration of said second leading electrolyte ions in said second leading electrolyte buffer by a factor of at least 1.5×. In some embodiments of aspects provided herein, said first leading electrolyte ions are different from said second leading electrolyte ions. In some embodiments of aspects provided herein, said first leading electrolyte ions are the same as said second leading electrolyte ions, and wherein a concentration of said first leading electrolyte ions in said first leading electrolyte buffer is the same as a concentration of said second leading electrolyte ions in said second leading electrolyte buffer, and wherein said first leading electrolyte buffer comprises third leading electrolyte ions. In some embodiments of aspects provided herein, said first leading electrolyte ions are the same as said second leading electrolyte ions, and wherein a concentration of said first leading electrolyte ions in said first leading electrolyte buffer is the same as a concentration of said second leading electrolyte ions in said second leading electrolyte buffer, and wherein said second leading electrolyte buffer comprises third leading electrolyte ions. In some embodiments of aspects provided herein, the method further comprises collecting said nucleic acids in said second leading electrolyte reservoir. In some embodiments of aspects provided herein, the method further comprises removing said nucleic acids from said second leading electrolyte reservoir. In some embodiments of aspects provided herein, said trailing electrolyte buffer is loaded into a trailing electrolyte reservoir that is separate from said first leading electrolyte reservoir and said second leading electrolyte reservoir. In some embodiments of aspects provided herein, said first conducting isotachophoresis and said second conducting isotachophoresis are performed by applying one electric field. In some embodiments of aspects provided herein, said first conducting isotachophoresis and said second conducting isotachophoresis are performed by applying more than one electric field.

An aspect of the present disclosure provides a fluidic device, comprising: a sample purification region, comprising: (a) a channel comprising a first zone and a second zone in fluid communication with said first zone; (b) a sample inlet, a trailing electrolyte reservoir comprising a trailing electrolyte buffer, and a first leading electrolyte reservoir comprising a first leading electrolyte buffer, each in fluid communication with said first zone; and (c) a second leading electrolyte reservoir comprising a second leading electrolyte buffer, wherein said second leading electrolyte buffer is in fluid communication with said second zone and wherein said second leading electrolyte buffer is different from said first leading electrolyte buffer.

In some embodiments of aspects provided herein, said sample inlet is capable of receiving a sample comprising at least some non-liquid biological material. In some embodiments of aspects provided herein, said second leading electrolyte buffer comprises a different leading electrolyte co-ion than said first leading electrolyte buffer. In some embodiments of aspects provided herein, said first leading electrolyte buffer comprises first leading electrolyte ions and said second leading electrolyte buffer comprises second leading electrolyte ions that are the same as said first leading electrolyte ions, and wherein a concentration of said first leading electrolyte ions in said first leading electrolyte buffer is different from a concentration of said second leading electrolyte ions in said second leading electrolyte buffer. In some embodiments of aspects provided herein, said first leading electrolyte buffer comprises first leading electrolyte ions and said second leading electrolyte buffer comprises second leading electrolyte ions, and wherein a concentration of said first leading electrolyte ions in said first leading electrolyte buffer is different from said concentration of said second leading electrolyte ions in said second leading electrolyte buffer by a factor of at least 1.5×. In some embodiments of aspects provided herein, said first leading electrolyte buffer comprises first leading electrolyte ions and said second leading electrolyte buffer comprises second leading electrolyte ions that are different from said first leading electrolyte ions. In some embodiments of aspects provided herein, said first leading electrolyte buffer comprises first leading electrolyte ions and said second leading electrolyte buffer comprises second leading electrolyte ions that are that same as said first leading electrolyte ions, and wherein a concentration of said first leading electrolyte ions in said first leading electrolyte buffer is the same as a concentration of said second leading electrolyte ions in said second leading electrolyte buffer, and wherein said first leading electrolyte buffer comprises third leading electrolyte ions. In some embodiments of aspects provided herein, said first leading electrolyte buffer comprises first leading electrolyte ions and said second leading electrolyte buffer comprises second leading electrolyte ions that are the same as said first leading electrolyte ions, and wherein a concentration of said first leading electrolyte ions in said first leading electrolyte buffer is the same as a concentration of said second leading electrolyte ions in said second leading electrolyte buffer, and wherein said second leading electrolyte buffer comprises third leading electrolyte ions.

An aspect of the present disclosure provides a method, comprising: (a) providing an electrokinetic fluidic device comprising a reservoir in fluidic communication with a channel; (b) loading a sample volume into said reservoir; (c) moving at least 50% of said sample volume from said reservoir to said channel; and (d) applying an ionic current through said channel.

In some embodiments of aspects provided herein, said moving is conducted with the aid of gravity. In some embodiments of aspects provided herein, said ionic current does not substantially pass through said reservoir. In some embodiments of aspects provided herein, said at least 50% of said sample volume comprises at least 80% of said sample volume. In some embodiments of aspects provided herein, said sample volume comprises nucleic acids. In some embodiments of aspects provided herein, said sample volume comprises a tissue sample. In some embodiments of aspects provided herein, said sample volume comprises a formalin-fixed paraffin-embedded (FFPE) sample. In some embodiments of aspects provided herein, said applying an ionic current comprises conducting isotachophoresis (ITP).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 27C shows the chip before ITP (blood lysate and ITP buffers loaded in chip; buffer only in elution well). FIG. 27D shows the chip after ITP (blood lysate and ITP buffers loaded in chip; purified DNA in elution well).

DETAILED DESCRIPTION

Overview

Figure 1A:
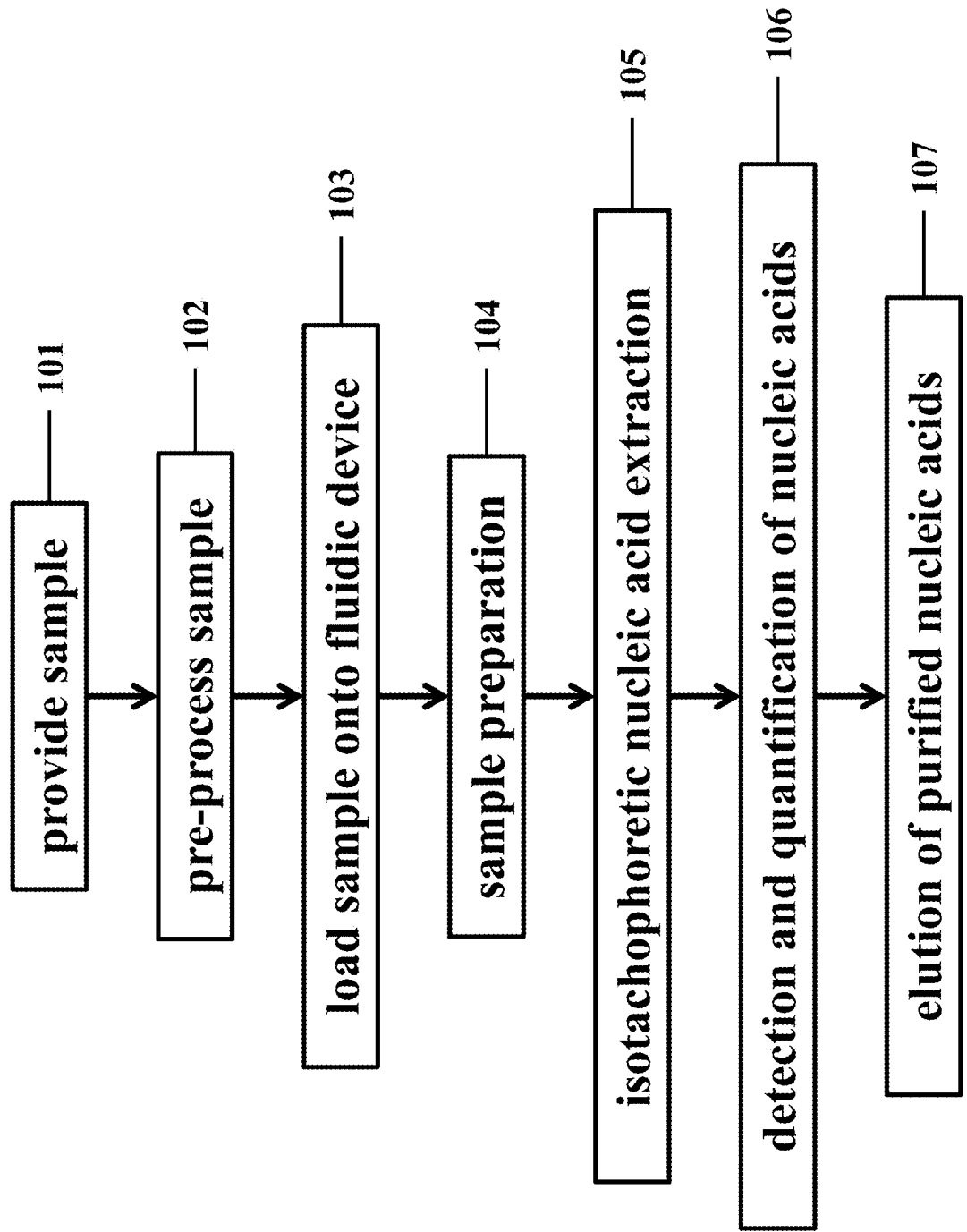
FIG. 1A shows an exemplary protocol for sample processing and nucleic acid extraction or purification.

Sample preparation is a first step to almost all genomic and transcriptomic analyses, and yet can be a primary source of analysis variability. Sample preparation can also be manually intensive, particularly when the sample is a formalin-fixed paraffin-embedded (FFPE) sample containing cross-linked proteins.

The present disclosure provides processes and devices to improve the efficiency of nucleic acid extraction and purification from tissue and cellular samples, including samples that have been processed in some way, such as paraffin-embedded samples or chemically-fixed samples (e.g., FFPE samples, samples that contain solid tissue). Methods provided herein include methods of on-chip or off-chip preparation of such processed samples prior to conducting isotachophoresis using methods that incorporate leading electrolyte ions and trailing electrolyte ions. In some instances, the methods include treating (e.g., by removal of embedding material, lysis, enzymatic disruption) a fixed solid tissue in a trailing electrolyte buffer or leading electrolyte buffer prior to conducting isotachophoresis on the sample. The methods can also include use of a second leading electrolyte buffer of lower ionic strength in order to produce a sample compatible with downstream processes like amplification or other enzymatic assays. The devices and systems provided herein include devices suitable for conducting isotachophoresis on samples derived from tissues, including microfluidic devices with parallel processing features and automated feedback-control mechanisms that may include thermal sensors that detect changes in temperature within sample processing channels.

The processes and devices of the present disclosure can provide improved nucleic acid recovery from a sample, especially from low abundance samples (e.g., less than 100 ng of nucleic acid), samples with relatively high volumes (e.g., total volume greater than 25 µl, total volume greater than 50 µl, total volume greater than 100 µl, or more) or liquid samples containing solid particles. The processes and devices provided herein also can provide high repeatability, and reduced bias for short nucleic acids. The devices provided herein can integrate sample preparation (e.g., removal of crosslinking or embedding material) and nucleic acid extraction operations within one device. Devices and processes of the present disclosure can also provide for compatibility with process automation, integration with downstream processes, integration with in-line quantitation (e.g., at single picogram resolution), and/or integration with nucleic acid length and sequence distribution analysis.

The methods provided herein are often methods of performing isotachophoresis under conditions suitable to extract nucleic acids from certain samples, especially FFPE samples. In some instances, the disclosed methods include methods of performing isotachophoresis using a trailing electrolyte buffer containing at least two ions with different magnitudes of effective mobilities. The methods may also include methods of conducting isotachophoresis using two different leading electrolyte buffers, one of which may serve as a sample elution buffer. The methods can include process automation and parallel processing of multiple samples.

The present disclosure also includes protocols using buffer and spacer chemistries. These buffer and spacer chemistries can include the use of multiple species of electrolytes for conducting ITP. For example, the trailing electrolytes can comprise a mixture of electrolyte species, capable of separating non-crosslinked nucleic acids from crosslinked nucleic acids, while separating either non-crosslinked nucleic acids or both crosslinked and non-crosslinked nucleic acids from contaminants within a sample.

The devices provided herein include injection-molded fluidic devices with parallel sample processing channels capable of performing ITP in a multiplexed fashion and ITP devices with two or more regions that are connected to a thermal device. Techniques of the present disclosure can employ ITP to simultaneously collect, purify, and focus extracted RNA and DNA, to quantify total extracted nucleic acid on-chip (e.g., via in-line ITP-aided concentration into very small volumes or labeling with an intercalating fluorescent dye), and to deliver nucleic acids downstream to parallel output reservoirs compatible with robotic pipetting.

Techniques of the present disclosure can enable purification of sample material (e.g., nucleic acids) without binding the sample material to a solid support. Techniques of the present disclosure can enable purification of sample material (e.g., nucleic acids) without the use of liquid-phase extraction. This can enable purification without dependence on solubility differences.

The operation of devices of the present disclosure can be automated, largely automated, or partly automated. In some cases, methods of the present disclosure involve only a single off-chip mixing step of dispensing a sample (e.g., FFPE section) into a solution (e.g., alkaline solution, lysis solution, or buffered solution comprising urea and/or thourea), followed by loading of the sample into a reservoir of a fluidic device for further on-device sample preparation (e.g. deparaffinization, tissue disruption and cell lysing, protease digestion, proteolytic digestion, or other treatment including protein denaturation, or nuclease digestion) and nucleic acid extraction, purification, enrichment, in-line quantitation, and sizing or fractionation (e.g., size selection). In some cases, methods of the present disclosure include dispensing a sample (e.g., FFPE section or other tissue sample) into a reservoir or channel of a fluidic device (e.g., cartridge) pre-filled with a solution (e.g., alkaline solution, lysis solution, or buffered solution comprising urea and/or thourea) for on-device sample preparation (e.g. deparaffinization, tissue disruption and cell lysing, protease digestion or other treatment including protein denaturation, or nuclease digestion) and nucleic acid extraction, purification, enrichment, in-line quantitation, and sizing or fractionation (e.g., size selection). In some cases, methods of the present disclosure include disruption tissue and/or lysing cells of a sample off-chip, followed by loading of the sample, which may be homogenous or a non-homogenous mixture of lysed solid tissue and nucleic acids, into a reservoir of a fluidic device for further on device sample preparation (e.g. deparaffinization, protease digestion or other treatment including protein denaturation, or nuclease digestion) and nucleic acid extraction, purification, enrichment, in-line quantitation, and sizing or fractionation (e.g., size selection). Nuclease digestion can include removal of DNA for DNA-free RNA extractions or removal of RNA for RNA-free DNA extractions. The fluidic devices provided herein can be used with a benchtop system to automate an electric-field-based method for the extraction of DNA and RNA from samples.

Devices of the present disclosure include systems that can automate and integrate on-chip heating (e.g., to a temperature from 37° C. to 80° C.), sample preparation (e.g., deparaffinization, tissue disruption and cell lysing), buffer exchange, nucleic acid extraction and purification, enrichment of uncrosslinked or amplifiable nucleic acids (e.g., by separating it away and delivering it separately from crosslinked nucleic acids), and delivery of purified nucleic acids to an output reservoir, such as an array compatible with manual or robotic pipetting. For example, the present disclosure includes an eight-channel cartridge in a standard, robotic automation compatible microtiter plate format, as well as integrated benchtop controller prototypes that can afford automated control of loading of buffers and other fluids, application of temperature and electric fields to the device, and automated start and end run processing of samples in parallel. This system can be easily modified in the future, as needed, to afford higher throughput for use in larger, diagnostic or clinical labs (e.g., 96-well sample format).

For example, FIG. 1A shows an exemplary process diagram for sample processing and nucleic acid extraction using techniques of the present disclosure. A sample can be provided 101 and subjected to any pre-processing steps 102, such as mixing with a buffer, lysis, or removal of embedding material (if present). The sample (and, for example, buffer) can then be loaded onto a fluidic device 103. Sample preparation steps 104 can then be performed on the fluidic device, such as removal of embedding material (if present and if not previously removed during pre-processing), tissue disruption, cell lysis, protein or proteolytic digestion and (for example) nuclease digestion. Isotachophoresis 105 can then be performed to separate and purify nucleic acids from contaminants within the sample (e.g. cell debris, embedding material, crosslinked nucleic acids, fixatives such as formalin, inhibitors, enzymes such as digestion or restriction enzymes). Other steps can occur concurrently with isotachophoresis, such as de-crosslinking of crosslinked nucleic acids (e.g. with heat or protease digestion). Nucleic acids can be detected and quantified 106 during or subsequent to isotachophoresis. Once extracted or purified, nucleic acids can then be eluted and recovered from the device 107.

Figure 1B:
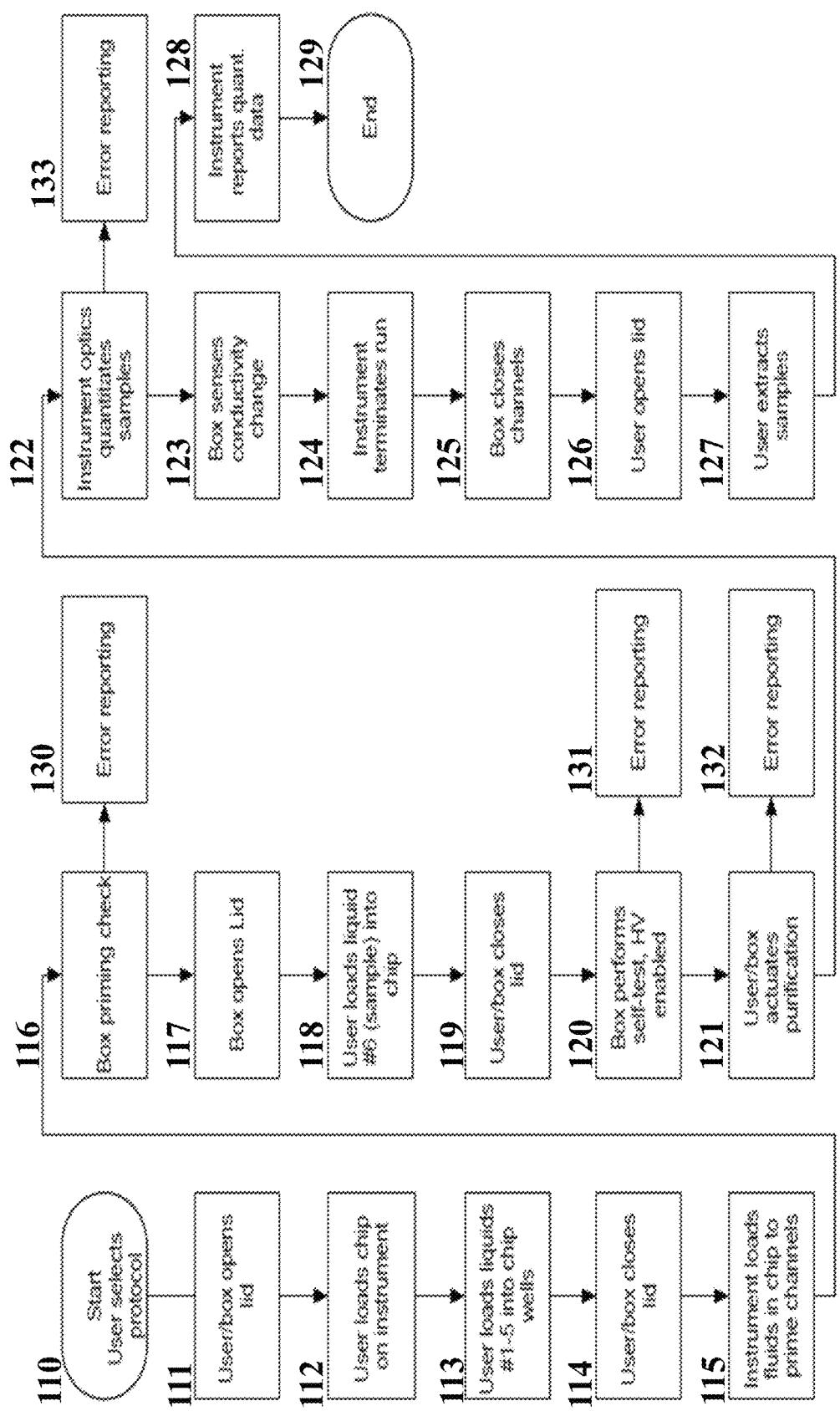
FIG. 1B shows an exemplary protocol for automated sample processing and nucleic acid extraction or purification.

FIG. 1B shows an exemplary process workflow for automated ITP. At step 110, a protocol can be selected, such as by using a graphical user interface on a benchtop device. The user interface software can enable ease of use or hands-free operation. For example, a user can select from a menu (e.g., drop-down menu). Alternatively, the device can scan a barcode (e.g., optical barcode, RFID chip) associated with a sample or a fluidic device chip which can indicate the protocol to be performed. At step 111, the instrument lid can be opened (e.g., manually or automatically via motor). Motorized lid opening can be compatible with robotic laboratory automation. At step 112, the user can load a chip (e.g., fluidic device) onto the benchtop instrument. The chip can comprise a monolithic, multichannel SLAS standard microtiter plate (MTP) footprint for automated ITP. At step 113, ITP liquids can be loaded into the chip wells. Reservoirs for ITP fluids and user samples can be designed for ease of loading, such as via a multichannel pipet (e.g., 9 mm pitch SLAS standard microtiter plate format). Geometrical designs (e.g., capillary barriers) of the channels connecting reservoirs to the ITP channel can resist gravimetric flow or wetting of liquids into the channel prior to operation. These structures can stop fluids in defined places within the ITP channel, including establishing the leading electrolyte/trailing electrolyte interface, as well as enable bubble-free loading. In some cases, prior to operation, pneumatic actuation can be applied to prime the channel. Chip material can be selected to prevent or resist wetting or wicking of fluids into channels (e.g., plastic with hydrophobic properties or a high contact angle). The user can load ITP reagents and buffers onto the chip (e.g., 5 different fluids); alternatively, the chip can be provided with reagents preloaded. At step 114, the user or the device can close the device lid. Sample loading can be actuated through gas or air ports on the chip. Wetting and/or gravity flow can be used to fill channels with liquids, for example without active pressure application.

At step 115, the instrument can apply pressure to load fluids in the chip to prime the channels. At step 116, the device can check that the channels have been appropriately primed. For example, optical (e.g., reflectance), electrical, pressure, and/or flow rate sensors can be used to check that fluids have been loaded to the correct locations within the chip. Sensors and device software can enable real time monitoring and control of liquid loading. ITP reagent and buffer loading can be conducted prior to loading sample onto the chip, so that in case of mis-loading, sample material is not wasted. If the channels are not appropriately primed, the device can perform error reporting 130. At step 117, the device lid can be opened. At step 118, the sample can be loaded onto the device. Sample loading can be performed manually by a user, or can be performed in an automated manner, such as via laboratory automation robotics. Other sample preparation steps can also be conducted. For example, a paraffin-embedded sample (e.g., FFPE) can be loaded, and then the device can control the temperature within the sample reservoir to deparaffinize the sample. At step 119, the device lid can be closed. At step 120, the device can perform a self-test. For example, electrical feedback from device electrodes interfacing with on-chip reservoirs can be used to self-test for successful priming of liquids (e.g., bubble detection). Optical sensors can be used to enable feedback on liquid priming status (e.g., whether or not a liquid has reached a designated capillary barrier). Other sensing mechanisms, such as those disclosed herein, can also be used. If the self-test determines that the device is not properly primed, the device can perform error reporting 131.

At step 121, ITP-based purification can be conducted. Feedback control and process timing using sensors (e.g. triggering) as described herein can be used to control and/or automate the ITP purification. The device can determine whether purification was successfully performed, and if not, the device can perform error reporting 132. At step 122, sensors on the device (e.g., optical sensors) can be used to quantitate the samples, for example by fluorescence, UV, or other optical detection. Sample sizing can also be performed. If the device determines that the sample was not properly quantitated or discovers other issues, the device can perform error reporting 133. At step 123, a conductivity change can be detected, which can be used to indicate timing for ending the ITP run (e.g., when the nucleic acids reach a designated elution location or reservoir). Other detection methods described herein, such as temperature or driving voltage, can also be used to determine end of run timing or other triggers. For example, a temperature or voltage sensor may be used to control an electric field applied to a channel within the device in order to automate the ITP process. As an example, an electric field may be applied to a channel to begin ITP purification. A sensed change in voltage may be used to trigger the start of temperature or other sensing at a fixed location within the channel such as at or near the elution reservoir. The voltage may change as the ITP zone comprising confined nucleic acids moves. Changes indicative of the ITP zone passing through channel features such as a section of decreased cross-sectional area may be sensed by a voltage sensor and feedback may be used to alter the electric field, for example by reducing the applied current. A change in temperature may be detected as the ITP zone passes a temperature sensor at or near the elution reservoir and feedback from the sensor may be used to control the electric field, for example by removing it to end the ITP run. At step 124, the device can terminate the run, for example based on a trigger signal. The nucleic acids may be positioned or isolated within the elution reservoir or region when the ITP run is terminated. At step 125, the device can close the channels, which can fix the elution volume to maintain a constant volume for the elution (e.g., by resisting or preventing flow into the elution reservoir or outlet reservoir during pipetting out of the eluted volume). Fixing the elution volume can aid ease of use and can help for reporting the concentration of the eluted sample material. At step 126, the device lid can be opened (e.g., by a user or automatically).

At step 127, purified samples can be extracted from the device. Chips and/or devices can be designed for a given elution volume, as discussed herein. Retrieval of purified material from the device can be performed via pipetting or otherwise removing the material from the chip. Alternatively, sample extraction can be performed by interfacing the ITP chip with another fluidic chip or system (e.g., in the absence of an elution reservoir). Other fluidic systems can then be used to perform other operations on the purified sample material, such as next generation sequencing (NGS) library preparation, sample analysis such as PCR, ddPCR, other sequencing operations, or other downstream processes. At step 128, the device can report quantitative data about the sample, such as sample amount and/or sample concentration. The device can contain an algorithm or other software for converting a measurement (e.g., a fluorescence signal) into a sample quantitation, and can report that data to a user. At step 129, the process ends.

These issues can be especially important to address for precious, difficult to collect, or low-abundance (e.g., less than 100 ng of nucleic acid or samples containing a low abundance of undamaged or uncrosslinked nucleic acids) samples. For such samples, current protocols may lack repeatability, introduce loss of sample material, introduce bias for short or long nucleic acid targets, introduce bias towards sequence of nucleic acid targets, and/or lack repeatability. Such protocols may also lack compatibility with process automation or downstream analyses. Current protocols for nucleic acid preparation can include liquid phase extraction (LPE) such as phenol-chloroform extraction or Trizol extraction, and solid phase extraction (SPE). SPE type approaches can use structures including packed beads, monolithic porous structures, and/or magnetic beads. In some cases, LPE and SPE type approaches can lead to mechanical shearing during processing which can cause fragmentation and/or reduce the yield of long or high molecular weight nucleic acids.

The isotachophoresis methods and devices provided herein are especially well-suited to performing extraction of nucleic acids from lysates of solid or semi-solid tissues. Solid phase extraction (SPE) techniques typically process lysates by pumping the entire lysate sample volume through a column in order to selectively adsorb nucleic acids onto the surfaces of the column. Such pumping of a complex lysate, which may comprise a liquid-particle mixture, through a porous column can result in clogging or fouling of the column which can reduce the efficiency of nucleic acid extraction. In contrast, the isotachophoresis methods and devices described herein often do not involve pumping or "filtering" the entire lysate sample volume through a column. Instead, an electric field may be applied to the lysate in order to cause the charged, solvated nucleic acids dispersed throughout the complex sample lysate to migrate through and out of the continuous liquid phase of the sample. Nucleic acids may comprise a relatively high electrophoretic mobility magnitude relative to other solutes, debris, or contaminants in the sample lysate. Solutes in the sample may have a relatively low electrophoretic mobility and be too low to focus into the isotachophoresis zone located at the interface between the leading electrolytes and trailing electrolytes. Application of an electric field may cause the nucleic acids to migrate while particles and/or other tissue debris (including for example cell debris, unlysed cells, or tissue which may connect cells to other cells) are left behind. The isotachophoresis methods and devices provided herein therefore can be well-suited to extract the charged, solvated nucleic acids out of the complex lysed solid tissue samples without having to process the entire mixture through a column as in SPE.

As used herein, "particles" may refer to components of a sample mixture or a sample lysate mixture which are a different phase than the continuous liquid phase of the sample (e.g., an aqueous solution). Particles may be non-liquid components of the sample mixture. Particles can be, for example, suspended solid particles or colloidal bodies suspended within a sample. Such particles can have a variety of characteristic length scales ranging from about 1 nanometer (nm) to about 1 millimeter (mm). In some instances, particles may not be single-celled organisms or cells.

The isotachophoresis methods and devices provided herein may provide for reduced rates of strain as the sample moves through the channel compared to typical SPE methods. In some cases, the methods and devices provided herein have rates of strain of less than about 250 $s^{-1}$, 500 $s^{-1}$, 750 $s^{-1}$ 1000 $s^{-1}$ 2000 $s^{-1}$ 3000 $s^{-1}$ 4000 $s^{-1}$ 5000 $s^{-1}$ 6000 $s^{-1}$ 7000 $s^{-1}$ 8000 $s^{-1}$ 9000 $s^{-1}$, or 10,000 $s^{-1}$. In some cases, the methods and devices provided herein have rates of strain of more than about 250 $s^{-1}$, 500 $s^{-1}$, 750 $s^{-1}$, 1000 $s^{-1}$, 2000 $s^{-1}$, 3000 $s^{-1}$, 4000 $s^{-1}$, 5000 $s^{-1}$, 6000 $s^{-1}$, 7000 $s^{-1}$, 8000 $s^{-1}$, 9000 $s^{-1}$, or 10,000 $s^{-1}$. In some cases, the methods provided herein may be performed without centrifugation.

Isotachophoresis Chemistry and Operation

Figure 2A:
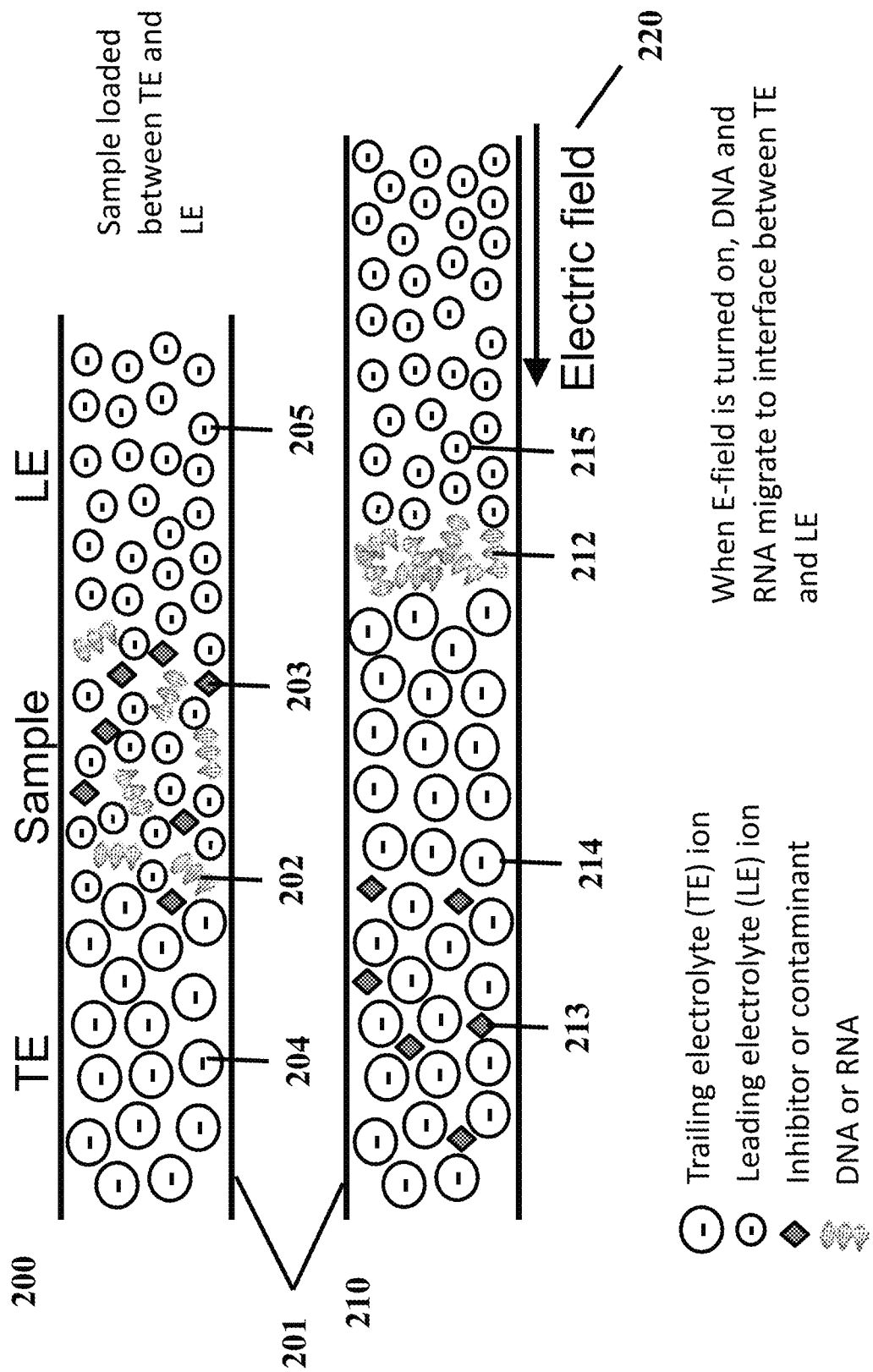
FIG. 2A shows an exemplary schematic of isotachophoretic separation and purification of DNA and RNA from contaminants.

FIG. 2A shows an exemplary schematic of an isotachophoresis (ITP) process purifying nucleic acid. A sample 201, for example a lysed solid tissue sample, comprising nucleic acids (DNA and RNA) 202 and contaminants 203 is loaded with trailing electrolytes (TE) 204 into an isotachophoresis channel 200 containing leading electrolytes (LE) 205. Under the influence of an electric field 220 applied to the isotachophoresis channel 210, the nucleic acids 212 migrate away from the contaminants 213. The electric field also causes the trailing electrolytes 214 to migrate through the channel in a position that is generally behind the nucleic acids, and causes the leading electrolytes 215 to migrate through the channel generally ahead of the nucleic acids. The magnitude of the effective mobility of the leading electrolytes is greater than the magnitude of the effective mobility of the nucleic acids, which in turn is greater than the magnitude of the effective mobility of the trailing electrolytes, which is greater than the magnitude of the effective mobility of the contaminants.

Figure 2B:
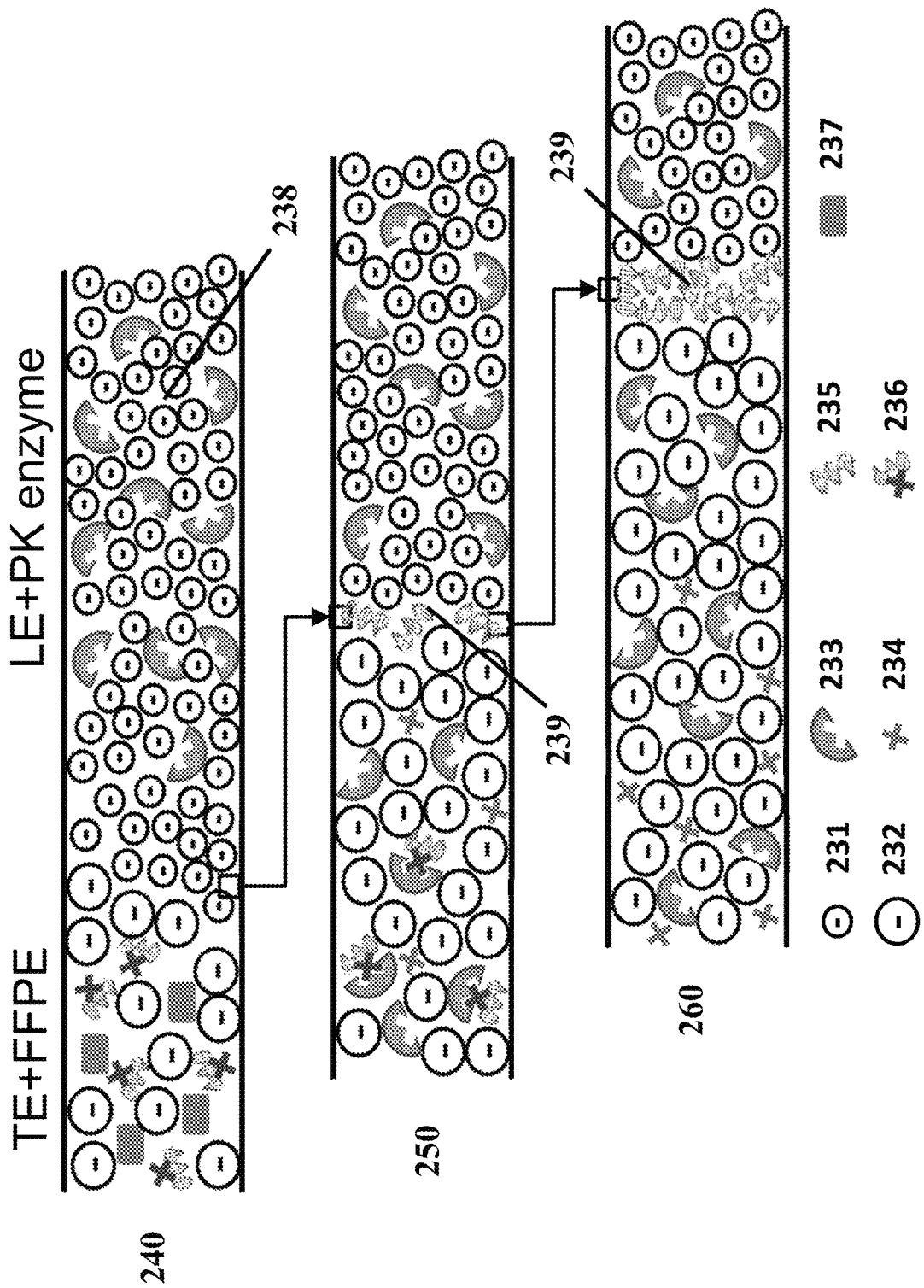
FIG. 2B shows an exemplary schematic of isotachophoretic separation and purification of nucleic acids from paraffin and other possible sample contaminants concurrent with proteinase-mediated tissue disruption and decrosslinking of nucleic acids.

FIG. 2B shows an exemplary schematic of a process to de-crosslink nucleic acids while separating de-crosslinked nucleic acids from crosslinked nucleic acids and contaminants (e.g., paraffin) using isotachophoresis (ITP) on a fluidic device. In some instances, the contaminants may comprise the crosslinked nucleic acids. A paraffin-embedded sample is loaded onto the fluidic device in an alkaline buffer and incubated for 10-30 minutes at about pH 10 and a temperature from about 50° C. to about 80° C. for tissue lysis and initial deparaffinization. Incubation may occur prior to or while applying an electric field to perform isotachophoresis. Alternatively, the sample can be loaded in a leading electrolyte buffer. After incubation, at a first time point 240, the sample comprising crosslinked nucleic acids 236 and paraffin 237 is located in an ITP channel with trailing electrolytes 232. Ahead in the ITP channel, in a leading electrolyte (LE) zone 238 are leading electrolytes 231 and Proteinase K enzymes 233. At a second time point 250, at 50° C., ITP-driven pH quenching reduces the pH, and Proteinase K enzymes are contacting and de-crosslinking the crosslinked nucleic acids, producing non-crosslinked nucleic acids 235 which focus at in the ITP zone 239 between the trailing electrolytes and leading electrolytes. Reduction of pH (e.g. to a range from about 10-12 to about 7 (or from about 6.5 to about 8.5)) can provide an environment appropriate for enzymatic activity and improved chemical stability of nucleic acids. At a third time point 260 the Proteinase K has de-crosslinked more nucleic acids, resulting in free protein 234, and the de-crosslinked nucleic acids have further migrated upstream from the paraffin, free protein, and other contaminants. The operation of such a process can be conducted automatically by the fluidic device or by a benchtop system.

In some cases, the sample may be loaded in a sample buffer comprising a concentration of leading electrolytes 205, 231 that differs from the concentration of leading electrolytes 205, 231 used to perform isotachophoresis. In some cases, the sample may be loaded in a sample buffer comprising a second leading electrolyte which differs from the leading electrolyte 215. The second leading electrolyte can have an effective mobility magnitude greater than the magnitude the effective mobility of the nucleic acid. The second leading electrolyte can have an effective mobility magnitude less than the effective mobility magnitude of the leading electrolyte 215.

In some cases, a pH of the sample may be quenched by conducting isotachophoresis. In some instances, the pH of the sample may be quenched within a range of about 6.5 to about 8.5, for example about 7 or 7.5.

Various leading electrolytes and trailing electrolytes can be used to conduct ITP. Leading electrolytes can be selected to have a greater effective mobility magnitude than the extraction target (e.g., nucleic acids), and trailing electrolytes can be selected to have a lesser effective mobility magnitude than the extraction target. Leading and/or trailing electrolytes can be present at a concentration from about 10 mM to about 200 mM. Leading and/or trailing electrolytes can be present at a concentration of about 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM. Leading and/or trailing electrolytes can be present at a concentration of at least about 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM. Leading and/or trailing electrolytes can be present at a concentration of at most about 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM. Leading electrolytes used in a particular instance of ITP can comprise 1, 2, 3, 4, 5, 6, 7, 8, 9, 10, or more different ion species. Trailing electrolytes used in a particular instance of ITP can comprise 1, 2, 3, 4, 5, 6, 7, 8, 9, 10, or more different ion species. Different species of ions in the leading electrolytes and/or trailing electrolytes can be present at different concentrations. Different concentrations of ions, such as within the trailing electrolytes or the leading electrolytes, can be selected to manipulate the size of a spacing zone. The spacing zone can be used to further separate one type of target from another, such as separating decrosslinked from protein crosslinked nucleic acids.

The trailing electrolytes can comprise a mixture of ions with different magnitudes of effective mobilities. Use of a first trailing electrolyte ion with a first effective mobility magnitude and a second trailing electrolyte ion with a second effective mobility magnitude lower than that of the first ion can be used to separate non-crosslinked nucleic acids from protein crosslinked nucleic acids, while separating both (or at least the decrosslinked nucleic acids) from contaminants. In such a case, the non-crosslinked nucleic acids can have a greater effective mobility magnitude than the first trailing electrolyte ions, which can have a greater effective mobility magnitude than the crosslinked nucleic acids, which in turn can have a greater effective mobility magnitude than the second trailing electrolyte ions, which in turn can have a greater effective mobility magnitude than the contaminants. For example, crosslinked and non-crosslinked nucleic acids can be enriched separately by conducting isotachophoresis using a leading electrolyte and two trailing electrolytes, such as caproic acid as the first ion and HEPES as the second ion.

Electrolyte ions can also be selected based on acidity (e.g., pKa). Ions with particular pKa can be selected, for example, to effect a pH change along an ITP channel. Ions can also be selected for non-electrophoretic reasons, such as compatibility with downstream processes (e.g., enzymatic processes such as PCR or next-generation sequencing library preparation). For example, caproic acid, MOPS, and HEPES can be selected for good downstream enzymatic compatibility.

Exemplary leading electrolyte ions include but are not limited to hydrochloric acid, acetic acid, 2-chloroisocrotonic acid, salicylic acid, chlorocrotonic acid, nicotinic acid, gallic acid, trichlorolactic acid, butyric acid, sulfanilic acid, benzoic acid, crotonic acid, trichloroacrylic acid, propionic acid, levulinic acid, sorbic acid, orotic acid, valeric acid, picric acid, 2-naphtalenesulfonic acid, saccharin, dinitrophenol, p-toluenesulfonic acid, aspartic acid, trimethylacrylic acid, isocaproic acid, caproic acid, octylsulfonic acid, nitrophenol, GABA, cacodylic acid, trimetylpyruvic acid, ethylmaleic acid, ethylfumaric acid, toluic acid, enanthylic acid, mandelic acid, cinnamic acid, cresol, glutamic acid, MES, isomers thereof, and combinations thereof.

Exemplary trailing electrolyte ions include but are not limited to caprylic acid, gluconic acid, vanillic acid, decylsulfonic acid, aspirin, glucuronic acid, pelargonic acid, benzylasparatic acid, ascorbic acid, dodecylsulfonic acid, MOPS (3-(N-morpholino)propanesulfonic acid), dichlorophenol, caproic acid, capric acid, tyrosine, HEPES (4-(2-hydroxyethyl)-1-piperazineethanesulfonic acid), isomers thereof, and combinations thereof.

Use of a mixture of different trailing electrolyte ions can be used to achieve mobility bracketed separations (e.g., separation of non-crosslinked nucleic acids from crosslinked nucleic acids from contaminants), compatibility with downstream assays, favorable surface energy or contact angles between fluids and fluidic device materials, buffering capacity, and total ion solubility.

Isotachophoresis can quench the pH of a sample to neutral or about neutral. Ions affecting the local pH (e.g., sodium ions (Na+)) can be displaced from the sample zone during isotachophoresis, thereby shifting the pH in the sample zone toward neutral.

Isotachophoresis can be conducted at a range of voltages, currents, and field strengths. For example, isotachophoresis can be conducted at a voltage from about 100 V and about 1500 V. Isotachophoresis can be conducted at a voltage of about 100 V, 200 V, 300 V, 400 V, 500 V, 600 V, 700 V, 800 V, 900 V, 1000 V, 1100 V, 1200 V, 1300 V, 1400 V, or 15000 V. Isotachophoresis can be conducted at a voltage of at least about 100 V, 200 V, 300 V, 400 V, 500 V, 600 V, 700 V, 800 V, 900 V, 1000 V, 1100 V, 1200V, 1300 V, 1400 V, or 15000 V. Isotachophoresis can be conducted at a voltage of at most about 100 V, 200 V, 300 V, 400 V, 500 V, 600 V, 700 V, 800 V, 900 V, 1000 V, 1100 V, 1200V, 1300 V, 1400 V, or 15000 V. Isotachophoresis can be conducted at a current from about 10 nA to about 10 mA. Isotachophoresis can be conducted at a current of about 10 nA, 20 nA, 30 nA, 40 nA, 50 nA, 60 nA, 70 nA, 80 nA, 90 nA, 100 nA, 200 nA, 300 nA, 400 nA, 500 nA, 600 nA, 700 nA, 800 nA, 900 nA, 1 mA, 2 mA, 3 mA, 4 mA, 5 mA, 6 mA, 7 mA, 8 mA, 9 mA, or 10 mA. Isotachophoresis can be conducted at a current of at least about 10 nA, 20 nA, 30 nA, 40 nA, 50 nA, 60 nA, 70 nA, 80 nA, 90 nA, 100 nA, 200 nA, 300 nA, 400 nA, 500 nA, 600 nA, 700 nA, 800 nA, 900 nA, 1 mA, 2 mA, 3 mA, 4 mA, 5 mA, 6 mA, 7 mA, 8 mA, 9 mA, or 10 mA. Isotachophoresis can be conducted at a current of at most about 10 nA, 20 nA, 30 nA, 40 nA, 50 nA, 60 nA, 70 nA, 80 nA, 90 nA, 100 nA, 200 nA, 300 nA, 400 nA, 500 nA, 600 nA, 700 nA, 800 nA, 900 nA, 1 mA, 2 mA, 3 mA, 4 mA, 5 mA, 6 mA, 7 mA, 8 mA, 9 mA, or 10 mA. Isotachophoresis can be conducted at a field strength of from about 10 V/cm to about 100 V/cm. Isotachophoresis can be conducted at a field strength of about 10 V/cm, 15 V/cm, 20 V/cm, 25 V/cm, 30 V/cm, 35 V/cm, 40 V/cm, 45 V/cm, 50 V/cm, 55 V/cm, 60 V/cm, 65 V/cm, 70 V/cm, 75 V/cm, 80 V/cm, 85 V/cm, 90 V/cm, 95 V/cm, or 100 V/cm. Isotachophoresis can be conducted at a field strength of at least about 10 V/cm, 15 V/cm, 20 V/cm, 25 V/cm, 30 V/cm, 35 V/cm, 40 V/cm, 45 V/cm, 50 V/cm, 55 V/cm, 60 V/cm, 65 V/cm, 70 V/cm, 75 V/cm, 80 V/cm, 85 V/cm, 90 V/cm, 95 V/cm, or 100 V/cm. Isotachophoresis can be conducted at a field strength of at most about 10 V/cm, 15 V/cm, 20 V/cm, 25 V/cm, 30 V/cm, 35 V/cm, 40 V/cm, 45 V/cm, 50 V/cm, 55 V/cm, 60 V/cm, 65 V/cm, 70 V/cm, 75 V/cm, 80 V/cm, 85 V/cm, 90 V/cm, 95 V/cm, or 100 V/cm.

Isotachophoresis can be used to concentrate nucleic acids in a sample. The concentration of nucleic acids in a sample can be increased after isotachophoresis by at least about 2-fold, 5-fold, 10-fold, 100-fold, 1,000-fold, 10,000-fold, 100,000-fold, 1,000,000-fold, 10,000,000-fold, 100,000,000-fold, or 1,000,000,000-fold. The operation time for concentration of nucleic acids with isotachophoresis can be less than or equal to about 5 hours, 4.5 hours, 4 hours, 3.5 hours, 3 hours, 2.5 hours, 2 hours, 1.5 hours, 1 hours, 50 minutes, 40 minutes, 30 minutes, 20 minutes, 10 minutes, 9 minutes, 8 minutes, 7 minutes, 6 minutes, 5 minutes, 4 minutes, 3 minutes, 2 minutes, 1 minute, 45 seconds, 30 seconds, 20 seconds 10 seconds, or 1 second. In some cases, isotachophoresis can be used to increase the concentration of nucleic acids in a sample by 1,000,000-fold in less than or equal to about 2 minutes. In some cases (e.g., from a sample of 25 µL blood lysate), isotachophoresis can be used to increase the concentration of nucleic acids in a sample by 100,000-fold in less than or equal to about 5 minutes.

Techniques of the present disclosure can be used to reduce the concentration of crosslinked nucleic acids in a sample. The concentration of crosslinked nucleic acids in a sample can be reduced after isotachophoresis by at least about 2-fold, 5-fold, 10-fold, 100-fold, 1,000-fold, 10,000-fold, 100,000-fold, 1,000,000-fold, 10,000,000-fold, 100,000,000-fold, or 1,000,000,000-fold. Isotachophoresis can be used to reduce the concentration of a contaminant in a sample. The concentration of contaminants in a sample can be reduced after isotachophoresis by at least about 2-fold, 5-fold, 10-fold, 100-fold, 1,000-fold, 10,000-fold, 100,000-fold, 1,000,000-fold, 10,000,000-fold, 100,000,000-fold, or 1,000,000,000-fold.

Nucleic acid samples can contain from about 0.1 picograms (pg) to about 25 micrograms (µg). For example, nucleic acid samples can contain from about 5 pg to about 5 µg. Nucleic acid samples can contain about 0.1 pg, 0.2 pg, 0.3 pg, 0.4 pg, 0.5 pg, 0.6 pg, 0.7 pg, 0.8 pg, 0.9 pg, 1 pg, 2 pg, 3 pg, 4 pg, 5 pg, 6 pg, 7 pg, 8 pg, 9 pg, 10 pg, 20 pg, 30 pg, 40 pg, 50 pg, 60 pg, 70 pg, 80 pg, 90 pg, 100 pg, 200 pg, 300 pg, 400 pg, 500 pg, 600 pg, 700 pg, 800 pg, 900 pg, 1 nanogram (ng), 2 ng, 3 ng, 4 ng, 5 ng, 6 ng, 7 ng, 8 ng, 9 ng, 10 ng, 20 ng, 30 ng, 40 ng, 50 ng, 60 ng, 70 ng, 80 ng, 90 ng, 100 ng, 200 ng, 300 ng, 400 ng, 500 ng, 600 ng, 700 ng, 800 ng, 900 ng, 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg, 21 µg, 22 µg, 23 µg, 24 µg, or 25 µg.

Nucleic acid samples can comprise deoxyribonucleic acids (DNA), single-stranded DNA, double-stranded DNA, genomic DNA, complementary DNA, ribonucleic acids (RNA), ribosomal RNA, transfer RNA, messenger RNA, micro RNA, or the like, or any combination thereof. Nucleic acid samples can comprise a length of at least about 0.5, 1, 2, 5, 10, 20, 30, 40, 50, 60, 70, 80, 90, 100, 150, 200, 250, 300, 350, 400, 450, or 500 kB or more. Techniques of the present disclosure can be used to extract different sample types in different channels of a fluidic device. For example, different channels may be used to extract nucleic acids of different lengths and/or different types.

In some instances, a characteristic of a nucleic acid sample may be compared to one or more nucleic acids from another sample. The characteristic may for example be an expression level, a nucleic acid sequence, a molecular weight, nucleic acid integrity, nucleic-acid stranded-ness, or nucleic acid purity.

Nucleic acid samples can be of a particular quality before and/or after extraction or other processing. Nucleic acid quality can be assessed by various metrics, including but not limited to RNA integrity number (RIN), DNA integrity number (DIN), size distribution (e.g., using electrophoresis), and ability to be amplified (e.g., by PCR) or otherwise enzymatically processed (e.g. fragmentation, ligation, a-tailing, or hybridization for next generation sequencing library preparation). Techniques of the present disclosure can be used to extract or process nucleic acids and provide extracted or processed nucleic acids with a RIN of at least about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. Techniques of the present disclosure can be used to extract or process nucleic acids and provide extracted or processed nucleic acids with a RIN of at most about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. Techniques of the present disclosure can be used to extract or process nucleic acids and provide extracted or processed nucleic acids with a DIN of at least about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. Techniques of the present disclosure can be used to extract or process nucleic acids and provide extracted or processed nucleic acids with a DIN of at most about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. Techniques of the present disclosure can be used to extract or process nucleic acids and provide extracted or processed nucleic acids such that at least 10%, 20%, 30%, 40%, 50%, 60%, 70%, 80%, 90%, 95%, 96%, 97%, 98%, 99%, 99.9%, or 99.99% of the mass of the nucleic acids of the sample has a molecular weight of at least about 0.5, 1, 2, 5, 10, 20, 30, 40, 50, 60, 70, 80, 90, 100, 150, 200, 250, 300, 350, 400, 450, or 500 kB or more. In some cases, about 90% to about 100% of the mass of the processed nucleic acids are from about 10 to about 1000 bp, from about 200 to about 2000 bp, or from about 200-5000 bp.

Figure 3:
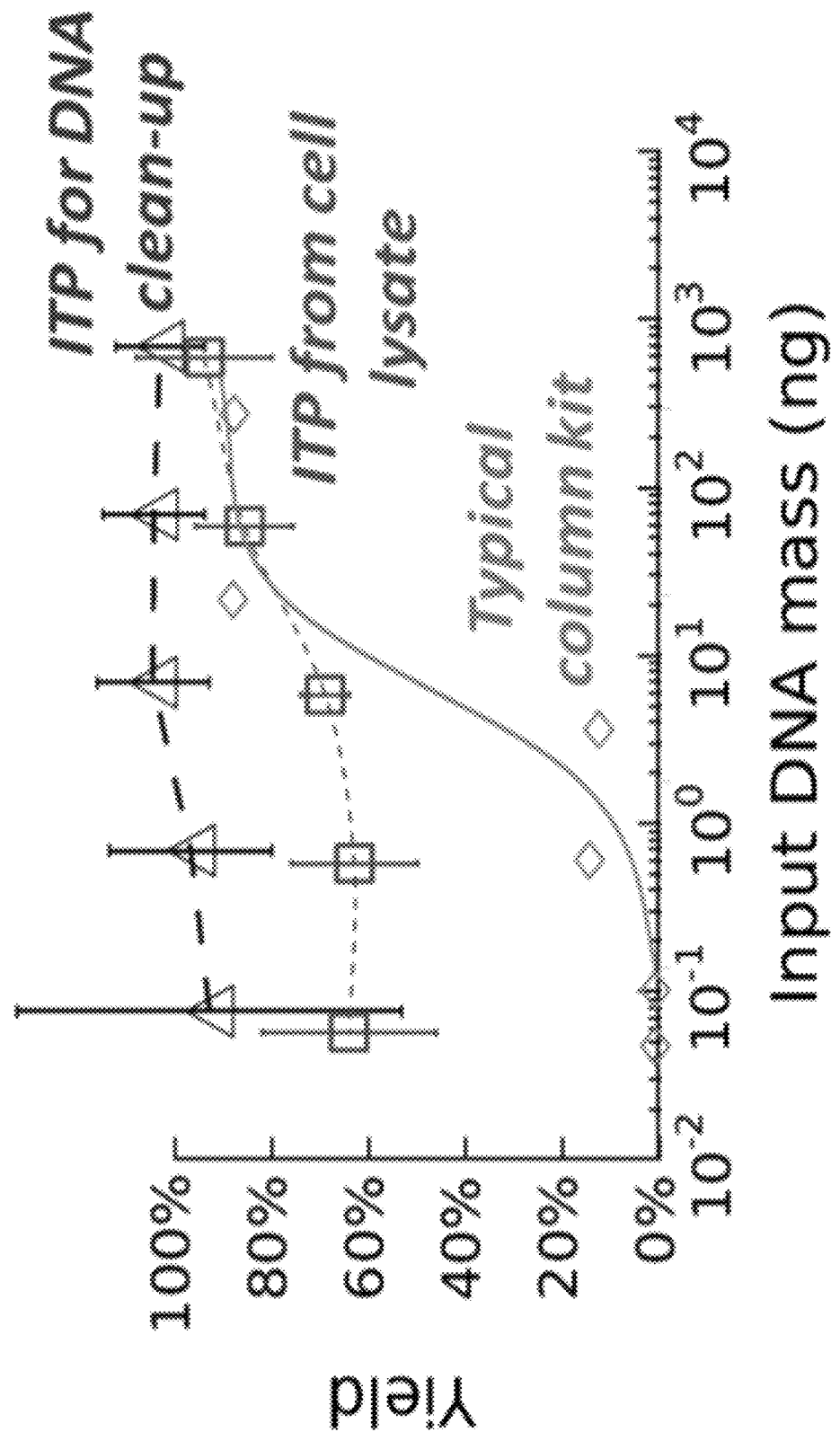
FIG. 3 shows exemplary results of DNA extraction and purification by automated isotachophoresis in a fluidic device compared to exemplary results from a typical solid phase column extraction kit.

Isotachophoresis can be used to extract nucleic acids at an extraction efficiency or yield, characterized as the percent yield of nucleic acid from a given starting amount of nucleic acid. Techniques of the present disclosure can provide extracted nucleic acids at a yield of at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9%. Techniques of the present disclosure can provide high yields even for low input amounts nucleic acid, including less than or equal to about $10^4$ nanograms (ng), $10^3$ ng, $10^2$ ng, $10^1$ ng, $10^0$ ng, $10^{-1}$ ng, or $10^{-2}$ ng. FIG. 3, for example, shows exemplary nucleic acid yields from a range of different input amounts and sources of nucleic acid. High yield and/or low loss of nucleic acids can be important for next generation sequencing library preparations. Recovery of nucleic acids can be at or near 100%.

Techniques of the present disclosure can extract nucleic acids with low or no sequence bias. That is, the sequence composition of the extracted and purified nucleic acids (e.g., ratio of GC-rich nucleic acids to AT-rich nucleic acids) can be similar to or the same as the sequence composition of the input nucleic acids (see, e.g., FIG. 4A). The difference in sequence composition of the extracted nucleic acids from the sequence composition of the input nucleic acids can be less than or equal to about 20%, 15%, 10%, 5%, 4%, 3%, 2%, or 1%.

Techniques of the present disclosure can extract nucleic acids with low or no length bias. That is, the length distribution of the extracted nucleic acids (e.g., the proportions of nucleic acids of different sizes) can be similar to or the same as the length distribution of the input nucleic acids (see, e.g., FIG. 4B). The difference in length distribution of the extracted nucleic acids from the length distribution of the input nucleic acids can be less than or equal to about 20%, 15%, 10%, 5%, 4%, 3%, 2%, or 1%. For example, short nucleic acids (e.g., about 10 to about 300 bp), long nucleic acids (e.g., about 10 kB, 20 kB, 30 kB, 40 kB, 50 kB, 60 kB, 70 kB, 80 kB, 90 kB, 100 kB, or greater), or both short and long nucleic acids can be extracted with reduced drop out or bias. Solid phase columns can, in some cases, lose up to 100% of short and/or long nucleic acid material. Techniques of the current disclosure can recover nucleotides from single base to hundreds of kilobases in size. Techniques of the present disclosure can recover at least about 10%, 20%, 30%, 40%, 50%, 60%, 70%, 80%, 90%, or 95%, 96%, 97%, 98%, 99%, 99.9%, or 100% of short and/or long nucleic acids present in the sample.

Techniques of the present disclosure can result in the removal of contaminants from the sample. Contaminants can include but are not limited to embedding material, cell debris, extracellular matrix components, tissue debris, embedding debris, lipids, carbohydrates, enzymes, ligation by-products, primers, unbound probes or ligators, divalent metals, detergents, preservatives, fixatives, anti-coagulants, collagen fibers, and PCR inhibitors. Contaminants can originate from the tissue or cells of the sample, from preservatives or embedding materials used on the sample, or from previous preparations, reactions, or assays performed on the sample. For example, enzymes such as restriction nucleases can be used to prepare DNA for a fingerprinting assay, and subsequent to digestion (e.g., DNase digestion), DNA can be separated from the enzyme.

Samples

The techniques of the present disclosure can be used to process different sample types, including but not limited to biological samples, solid tissue, biopsies, tissue biopsies, liquid biopsies, organs, tumors, fresh tissue, solid organs, preserved tissue (e.g., FFPE), dissected FFPE, fresh frozen tissue, fixed samples, fixed tissue, embedded samples, lysed samples, un-lysed samples, samples comprising connections between cells (e.g. gap junctions, tight junctions, adherent junctions), samples comprising lysed solid tissue and nucleic acids, multiphasic samples, inhomogeneous liquids or solutions (such as tissue, whole blood, or unlysed cell suspensions), biological samples comprising genomic DNA, lysed and un-lysed whole blood, plasma and serum, buccal swabs, dried blood spots and other forensic samples, fresh or fresh frozen (FF) tissues, cultured or harvested cells (lysed and un-lysed) from blood or tissues, fixed cells, stool, and bodily fluids (e.g., saliva, urine), or any combination thereof. Non-limiting examples of solid organs include liver, pancreas, brain, heart, gall bladder, colon, lung and reproductive organs. Samples can include cellular and cell-free nucleic acids, for both eukaryotic and prokaryotic organisms. Fixed samples can be chemically fixed or physically fixed (e.g., heating or freezing). For example, samples can be chemically fixed with a chemical fixative such as formalin, neutral buffered formalin (NBF), formaldehyde, paraformaldehyde, glutaraldehyde, glyoxal, mercuric chloride, zinc salts, Bouin's fluid, alcohol-formalin-acetic acid (AFA or FAA), citrate-acetone-formalin (CAF), acetone, methanol, ethanol, Clarke's fluid, Carnoy's fluid, or Puchtler's methacarn. Embedded samples can be embedded in materials including but not limited to wax (e.g., paraffin), agar, gelatin, or plastic resins. Formalin-fixed paraffin-embedded (FFPE) samples can be processed using techniques of the present disclosure. Samples can comprise buccal swabs, blood spots, and other forensic samples. Samples can comprise clinical samples, fine needle aspirates, biopsies, whole blood, lysed blood, serum, plasma, urine, cell culture lysate or freshly harvested cell (e.g., blood cell, dissociated fresh tissue, stem cell) lysate, blood cells, circulating cells (e.g., circulating tumor cells (CTCs)), nucleic acids from blood or other bodily fluid, and other sample categories. Cell-free nucleic acids (e.g., cfDNA or cfRNA) can be recovered, such as from whole un-lysed blood, using techniques of the present disclosure; often the cell-free nucleic acids are circulating cell-free nucleic acids. Samples can be from a variety of sources, including but not limited to normal tissue, benign neoplasms, malignant neoplasms, stem cells, human tissue, animal tissue, plant tissue, bacteria, viruses, and environmental sources (e.g., water). Human or animal tissues can include but are not limited to epithelial tissue, connective tissue (e.g., blood, bone), muscle tissue (e.g., smooth muscle, skeletal muscle, cardiac muscle), and nervous tissue (e.g., brain, spinal cord).

Samples can comprise one or more particles in suspension. The one or more particles may range from colloidal size to visible. The one or more particles can have a size of at least about 1 nanometer (nm), 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 600 nm, 700 nm, 800 nm, 900 nm, 950 nm, 1 micrometer ($\mu$m), 10 $\mu$m, 20 $\mu$m, 30 $\mu$m, 40 $\mu$m, 50 $\mu$m, 60 $\mu$m, 70 $\mu$m, 80 $\mu$m, 90 $\mu$m, 100 $\mu$m, 150 $\mu$m, 175 $\mu$m, 200 $\mu$m, 225 $\mu$m, 250 $\mu$m, 275 $\mu$m, 300 $\mu$m, 350 $\mu$m, 400 $\mu$m, 450 $\mu$m, 500 $\mu$m, 550 $\mu$m, 600 $\mu$m, 650 $\mu$m, 700 $\mu$m, 750 $\mu$m, 800 $\mu$m, 850 $\mu$m, 900 $\mu$m, 950 $\mu$m, or 1 millimeter (mm). The one or more particles can have a size of at most about 1 nanometer (nm), 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 600 nm, 700 nm, 800 nm, 900 nm, 950 nm, 1 micrometer ($\mu$m), 10 $\mu$m, 20 $\mu$m, 30 $\mu$m, 40 $\mu$m, 50 $\mu$m, 60 $\mu$m, 70 $\mu$m, 80 $\mu$m, 90 $\mu$m, 100 $\mu$m, 150 $\mu$m, 175 $\mu$m, 200 $\mu$m, 225 $\mu$m, 250 $\mu$m, 275 $\mu$m, 300 $\mu$m, 350 $\mu$m, 400 $\mu$m, 450 $\mu$m, 500 $\mu$m, 550 $\mu$m, 600 $\mu$m, 650 $\mu$m, 700 $\mu$m, 750 $\mu$m, 800 $\mu$m, 850 $\mu$m, 900 $\mu$m, 950 $\mu$m, or 1 millimeter (mm). The one or more particles can be the same size or different sizes. A sample may for example comprise a plurality of particles ranging in size from 1 nm to 500 $\mu$m.

Samples of various volumes can be processed on a fluidic device (e.g., to extract and purify nucleic acids). For example, a sample volume (with or without buffer) can be at least about 1 nanoliter (nL), 10 nL, 20 nL, 50 nL, 100 nL, 200 nL, 500 nL, 1 microliter ($\mu$L), 10 $\mu$L, 20 $\mu$L, 30 $\mu$L, 40 $\mu$L, 50 $\mu$L, 60 $\mu$L, 70 $\mu$L, 80 $\mu$L, 90 $\mu$L, 100 $\mu$L, 150 $\mu$L, 175 $\mu$L, 200 $\mu$L, 225 $\mu$L, 250 $\mu$L, 275 $\mu$L, 300 $\mu$L, 350 $\mu$L, 400 $\mu$L, 450 $\mu$L, 500 $\mu$L, 600 $\mu$L, 700 $\mu$L, 800 $\mu$L, 900 $\mu$L, 1 milliliter (mL), 2 mL, 3 mL, 4 mL, 5 mL, 6 mL, 7 mL, 8 mL, 9 mL, or 10 mL. A sample volume (with or without buffer) can be at most about 1 nanoliter (nL), 10 nL, 20 nL, 50 nL, 100 nL, 200 nL, 500 nL, 1 microliter ($\mu$L), 10 $\mu$L, 20 $\mu$L, 30 $\mu$L, 40 $\mu$L, 50 $\mu$L, 60 $\mu$L, 70 $\mu$L, 80 $\mu$L, 90 $\mu$L, 100 $\mu$L, 200 $\mu$L, 300 $\mu$L, 400 $\mu$L, 500 $\mu$L, 600 $\mu$L, 700 $\mu$L, 800 $\mu$L, 900 $\mu$L, 1 milliliter (mL), 2 mL, 3 mL, 4 mL, 5 mL, 6 mL, 7 mL, 8 mL, 9 mL, or 10 mL. In some cases, a sample volume can be from about 1 nL to about 10 nL. A sample volume (with or without buffer) can be at least about 1 nanoliter (nL), 10 nL, 20 nL, 50 nL, 100 nL, 200 nL, 500 nL, 1 microliter ($\mu$L), 10 $\mu$L, 20 $\mu$L, 30 $\mu$L, 40 $\mu$L, 50 $\mu$L, 60 $\mu$L, 70 $\mu$L, 80 $\mu$L, 90 $\mu$L, 100 $\mu$L, 200 $\mu$L, 300 $\mu$L, 400 $\mu$L, 500 $\mu$L, 600 $\mu$L, 700 $\mu$L, 800 $\mu$L, 900 $\mu$L, 1 milliliter (mL), 2 mL, 3 mL, 4 mL, 5 mL, 6 mL, 7 mL, 8 mL, 9 mL, or 10 mL. In some cases, a sample volume can be from about 1 nL to about 10 nL.

Samples with different numbers of cells can be processed on a fluidic device (e.g., to extract and purify nucleic acids). For example, a sample can contain less than or equal to about 20,000 cells, 15,000 cells, 10,000 cells, 9,000 cells, 8,000 cells, 7,000 cells, 6,000 cells, 5,000 cells, 4,500 cells, 4,000 cells, 3,500 cells, 3,000 cells, 2,500 cells, 2,000 cells, 1,500 cells, 1,000 cells, 900 cells, 800 cells, 700 cells, 600 cells, 500 cells, 400 cells, 300 cells, 200 cells, 100 cells, 90 cells, 80 cells, 70 cells, 60 cells, 50 cells, 40 cells, 30 cells, 20 cells, 10 cells, 5 cells, 2 cells, or 1 cell. In some cases, a sample contains at least about 10,000,000 cells, 5,000,000 cells, 1,000,000 cells, 500,000 cells, 100,000 cells, 50,000 cells, 20,000 cells, 15,000 cells, 10,000 cells, 9,000 cells, 8,000 cells, 7,000 cells, 6,000 cells, 5,000 cells, 4,500 cells, 4,000 cells, 3,500 cells, 3,000 cells, 2,500 cells, 2,000 cells, 1,500 cells, 1,000 cells, 900 cells, 800 cells, 700 cells, 600 cells, 500 cells, 400 cells, 300 cells, 200 cells, or 100 cells.

Samples of different masses can be processed on a fluidic device (e.g., to extract and purify nucleic acids). For example, a sample can contain from about 0.001 milligrams (mg) and about 10 mg of tissue. A sample can contain at most about 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, or 10 mg of tissue. A sample can contain at least about 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, or 10 mg of tissue. A sample can contain about 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, or 10 mg of tissue.

Samples with different amounts of nucleic acid can be processed on a fluidic device (e.g., to extract and purify nucleic acids). For example, samples can contain less than or equal to about 1 microgram (1 $\mu$g), 100 nanograms (ng), 10 ng, 1 ng, 100 picograms (pg), 10 pg, or 1 pg of nucleic acid. In some cases, samples can contain greater than or equal to about 1 microgram (1 $\mu$g), 100 nanograms (ng), 10 ng, 1 ng, 100 picograms (pg), 10 pg, or 1 pg of nucleic acid.

Samples can be loaded in a buffer comprising trailing electrolyte or leading electrolyte. Samples can be loaded in a buffer comprising a second leading electrolyte which differs from the leading electrolyte used to perform ITP. Samples can be loaded in a buffer, such as an aqueous alkaline or a neutral aqueous buffer. Exemplary alkaline solutions or buffers (e.g., for DNA extraction) can comprise 30-120 mM NaOH (in some cases, 40-80 mM NaOH) at a pH of about 10-13 (in some cases, with at least one additional component). In some instances, when the sample is lysed via treatment with an alkaline solution or buffer prior to loading onto the chip, the lysed sample may subsequently be quenched by adding an acidic solution or buffer to bring the pH of the lysed sample within a range of about 7.5 to about 8.5 prior to performing isotachophoresis. Exemplary aqueous buffers (e.g., for DNA or RNA extraction) can comprise 2-150 mM Tris-HCl (at a pH of about 7 to about 8) or BisTris-HCl at a pH of about 5.8 to about 7.3, with at least one additional component. Additional components used in buffers can include non-ionic surfactants or detergents, ionic or zwitter-ionic surfactants or detergents, chaotropic agents, disulfide bond reducing agents, proteases, nucleases, and other additives or components that digest, denature, disrupt, or degrade for the purpose of extracting, purifying, enriching, or otherwise isolating nucleic acids.

Non-ionic surfactants or detergents can include but are not limited to surfactants from the following classes: octylphenol ethoxylate, polysorbate, poloxamer, or polyoxyethylene. Octylphenol ethoxylate surfactants can include but are not limited to branched octylphenoxy polyethoxy ethanol (IGEPAL CA-630), t-octylphenoxypolyethoxyethanol (Triton™ X-100), or other polyethylene oxide chains with an aromatic hydrocarbon lipophilic or hydrophobic group. Polysorbate surfactants can include but are not limited to polyethylene glycol sorbitan monolaurate (Tween® 20), polyethylene glycol sorbitan monooleate (Tween® 80), or sorbitan monooleate (Span® 80). Poloxamer surfactants (i.e. block copolymers based on ethylene oxide and propylene oxide) can include but are not limited to polyoxyethylene-polyoxypropylene block copolymer (Pluronic® F-68) or polyethylene-polypropylene glycol block copolymer (Pluronic® F-127). Polyoxyethylene surfacts can include but are not limited to nonyl phenoxypolyethoxylethanol (NP-40).

Non-ionic surfactants or detergents can include but are not limited to IGEPAL® (e.g., IGEPAL® CA-630), Triton™ X-100, Tween® 20, Tween® 80, NP-40, other block copolymers including Pluronic® (e.g., F-68 or F-127), Span® 80, and pegylated polymers or copolymers. Non-ionic surfactants or detergents can be used to reduce or prevent biological molecule adsorption to channel walls, or to control wetting and/or surface tension properties of fluids to control loading of sample into fluidic devices. Non-ionic surfactants or detergents can be present at concentrations from about 0.0005-5% v/v or w/v. For example, IGEPAL CA-630 can be used at about 0.05-0.5% v/v. Ionic surfactants or detergents can include but are not limited to sodium dodecyl sulfate (e.g., at 0.01-2% w/v), sodium dodecylbenzenesulfonate (e.g., at 0.01-2% w/v), sodium cholesteryl sulfate (e.g., at 0.01%-2% w/v), and sodium deoxycholate (e.g., at about 10-1000 mM). Chaotropic agents can include but are not limited to urea (e.g., at about 0.5-9.5 M, or in some cases, 5-9.5 M) thiourea, butanol, ethanol, guanidinium chloride, lithium perchlorate, lithium acetate, lithium chloride, magnesium chloride, phenol, and propanol. For example, 7.0 M urea and 2.0 M thiourea can be used in a 5-50 mM Tris-HCl (in some cases, 10-20 mM Tris-HCl) buffered solution for either RNA or DNA extractions, or for total nucleic acid extractions. The ratio of urea to thiourea can be at least about 1:1, 1.5:1, 2:1, 2.5:1, 3:1, 3.5:1, 4:1, 4.5:1, 5:1, 6:1, 6.5:1, 7:1, 7.5:1, or 8:1. Disulfide bond reducing agents can include but are not limited to DTT (e.g. at about 0.1-40 mM, or in some cases about 10 mM) and betamercaptoethanol (e.g., at about 0.5-2%, or in some cases about 1%). Proteases can include but are not limited to Proteinase K, proteases, endoproteinases (e.g., trypsin, LysC, GluC, AspN), peptidases, pepsin, and papain. Nucleases can include but are not limited to non-specific nucleic acid digestion enzymes such as DNases including DNase I (e.g., to prepare DNA-free RNA extractions) and RNase, such as RNase A, RNase T, or combinations thereof (e.g., to prepare RNA-free DNA extractions). Nucleases can also include specific nucleic acid digestion enzymes (e.g., restriction enzymes) which can cut at specific nucleic acid sequences and can produce predictable fragment sizes and fragment size distributions. In some cases, one or more methods or processes provided herein are performed without use of a nuclease, without use of a DNAse, or without use of an RNAase. For example, the methods provided herein include extraction of RNA without use of DNAase.

Restriction enzymes can include but are not limited to Type 1 through Type V restriction enzymes, BamHI, EcoP15I, EcoRI, EcoRII, EcoRV, HaeIII, HgaI, HindIII, HinFI, KpnI, NotI, PstI, PvuII, SacI, SalI, SmaI, SpeI, SphI, XbaI, and StuI. Nucleases can be used at concentrations including 50-400 µg/mL. Nuclease digestions can be performed at temperatures including from about 20° C. to about 37° C. Other nucleic acid modifying enzymes can be used, such as transposases, ligases, polymerases, and phosphatases. Other protein or polynucleotide digestion or degradation agents can be used, such as lysozymes.

Prior to loading onto a fluidic device, samples can be subjected to various degrees of pre-processing. In some cases, a sample can be simply loaded into buffer prior to loading onto a fluidic device, and any other necessary or desired sample preparation steps can be conducted on the device. In other cases, sample can be added to a sample reservoir that is prefilled with a processing fluid such as a solution or buffer. In other cases, a sample can be subjected to removal of embedding material, tissue disruption, cell lysis, or digestion prior to loading on a fluidic device. In one example, a sample is deparaffinized prior to loading onto a fluidic device, and de-crosslinking of nucleic acids is conducted on the fluidic device. In another example, a sample is deparaffinized, disrupted, and lysed prior to loading onto a fluid device, and, optionally, de-crosslinking of nucleic acids is conducted on the fluidic device. In another example, a sample is deparaffinized prior to loading onto a fluidic device, and tissue disruption and cell lysis are conducted on the fluidic device. In another example, a sample is loaded onto a fluidic device, and deparaffinization, tissue disruption, cell lysis, and de-crosslinking of nucleic acids are all conducted on the fluidic device. Sample preparation steps are discussed further in this disclosure.

Sample Preparation

Samples can be prepared prior to isotachophoresis. Sample preparation can involve steps including but not limited to removal of embedding material, tissue disruption, cell lysis, digestion of proteins, removal of nucleic acid crosslinking, isothermal enzymatic process, enzymatic amplification, enzymatic digestion, disruption of cell-cell junctions, disruption of extracellular matrix, disruption of connective tissue, and combinations thereof. Sample preparation can involve techniques such as polymerase chain reaction (PCR) or other nucleic acid amplification, isolation or purification of material (e.g., cells, nucleic acids) of interest, probe hybridization, and antibody hybridization (e.g., hybridization of antibodies to nucleosomes). In some cases, samples can be prepared by isolating a portion of material from cells from the sample for further analysis. For example, circulating tumor cells can be isolated from a heterogenous population of cells using a cell sorting devices such as a flow cytometer or magnetized column. In another example, peripheral blood lymphocytes (PBLs) or peripheral blood mononuclear cells (PBMCs) can be isolated from a blood sample. Sample preparation can be conducted on-device or off-device. In some cases, some sample preparation steps are conducted off-device, and then the sample is loaded onto a fluidic device where additional sample preparation steps are conducted.

Biological material (e.g., cells, tissue, nucleic acids) in an embedded sample can be removed from the embedding material. For example, a paraffin-embedded sample can be deparaffinized. Removal of embedding material can be conducted using techniques including but not limited to heat treatment, chemical treatment (e.g., acid or base), enzymatic treatment, and combinations thereof. Deparaffinization can be performed by chemical treatment of a sample, by heat-treating a sample, by enzymatic treatment of a sample, or by other methods. For example, deparaffinization can be conducted at an elevated temperature (e.g. from about 50° C. to about 80° C.) in the presence of a neutral buffer or somewhat acidic buffer (e.g., down to pH about 5.5) buffer or somewhat basic (up to pH about 9) or alkaline solution (e.g., pH from about 12 to about 13). Removal of embedding material can be conducted off-device or on-device. In one example, an embedded sample can be incubated at an elevated temperature in a vessel and subsequently loaded onto a fluidic device. In another example, an embedded sample can be loaded onto a fluidic device and incubated at an elevated temperature on the device, for example in the channel or a reservoir.

Removal of embedding material can be conducted by heat treatment. Incubation for removal of embedding material can be conducted at a temperature of at least about 35° C., 37° C., 40° C., 45° C., 50° C., 55° C., 60° C., 65° C., 70° C., 75° C., 80° C., 85° C., 90° C., 95° C., 96° C., 97° C., 98° C., 99° C., 99.5° C., or 100° C. Incubation for removal of embedding material can be conducted at a temperature from about 40° C. to about 80° C., from about 50° C. to about 80° C., from about 50° C. to about 99.9° C., or about 95 to about 99.5° C. Incubation for removal of embedding material can be conducted for a duration of at least about 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, or 120 minutes. Incubation for removal of embedding material can be conducted for a duration from about 1 minute to about 20 minutes, from about 1 minute to about 30 minutes, from about 1 minute to about 60 minutes, from about 1 minute to about 120 minutes, or from about 5 minutes to about 20 minutes. Incubation for removal of embedding material can for example be conducted at a temperature of at least about 37° C. for a duration of at least about 1 minute. Incubation for removal of embedding material can be conducted in the presence of an alkaline buffer or a neutral buffer (e.g. lysis buffer). An alkaline buffer (e.g. lysis buffer) can have a pH of at least about 8.5, 9.0, 9.5, 10.0, 10.5, 11.0, 11.5, 12.0, 12.5, 13.0, or 13.5. A neutral buffer can have a pH of about 7.0 (e.g., from about 7 to about 8).

Tissues or cells can be disrupted or lysed, releasing nucleic acids for separation, purification, or extraction. Tissue disruption or cell lysis can be conducted using techniques including but not limited to mechanical stress, sonication, electroporation, osmotic pressure, chemical treatment (e.g., acid or base), enzymatic treatment, heat treatment, and combinations thereof. For example, pressure can be used to drive tissue through a structure (e.g., a channel, a resin such as a frit or porous resin, or a glass material) to mechanically disrupt tissue or lyse cells. In some cases, the trailing electrolyte buffer can comprise one or more tissue disruption agents and/or cell lysis agents. In some cases, the leading electrolyte buffer can comprise one or more tissue disruption agents and/or cell lysis agents. In some cases, removal of embedding material can be achieved by the same process as tissue disruption or cell lysis. For example, incubation at an elevated temperature (e.g. from about 30° C. to about 80° C., from about 50° C. to about 80° C., or from about 30° C. to about 65° C.) can achieve removal of embedding material, tissue disruption, and cell lysis. Tissue disruption or cell lysis can be conducted off-device or on-device. In one example, a tissue sample is disrupted in a vessel and subsequently loaded onto a fluidic device. In another example, a tissue sample previously loaded onto a fluidic device is disrupted on the device.

Samples comprising tissue or cells can be lysed before or after loading onto a fluidic device using a lysis solution or buffer compatible with isotachophoresis. Lysis buffers compatible with isotachophoresis can include non-ionic surfactants or detergents, ionic or zwitter-ionic surfactants or detergents, chaotropic agents, disulfide bond reducing agents, proteases, nucleases, and other additives or components that digest, denature, disrupt, or degrade for the purpose of extracting, purifying, enriching (concentrating), or otherwise isolating nucleic acids. In some cases, a lysis buffer may comprise an alkaline buffer. In some cases, a lysis buffer may not comprise an alkaline buffer. An exemplary lysis buffer may include 0.5 M to 9.5 M, 4M to 9 M, or 6.5M to 7 M urea as described herein. An exemplary lysis buffer may include 0.5 M to 3.5 M or 1.5 M to 2.5 M thiourea as described herein. An exemplary lysis buffer may include 0.5-9.5 M urea and thiourea, for example 7M urea and 2M thiourea with a non-ionic surfactant as described herein. The use of urea alone or in combination with thiourea may be used to lyse cells for nucleic acid purification. In combination, urea and thiourea may act synergistically to lyse cells and may provide an uncharged isotachophoresis-compatible buffer for nucleic acid purification.

An exemplary lysis buffer may include a non-ionic surfactant such as 0.05-0.5% v/v IGEPAL CA-630 as described herein. In some cases, the lysis buffer may comprise one or more trailing electrolytes. In some cases, the lysis buffer may comprise a trailing electrolyte buffer with additives for tissue disruption or cell lysis as described herein. In some cases, the lysis buffer may comprise one or more leading electrolytes. In some cases, the lysis buffer may comprise a leading electrolyte buffer with additives for tissue disruption or cell lysis as described herein. In some cases, the lysis buffer may comprise one or more leading electrolyes and one or more trailing electrolytes. In some cases, the lysis buffer may comprise one or more leading electrolyes and one or more trailing electrolytes with additives for tissue disruption or cell lysis as described herein.

In some cases, a method or process herein may involve lysing a cell or tissue sample using a lysis buffer that minimizes mechanical disruption of DNA and/or RNA during the lysis reaction. For example, cells or tissue may be lysed in a buffer solution containing Tris (e.g., 5 mM, 10 mM, 20 mM, 30 mM Tris) with HCl (e.g., 1 mM, 5 mM, 10 mM HCl) and a non-ionic surfactant. The non-ionic detergent (e.g., IGEPAL CA-630) may be present at about 1%, about 2%, about 3%, about 4%, or greater in the lysis buffer, or less than about 1%. Cells or tissue may be lysed in the lysis buffer by gentle mixing such as by inversion and low-speed (automated pipette). An enzyme such as proteinase K may, in some cases, be included in the lysate or lysis buffer. In some cases, the lysis is conducted without centrifugation. In some cases, centrifugation is used in the lysis method. The lysate may be introduced into an isotachophoresis device in order to purify a desired analyte such as high molecular weight DNA fragments.

Proteins in a sample can be digested, for example via enzymatic digestion with proteases. Proteases can include but are not limited to Proteinase K, proteases, endoproteinases (e.g., trypsin, LysC, GluC, AspN), peptidases, pepsin, and papain. Other protein or polynucleotide digestion or degradation agents can be used, such as lysozymes. Digestion of proteins can remove crosslinking proteins from crosslinked nucleic acids, converting them into non-crosslinked nucleic acids. Digestion of proteins can occur at room temperature or at elevated temperatures described herein (e.g. greater than about 25° C.).

Sample can be processed on a device (e.g., an electrokinetic device or system with at least one reservoir connected to at least one channel), such that the sample volume passes through the reservoir into the channel with less than 20% of the sample volume left behind in the reservoir, and subsequently an ionic current can be applied through the sample volume in the channel. The ionic current may not substantially pass through the channel. In some cases, less than 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, or 1% of the sample volume is left behind in the reservoir.

Sample can be processed on a device (e.g., an electrokinetic device or system with at least one reservoir connected to at least one channel), such that the sample volume which passes through the reservoir into the channel is at least 50% of the sample volume loaded into the reservoir, and subsequently an ionic current can be applied through the sample volume in the channel. In some cases, at least 50%, 55%, 60%, 65%, 70%, 75%, 80%, 85%, 90%, 95%, 99%, or more of the sample volume is moved from the reservoir to the channel. In some instances, the total volume loaded into the reservoir is less than or equal to an internal volume of the reservoir. The ionic current may not substantially pass through the channel. In some cases, applying an ionic current comprises conducting isotachophoresis.

Isotachophoresis Devices

Figure 5A:
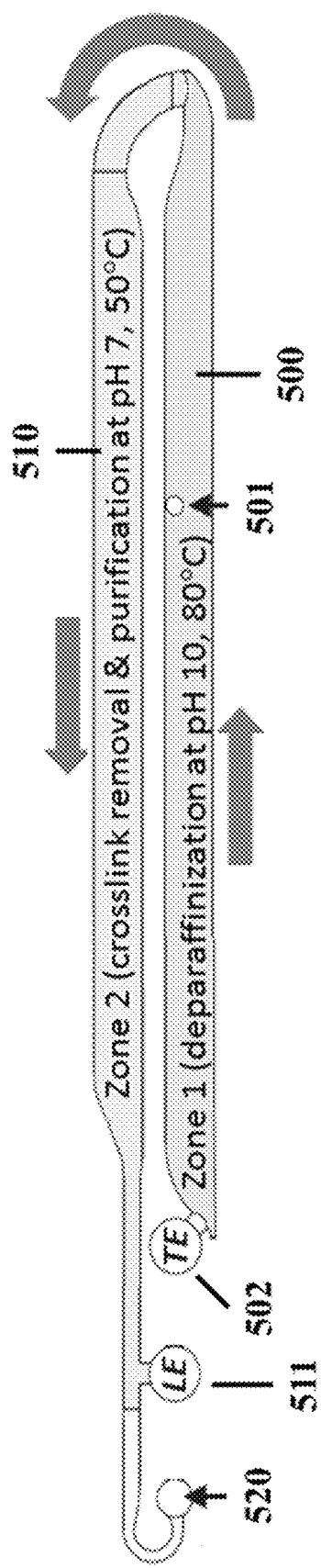
FIG. 5A shows an exemplary schematic of a channel with a sample preparation zone and an isotachophoretic purification zone.
Figure 5B:
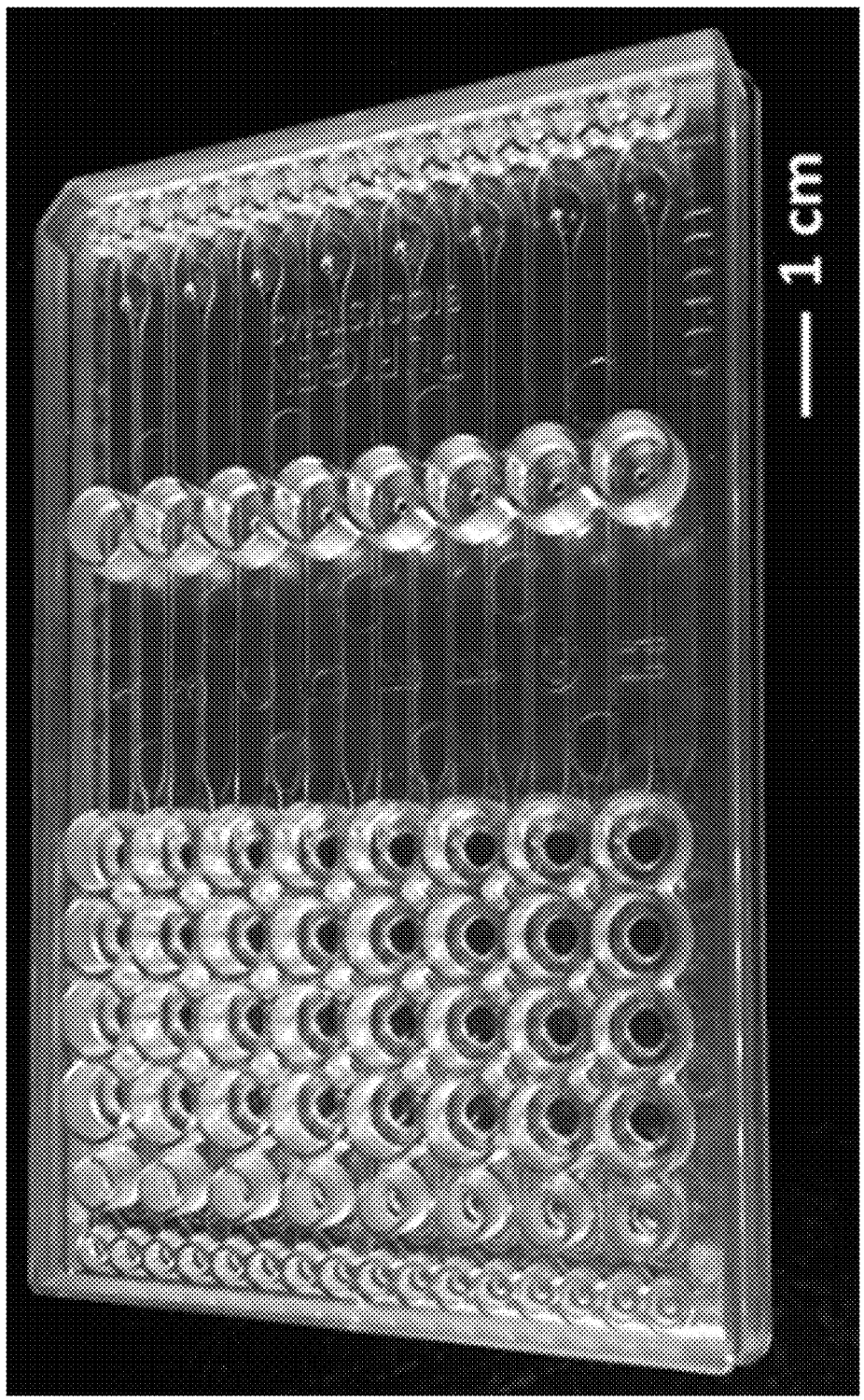
FIG. 5B shows an exemplary fluidic device cartridge comprising eight parallel fluidic channels and reservoirs for simultaneous processing of up to eight samples as shown in FIG. 5A.
Figure 5C:
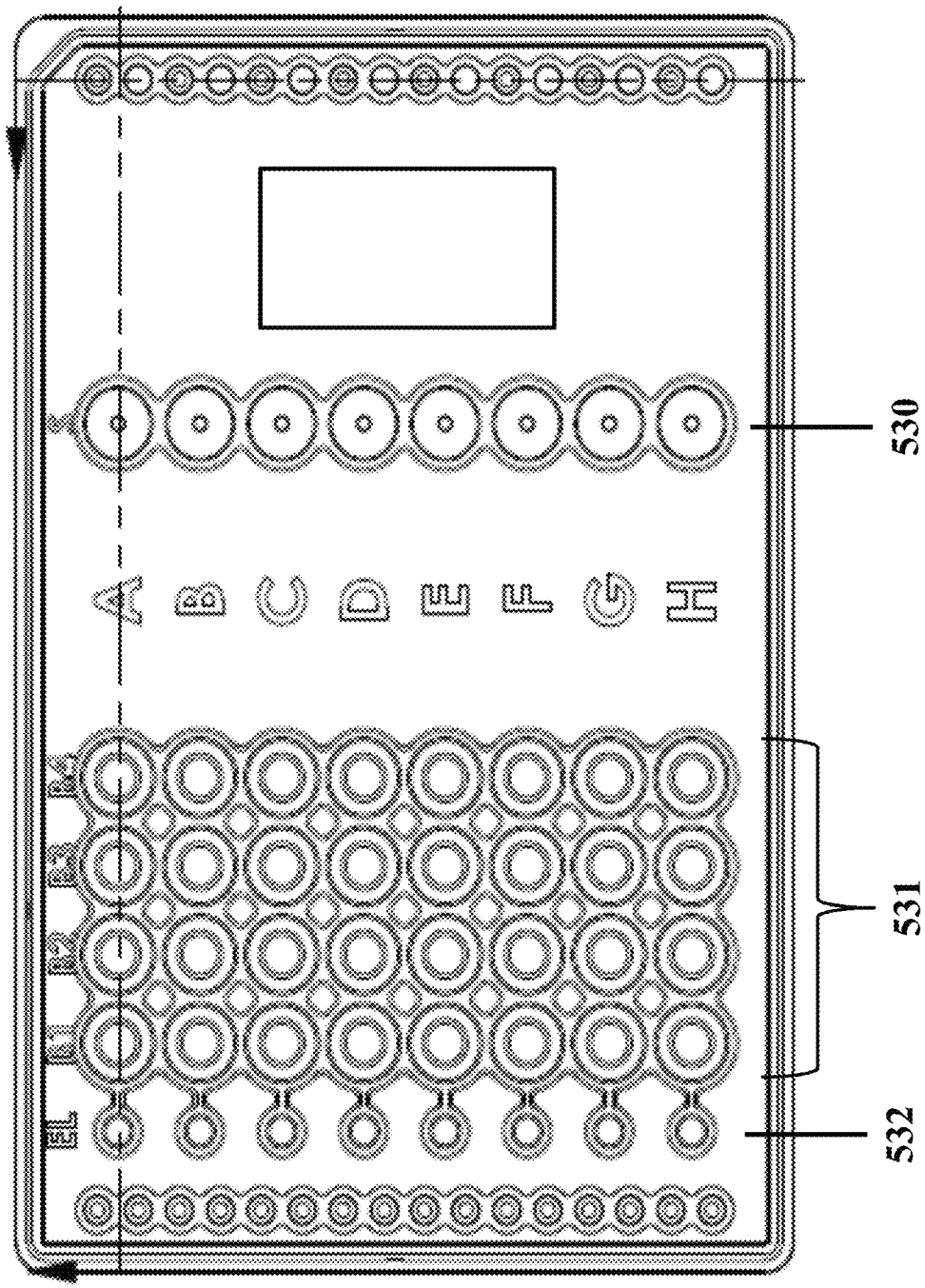
FIG. 5C shows an exemplary top view schematic of one channel and its connected reservoirs for a fluidic device cartridge as shown in FIG. 5B, further exemplifying use of gas ports for external pressure or vacuum application to the channels within the fluidic device cartridge.
Figure 5D:
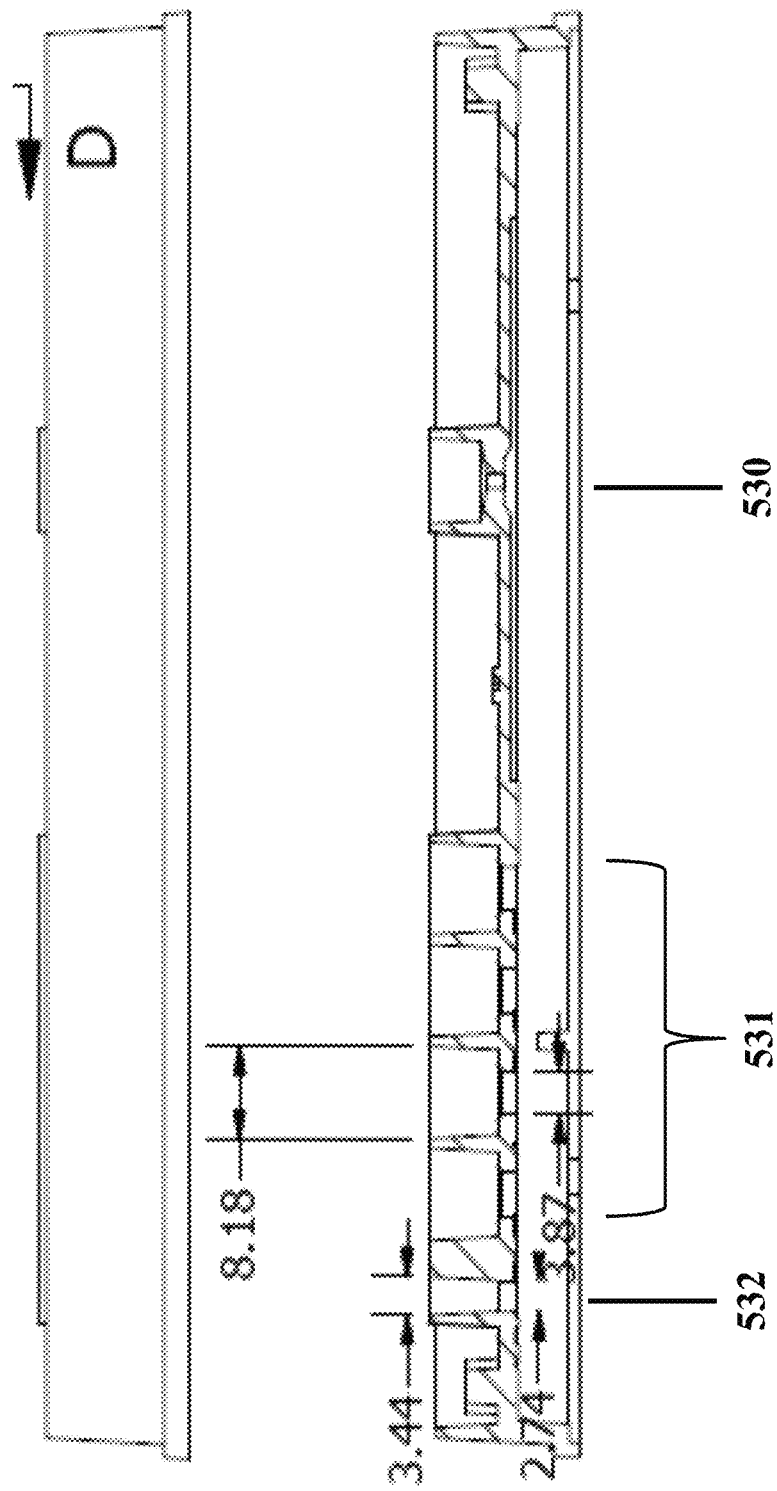
FIG. 5D shows an exemplary side view schematic of a fluidic device cartridge as shown in FIG. 5B.
Figure 5E:
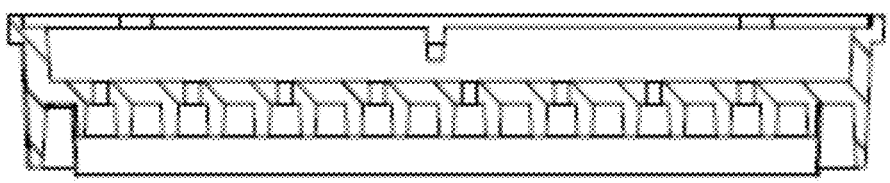
FIG. 5E shows an exemplary end view schematic of a fluidic device cartridge as shown in FIG. 5B.

Isotachophoresis and/or sample preparation (e.g., deparaffinization, digestion, lysis) can be conducted in a fluidic device, for example a microfluidic chip. For example, FIG. 5A shows a schematic of a channel with a sample preparation (e.g., deparaffinization) zone 500 with a sample inlet 501 and a trailing electrolyte reservoir 502, a purification (e.g., isotachophoresis) zone 510 with a leading electrolyte reservoir 511, and an elution outlet 520. A capillary barrier may provide an interface between the sample fluid and the leading electrolyte buffer prior to applying voltage. A capillary barrier may be provided between the sample preparation zone 500 and the trailing electrolyte reservoir 502 in order to limit, reduce, or prevent mixing or pressure-driven flow of the sample fluid and the trailing electrolyte buffer. A capillary barrier may be provided between the purification zone 510 and the leading electrolyte reservoir 511 so as to limit, reduce, or prevent mixing or pressure-driven flow of the contents of zone 510 and the leading electrolyte reservoir 511. In another example, deparaffinization can be performed first off-chip, or can be unnecessary due to the starting material, in which case the channel can comprise a lysis and digestion zone (e.g., pH 7, 56° C.) and a crosslink removal and purification (e.g., isotachophoresis) zone (e.g., pH 7, 80° C.). In another example, deparaffinization can be performed first off-chip, or can be unnecessary due to the starting material, in which case the channel can comprise a lysis and digestion zone (e.g., pH 7, temperature T1) and a crosslink removal and/or purification (e.g., isotachophoresis) zone (e.g., pH 7, temperature T2). In another example, deparaffinization can be performed first off-chip, or can be unnecessary due to the starting material, in which case the channel can comprise a disruption and/or lysis zone (e.g., pH 7, temperature T1) and a digestion and/or purification (e.g., isotachophoresis) zone (e.g., pH 7, temperature T2). In another example, deparaffinization can be performed first of-chip, or can be unnecessary due to the starting material, in which case the channel can comprise a disruption and/or lysis zone (e.g., pH 7, temperature T1) and an isothermal enzymatic amplification zone (e.g., pH 7, temperature T2). In another example, deparaffinization can be performed first of-chip, or can be unnecessary due to the starting material, in which case the channel can comprise a disruption and/or lysis zone (e.g., pH 7, temperature T1) and an isothermal enzymatic digestion zone (e.g., pH 7, temperature T2). In some cases, the channel may comprises three zones, for example a disruption and/or lysis zone (e.g. pH 7, temperature T1), an isothermal enzymatic amplification zone (e.g., pH 7, temperature T2), and a purification (e.g. isotachophoresis) zone (e.g. pH 7, temperature T3). FIG. 5B shows an exemplary fluidic device cartridge with eight parallel channels each as shown in FIG. 5A. FIG. 5C shows a top-view schematic of the fluidic device shown in FIG. 5B, while FIG. 5D and FIG. 5E show side and end views, respectively. The devices can comprise sample inlets or reservoirs 530, ITP electrolyte buffer reservoirs 531, and sample elution outlets or reservoirs 532. The channels and/or reservoirs may be coupled to one or more pneumatic ports. Each of the eight parallel channels of the fluidic device may be independently operated from each of the other channels. In some cases, each channel has a dedicated set of electrodes and electric circuitry to drive ITP. Electrodes may for example be located in the trailing electrolyte reservoir 502 and the leading electrolyte reservoir 511 such that the electrodes do not directly contact sample material.

In some instances, there is little or no fluid or ion flow between parallel channels. In some cases, the parallel channels may not be in fluid communication with one another. The fluid leakage rate between parallel channels may be less than about 0.1, 0.2, 0.3, 0.4, 0.5, 0.6, 0.7, 0.8, 0.9, or 1 μL per hour.

In some instances, there is little or no electrical communication between parallel channels such that the parallel channels are electrically isolated from one another. Each of the parallel channels may be independently electrically controlled so as to apply an independent electric field to each of the channels. In some instances, current leakage between the channels is less than about 0.1 microamperes (μA), 0.2 μA, 0.3 μA, 0.4 μA, 0.5 μA, 0.6 μA, 0.7 μA, 0.8 μA, 0.9 μA, or 1 μA. In some instances, the impedance between channels may be greater than 0.1 mega Ohm (MOhm), 0.2 MOhm, 0.3 MOhm, 0.4 MOhm, 0.5 MOhm, 0.6 MOhm, 0.7 MOhm, 0.8 MOhm, 0.9 MOhm, 1 MOhm, 5 MOhm, 10 MOhm, 20 MOhm, 30 MOhm, 40 MOhm, or 50 MOhm.

In some instances, each zone on the isotachofluidic device can be heated. In some instances, the zones are heated to the same temperature. In some instances, individual zones are heated to different temperatures. In some instances, a first zone may be heated to a temperature above 37° C., for example within a range of about 60° C. to about 100° C. In some instances a second zone may be heated to a temperature above 37° C., for example within a range of about 40° C. to about 60° C.

An isotachophoresis fluidic device can comprise one or more reservoirs, including but not limited to buffer loading reservoirs, sample loading reservoirs (including reservoirs that accept solid, multiphasic, or other inhomogeneous liquids or solutions such as tissue, whole blood, or unlysed cell suspensions), leading electrolyte reservoirs, trailing electrolyte reservoirs, reagent reservoirs, elution reservoirs (e.g., for unloading processed samples), and gas or air reservoirs. In some cases, one physical reservoir can be used for multiple purposes, such as buffer loading and sample loading. Liquid or air reservoirs can be used to apply external pressure for liquid loading (e.g., positive pressure on liquid wells or vacuum on gas only reservoirs).

Reservoirs can be in thermal communication with a heating or cooling source, allowing control of the temperature of the reservoir and any material within (e.g., reagent, sample, product). For example, an elution reservoir can be thermally controlled to control the temperature of the eluted product (e.g., for preservation of structure, integrity) while within the fluidic device.

Reagent reservoirs can be used to load one or more reagents for processing the sample before, during, or after isotachophoresis. Reagents can include digestion reagents, amplification reagents, reverse transcription reagents, linear polymer solutions for size-based separations, probes for hybridization reactions, ligation reagents, dyes, tracers, labels, and other reagents. Reagent reservoirs can be connected to a reaction channel, or a reaction section of another channel, where reactions can occur. Heating or cooling can be applied (e.g., with thermal controllers as discussed herein) to catalyze reactions (such as enzymatic reactions with nucleic acids or proteins), to hybridize or melt nucleic acids, or remove intercalated dyes from nucleic acids (for example, prior to elution). Heating and cooling can also be used to control a fixed operating temperature for conducting ITP (e.g., cooling can be applied to reduce effects of Joule heating), or to keep a reservoir (e.g., an elution reservoir) at a fixed temperature (e.g., cooler than room temperature), such as for stable storage of purified nucleic acids. Light can be applied (e.g., with light sources as discussed herein) for purposes including optical interrogation, fluorescent excitation, and reaction energy or catalysis.

Gas or air reservoirs, or gas or air outlets, can be connected via gas channels to liquid channels within a fluidic device to allow purging of air or other gases from the fluidic device (e.g., during liquid filling of the fluidic device). Gas or air reservoirs, or pneumatic pressure ports, can be connected via gas channels to liquid channels to allow for pumping of fluids onto or within the fluidic device (e.g., for pumping of fluids from reservoirs into channels).

A device can comprise multiple purification (e.g., isotachophoresis) zones in connection with each other. For example, a second isotachophoresis zone can split from and run in parallel to a first isotachophoresis zone, allowing splitting of a sample band at a specified ratio (e.g., based on a ratio of currents between the two zones) for parallel processing.

A fluidic device can comprise multiple purification zones in parallel (see, e.g., FIG. 5C). For example, a fluidic device can comprise more than one set of purification zones, each with associated reservoirs, inlets, outlets, channels, and any other components described herein (e.g., sample preparation zones, electrodes, heaters, detectors) in parallel, separate from each other and each capable of independently processing a sample. A fluidic device can comprise at least 2, 3, 4, 5, 6, 7, 8, 9, 10, 11, 12, 13, 14, 15, 16, 17, 18, 19, 20, 24, 48, 96, or more purification zones in parallel. A fluidic device can comprise multiple channels in parallel. A fluidic device can comprise at least 2, 3, 4, 5, 6, 7, 8, 9, 10, 11, 12, 13, 14, 15, 16, 17, 18, 19, 20, 24, 48, 96, or more channels in parallel. Components, such as purification zones or channels, located in parallel can be side-by-side, located in different device layers (e.g., horizontal or vertical layers), or placed in different arrangements. Parallel components can be identical, or can be designed differently but function equivalently or nearly equivalently. For example, parallel channels can have different geometries to allow a smaller overall fluidic device footprint, but still function similarly. Alternatively, parallel components can be designed to function differently, for example to process different types of samples in parallel, or to subject samples to different operations. In some cases, parallel components can be designed to subject different sample types to different operations in parallel. In some cases, parallel components can be designed to subject the same sample types to different operations in parallel. In some cases, parallel components can be designed to subject different sample types to the same operations in parallel. In some cases, parallel components can be designed to subject the same sample types to the same operations in parallel. In some cases, parallel components can be designed to simultaneously and/or independently subject two or more samples to one or more operations in parallel. In some cases, a leakage rate between two or more channels (or between two or more purification zones) is less than 0.5 µl per hour, less than 1 µl per hour, less than 5 µl per hour, less than 10 µl per hour. In some embodiments, a current leakage rate between two or more channels (or between two or more purification zones) is less than 0.5 µA, less than 1 µA, less than 5 µA, or less than 10 µA. In some embodiments, an impedance between channels or zones is greater than 0.5 megaOhm, greater than 1 megaOhm, greater than 5 megaOhm, or greater than 10 megaOhm.

As discussed herein, a fluidic device can be designed to process different sample volumes. For example, FIG. 6A, FIG. 6B, FIG. 6C, and FIG. 6D show top, side, bottom, and top three-quarters views, respectively, of a rapid purification ITP fluidic device 600 for sample volumes greater than or equal to about 200 µL. The device comprises a channel 600 connected to sample input wells 601, ITP buffer wells 602, and sample output (elution) wells 603. The ITP buffer wells 602 can include an elution buffering reservoir 605, a leading electrolyte reservoir 606, a leading electrolyte buffering reservoir 607, and a trailing electrolyte reservoir 608. Elution reservoir 603 may be connected to elution buffering reservoir 605 by an elution buffering channel 609. A capillary barrier may be provided in the elution buffering channel 609 to reduce or prevent mixing or pressure driven flow between the contents of the elution buffering reservoir 605 and the elution reservoir 603. Leading electrolyte reservoir 606 may be connected to leading electrolyte buffering reservoir 607 by a leading electrolyte buffering channel 610. A capillary barrier may be provided in the leading electrolyte buffering channel 610 to reduce or prevent mixing or pressure driven flow between the contents of the leading electrolyte buffering reservoir 607 and the leading electrolyte reservoir 606. Buffering reservoir 605 may contain elution buffer electrolytes at a higher ionic strength than those in elution reservoir 603, while buffering reservoir 607 may contain leading electrolytes at a higher ionic strength than those in leading electrolyte reservoir 606. The device may further comprise pneumatic ports 604 along its edges which are configured to couple to a pneumatic device, for example a vacuum source on a benchtop instrument. The pneumatic ports 604 may be coupled to the channel 600 and reservoirs by gas channels as described herein. Application of suction at the pneumatic ports 604 may load the sample, leading electrolyte, and elution buffer into the channel 600. In some cases, the trailing electrolyte buffer fluid remains in the trailing electrolyte reservoir 608. Suction may be applied simultaneously or sequentially to the pneumatic ports 604 so as to load the channel 600 simultaneously or in stages, respectively. The sample may be loaded into a first zone or sub-channel of channel 600 which extends from the trailing electrolyte reservoir 608 to a capillary barrier 611 at a 180° low dispersion turn in the channel 600. The capillary barrier 611 may provide an interface between the sample and the leading electrolyte buffer during loading so as to limit, reduce, or prevent mixing or pressure-driven flow. A capillary barrier may be provided between the trailing electrolyte reservoir 608 and the first zone or sub-channel so as to limit, reduce, or prevent mixing or pressure-driven flow between the contents of the trailing electrolyte reservoir 608 and the sample. The leading electrolyte may be loaded into the second zone or sub-channel of the channel 600 which extends from capillary barrier 611 to capillary barrier 612. The capillary barrier 612 may provide an interface between the leading electrolyte buffer and the elution buffer. The elution buffer may be loaded into a third zone or sub-channel of channel 600 which extends from capillary barrier 612 to elution reservoir 603. In some embodiments, the ITP buffer wells 602 may further comprise a trailing electrolyte buffering reservoir (not shown) containing trailing electrolytes at a higher ionic strength than those in the trailing electrolyte reservoir 608. The trailing electrolyte buffering reservoir may be connected to the trailing electrolyte reservoir 608 by a trailing electrolyte buffering channel (not shown). The trailing electrolyte buffering channel may comprise a capillary barrier to limit, reduce, or prevent mixing or pressure-driven flow between the contents of the trailing electrolyte buffering reservoir and the trailing electrolyte reservoir 608.

Electrodes may for example be located in the trailing electrolyte reservoir 608, a trailing electrolyte buffering reservoir (not shown), the leading electrolyte reservoir 606, and/or the leading electrolyte buffering reservoir 607 such that the electrodes do not directly contact sample material. The electrodes may be triggered to alter or control the applied electric field in response to feedback from a sensor, for example a voltage, current, conductivity, or temperature sensor as described herein. For example, passage of the nucleic acids within the ITP zone from the second zone of channel 600 to the third zone of channel 600 may be detected and feedback from the detector may trigger the applied current to change. The current may for example be increased, decreased, or ended according to the protocol of the instrument. The current may for example be paused (e.g. dropped temporarily to zero) in order to enable on-chip quantification of the nucleic acids. Alternatively or in combination, the current may be decreased in order to slow isotachophoresis within the third zone to allow the nucleic acids which may have dispersed upon transition from the leading electrolyte buffer to the elution buffer (or second leading electrolyte buffer) time to concentrate further before reaching the elution well 603.

The methods and processes provided herein include methods and processes that use any of the devices provided herein. Devices provided herein with multiple channels for processing multiple samples in parallel may be used in a variety of contexts. In some cases, a method may include use of a device to process multiple samples (e.g., by conducting isotachophoresis on such samples) that share a certain feature (e.g., solid tissue lysate, cell lysate, solid tissue, fixed tissue). In some cases, the multiple samples may be different samples. For example, the method may involve performing isotachophoresis on a tissue sample in one zone of the device while simultaneously, but independently, conducting isotachophoresis on a different sample such as a cellular sample or sample comprising cross-linked nucleic acids.

In some cases, a method or multiplexing process provided herein may involve conducting isotachophoresis on a sample in a channel in parallel with conducting isotachophoresis on a second sample in a second channel using leading electrolyte and/or trailing electrolyte buffers that are the same or similar. In some cases, a sample in one of the channels is processed using a first leading electrolyte buffer and a sample in a different channel is processed using a second leading electrolyte buffer that is different from the first. For example, the first leading electrolyte buffer can contain one or more leading electrolyte ions that are different from those contained in the second leading electrolyte buffer. In another example, the first leading electrolyte buffer can contain one or more leading electrolyte ions that are the same as those contained in the second leading electrolyte buffer but the concentration of such leading electrolyte ions in the first leading electrolyte buffer is different from the concentration of such ions in the second leading electrolyte buffer. In some cases, a method or process provided herein may involve conducting isotachophoresis on a sample in a channel in parallel with conducting isotachophoresis on a second sample in a second channel using trailing electrolyte or trailing electrolyte buffers that are the same or similar. In some cases, a sample in one of the channels is processed using a first trailing electrolyte buffer and a sample in a different channel is processed using a second trailing electrolyte buffer that is different from the first. For example, the first trailing electrolyte buffer can contain one or more trailing electrolyte ions that are different from those contained in the second trailing electrolyte buffer. In another example, the first trailing electrolyte buffer can contain one or more trailing electrolyte ions that are the same as those contained in the second trailing electrolyte buffer the concentration of such trailing electrolyte ions is different in the first trailing electrolyte buffer is different from the concentration in the second trailing electrolyte buffer.

In some embodiments, one or more reservoirs may be connected to two channels or sub-channels. For example, elution reservoir 603 may be connected to both channel 600 and elution buffering channel 609. Alternatively or in combination, leading electrolyte reservoir 606 may be connected to both channel 600 and leading electrolyte buffering channel 610. Alternatively or in combination, trailing electrolyte reservoir 608 may be connected to both 600 and a trailing electrolyte buffering channel. Alternatively or in combination, sample input well 601 may be connected to a mid-point in channel 600 such that channel 600 extends to the left (as a first sub-channel) and right (as a second sub-channel) of the input well 601. The two channels or sub-channels may be connected to the one or more reservoirs with an angle between the two channels (swept in the major plane of the fluidic device) of at least about 5°, 10°, 20°, 30°, 40°, 45°, 50°, 60°, 70°, 80°, 90°, 100°, 110°, 120°, 130°, 135°, 140°, 150°, 160°, 170°, or 180°. The two channels or sub-channels may be connected to the one or more reservoirs with an angle between the two channels (swept in the major plane of the fluidic device) of at most about 5°, 10°, 20°, 30°, 40°, 45°, 50°, 60°, 70°, 80°, 90°, 100°, 110°, 120°, 130°, 135°, 140°, 150°, 160°, 170°, or 180.

The device may comprise, for example, 8 channels as shown. Each channel may hold a sample volume of about 50 µL to about 275 µL and a total volume of about 500 µL. The 180° low dispersion turn in each channel may facilitate such large sample volumes in an 8-channel multi-channel plate with a standard SLAS footprint.

FIG. 7A, FIG. 7B, FIG. 7C, and FIG. 7D show top, side, bottom, and bottom three-quarters views, respectively, of a rapid purification ITP fluidic device 700 for sample volumes less than or equal to about 100 µL. The device comprises sample input wells 701, ITP buffer wells 702, and sample output (elution) wells 703. The device 700 may be substantially similar to device 600 but with different channel geometry (and corresponding reservoir geometry) that does not include a 180° turn in the channel.

The device may comprise, for example, 8 channels as shown. Each channel may hold a sample volume of about 10 µL to about 100 µL. A device with smaller sample volumes may be useful for PCR cleanup or other reaction cleanup applications or for smaller sample sizes (for example a sample with a low number of cells or a small amount of tissue).

FIG. 8A, FIG. 8B, FIG. 8C, and FIG. 8D show top, side, bottom, and three-quarters bottom views, respectively, of another rapid purification ITP fluidic device 800 for sample volumes less than or equal to about 100 μL. The device comprises sample input wells 801, ITP buffer wells 802, and sample output (elution) wells 803. The device 800 may be substantially similar to devices 600 and 700 but comprises multiple different channel geometries on a single chip.

The fluidic device can comprise one or more electrodes that apply an electric field to a fluidic device or a part of the fluidic device. Applied electric fields can be used for conducting isotachophoresis. The fluidic device may comprise one or more electrodes that apply a single electric field to all channels of the fluidic device. The fluidic device may comprise one or more electrodes that apply more than one electric field to the fluidic device, for example one electric field per channel on the device. In some instance, a first and second electric field are generated from a single electrode pair. In some instances, a first and second electric field are generated from different electrode pairs. The electric fields may be applied simultaneously, sequentially, and/or independently or one another. Electrodes can be external, such as a wire that drops into a reservoir. Electrodes can be internal, such as a microfabricated, printed, or other embedded element included within the fabrication of the fluidic device. Electrode materials can include but are not limited to metals (e.g., platinum, titanium), and carbon.

The one or more electrodes of the fluidic device may be part of one or more electric circuits that apply an electric field to a fluidic device or part of a fluidic device. The fluidic device may comprise one or more electric circuits that apply a single electric field to all channels or isotachoporesis regions of zones of the fluidic device. The fluidic device may comprise one or more electric circuits that apply more than one electric field to the fluidic device, for example one electric field per channel on the device. In some instance, first and second electric fields may be generated from a single electric circuit. In some instances, first and second electric fields may be generated from different electric circuits. The electric fields may be applied simultaneously, sequentially, and/or independently or one another by the one or more electric circuits. In some instances the device (or benchtop instrument) may be configured to control a first electric circuit simultaneously with and independently of a second electric circuit.

Electrodes can be located in reservoirs, such as trailing and leading electrolyte reservoirs, which can be separated from sample reservoirs by buffering channels. In some cases, electrodes are located in buffering channels or buffering reservoirs. Location of electrodes in electrolyte reservoirs or electrolyte buffering reservoirs can isolate the electrodes from analytes such as nucleic acids to reduce or eliminate contamination of electrodes by sample material. This approach can allow reuse of electrodes without cross-contamination between samples. In one example, a trailing electrolyte reservoir or trailing electrolyte channel is connected by a buffering channel to a buffering reservoir which contains trailing electrolyte ions and an electrode, and the trailing electrolyte reservoir is also connected to a sample reservoir or sample channel, which in turn is connected to a leading electrolyte reservoir by a leading electrolyte channel; the leading electrolyte reservoir is also connected by a buffering channel to a buffering reservoir which also contains leading electrolytes and an electrode. In another example, or as a continuation of the previous example, an elution reservoir containing elution buffer is connected to a leading electrolyte reservoir by an elution channel and is also connected to a buffering reservoir containing elution buffer electrolytes and an electrode. The buffering channels between the buffering reservoirs and their corresponding reservoirs can include capillary barriers and/or a low cross-sectional area to limit, reduce, or prevent mixing and pressure-driven flow as described herein. The buffering reservoirs may contain electrolytes at the same or higher ionic strength as their corresponding reservoirs. For example, the elution reservoir can be connected to a buffering reservoir containing elution buffer electrolytes at the same or higher ionic strength or concentration as the elution reservoir. The trailing electrolyte reservoir can be connected to a buffering reservoir containing trailing electrolytes at the same or higher ionic strength or concentration as the trailing electrolyte reservoir. The leading electrolyte reservoir can be connected to a buffering reservoir containing leading electrolytes at the same or higher ionic strength or concentration as the leading electrolyte reservoir. Providing dedicated buffering reservoirs connected to the elution reservoir, trailing electrolyte reservoir, and/or leading electrolyte reservoir with higher ionic strengths can provide a pool of additional ions to maintain pH and conductivity in the channel as the sample moves through the channel.

Figure 9B:
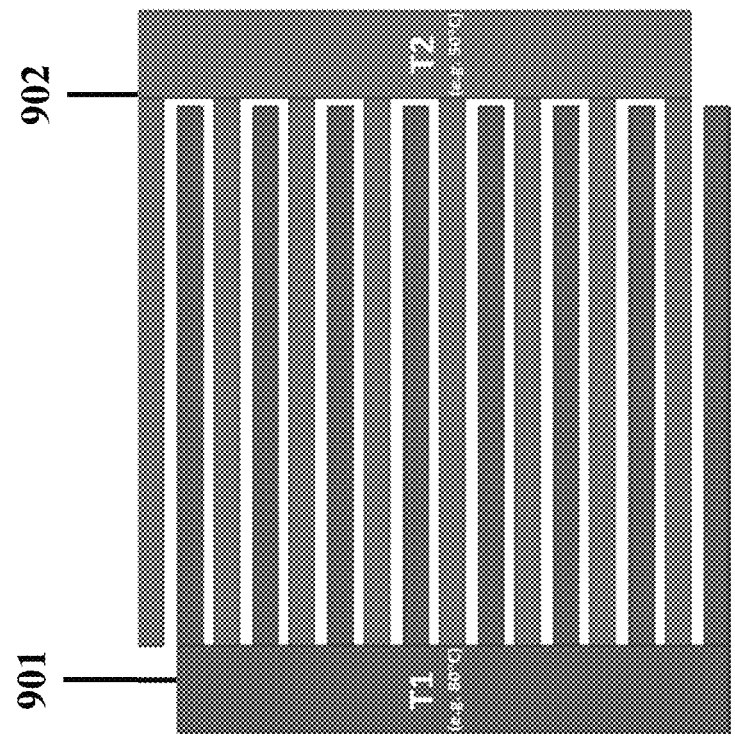
FIG. 9B shows an exemplary schematic of two thermal controllers, each aligned with a zone of the eight parallel channels shown in FIG. 9A.
Figure 9A:
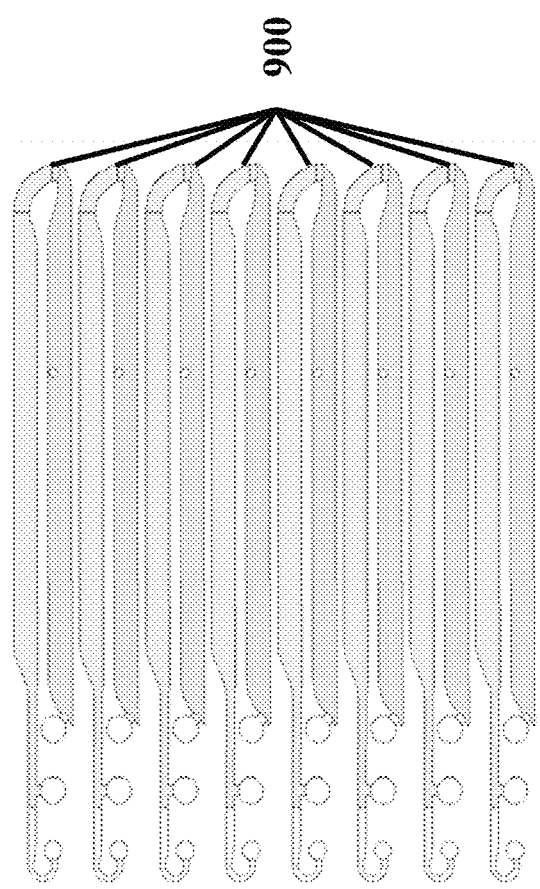
FIG. 9A shows an exemplary schematic of fluidic device cartridge comprising eight parallel channels as shown in FIG. 5B.

Fluidic devices can be used with one or more thermal controllers. For example, FIG. 9A shows a schematic of an eight-plex sample preparation and isotachophoresis device, comprising eight parallel channels 900 of the design shown in FIG. 5A. FIG. 9B shows a schematic of a first and a second thermal controller 901, 902. A first thermal controller 901 at temperature T1 (e.g., 80° C.) is aligned with the sample preparation zones of the channels and a second thermal controller 902 at temperature T2 (e.g., 50° C.) is aligned with the isotachophoresis zones of the channels. In some cases, additional thermal controllers may be aligned with additional zones of the channels (not shown), for example a third thermal controller at temperature T3 may be aligned with a third zone at temperature T3. In some cases, each zone of each channel can have its own separate thermal controller, rather than sharing a common thermal controller with the respective zones of the other channels. In other cases, all the zones or channels can share one thermal controller. In other cases, more than one but less than all the zones or channels can share one thermal controller. Thermal controllers can comprise components including but not limited to resistive heaters, fluid-based heating or cooling systems, and Peltier devices. Thermal controllers can be fabricated from materials including but not limited to metals (e.g., platinum, titanium, copper, gold), carbon, and indium tin oxide (ITO). Thermal controllers can comprise temperature sensors, which can be used to monitor the temperature being controlled and provide temperature feedback for thermal control. Thermal controllers can be used with computer control systems, as discussed further in this disclosure. In some cases, thermal controllers are operated without temperature feedback. Thermal controllers can be integrated into fluidic devices or located externally, such as within a benchtop system.

Fluidic devices can be used with one or more light sources. Light sources can be integrated into fluidic devices or located externally to a fluidic device, such as within a benchtop system or in a separate device. Light sources can provide light for optical interrogation, fluorescent excitation, temperature sensing, reaction energy or catalysis, and other purposes.

Fluidic devices can be designed such that their outermost frame or dimensions meet microtiter plate standards (e.g., SLAS microtiter plate standards). Fluidic devices can be designed to use the defined ports of a microtiter plate (e.g., SLAS standard microtiter plate) as liquid reservoirs, with pneumatic actuation ports located on the unused surface external to the liquid reservoirs. Pneumatic ports can be arranged at the edges of a fluidic device with a microtiter plate-compatible layout such that cross-contamination through pneumatic actuation across liquid reservoirs is avoided, and such that the ports are easy to access with pneumatic hardware. A subset of defined ports can also be used for pneumatic actuation in addition to their other functions. In some cases, a fluidic device can be designed and fabricated in two interlocking parts: first, an insert that includes a channel unit (e.g. a layer with a flat surface enabling ease of film bonding), wells, and pneumatic ports; and second, an outer ring to provide conformity to a microtiter plate standard (e.g., SLAS microtiter plate dimensional standards), including alignment features for aligning the fluidic device to a benchtop system and mating features to interlock with the first part. Wells can be connected to form bosses, which can be more compatible with injection molding.

Fluidic devices can be made from a variety of materials, including but not limited to, glass (e.g., borosilicate glass), silicon, plastic, and elastomer. Plastics can include polymethylmethacrylate (PMMA), cyclic olefin copolymer (COC), cyclic olefin polymer (COP), polyethylene, polyethylene terephthalate (PET), high-density polyethylene (HDPE), and low-density polyethylene (LDPE). Elastomers can include polydimethylsiloxane (PDMS).

Materials used for the fabrication of fluidic devices can be selected for their optical properties. For example, materials can be used that exhibit low auto-fluorescence, low scatter, and high transmission at wavelengths of interest (e.g., excitation and emission wavelengths for nucleic acid labels or dyes). Different materials can be used in one fluidic device; for example, a detection region can be fabricated with materials exhibiting useful optical properties, while other regions of the device can comprise other materials.

Materials used for the fabrication of fluidic devices can be selected for their thermal properties. For example, materials can be selected for high thermal conductivity. Alternatively, materials can be selected for low thermal conductivity (e.g., to thermally insulate a fluidic device or a region of a fluidic device. Different materials can be used in one fluidic device; for example, a heating region can have materials with high thermal conductivity for improved thermal communication with a thermal controller, while the heating region is surrounded by materials with low thermal conductivity for thermal isolation from other regions of the device.

Materials used for the fabrication of fluidic devices or microchannels therein can be selected for their elastomeric or deformation properties. For example, materials can be selected for low elasticity so as to allow for plastic channel closure as described herein. Alternatively, materials can be selected for high elasticity. Different materials can be used in one fluidic device; for example poly(methyl methacrylate) (PMMA), cyclic olefin copolymer (COC), cyclo-olefin polymer (COP), or the like can be used in a single fluidic device. Materials may have a modulus of elasticity of at least 1 GPa, 1.5 GPa, 2 GPa, 2.5 GPa, 3 GPa, 3.5 GPa, 4 GPa, 4.5 GPa, or 5 GPa. Materials may have a modulus of elasticity of at most 1 GPa, 1.5 GPa, 2 GPa, 2.5 GPa, 3 GPa, 3.5 GPa, 4 GPa, 4.5 GPa, or 5 GPa. Materials may have a tensile strength of at least 10 MPa, 20 MPa, 30 MPa, 40 MPa, 50 MPa, 60 MPa, 70 MPa, 80 MPa, 90 MPa, 100 MPa, 110 MPa, 120 MPa, 130 MPa, 140 MPa, 150 MPa, 160 MPa, 170 MPa, 180 MPa, 190 MPa, 200 MPa. Materials may have a tensile strength of at most 10 MPa, 20 MPa, 30 MPa, 40 MPa, 50 MPa, 60 MPa, 70 MPa, 80 MPa, 90 MPa, 100 MPa, 110 MPa, 120 MPa, 130 MPa, 140 MPa, 150 MPa, 160 MPa, 170 MPa, 180 MPa, 190 MPa, 200 MPa.

In some cases, surfaces of a fluidic device can be used without surface treatments or coatings. In other cases, surfaces of a fluidic device can be used with surface coatings, such as hydrophobic treatments, hydrophilic treatments, or selective binding agents (e.g., antibodies). Different regions of a fluidic device can comprise different surface treatments (or the lack thereof). For example, some channels, reservoirs, or parts thereof can be hydrophobic, while others are hydrophilic.

Fluidic devices can include a range of flow control units and techniques, including but not limited to capillary barriers, air outlet reservoirs, gas/air lines, fill level monitors (e.g., by electrode measurement), particular reservoir geometries, particular fluidic resistances of channels, and fluid loading orders.

Capillary barriers can be paired with air outlet reservoirs to purge air (e.g., to prevent bubbles), thereby positioning and successfully establishing a liquid-liquid interface (i) between leading and trailing electrolyte solutions that is required for isotachophoresis, and (ii) between buffering reservoirs and leading electrolyte or trailing electrolyte and/or sample solutions. Capillary barriers can be designed in combination with channel geometry to automate filling of channels in a preferred order. Channel resistances can be selected, such as by design of channel dimensions, to provide differential fluidic resistances. Ordering of liquid loading can allow the correct formation of liquid-liquid interfaces without air bubbles for performing electrokinetic processes. In one example, a trailing ion reservoir is directly connected to the analyte or sample channel.

Figure 10B:
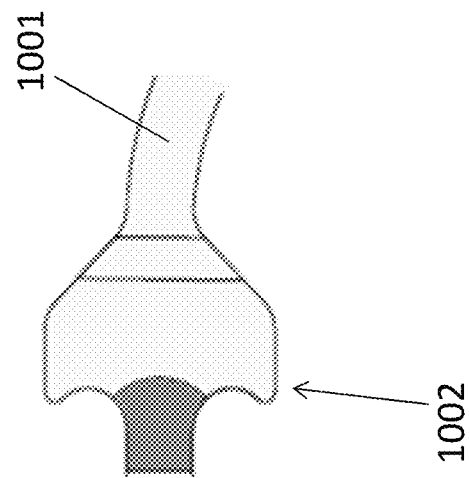
FIG. 10B is a magnified schematic of the gas channel of FIG. 10A.
Figure 10A:
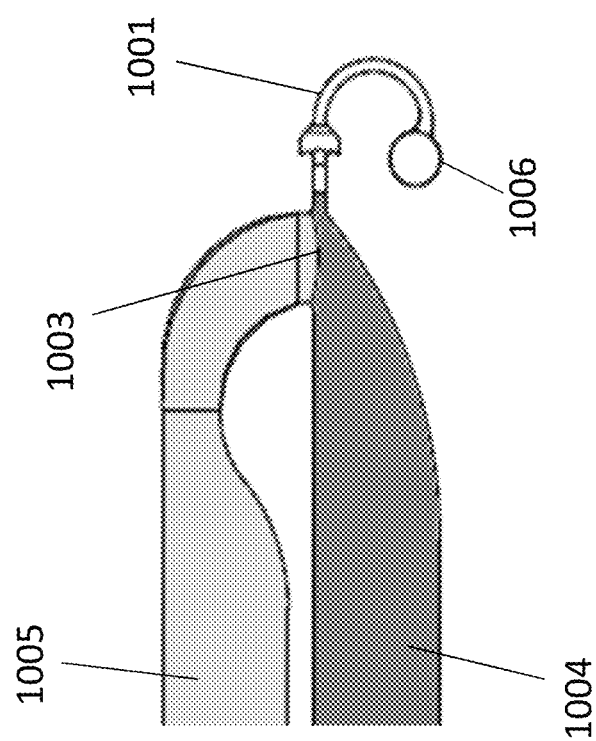
FIG. 10A shows an exemplary gas channel which may comprise a capillary barrier.

Gas (e.g., air) channels or lines can be used to provide actuated pneumatic pressure to capillary barriers or other regions of a fluidic device. Gas channels can connect to external gas pressure sources via pneumatic ports. Gas channels can have higher fluidic resistance than the liquid channels they provide pressure to, for example to reduce or prevent liquid flow into the gas channel. For example, gas channels can have less than half the cross sectional area of a main isotachophoresis channel. Multiple gas channels can be connected to a single gas reservoir or port (e.g., with branching channels). Capillary valves can be employed with branched air lines to prevent upstream liquid movement. FIG. 10A shows an exemplary gas channel 1001 which may comprise a capillary barrier 1002 connected to the liquid channel interface 1003 between the sample 1004 and leading electrolyte buffer 1005 sub-channels. FIG. 10B is a magnified schematic of the gas channel 1001 highlighting the capillary barrier 1002 which prevents upstream liquid movement towards the pneumatic port 1006.

Negative pressure or vacuum can be applied to the gas channels via the gas ports in order to load a fluidic channel. Each fluidic channel on a microfluidic device may be loaded simultaneously or independently (e.g. sequentially) of one another. Within a channel, the fluids may be loaded simultaneously or independently of one another. For example, leading electrolyte buffer, high concentration leading electrolyte buffer, trailing electrolyte buffer, high concentration trailing electrolyte buffer, the elution buffer, high concentration elution buffer, or any combination thereof may be loaded prior to, simultaneously with, or after loading the sample. For example, negative pressure may be applied to the gas ports on one side of the chip to load one or more fluids (e.g. trailing electrolyte buffer, elution buffer, etc.). Subsequently, negative pressure may be applied to the gas ports on the other side of the chip to load additional fluids (e.g. leading electrolyte buffer). Alternatively, negative pressure may be applied to all of the gas ports connected to a channel at the same time. The sample may be loaded by applying negative pressure or vacuum before, during, or after loading of the isotachophoresis buffers. The sample may be loaded without applying negative pressure or vacuum, for example by wetting or gravity.

Sensors (e.g., electrodes) can be used to detect liquid filling levels or bubbles (e.g., via current or voltage sensing) and provide feedback. Geometric features (e.g. constrictions, expansions, or turns) can be used in combination with electrodes to monitor impedance of channels and thereby the time progression of isotachophoresis. For example, during ITP the nucleic acids are focused, and voltage can be used to track the focused band location in the channel from start to finish. In one example, monitoring of fluid expansion into a reservoir (such as an elution reservoir) from a connected channel with smaller cross sectional area can be used to determine the time the analyte is eluting, thereby allowing for automated elution and end-process control. In another example, a channel constriction can be designed to allow detection of the timing (or triggering) of a step in an electrokinetic process, such as when the focused analyte is entering a channel zone where a reaction is to take place or where an optical detection event is to take place, allowing control of reaction timing or detector triggering.

Figure 11:
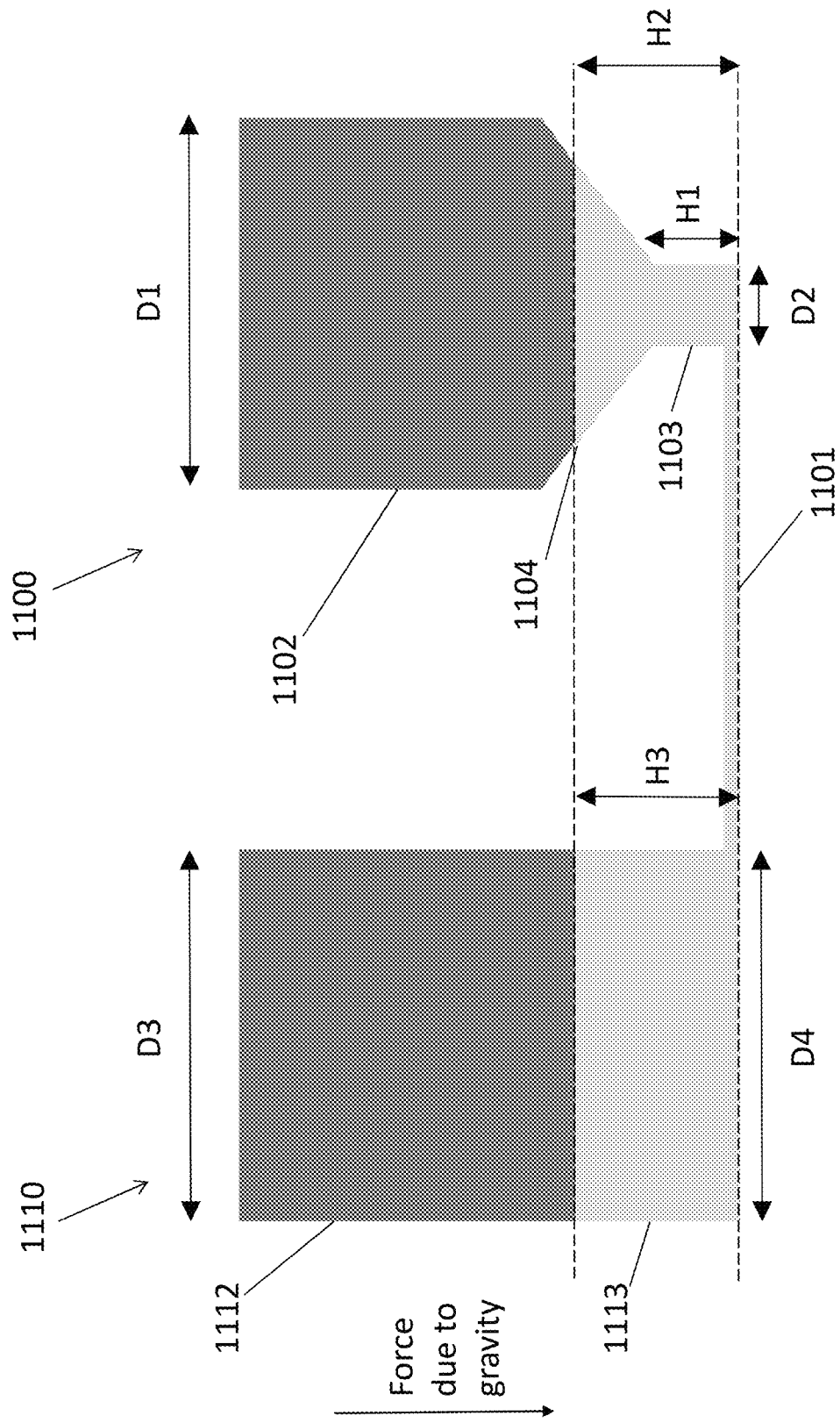
FIG. 11 shows an exemplary low-loss sample reservoir.

Reservoir and channel features can be designed to control or prevent pressure driven flow. For example, a reservoir (e.g., sample and elution reservoirs) can have an internal shape designed so that large changes in liquid height produce only small variations in internal volume at the intended head height as shown in FIG. 11. This can provide more precise control of the liquid volume contained in the reservoir. For other reservoirs, liquid volume can vary without detriment to a separation process; such reservoirs can be designed to have large volume changes in response to small liquid height changes, and can help stabilize liquid height throughout the fluidic device. Low fluidic resistances between reservoirs can be used to enable fast equilibration times of head pressures and to enable minimal flow of liquids in channels before, during, or after an electrokinetic process.

Reservoirs can be designed to minimize evaporation, for example by controlling the surface area within the reservoir to maintain a constant or fixed volume. Reservoirs can be designed to maximize liquid recovery from the reservoirs, for example by using drafted angle wall designs to minimize dead zones. Reservoirs can be designed to prevent the flow of liquids in connecting channels into the reservoir during unloading, which can help maintain purity or separation of material (e.g., nucleic acids) being unloaded. Reservoirs can be designed for easy loading or unloading via pipetting, for example by having dimensions amenable to admitting a pipet tip or having volumes within typical pipet operation. For example, the elution reservoir may be configured to admit a pipet tip for extraction of nucleic acids. Reservoirs can be designed or spaced to accept multi-channel pipettors (e.g., having a pitch of about 9 mm).

Reservoirs (e.g., sample reservoirs) can be located directly above the channels to be filled, which can minimize liquid lost in connecting channels between reservoirs and the channels they fill. Reservoirs (e.g., sample reservoirs) can have a conical shaped bottom and a cylindrical through-hole; the large inner diameter at the top of such a reservoir can allow it to contain a large volume while the liquid meniscus at the bottom of the reservoir has a smaller inner diameter, reducing the amount of liquid left behind after dispensing. Such a design can also reduce or prevent wicking of wetting fluids into concave corners. In some cases, a through-hole from a reservoir (e.g., sample reservoir) into a channel is less than or equal to about 2 millimeters (mm).

FIG. 11 shows a sample reservoir 1100 configured to reduce the amount of sample left behind (or lost) in the reservoir 1100 after moving the sample to the connected channel 1101. The low-loss sample reservoir 1100 may reduce the amount of sample left in the reservoir 1100 after moving the sample to the connected channel 1101 without adding or pumping in additional volume (of sample or other fluid) in to the sample reservoir 1100 following or during delivery of the sample into the connected channel 1101. The low-loss sample reservoir 1100 may comprise an upper or top portion 1102 with an inner hydraulic diameter $D_1$ configured to contain a sample volume prior to loading the sample into the channel 1101, a lower or bottom portion 1103 with an inner hydraulic diameter or through-hole $D_2$ and height $H_1$ configured to contain a sample volume after loading the sample into the channel 1101, and a tapered or conical portion 1104 therebetween. In some cases, the upper portion 1102 and/or the lower portion 1103 are non-symmetrical, in which case the dimensions $D_1$ to $D_2$ may represent the maximum dimension across of the upper and/or lower portions 1102, 1103, respectively.

The sample reservoir 1100 may be configured to produce a head height $H_2$ of sample left behind which equals or nearly equals the head height $H_3$ of the buffers in the other reservoirs 1110 connected to the channel 1101 in order to limit, prevent, or reduce pressure-driven flow and mixing in the channel 1101. A standard buffer reservoir 1110 may comprise an upper portion 1112 with an inner hydraulic diameter $D_3$ and a lower portion 1113 with an inner hydraulic diameter $D_4$. Unlike in the sample well, $D_3$ may be substantially similar to $D_4$ such that a larger volume of fluid is held within the buffer well 1110 compared to the sample well 1100 when the head heights $H_2$ and $H_3$ are equal or nearly equal.

The sample reservoir 1100 may be configured to hold a sample volume (with or without buffer) of at least about 1 nanoliter (nL), 10 nL, 20 nL, 50 nL, 100 nL, 200 nL, 500 nL, 1 microliter (µL), 10 µL, 20 µL, 30 µL, 40 µL, 50 µL, 60 µL, 70 µL, 80 µL, 90 µL, 100 µL, 200 µL, 300 µL, 400 µL, 500 µL, 600 µL, 700 µL, 800 µL, 900 µL, 1 milliliter (mL), 2 mL, 3 mL, 4 mL, 5 mL, 6 mL, 7 mL, 8 mL, 9 mL, or 10 mL. In some cases, the sample reservoir 1100 may be configured to hold a sample volume within a range of from about 1 nL to about 10 nL.

The inner hydraulic diameter $D_1$ may be larger than the through-hole hydraulic diameter $D_2$. The inner hydraulic diameter $D_1$ of the upper portion may be at least about 1 mm, 2 mm, 3 mm, 4 mm, 5 mm, 6 mm, 7 mm, 8 mm, 9 mm, 10 mm, 11 mm, 12 mm, 13 mm, 14 mm, or 15 mm. The inner hydraulic diameter $D_1$ of the upper portion may be at most about 1 mm, 2 mm, 3 mm, 4 mm, 5 mm, 6 mm, 7 mm, 8 mm, 9 mm, 10 mm, 11 mm, 12 mm, 13 mm, 14 mm, or 15 mm. The inner hydraulic diameter $D_2$ of the lower portion may be at least about 0.5 mm, 1 mm, 1.5 mm, 2 mm, 2.5 mm, 3 mm, 3.5 mm, 4 mm, 4.5 mm, or 5 mm. The inner hydraulic diameter $D_2$ of the lower portion may be at most about 0.5 mm, 1 mm, 1.5 mm, 2 mm, 2.5 mm, 3 mm, 3.5 mm, 4 mm, 4.5 mm, or 5 mm.

The ratio of $D_1$ to $D_2$ may determine the amount of sample left in the sample reservoir after the sample is moved into the channel. In some cases the ratio of $D_1$ to $D_2$ is at least about 2:1, 5:1, 10:1, 15:1, 20:1, 25:1, 30:1, 35:1, 40:1, 45:1, or 50:1. In some cases the ratio or $D_1$ to $D_2$ is at most about 2:1, 5:1, 10:1, 15:1, 20:1, 25:1, 30:1, 35:1, 40:1, 45:1, or 50:1. A ratio of $D_1$ to $D_2$ may be greater than 2:1 in order to facilitate moving at least 50% of the sample volume from the low-loss sample reservoir 1100 into the channel 1101.

The cross-sectional area of the upper portion may be at least about 3 mm$^2$, 5 mm$^2$, 10 mm$^2$, 15 mm$^2$, 20 mm$^2$, 25 mm$^2$, 30 mm$^2$, 35 mm$^2$, 40 mm$^2$, 45 mm$^2$, 50 mm$^2$, 55 mm$^2$, 60 mm$^2$, 65 mm$^2$, 70 mm$^2$, 75 mm$^2$. The cross-sectional area of the upper portion may be at most about 3 mm$^2$, 5 mm$^2$, 10 mm$^2$, 15 mm$^2$, 20 mm$^2$, 25 mm$^2$, 30 mm$^2$, 35 mm$^2$, 40 mm$^2$, 45 mm$^2$, 50 mm$^2$, 55 mm$^2$, 60 mm$^2$, 65 mm$^2$, 70 mm$^2$, 75 mm$^2$. The cross-sectional area of the lower portion may be at least about 0.2 mm$^2$, 0.3 mm$^2$, 0.4 mm$^2$, 0.5 mm$^2$, 1 mm$^2$, 1.5 mm$^2$, 2 mm$^2$, 2.5 mm$^2$, 3 mm$^2$, 3.5 mm$^2$, 4 mm$^2$, 4.5 mm$^2$, 5 mm$^2$, 6 mm$^2$, 7 mm$^2$, 8 mm$^2$, 9 mm$^2$, 10 mm$^2$, 11 mm$^2$, 12 mm$^2$. The cross-sectional area of the lower portion may be at most about 0.2 mm$^2$, 0.3 mm$^2$, 0.4 mm$^2$, 0.5 mm$^2$, 1 mm$^2$, 1.5 mm$^2$, 2 mm$^2$, 2.5 mm$^2$, 3 mm$^2$, 3.5 mm$^2$, 4 mm$^2$, 4.5 mm$^2$, 5 mm$^2$, 6 mm$^2$, 7 mm$^2$, 8 mm$^2$, 9 mm$^2$, 10 mm$^2$, 11 mm$^2$, 12 mm$^2$.

The ratio of the cross-sectional area of the upper portion to the cross-sectional area of the lower portion may determine the amount of sample left in the sample reservoir after the sample is moved into the channel. In some cases, the ratio for the upper portion cross-sectional area to the lower portion cross-sectional area is at least about 4:1, 5:1, 10:1, 20:1, 30:1, 40:1, 50:1, 60:1, 70:1, 80:1, 90:1, 100:1, 150:1, 200:1, 250:1, 300:1, 350:1, 400:1, 450:1, 500:1, 600:1, 700:1, 800:1, 900:1, 1000:1, 1500:1, 2000:1, or 2500:1. In some cases, the ratio for the upper portion cross-sectional area to the lower portion cross-sectional area is at most about 4:1, 5:1, 10:1, 20:1, 30:1, 40:1, 50:1, 60:1, 70:1, 80:1, 90:1, 100:1, 150:1, 200:1, 250:1, 300:1, 350:1, 400:1, 450:1, 500:1, 600:1, 700:1, 800:1, 900:1, 1000:1, 1500:1, 2000:1, or 2500:1.

The tapered portion between the upper portion and the lower portion may comprise an angle so as to facilitate wetting of sample into the lower portion and movement of the sample from the low-loss sample well to the channel. In some cases, the tapered portion of the low-loss sample reservoir may comprise a half-angle between the upper portion and the lower portion of less than about 10°, 20°, 30°, 40°, 45°, 50°, 60°, 70°, 80°, or 90°. In some cases, the tapered portion of the low-loss sample reservoir may comprise a half-angle between the upper portion and the lower portion of more than about 10°, 20°, 30°, 40°, 45°, 50°, 60°, 70°, 80°, or 90°.

In some cases, the height $H_1$ of the lower portion can be configured so as to produce a head height of sample left behind which equals or nearly equals the head height of the buffers in the other reservoirs connected to the channel in order to limit, prevent, or reduce pressure-driven flow and mixing in the channel. The height $H_1$ of the lower portion may be at least about 1 mm, 2 mm, 3 mm, 4 mm, 5 mm, 6 mm, 7 mm, 8 mm, 9 mm, or 10 mm. The height $H_2$ of the lower portion may be at most about 1 mm, 2 mm, 3 mm, 4 mm, 5 mm, 6 mm, 7 mm, 8 mm, 9 mm, or 10 mm.

Reservoirs (e.g., elution reservoirs) can have diameters that are large compared to the diffusion length scale of analytes (e.g., nucleic acids) to reduce the diffusion of analytes out of a reservoir. In some cases, the reservoir diameter length scale can be on the order of millimeters, and the resulting diffusion time of analyte from the reservoir can be on the order of hours. Connections between channels and reservoirs (e.g., elution reservoirs) can be designed without sharp corners, thereby reducing the prevalence of high electric field regions at these connections and increasing the residence time of analytes within the reservoir. In some cases, the cross section of a reservoir (e.g., elution reservoir) normal to the electric field can be significantly greater than the cross section of the channel normal to the electric field, thereby reducing the electric field strength in the reservoir and increasing the residence time of analyte within the reservoir.

In some cases, an elution channel and/or an elution reservoir can comprise a second leading electrolyte buffer, different in type or concentration from the first leading electrolyte buffer used in the main channel. This can allow purified material to be eluted in the second leading electrolyte buffer (e.g., an elution buffer or output solution). The effective mobility magnitude of the second leading electrolyte ions within the second leading electrolyte buffer can be greater than the effective mobility magnitude of the nucleic acids. The second leading electrolyte buffer can have low ionic strength, for example an ionic strength compatible with downstream assays (e.g., qPCR, next generation sequencing). In some cases, the second leading electrolyte buffer is the same as the first leading electrolyte buffer but present at a different concentration or ionic strength (e.g., an ionic strength lower than that of the first leading electrolyte buffer). For example, the first leading electrolyte buffer may have an electrolyte ion concentration of 70-100 mM (e.g. 70-100 mM Tris HCl) while the second leading electrolyte buffer may have an electrolyte ion concentration of less than 70 mM, less than 60 mM, or less than 50 mM (e.g., less than 50 mM Tris HCl).

Channels on a fluidic device can be closed. For example, a mechanical actuator coupled to a mechanical member can be used to apply pressure to completely or partially close a channel (e.g., by deformation of the channel). Elution reservoirs can be closed off from the ITP channel to define a fixed elution volume. Channel closing can result in reduced flow or completely blocked flow. Channel closing can result in increased resistance to fluid flow. In some instances, channel closing can increase fluidic resistance by a factor of at least 2, 3, 4, 5, 10, 20, 30, 40, 50, 60, 70, 80, 90, or 100.

Figure 6A:
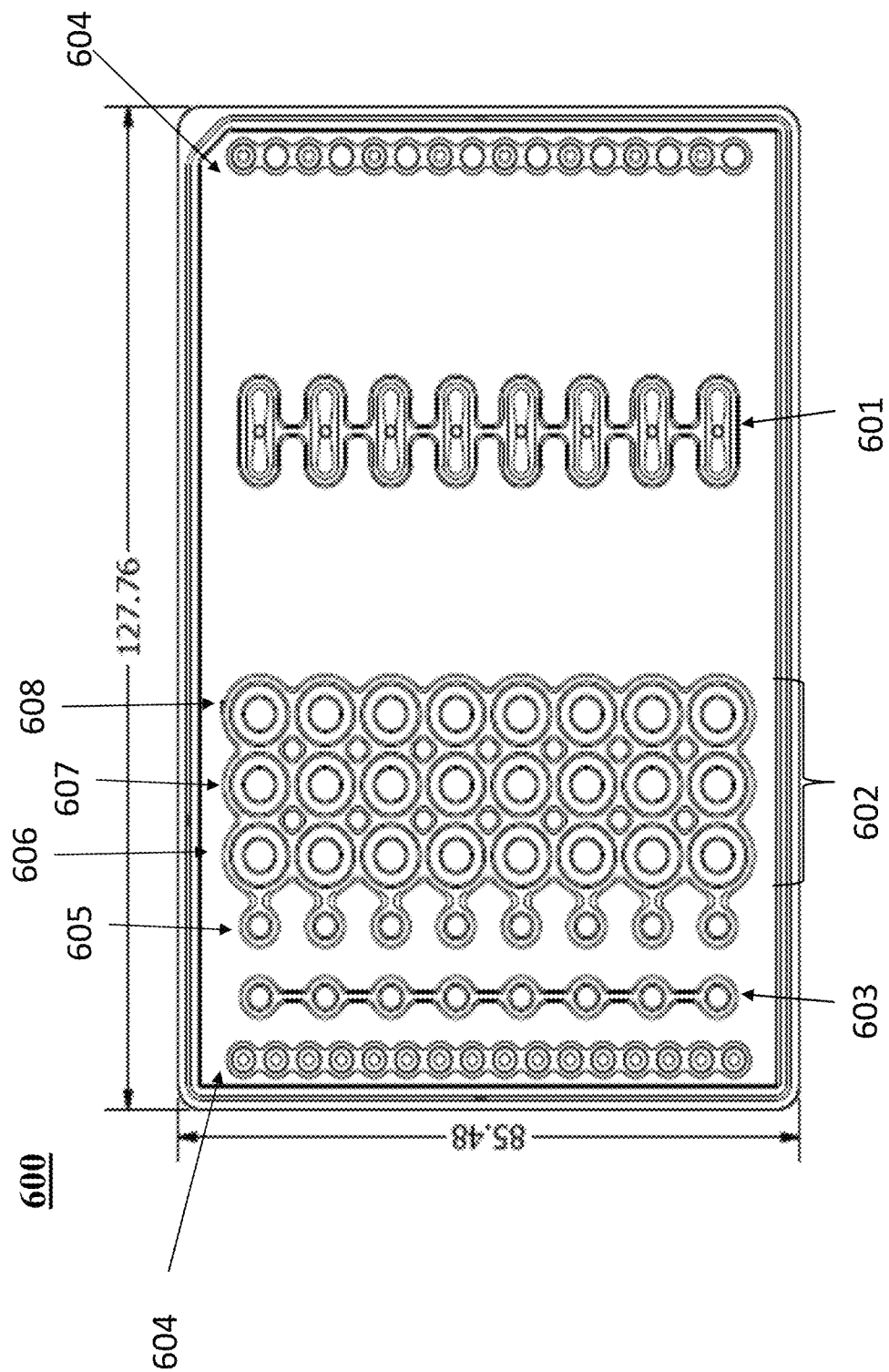
FIG. 6A shows an exemplary top view schematic of a fluidic device cartridge.
Figure 6B:
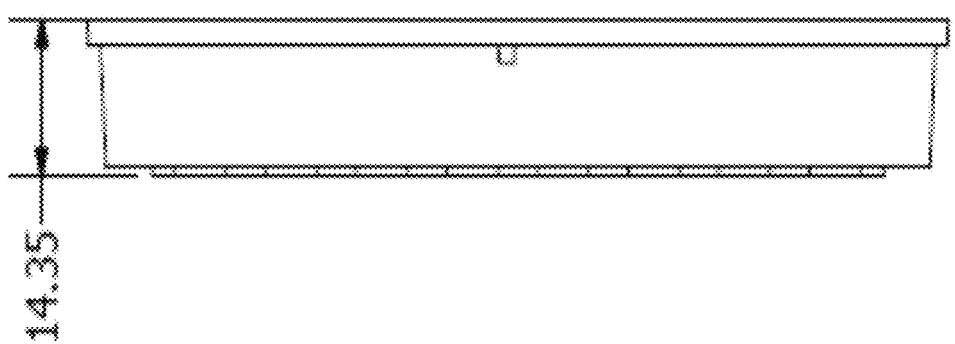
FIG. 6B shows an exemplary side view schematic of a fluidic device cartridge.
Figure 6C:
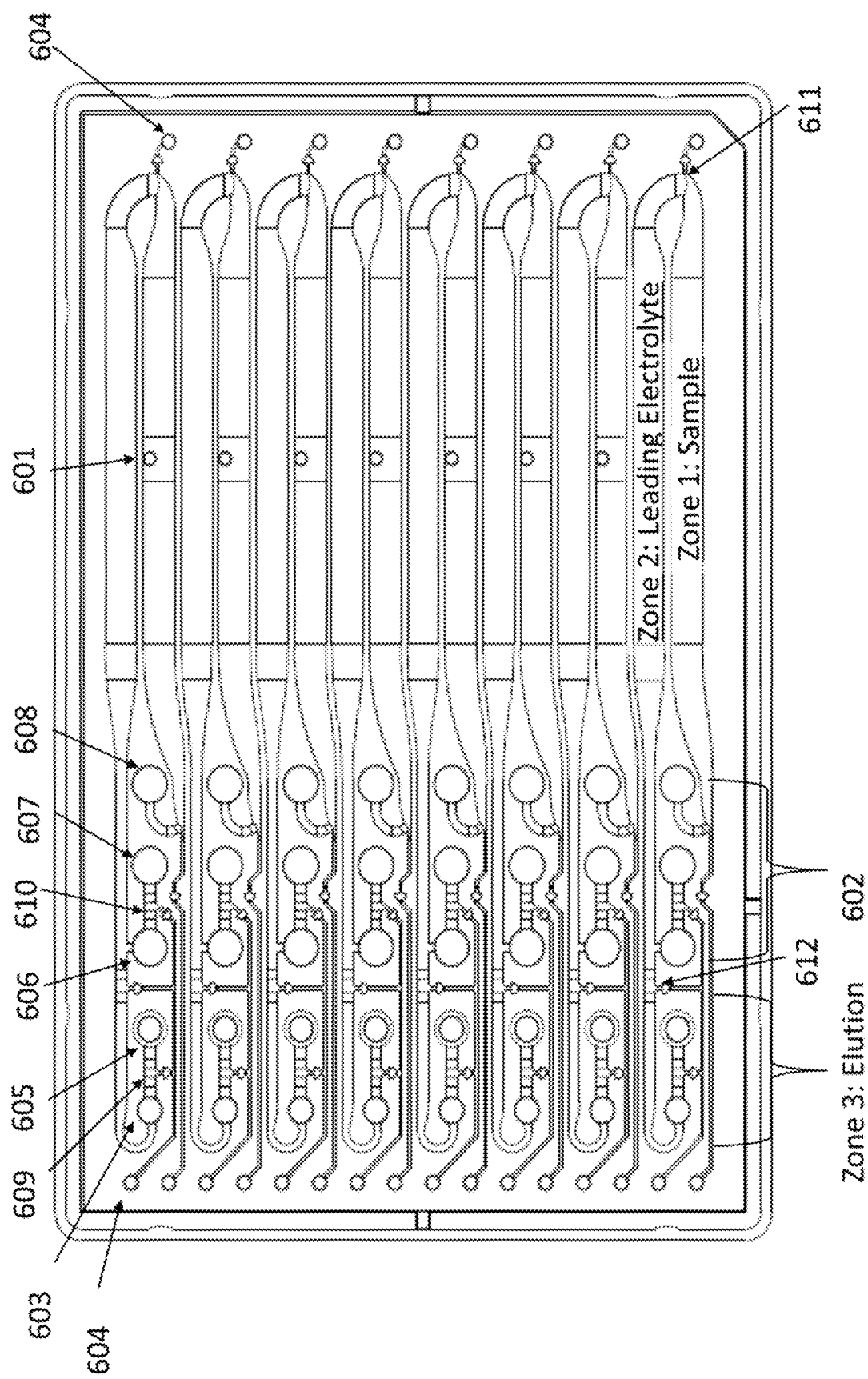
FIG. 6C shows an exemplary bottom view schematic of a fluidic device cartridge.
Figure 6D:
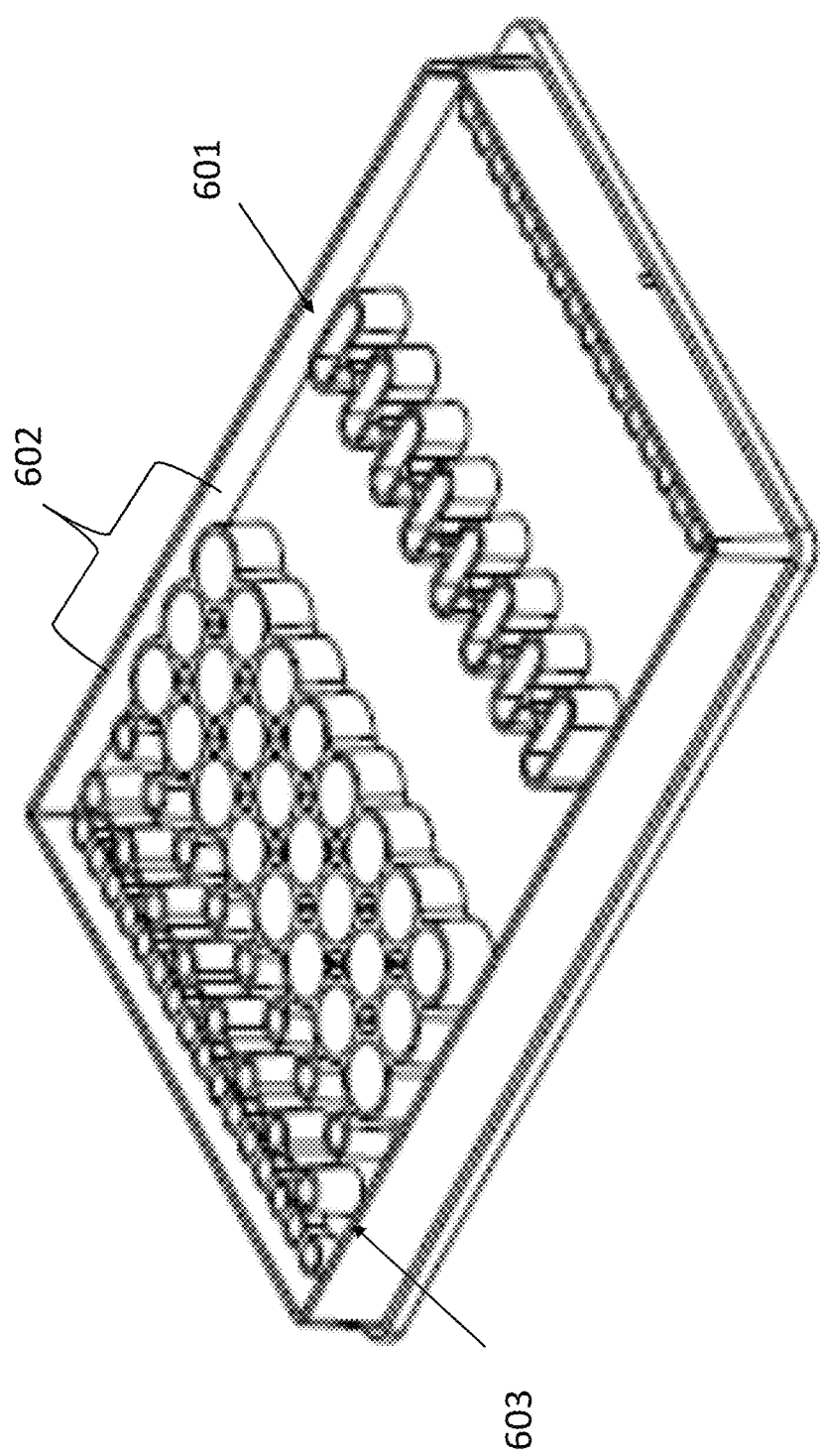
FIG. 6D shows an exemplary top full view schematic in three dimensions of a fluidic device cartridge.
Figure 7A:
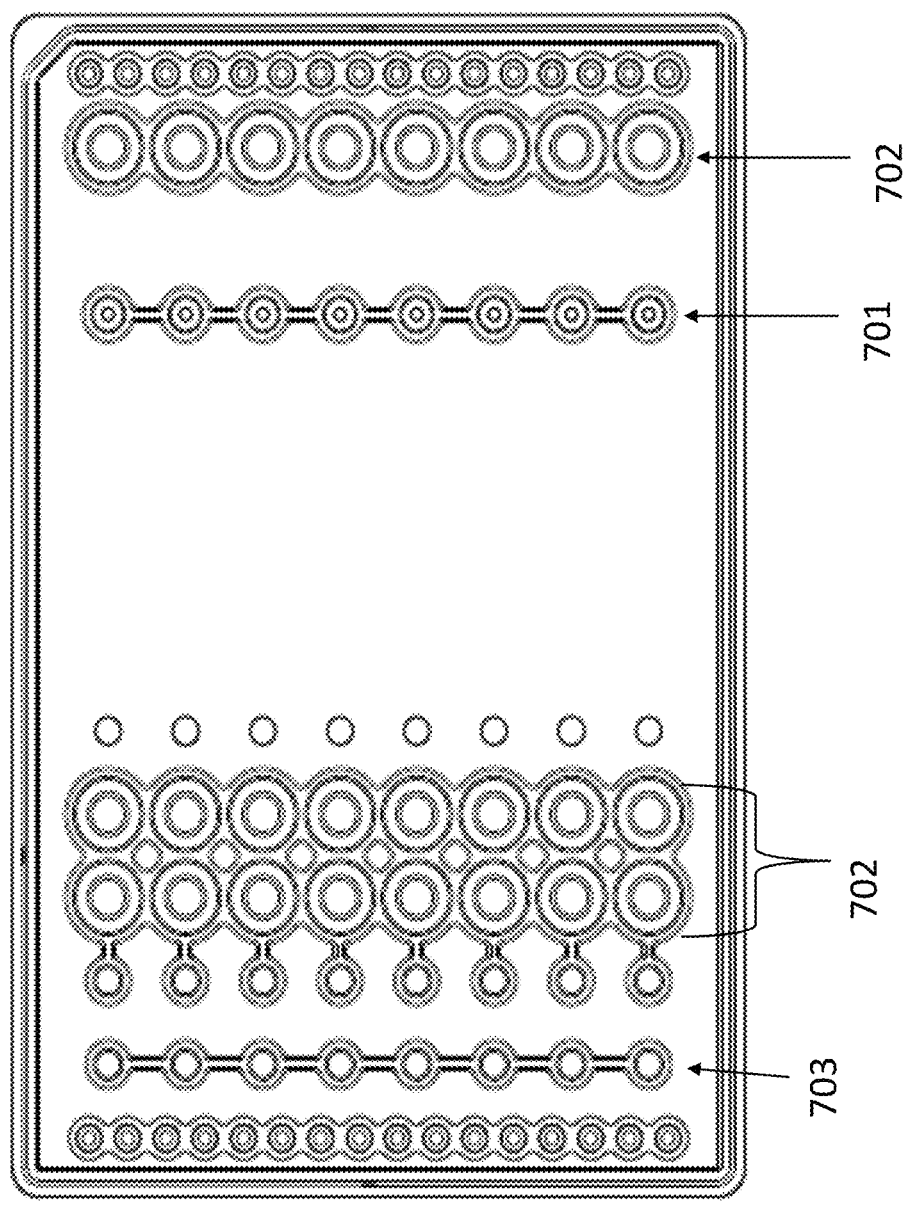
FIG. 7A shows an exemplary top view schematic of a fluidic device cartridge.
Figure 7B:
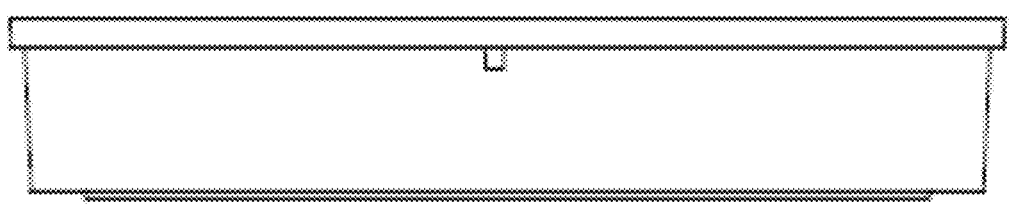
FIG. 7B shows an exemplary side view schematic of a fluidic device cartridge.
Figure 7C:
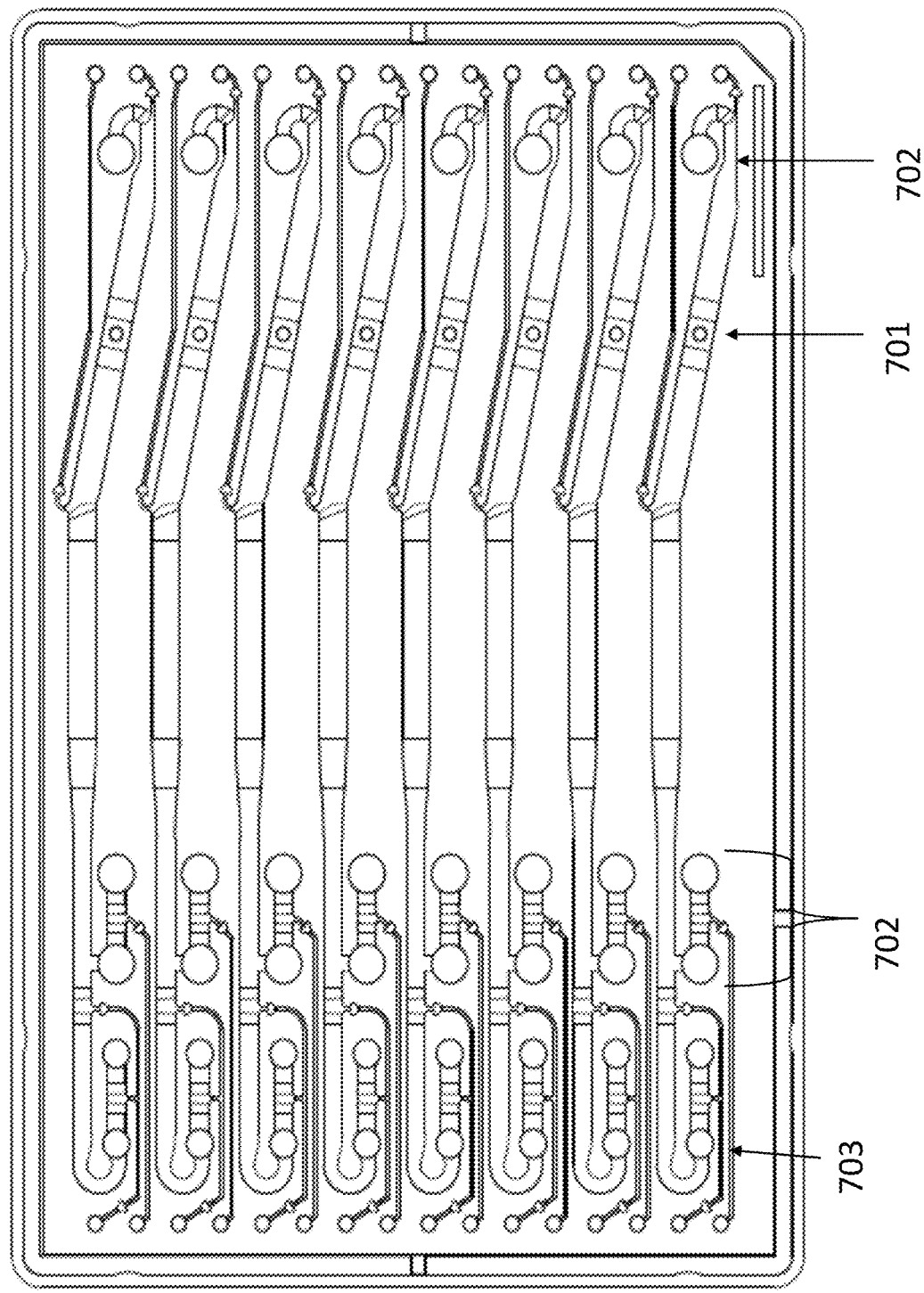
FIG. 7C shows an exemplary bottom view schematic of a fluidic device cartridge.
Figure 7D:
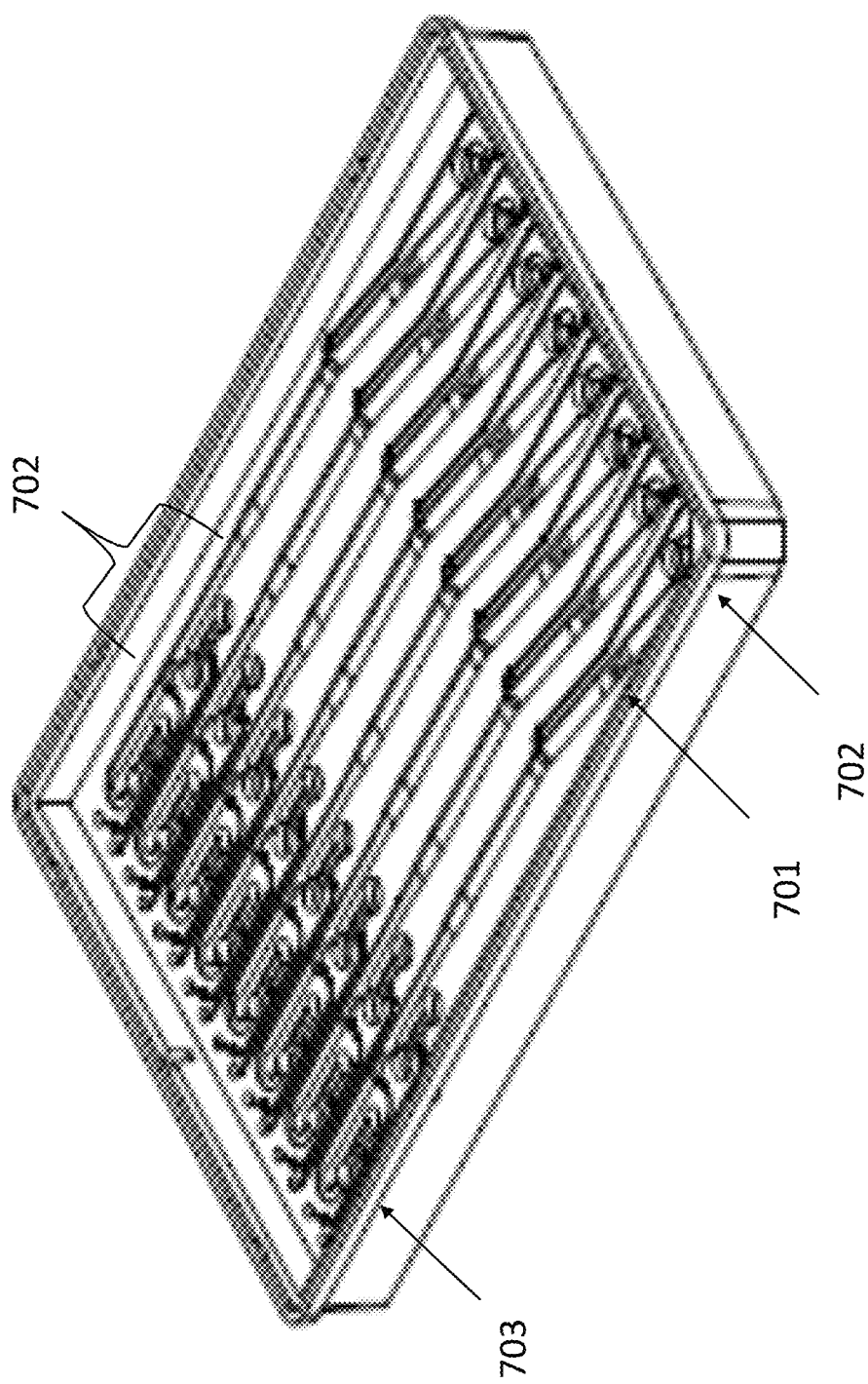
FIG. 7D shows an exemplary bottom full view schematic in three dimensions of a fluidic device cartridge.
Figure 8A:
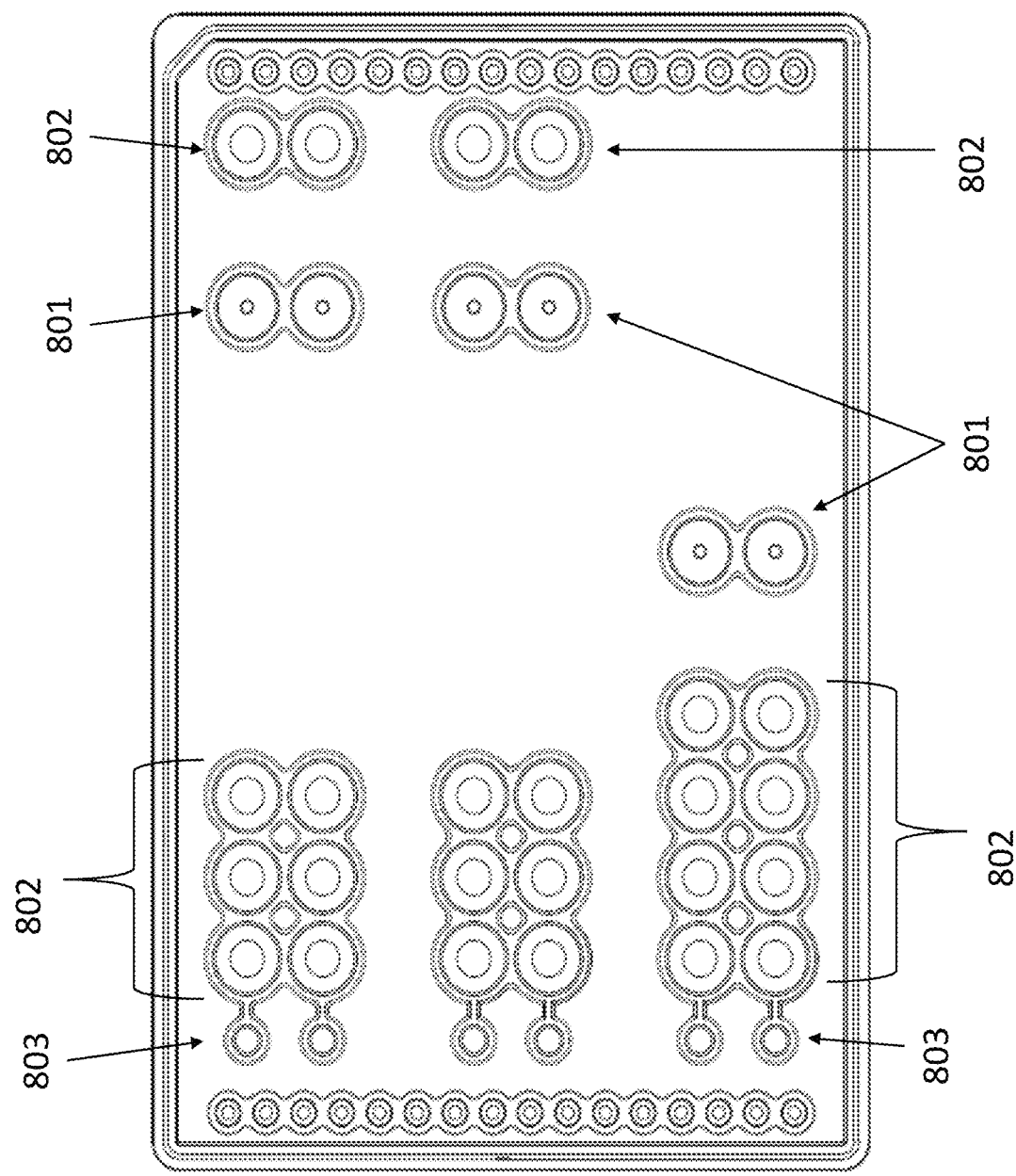
FIG. 8A shows an exemplary top view schematic of a fluidic device cartridge.
Figure 8B:
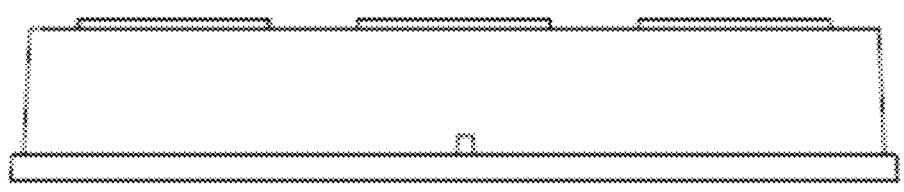
FIG. 8B shows an exemplary side view schematic of a fluidic device cartridge.
Figure 8C:
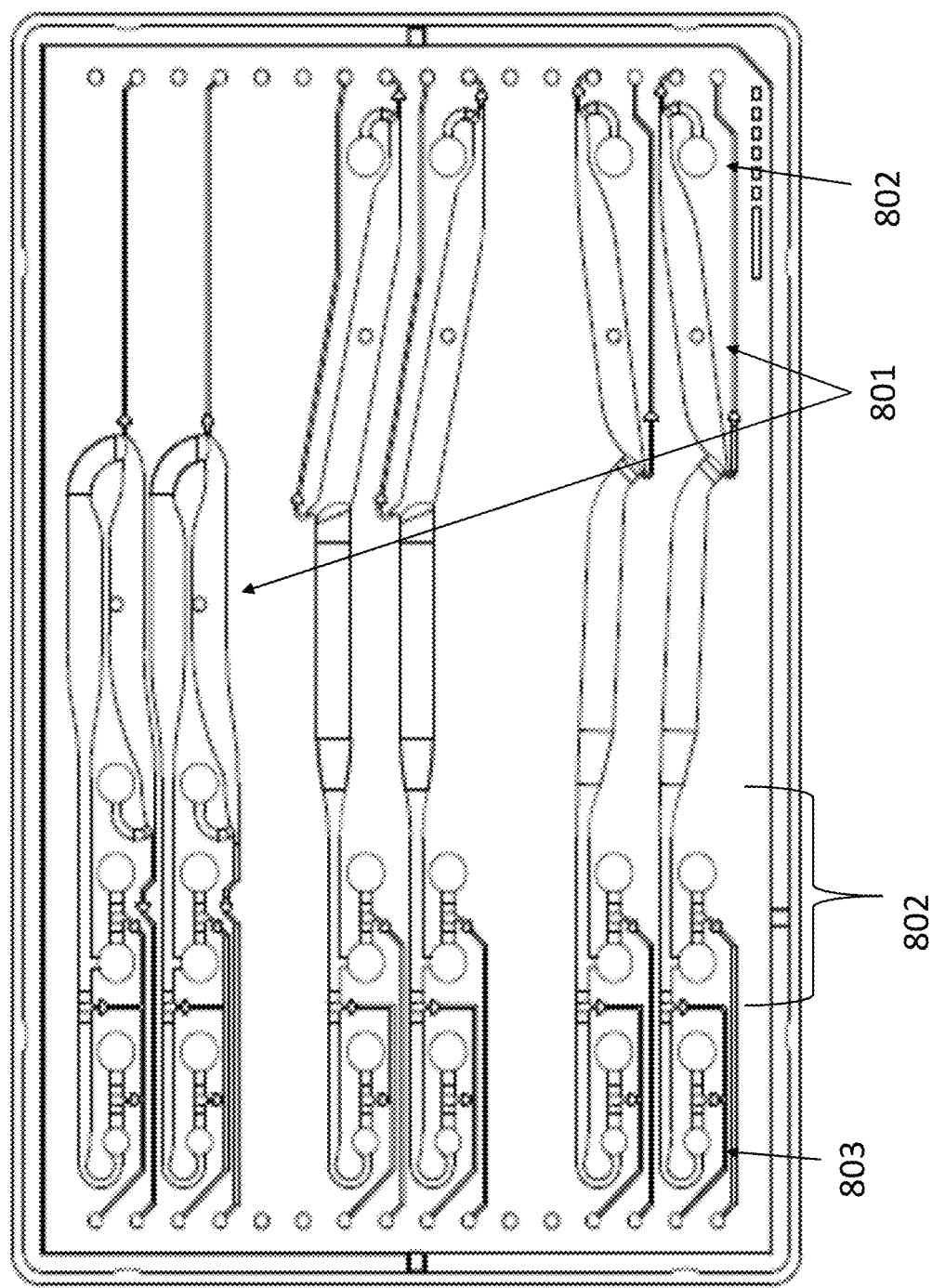
FIG. 8C shows an exemplary bottom view schematic of a fluidic device cartridge.
Figure 8D:
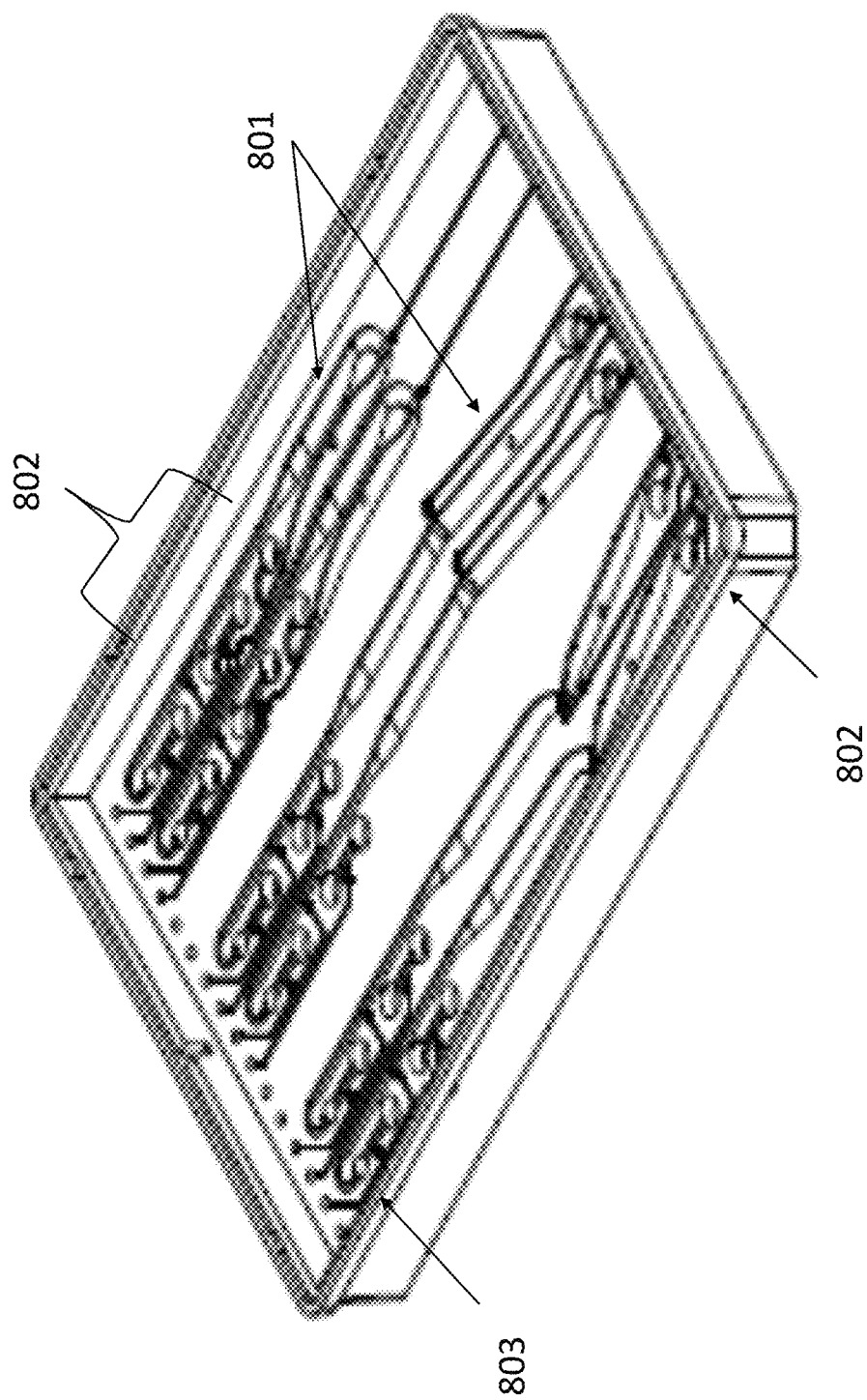
FIG. 8D shows an exemplary bottom full view schematic in three dimensions of a fluidic device cartridge.
Figure 12B:
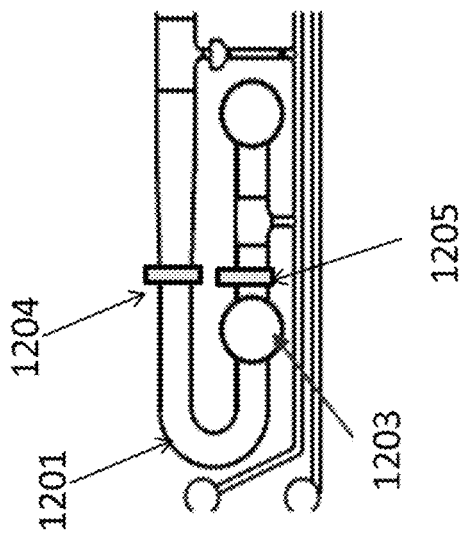
FIG. 12B shows an exemplary comb-like mechanical member.
Figure 12A:
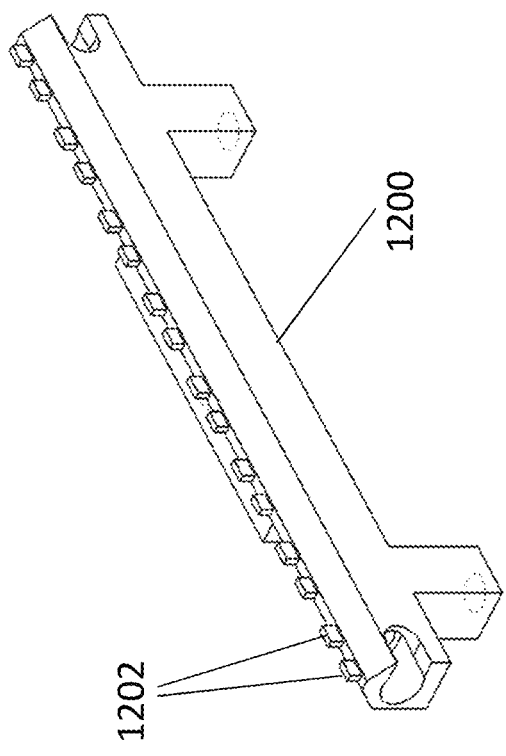
FIG. 12A shows an exemplary mechanical member which can be used to apply pressure to close the channels of a fluidic device.

FIG. 12A shows an exemplary mechanical member 1200 which can be used to apply pressure to close or at least partially close the channels 1201 of a fluidic device 1210, the fluidic device 1210 comprising multiple channels in parallel (for example the device of FIG. 6C comprising eight independent parallel channels). The mechanical member 1200 can comprise a comb-like structure with teeth 1202 that line up with two locations 1204, 1205 in each of the eight channels of the chip as shown in FIG. 12B. Mechanical pressure can be applied by the teeth 1202 to permanently or plastically close or at least partially close the channels 1201 to limit, reduce, or prevent liquid flow to or from the elution reservoirs 1203 and control the elution volume. At least partially closing the channels 1201 may increase resistance to fluid flow between the channels 1201 and the elution reservoirs 1203. The mechanical member 1200 may be coupled to a mechanical actuator which generates the force applied to the channel 1201 by the teeth 1202 of the mechanical member 1200. The mechanical member 1200 may comprise a material with a Young's modulus of elasticity greater than a Young's modulus of elasticity of the channel 1201. One or more teeth 1202 of the mechanical member 1200 may be configured to heat a channel 1201.

Figure 12C:
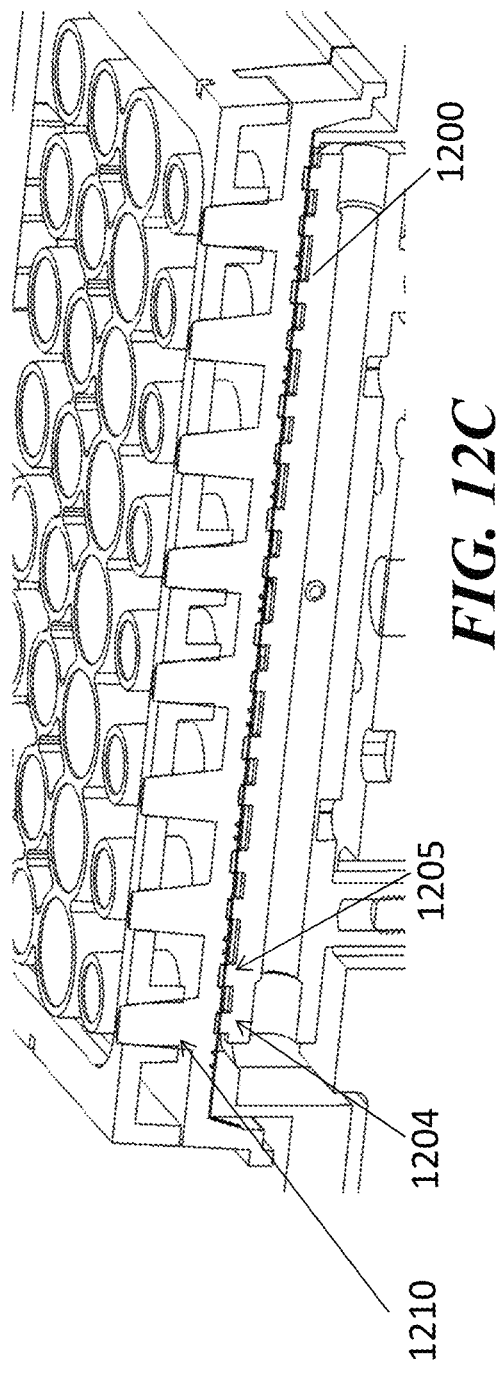
FIG. 12C shows the alignment of a comb-like mechanical member and the channels of a fluidic device.

One or more teeth 1202 of the mechanical member 1200 may be thermally coupled to a heater or heating element. The mechanical member 1200 may optionally comprise a heater or heating element. Heat can optionally be applied by the teeth 1202 to permanently or plastically close the channels 1201. One or more teeth 1202 may be heated to a temperature greater than the glass transition temperature of at least one wall of one or more channels 1201. FIG. 12C shows how the sixteen teeth 1202 of the mechanical member 1200 line up with the sixteen locations 1204, 1205 on the chip 1210 (two per channel). Each tooth 1202 may be configured to deliver mechanical pressure to the channel 1201 in order to plastically deform at least one wall of the channel 1201. Each channel 1201 is contacted by the mechanical member 1200 and plastically deformed at a first close location 1204 and a second close location 1205 to isolate the elution reservoir volume and increase fluid resistance between the channel 1201 and the reservoir 1203. In some instances, a tooth 1202 may apply mechanical pressure to the channel location 1204 upstream of the reservoir 1203. In some instances, a tooth 1202 may apply mechanical pressure to a junction where the reservoir 1203 and the channel 1201 meet. In some instances, a tooth 1202 may apply mechanical pressure to a junction 1205 where the reservoir and a buffering channel meet to prevent fluid communication between the reservoir 1203 and a buffering reservoir.

In some cases, the mechanical member 1200 may comprise one tooth 1202 per channel which aligns with the first close location 1204. For example, the channel shown in FIG. 5A does not comprise a buffer channel or reservoir connected to the elution reservoir and thus may not need a second close location 1205 beyond the elution reservoir. In some cases, the mechanical member 1200 is configured to close each of the channels 1201 on a chip 1210 at one or more locations. In some cases, the mechanical member 1200 is configured to leave one or more channel 1201 on the chip 1210 open such that only a fraction of channels 1201 on the chip 1210 are closed.

The mechanical member 1200 may apply a force of at least 0.25 lbs per channel via teeth 1202. Each tooth 1202 of the mechanical member 1200 may apply a force of at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, or 5 pounds to a channel 1201.

Channels on a fluidic device (e.g., sample preparation zones, isotachophoresis zones) can have a large enough width, height, or diameter such that contaminants, such as embedding material (e.g., paraffin), can deposit on the channel walls while still leaving adequate room for fluid flow within the channel. In some cases, a channel on a fluidic device has a width, height, or diameter of less than or equal to 20 millimeters (mm), 19 mm, 18 mm, 17 mm, 16 mm, 15 mm, 14 mm, 13 mm, 12 mm, 11 mm, 10 mm, 9 mm, 8 mm 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, or 0.1 mm. In some cases, a channel on a fluidic device has a width, height, or diameter of at least 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. In some cases, a channel on a fluidic device has a width within a range of about 1 mm to about 3.8 mm. In some cases, a channel on a fluidic device has a height within a range of about 0.1 mm to about 1.2 mm.

In some cases, a channel on a fluidic device has a length of at least about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 25 mm, 30 mm, 35 mm, 40 mm, 45 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, 300 mm, 310 mm, 320 mm, 330 mm, 340 mm, 350 mm, 360 mm, 370 mm, 380 mm, 390 mm, 400 mm, 410 mm, 420 mm, 430 mm, 440 mm, 450 mm, 460 mm, 470 mm, 480 mm, 490 mm, or 500 mm. In some cases, a channel on a fluidic device has a length of less than or equal to about 500 mm, 490 mm, 480 mm, 470 mm, 460 mm, 450 mm, 440 mm, 430 mm, 420 mm, 410 mm, 400 mm, 390 mm, 380 mm, 370 mm, 360 mm, 350 mm, 340 mm, 330 mm, 320 mm, 310 mm, 300 mm, 290 mm, 280 mm, 270 mm, 260 mm, 250 mm, 240 mm, 230 mm, 220 mm, 210 mm, 200 mm, 190 mm, 180 mm, 170 mm, 160 mm, 150 mm, 140 mm, 130 mm, 120 mm, 110 mm, 100 mm, 90 mm, 80 mm, 70 mm, 60 mm, 50 mm, 45 mm, 40 mm, 35 mm, 30 mm, 25 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm.

Channels on a fluidic device can have a large enough width, height, or diameter so as to accommodate a large sample volume. In some cases, a channel on a fluidic device has a width greater than its height so as to reduce a temperature rise due to Joule heating in the channel. In some cases, a channel on a fluidic device has a ratio of width to height of at least 2:1, 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1. In some cases, a channel on a fluidic device has a ratio of width to height of at most 2:1, 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1. In some cases, a channel on a fluidic device has a cross-sectional area less than about 0.1 $mm^2$, 0.2 $mm^2$, 0.3 $mm^2$, 0.4 $mm^2$, 0.5 $mm^2$, 0.6 $mm^2$, 0.7 $mm^2$, 0.8 $mm^2$, 0.9 $mm^2$, 1 $mm^2$, 1.1 $mm^2$, 1.2 $mm^2$, 1.3 $mm^2$, 1.4 $mm^2$, 1.5 $mm^2$, 1.6 $mm^2$, 1.7 $mm^2$, 1.8 $mm^2$, 1.9 $mm^2$, 2 $mm^2$, 2.1 $mm^2$, 2.2 $mm^2$, 2.3 $mm^2$, 2.4 $mm^2$, 2.5 $mm^2$, 2.6 $mm^2$, 2.7 $mm^2$, 2.8 $mm^2$, 2.9 $mm^2$, 3 $mm^2$, 3.1 $mm^2$, 3.2 $mm^2$, 3.3 $mm^2$, 3.4 $mm^2$, 3.5 $mm^2$, 3.6 $mm^2$, 3.7 $mm^2$, 3.8 $mm^2$, 3.9 $mm^2$, 4 $mm^2$, 4.1 $mm^2$, 4.2 $mm^2$, 4.3 $mm^2$, 4.4 $mm^2$, 4.5 $mm^2$, 4.6 $mm^2$, 4.7 $mm^2$, 4.8 $mm^2$, 4.9 $mm^2$, 5 $mm^2$, 6 $mm^2$, 7 $mm^2$, 8 $mm^2$, 9 $mm^2$, 10 $mm^2$, 11 $mm^2$, 12 $mm^2$, 13 $mm^2$, 14 $mm^2$, or 15 $mm^2$. In some cases, a channel on a fluidic device has a cross-sectional area more than about 0.1 $mm^2$, 0.2 $mm^2$, 0.3 $mm^2$, 0.4 $mm^2$, 0.5 $mm^2$, 0.6 $mm^2$, 0.7 $mm^2$, 0.8 $mm^2$, 0.9 $mm^2$, 1 $mm^2$, 1.1 $mm^2$, 1.2 $mm^2$, 1.3 $mm^2$, 1.4 $mm^2$, 1.5 $mm^2$, 1.6 $mm^2$, 1.7 $mm^2$, 1.8 $mm^2$, 1.9 $mm^2$, 2 $mm^2$, 2.1 $mm^2$, 2.2 $mm^2$, 2.3 $mm^2$, 2.4 $mm^2$, 2.5 $mm^2$, 2.6 $mm^2$, 2.7 $mm^2$, 2.8 $mm^2$, 2.9 $mm^2$, 3 $mm^2$, 3.1 $mm^2$, 3.2 $mm^2$, 3.3 $mm^2$, 3.4 $mm^2$, 3.5 $mm^2$, 3.6 $mm^2$, 3.7 $mm^2$, 3.8 $mm^2$, 3.9 $mm^2$, 4 $mm^2$, 4.1 $mm^2$, 4.2 $mm^2$, 4.3 $mm^2$, 4.4 $mm^2$, 4.5 $mm^2$, 4.6 $mm^2$, 4.7 $mm^2$, 4.8 $mm^2$, 4.9 $mm^2$, 5 $mm^2$, 6 $mm^2$, 7 $mm^2$, 8 $mm^2$, 9 $mm^2$, 10 $mm^2$, 11 $mm^2$, 12 $mm^2$, 13 $mm^2$, 14 $mm^2$, or 15 $mm^2$. In some cases, a channel on a fluidic device has a minimum length scale for heat dissipation less than about 1 micrometer ($\mu m$), 5 $\mu m$, 10 m, 20 $\mu m$, 30 $\mu m$, 40 $\mu m$, 50 $\mu m$, 100 $\mu m$, 150 $\mu m$, 200 $\mu m$, 250 $\mu m$, 300 $\mu m$, 350 $\mu m$, 400 $\mu m$, 450 $\mu m$, 500 $\mu m$, 550 $\mu m$, or 600 $\mu m$. In some cases, a channel on a fluidic device has a minimum length scale for heat dissipation more than about 1 micrometer ($\mu m$), 5 $\mu m$, 10 $\mu m$, 20 $\mu m$, 30 $\mu m$, 40 $\mu m$, 50 $\mu m$, 100 $\mu m$, 150 $\mu m$, 200 $\mu m$, 250 $\mu m$, 300 $\mu m$, 350 $\mu m$, 400 $\mu m$, 450 $\mu m$, 500 $\mu m$, 550 $\mu m$, or 600 $\mu m$.

In some cases, a channel on a fluid device has a total volume of at least about 1 microliter (μL), 10 μL, 20 μL, 30 μL, 40 μL, 50 μL, 60 μL, 70 μL, 80 μL, 90 μL, 100 μL, 150 μL, 175 μL, 200 μL, 225 μL, 250 μL, 275 μL, 300 μL, 350 μL, 400 μL, 450 μL, 500 μL, 600 μL, 700 μL, 800 μL, 900 μL, 1 milliliter (mL), 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 50 mL, 55 mL, 60 mL, 65 mL, 70 mL, 75 mL, 80 mL, 85 mL, 90 mL, 95 mL, or 100 mL. In some cases, a channel on a fluid device has a total volume of at most about 1 microliter (μL), 10 μL, 20 μL, 30 μL, 40 μL, 50 μL, 60 μL, 70 μL, 80 μL, 90 μL, 100 μL, 150 μL, 175 μL, 200 μL, 225 μL, 250 μL, 275 μL, 300 μL, 350 μL, 400 μL, 450 μL, 500 μL, 600 μL, 700 μL, 800 μL, 900 μL, 1 milliliter (mL), 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 50 mL, 55 mL, 60 mL, 65 mL, 70 mL, 75 mL, 80 mL, 85 mL, 90 mL, 95 mL, or 100 mL.

In some cases, a fluidic device comprises more than one channel. The channels may be spaced within the fluidic device at a given density. In some cases, the edge to edge distance between channels is at least about 0.2 mm, 0.3 mm, 0.4 mm, 0.5 mm, 0.6 mm, 0.7 mm, 0.8 mm, 0.9 mm, 1 mm, 1.25 mm, 1.5 mm, 1.75 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, or 10 mm. In some cases, the edge to edge distance between channels is at most about 0.2 mm, 0.3 mm, 0.4 mm, 0.5 mm, 0.6 mm, 0.7 mm, 0.8 mm, 0.9 mm, 1 mm, 1.25 mm, 1.5 mm, 1.75 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, or 10 mm. The density of channels may be defined as a ratio of the width of the channels to the space (or distance) between channels. In some cases, the ratio of channel width to distance between channels is at least about 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, 11:1, 12:1, 13:1, 14:1, 15:1, 16:1, 17:1, 18:1, 19:1, or 20:1.

In some cases, the total volume of all channels within a microfluidic device (e.g., chip) is 1 microliter (μL), 10 μL, 20 μL, 30 μL, 40 μL, 50 μL, 60 μL, 70 μL, 80 μL, 90 μL, 100 μL, 150 μL, 175 μL, 200 μL, 225 μL, 250 μL, 275 μL, 300 μL, 350 μL, 400 μL, 450 μL, 500 μL, 600 μL, 700 μL, 800 μL, 900 μL, 1 milliliter (mL), 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 50 mL, 55 mL, 60 mL, 65 mL, 70 mL, 75 mL, 80 mL, 85 mL, 90 mL, 95 mL, or 100 mL. In some cases, the total volume of all channels within a microfluidic device (e.g., chip) is at most about 1 microliter (μL), 10 μL, 20 μL, 30 μL, 40 μL, 50 μL, 60 μL, 70 μL, 80 μL, 90 μL, 100 μL, 150 μL, 175 μL, 200 μL, 225 μL, 250 μL, 275 μL, 300 μL, 350 μL, 400 μL, 450 μL, 500 μL, 600 μL, 700 μL, 800 μL, 900 μL, 1 milliliter (mL), 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 50 mL, 55 mL, 60 mL, 65 mL, 70 mL, 75 mL, 80 mL, 85 mL, 90 mL, 95 mL, or 100 mL.

Inlets and/or outlets of a fluidic device can be arranged and spaced such that they are compatible with standard fluid handling formats. For example, inlets and/or outlets can be spaced to line up with wells on a 5"×3.33" titer plate. A device can comprise eight inlets and/or outlets, spaced to correspond with a standard eight-tip pipettor and/or the eight wells in a dimension of a standard 24-, 48-, or 96-well plate. A device can comprise twelve inlets and/or outlets, spaced to correspond with a standard twelve-tip pipettor and/or with the twelve wells in a dimension of a standard 96-well plate. A device can comprise sixteen inlets and/or outlets, spaced to correspond with a standard sixteen-tip pipettor and/or with the sixteen wells in a dimension of a standard 384-well plate. A device can comprise twenty-four inlets and/or outlets, spaced to correspond with a standard twenty-four-tip pipettor and/or with the twenty-four wells in a dimension of a standard 384-well plate. This can enable easier fluid handling from such plates onto the device, for example via robotic pipet systems or other multi-pipets.

Figure 13A:
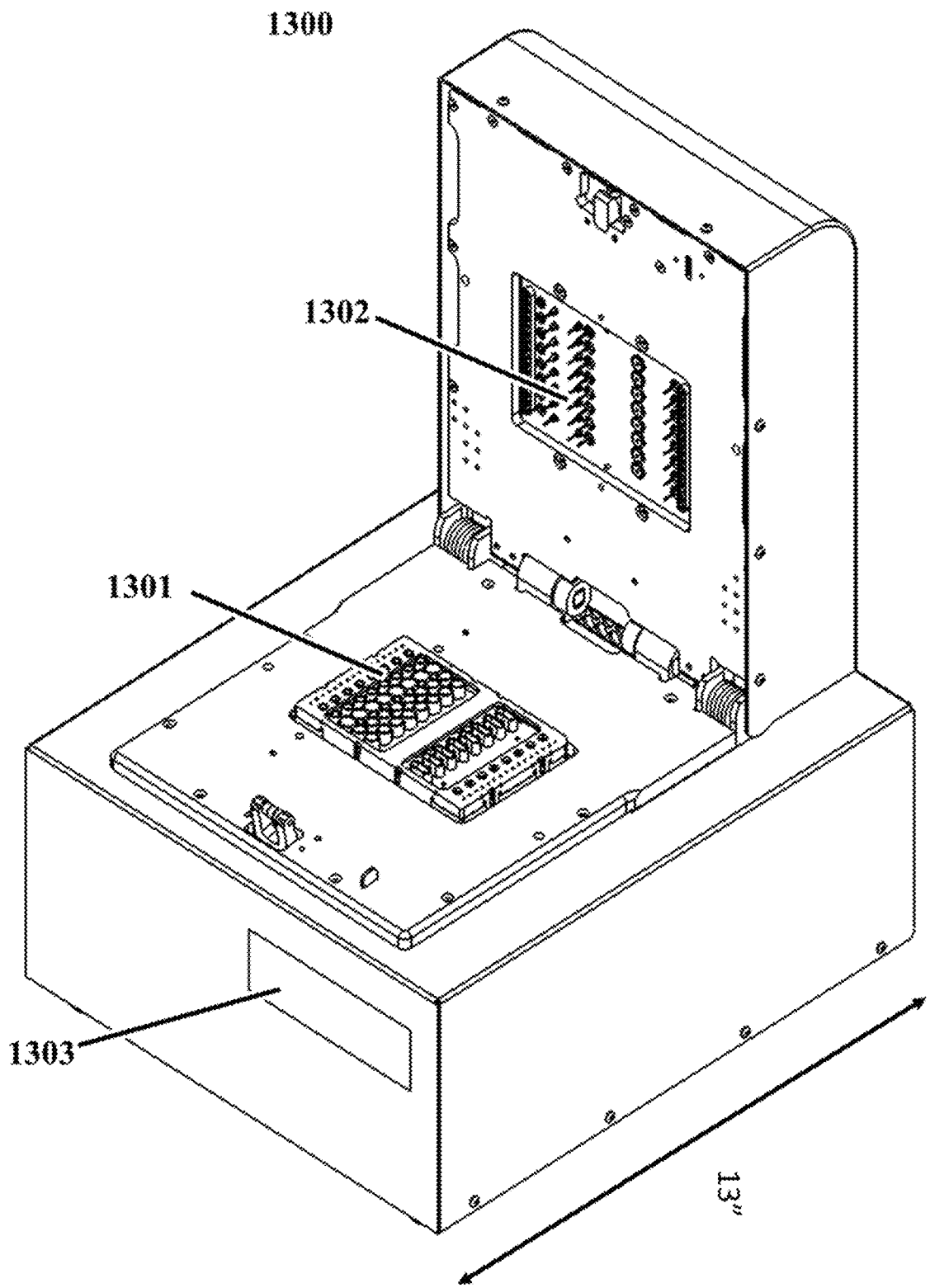
FIG. 13A shows an exemplary benchtop device for conducting automated sample preparation and isotachophoresis on a fluidic device cartridge.

Isotachophoresis can be conducted using a benchtop system or base station. For example, FIG. 13A shows a benchtop system 1300 for conducting sample preparation and isotachophoresis on a fluidic device cartridge 1301. The fluidic device cartridge can be loaded onto the benchtop system as shown, and a lid with matching covers and controls 1302 can be lowered onto the fluidic device cartridge. The benchtop system can also include a control panel 1303 with a user interface (e.g., touch screen) for operation of the system.

The benchtop system can comprise pressure controls that provide pressure to handle fluids (e.g., sample, buffer, reagents, enzyme solutions, electrolyte solutions) on a fluidic device. The benchtop system can receive pressure feedback signals to regulate or control the fluid handling. Fluid handling can be used to load fluids onto a fluidic device (e.g., reagents, buffers, samples). Fluid handling can be used to prime fluids (e.g., reagent solutions) into dry channels on a fluidic device. Pressure can be regulated using, for example, solenoid valves.

The benchtop system can comprise electrodes or electrical contacts. Electrodes can be part of an electric circuit and can insert into reservoirs or other openings on a fluidic device to allow application of an electric field within the fluidic device by the completed circuit. Electrical contacts can couple to corresponding contacts on a fluidic device, for example a fluidic device with integrated electrodes.

The benchtop system can comprise one or more detectors or sensors, such as optical detectors, reflectance sensors, infrared (IR) detectors, electrical detectors, thermal sensors, flow sensors, and pressure sensors, including detectors described further in this disclosure. Optical detectors can include but are not limited to three-axis point detectors, complementary metal-oxide semiconductor (CMOS) detectors, charge-coupled device (CCD) detectors, photodiode light sensors, photoresistors, photomultiplier tubes, and phototransistors. Electrical detectors can include electrodes or other detectors capable of detecting a voltage, voltage differential, current, charge, or other electrical property. Electrical detectors can be used to detect the passage of a band of extracted or purified nucleic acids, for example by detecting a change in conductivity at the interface between trailing electrolytes and leading electrolytes. Thermal sensors can include infrared (IR) sensors, probe temperature sensors, thermistors, negative temperature coefficient (NTC) thermistors, resistance temperature detectors (RTDs), thermocouples, semiconductor-based sensors, or the like.

The one or more detectors or sensors can be simultaneously or independently operated and controlled. In some instances, a single channel may have a dedicated sensor, for example a thermal or voltage sensor, which operates independently of other sensors dedicated to other channels on the microfluidic device. Feedback from the independent sensor may be used to independently control one or more electric fields on the device. For example, a sensor may detect a change in voltage over time within a well as described herein and feedback from that sensor may be used to control the current within the channel. A second sensor may act on a second channel in a similar, but independent, manner. In some instances, a sensor may detect a change in current over time within a well and feedback from that sensor may be used to control the voltage within the cannel.

The benchtop system can comprise one or more thermal controllers that control a temperature on a fluidic device or a part of a fluidic device. Thermal controllers can comprise components including but not limited to resistive heaters, fluid-based heating or cooling systems, and Peltier devices. Thermal controllers can be fabricated from materials including but not limited to metals (e.g., platinum, titanium, copper, gold), carbon, and indium tin oxide (ITO). Thermal controllers can comprise temperature sensors, which can be used to monitor the temperature being controlled and provide temperature feedback for thermal control. Thermal controllers can be used with computer control systems, as discussed further in this disclosure. For example, temperature sensors (e.g., infrared sensors) can be used to monitor a change in temperature in channels on a chip. Such temperature changes can be indicative of a location of an ITP band (e.g., a band of nucleic acid) during an ITP process, which temperature difference can be due to a change in conductivity between the leading electrolytes and trailing electrolytes. In some cases, thermal controllers are operated without temperature feedback.

Techniques of the present disclosure (including, e.g., the use of fluidic devices and/or benchtop systems discussed herein) can provide quick processing times. For example, a sample comprising nucleic acids can be prepared (e.g., removal of embedding material, tissue disruption, cell lysis, nucleic acid de-crosslinking) and have nucleic acids extracted or purified for subsequent analysis, use, or storage.

Detection and Quantitation

Techniques of the present disclosure can employ one or more detectors. Detectors can be integrated into fluidic devices or located externally to a fluidic device. Detectors can be used for quantitation of nucleic acid in a sample, for example by fluorescent measurement or ultraviolet (UV) radiation (e.g., for measurement of quantity or purity, such as by measurement of A260/A280), or for providing a qualitative measure of the nucleic acids in the sample. Nucleic acids can be detected while located on a fluidic device, for example while within a purification zone (e.g., ITP channel) or reservoir (e.g., elution reservoir). The concentration of the nucleic acids may be detected (or calculated based on a quantity measurement in a known volume such as in the elution well as described herein). Nucleic acids can be labeled, such as with dyes, and the fluorescence intensity of the nucleic acids can be measured by a detector and used to quantify the nucleic acids present (see, e.g., FIG. 14). Nucleic acids can be labeled prior to loading on a fluidic device, while in a fluidic device, or after recovery from a fluidic device.

Use of a detector can enable quantitation of nucleic acids from samples with a high sensitivity or a low limit of detection. For example, nucleic acids can be detected (e.g., in-line in an isotachophoresis channel) at limit of detection of less than or equal to about 1000 picograms per microliter (pg/µL), 100 pg/µL, 10 pg/µL, 1 pg/µL, 0.9 pg/µL, 0.8 pg/µL, 0.7 pg/µL, 0.6 pg/µL, 0.5 pg/µL, 0.4 pg/µL, 0.3 pg/µL, 0.2 pg/µL, or 0.1 pg/µL. Nucleic acids can be detected (e.g., in-line in an isotachophoresis channel) at a limit of detection of less than or equal to about 1000 picograms (pg), 100 pg, 10 pg, 1 pg, or 0.1 pg.

Use of a detector can enable identification or qualification of nucleic acids in a sample. For example, techniques such as nucleic acid amplification (including, e.g., PCR, real-time PCR, and reverse-transcription PCR), hybridization (including, e.g., fluorescent in situ hybridization (FISH) and Q-FISH), and sequencing can be used to identify the presence or absence of, and optionally quantify, a particular sequence within nucleic acids in a sample.

Detectors can be used in the control of nucleic acid extraction or purification operations. For example, a detector can detect a band of nucleic acids concentrated by isotachophoresis. When the concentrated nucleic acids reach a certain location within the device, the process can be ended (e.g., electric fields can be turned off) and extracted or purified sample can be recovered from the device.

Detectors can include but are not limited optical detectors and electrical detectors, thermal sensors, and pressure sensors (e.g., pressure transducers). Optical detectors can include but are not limited to three-axis point detectors, complementary metal-oxide semiconductor (CMOS) detectors, charge-coupled device (CCD) detectors, photodiode light sensors, photoresistors, photomultiplier tubes, and phototransistors. Optical detection can be achieved by LED illumination paired with photodiode detection. Electrical detectors can include electrodes or other detectors capable of detecting a voltage, voltage differential, current, charge, or other electrical property. For example, electrical detectors can be used to detect the passage of a band of extracted or purified nucleic acids.

End of Run Triggering

When purifying a sample using ITP, it can be important to accurately stop applying current when the sample ITP zone is in the elution location (e.g., a channel or a reservoir). The present disclosure provides techniques for assessing the ITP zone position, which can be used to trigger the end of a purification run. These techniques can include measurement of driving voltage, measurement of conductivity, and measurement of temperature.

Figure 15:
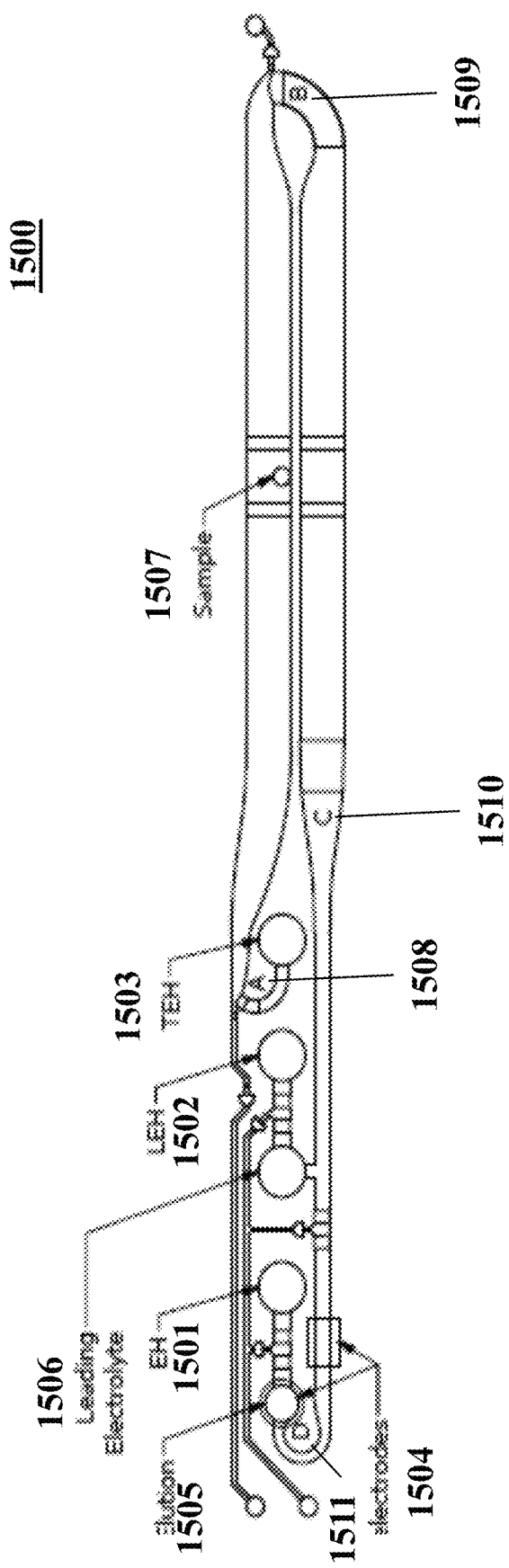
FIG. 15 shows a schematic of an exemplary design of a fluidic channel with connected reservoirs, contactless electrode(s) (may be used as conductivity sensor) and gas port(s) for conducting automated fluid loading into channel/device and automated isotachophoresis.

FIG. 15 shows a schematic of an ITP channel 1500, with driving electrodes placed in the buffered elution electrode (EH) reservoir 1501 and the buffered leading electrolyte (LEH) reservoir 1502, and a ground electrode placed in the buffered trailing electrolyte (TEH) reservoir 1503. Conductivity detector (e.g., capacitively-coupled contactless conductivity detector (C4D)) electrodes 1504 can be placed outside of the chip, such as near the elution reservoir 1505, as shown on the left side of the figure. The channel can also comprise a leading electrolyte reservoir 1506 and a sample reservoir or injection point 1507. Gas ports are indicated by small circles on the far left and right edges of the channel. Gas ports can be used to automatically load or prime fluids into the channels from the attached reservoirs, for example using vacuum or applied pressure.

One method for measuring the position of an ITP band is to measure the voltage or the resistance of the channel, such as between the driving electrode and the ground electrode. In systems with more than two electrodes, this measurement may be taken between any pair of electrodes. This measurement can be made readily, as the voltage driving electrophoresis is also the measurement voltage. Throughout the purification process, the voltage can increase as the trailing ion fills the channel. However, the elution reservoir can have a large cross-section, so the contribution to overall resistance can be small. Hence, changes in the buffer conductivity in this region may not strongly impact the overall channel resistance, and the voltage can stop rising when the ITP zone enters the elution reservoir. This can be used as a signal to stop applying current and end the run.

Figure 16:
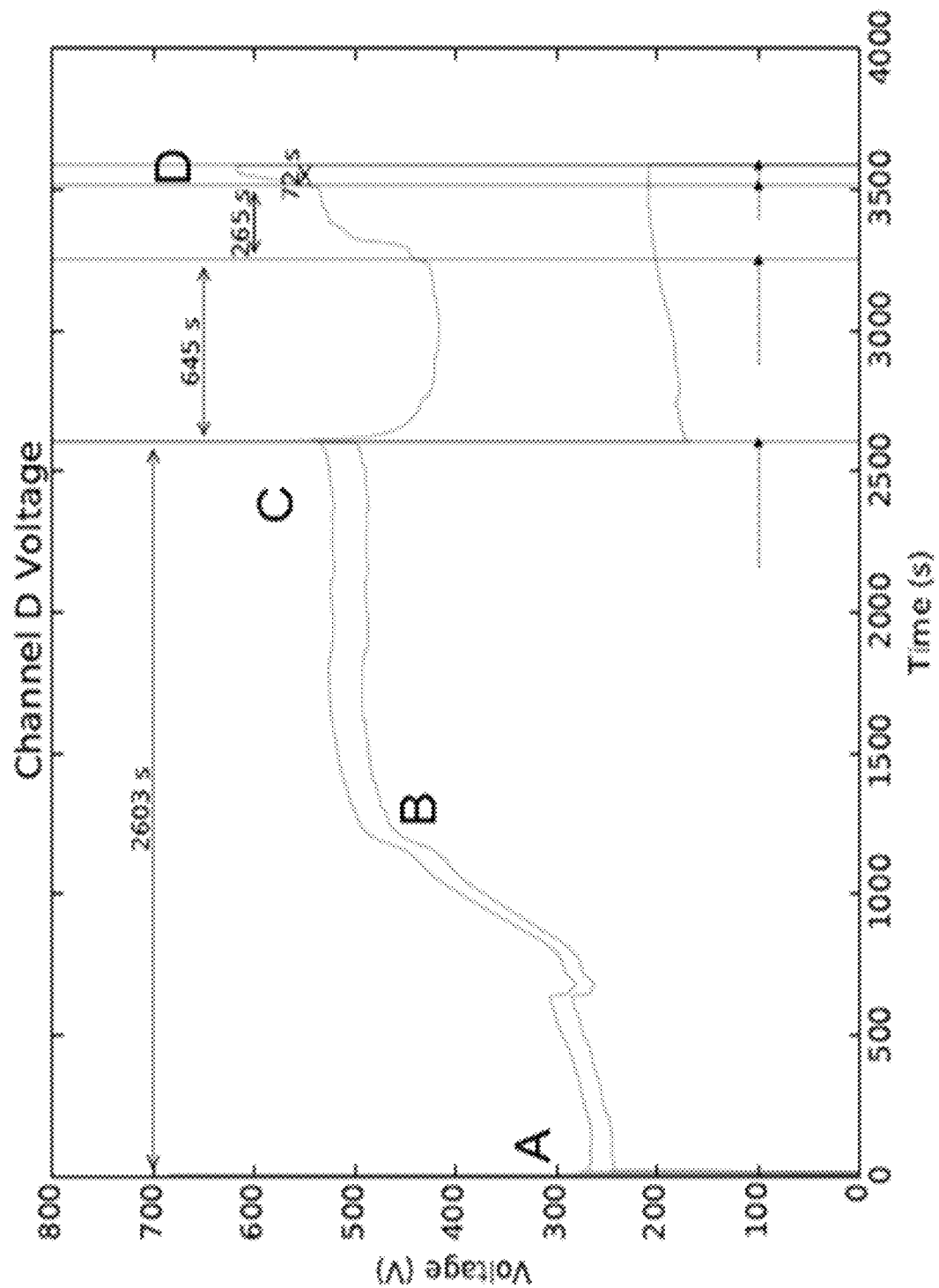
FIG. 16 shows a graph of voltage measurement over time in an ITP channel during a run.
Figure 17:
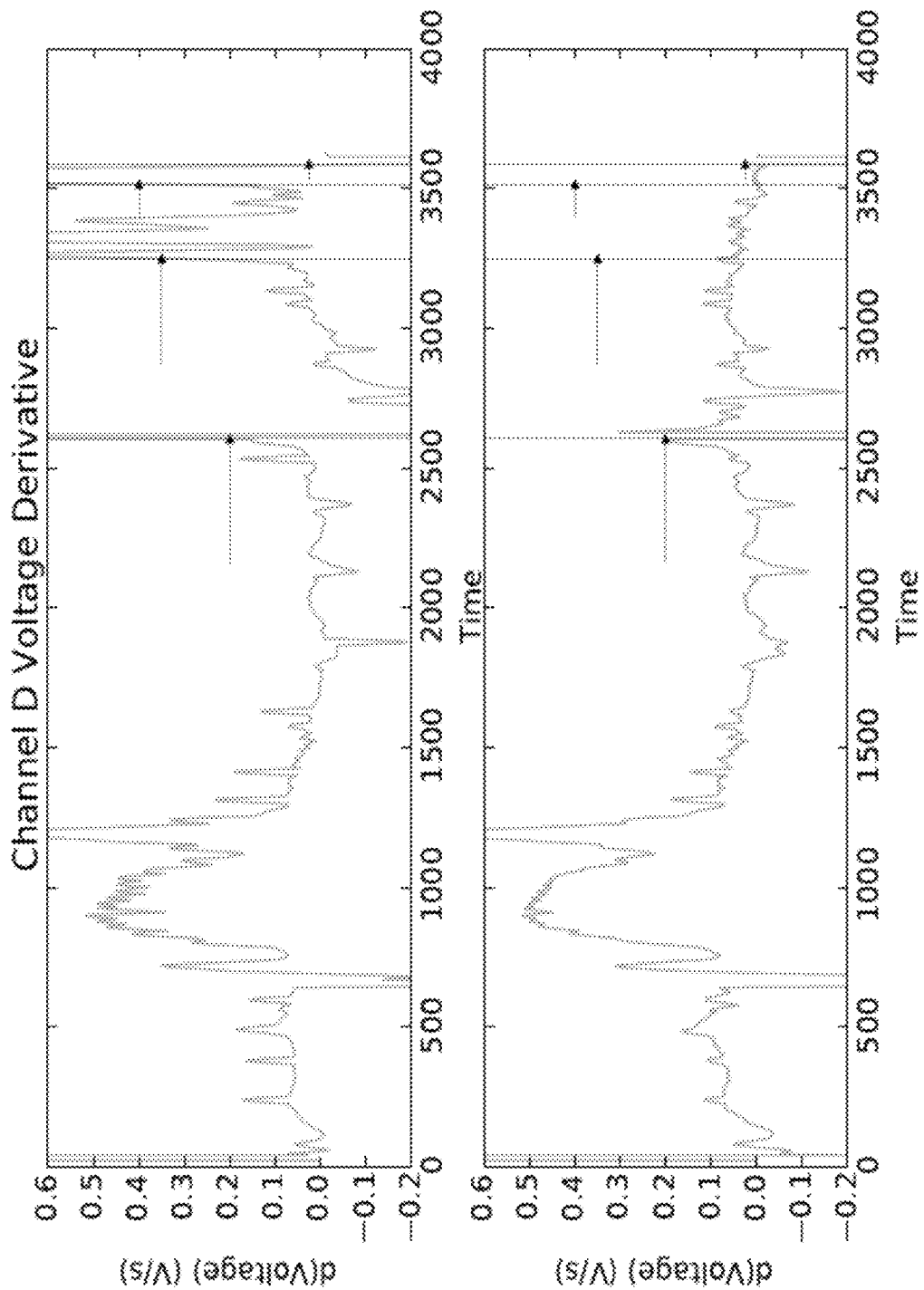
FIG. 17 shows two graphs of derivative analysis of the voltage measurements from FIG. 16.

To assess this voltage change, the derivative of voltage can be calculated, for example as shown in FIG. 16. The Lanzcos differentiation method can be used to suppress high frequency noise. Thresholds can be set for the derivative, and when the derivative passes the threshold, a trigger is performed. In some cases, introducing additional triggers can improve the robustness of the control. For example, FIG. 16 shows four trigger points. In some cases only two of these triggers are used to change the driving current (e.g., triggers 1 and 4), while the others (e.g., triggers 2 and 3) are used to mark time points in the run, which can improve the timing of trigger 4. FIG. 17 shows derivative analysis of the voltages in FIG. 16, with arrows representing the derivative thresholds used to choose the trigger points.

FIG. 16 shows example data from measuring the driving voltage. Each vertical line represents a trigger point. The two lines represent two electrodes, the electrodes in the EH and LEH reservoirs, with respect to the ground electrode. Points A, B, C, and D show to the time at which the ITP zone is in the corresponding location marked in FIG. 15 (A, B, C, and D; labeled 1508, 1509, 1510, and 1511, respectively). In some cases, the conductivity everywhere in the channel can affect the overall driving voltage, which may make it more difficult to assess what is happening near the elution reservoir.

Figure 18:
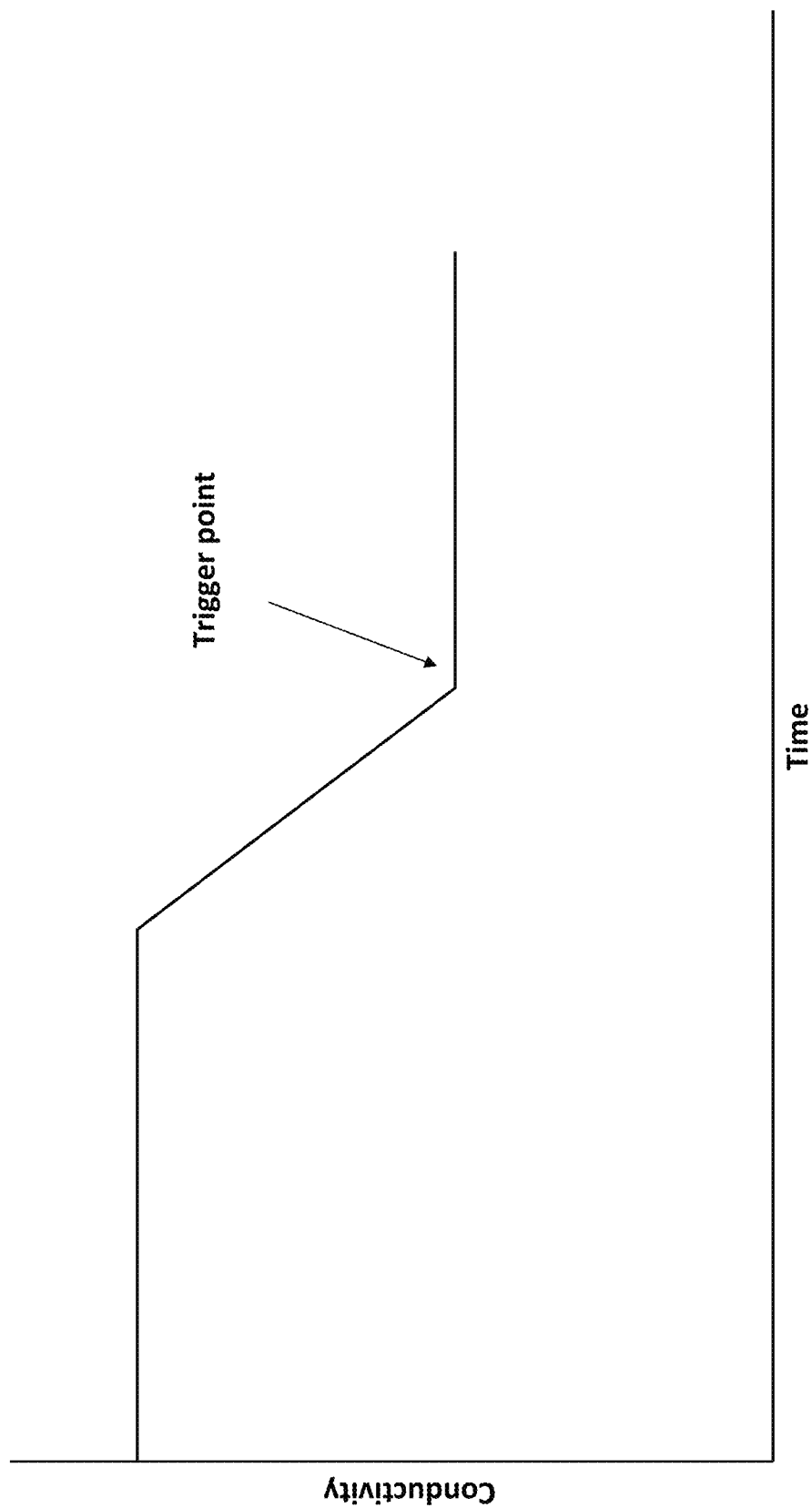
FIG. 18 shows an example of conductivity measurement over time in an ITP channel near an elution reservoir.

A second method for detecting the position of an ITP band is to make a localized measurement of the conductivity. This can be done using a capacitively coupled contactless conductivity detector (C4D). This method can use high frequency alternating current to pass through the channel wall and couple to the electrolyte. This localized measurement can be taken at the elution reservoir itself. This technique can reduce or remove the ambiguity associated with measurements taken over the entire channel. In this technique, the end of run trigger can be chosen as soon as a change is seen in the conductivity at the elution reservoir conductivity detector, for example as shown in FIG. 18.

Figure 19:
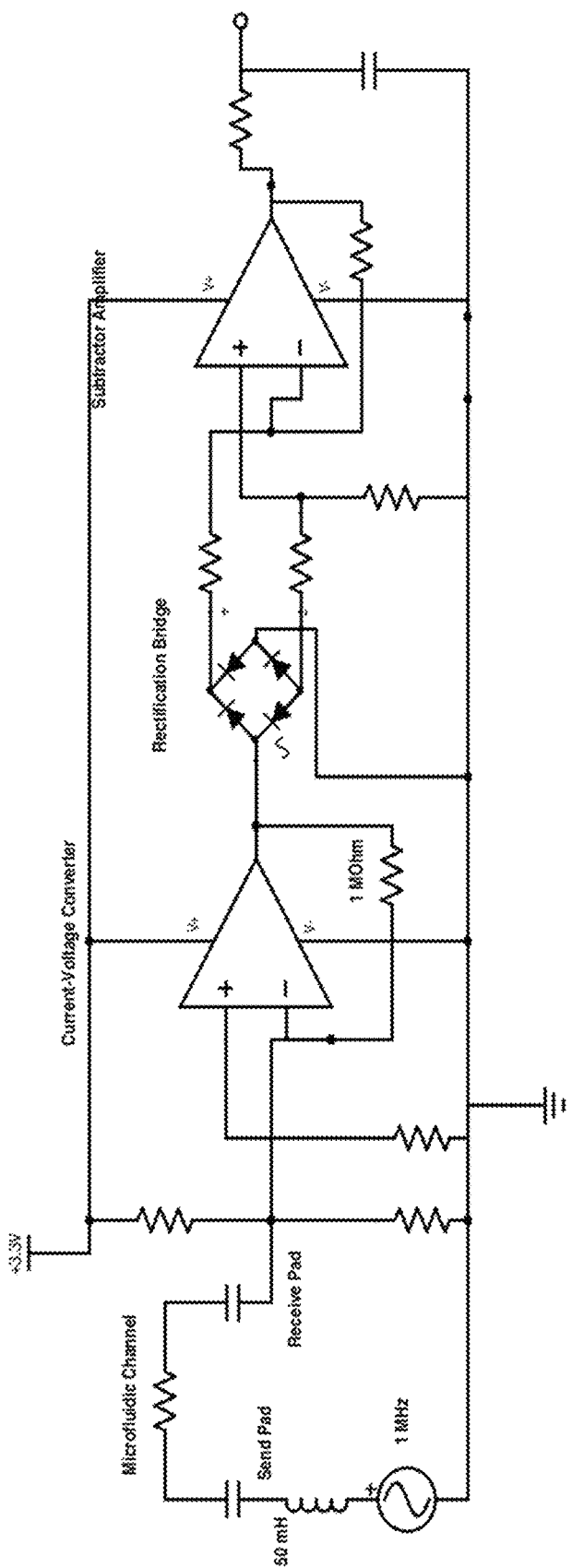
FIG. 19 shows an exemplary schematic of a C4D sensor implementation.

C4D detection can be performed with electrodes placed below the elution channel. Maximizing the electrode area can reduce the necessary driving frequency. For example, driving frequencies can be used from about 100 kHz to about 10 MHz, with electrode contact pads between about 0.2 mm$^2$ and about 50 mm$^2$. C4D sensors can be implemented with electrical components including resistors, capacitors, a diode bridge, and high-frequency operational amplifiers, with a high frequency signal source such as from a direct digital synthesizer. FIG. 19 shows an exemplary schematic of a C4D sensor implementation.

A third method for detecting the position of an ITP band is to make a localized measurement of temperature near the elution reservoir. This measurement can be made with temperature sensors including a thermocouple or an infrared temperature sensor. The sensor can be placed under the channel near the elution reservoir and can monitor the temperature over time. When the lower-mobility trailing ions displace the higher-mobility leading ions (e.g. the LE-TE interface of the ITP zone), the electric field in the channel can increase, and the temperature can rise. During isotachophoresis, lower mobility trailing electrolyte ions and higher mobility leading electrolyte ions may meet at an isotachophoresis interface. The ITP interface may comprise the sample nucleic acids concentrated between the leading electrolyte ions and trailing electrolyte ions. A temperature rise can detect the presence of the ITP interface between the higher-mobility leading ions and the lower-mobility trailing ions, and thus also indicates the presence of the nucleic acids therebetween. This temperature rise can be 1-10° C.

Figure 20A:
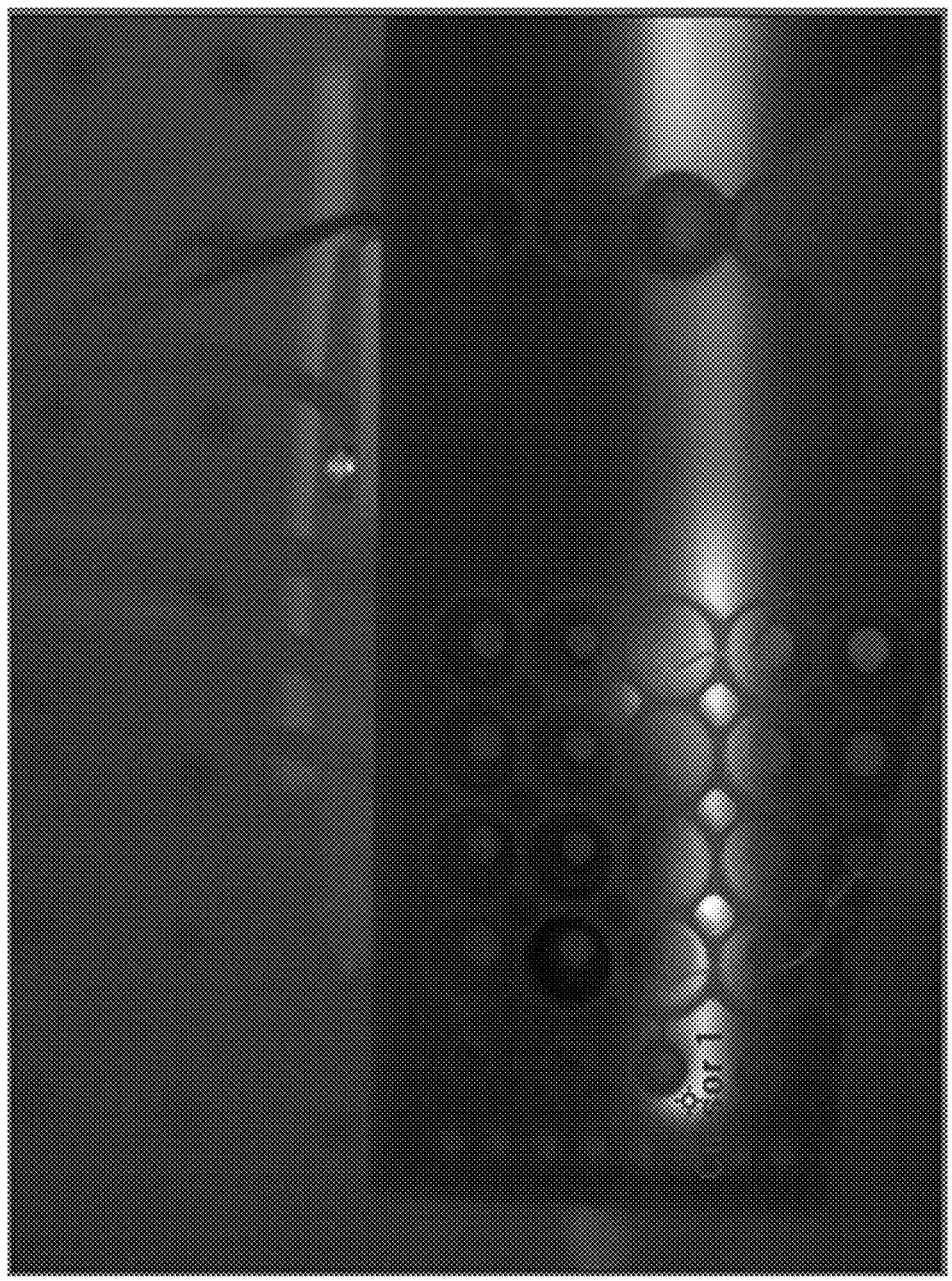
FIG. 20A shows an exemplary temperature map of an ITP channel taken using a thermal imaging camera.
Figure 20B:
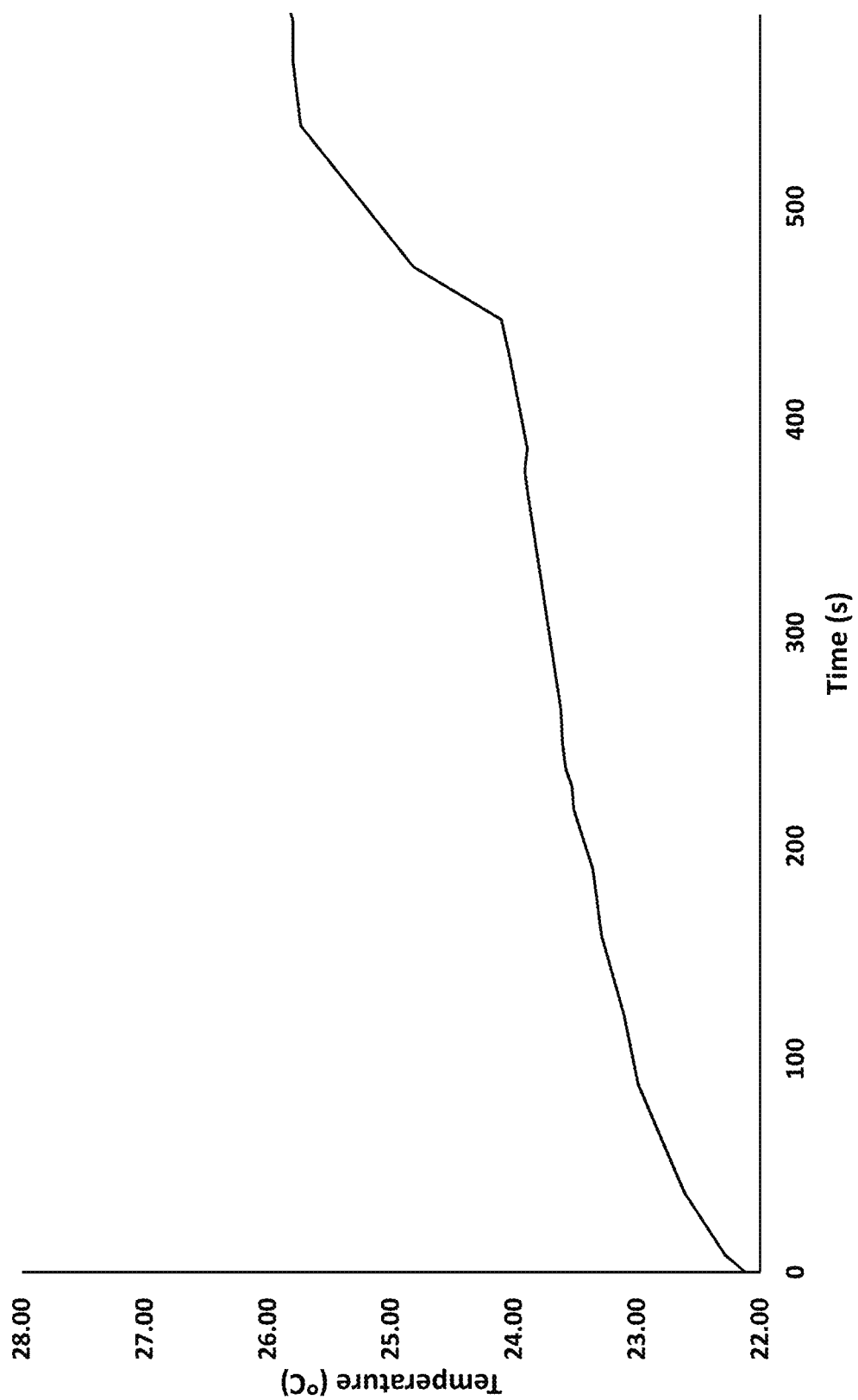
FIG. 20B shows a plot of temperature over time at the position of Cursor 1 in FIG. 20A.

FIG. 20A and FIG. 20B show exemplary temperature measurement results using a thermal imaging camera. These images show a clear rise in temperature as the trailing ion enters the channel. FIG. 20A shows a temperature map of an ITP channel taken using a thermal imaging camera; the orientation of the channel is the same as in FIG. 15. FIG. 20B shows a plot of temperature over time at the position of Cursor 1 in FIG. 20A. At about 450 seconds, the ITP interface and trailing ion enters the region, causing an increase in temperature. This temperature rise can be detected and used as a triggering signal to alter the electric current applied to the channel.

Figure 21:
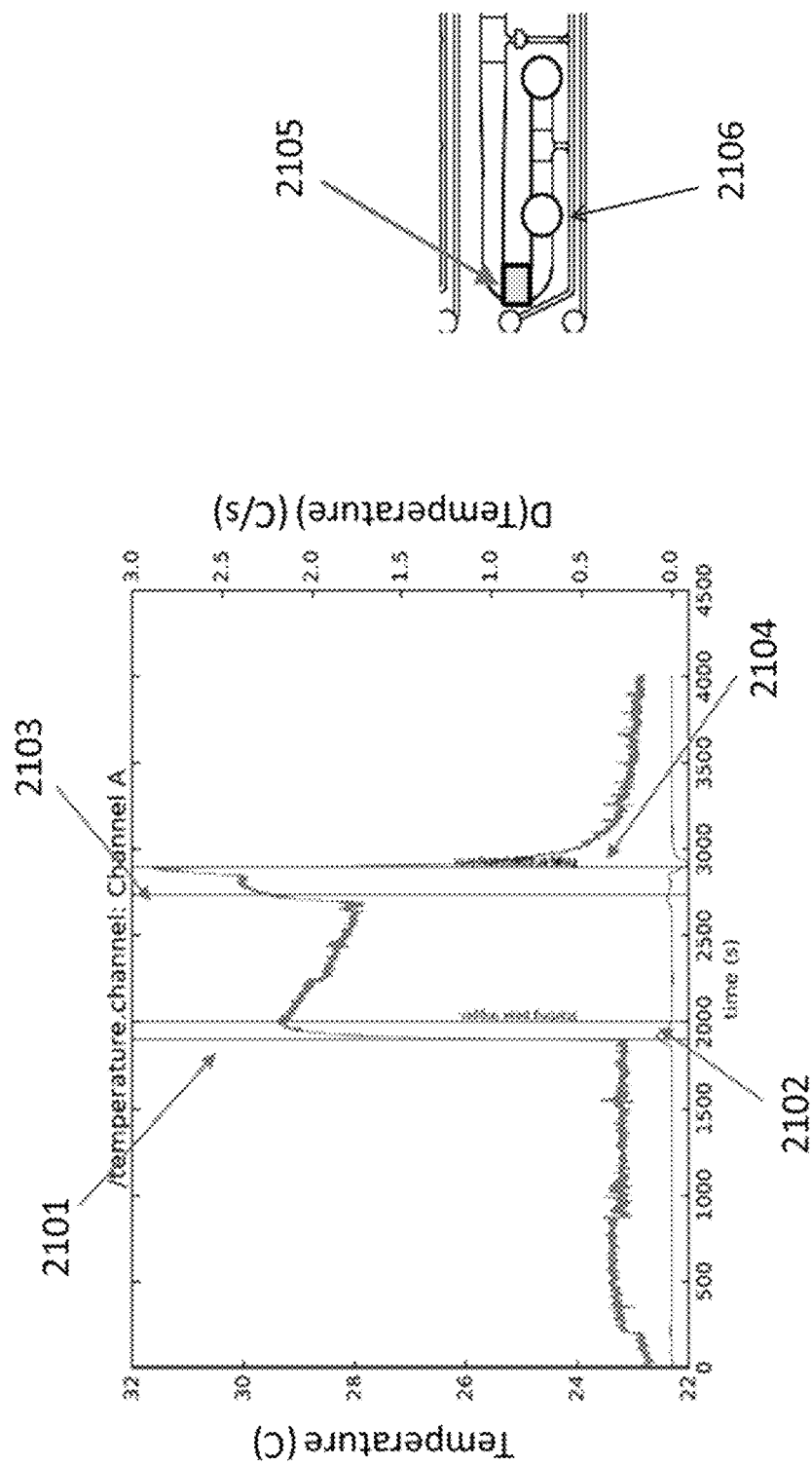
FIG. 21 shows a graph of temperature measurement and temperature derivative over time during an ITP run.

The temperature may be measured at a detection location at or near the elution reservoir (e.g. as shown in FIG. 21). In some instances, the detection location may be located at least about 5 mm from the elution reservoir. In some instances, the detection location may be located at least about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm from the elution reservoir. In some instances, the detection location may be located at most about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm from the elution reservoir. In some instances, the temperature sensor may be located at least about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm from the elution reservoir. In some instances, the temperature sensor may be located at most about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm from the elution reservoir.

The temperature sensor may trigger a change in electric current when a change in temperature is sensed. In some instances, the detected change in temperature is within a range of about 0.2° C. to about 5° C. In some instances, the detected change in temperature is at least about 0.2° C., 0.3° C., 0.4° C., 0.5° C., 1° C., 2° C., 3° C., 4° C., 5° C., 6° C., 7° C., 8° C., 9° C., or 10° C. In some instances, the detected change in temperature is at most about 0.2° C., 0.3° C., 0.4° C., 0.5° C., 1° C., 2° C., 3° C., 4° C., 5° C., 6° C., 7° C., 8° C., 9° C., or 10° C.

In some cases, detection of the ITP zone, for example by voltage monitoring, conductivity measurements, or temperature sensing, at one or more trigger points may cause the benchtop controller to alter the electric current applied to the microfluidic chip. The change may be applied immediately upon detection or after a pre-determined delay. Detection of the ITP zone may trigger a decrease, increase, or removal of current. For example, detection of the ITP zone at point C 1510 may trigger a decrease in current in order to increase the residence time of the ITP zone in the channel leading to the elution reservoir. Alternatively or in combination, detection of the ITP zone at point D 1511 located at or near the elution reservoir may trigger the removal of electric current in order to position the ITP zone (and nucleic acids) or a portion thereof within the elution reservoir, well, or region of the channel or chip. In some instances, detection of the ITP zone may trigger a change in electric current after a pre-determined amount of time. For example, a detection location (for example 1504 or the position of cursor 1) may be positioned at or near the elution reservoir at a known distance such that the time needed for the ITP zone to travel between the detection location and the elution reservoir can be calculated for a given current. The controller may pre-determine a travel time and detection of the ITP zone at the detection location may trigger a delayed removal of the current after the pre-determined amount of time. In some instances—detecting the ITP zone at a specific detection location may offer a space-time relationship of the ITP zone which may result in more precise triggering than other sensing methods.

In some cases, detection of the ITP zone at a trigger point may cause the electric current applied to the microfluidic chip to change directions or paths. For example, the electric current may be triggered to reverse such that the ITP zone reverses direction of travel within the channel. In another example, the system may be triggered to stop applying current between a first pair of electrodes and begin applying current to a second pair of electrodes to drive the flow of ions along a different path. For example, a channel may be "y-shaped" with a first channel leading into two side channels which split from the first channel at different directions. Current may initially be driven between first and second electrodes connected to the first channel and a first side channel, respectively. Without interruption of current, the ITP zone may travel from the first channel to the first side channel. Detection of the ITP zone at a connection between a first channel and two side channels may trigger the first and second electrodes to stop driving current and third and fourth electrodes connected to the first channel and a second side channel, respectively, to begin driving current. The ITP zone will then travel from the first channel to the second side channel. In some cases, the first and third electrodes are the same electrode. In this way, the trigger may cause the current to change such that the path of the ITP zone changes along the channel.

Further Processing and Use of Purified Samples

Extracted or purified nucleic acids can be used for sequencing, genotyping, analysis of mutations or polymorphisms, analysis of gene expression levels, disease diagnosis, disease prediction, cytological classification, paternity or genealogical analysis, or indication of suggested treatment modalities.

Extracted or purified nucleic acids can be used in amplification reactions, including but not limited to loop-mediated isothermal amplification (LAMP), strand displacement amplification (SDA), helicase-dependent amplification (HDA), rolling circle amplification (RCA), nicking enzyme amplification reaction (NEAR), PCR, reverse transcription PCR, real-time PCR, quantitative PCR (qPCR), digital PCR, and methylation-specific PCR.

Extracted or purified nucleic acids can be used in sequencing reactions, including Maxam-Gilbert sequencing, chain termination sequencing (e.g., Sanger sequencing), shotgun sequencing, pyrosequencing, bridge PCR, colony sequencing, polony sequencing, sequencing by synthesis, ion semiconductor sequencing, nanopore sequencing, nanoball sequencing, sequencing by ligation, sequencing by hybridization, and single molecule real-time sequencing.

Extracted or purified nucleic acids can be used in protein binding assays, such as DNA footprinting assays. For example, DNase (e.g., DNase I) can be used to randomly cut DNA molecules of interest. The techniques of the present disclosure can be used to separate digested DNA from the DNase enzymes, preventing further digestion. In some cases, DNase digestion can be performed off of a fluidic device, and then the sample can be loaded onto a fluidic device for purification. In other cases, DNase digestion can be performed on a fluidic device, and once digestion is performed, the nucleic acids can be purified on the fluidic device.

Samples, such as fixed or embedded samples (e.g., FFPE samples), can be used for longitudinal studies, genome-wide association studies, and other large-scale analysis across populations.

Vertical or Column ITP

Planar ITP device designs, such as discussed herein, can utilize horizontal space for ITP bands to travel. To process samples at high throughput, such as in the 96-well plate format, it can be advantageous to fit an entire ITP separation system for a sample in a given footprint, such as 9 mm×9 mm footprint. One way of doing this is to increase the height of the system to accommodate more sample volume. This can provide the option to increase total sample volumes into the milliliter range and still process samples with reasonable run times.

In some cases, it can be important to reduce or prevent gravity-driven flow and/or buoyant flow through such a system. It can also be important to assemble the electrolyte zones needed for ITP without mixing the electrolytes.

A vertical or column ITP system can comprise several ITP stages, where each stage comprises a column (e.g., plastic) with gel (e.g., agarose) or similar material at the bottom. The gel can have high electrolytic conductivity. Each stage can be prepared by introducing an electrolyte on top of the gel. The gel can slow or prevent liquid flow. To create the column, the stages can be stacked with the trailing electrolyte at the top and the leading electrolyte at the bottom. Current can then be driven through the system. Purified analyte can be recovered by de-stacking the columns and pipetting out.

Figure 22B:
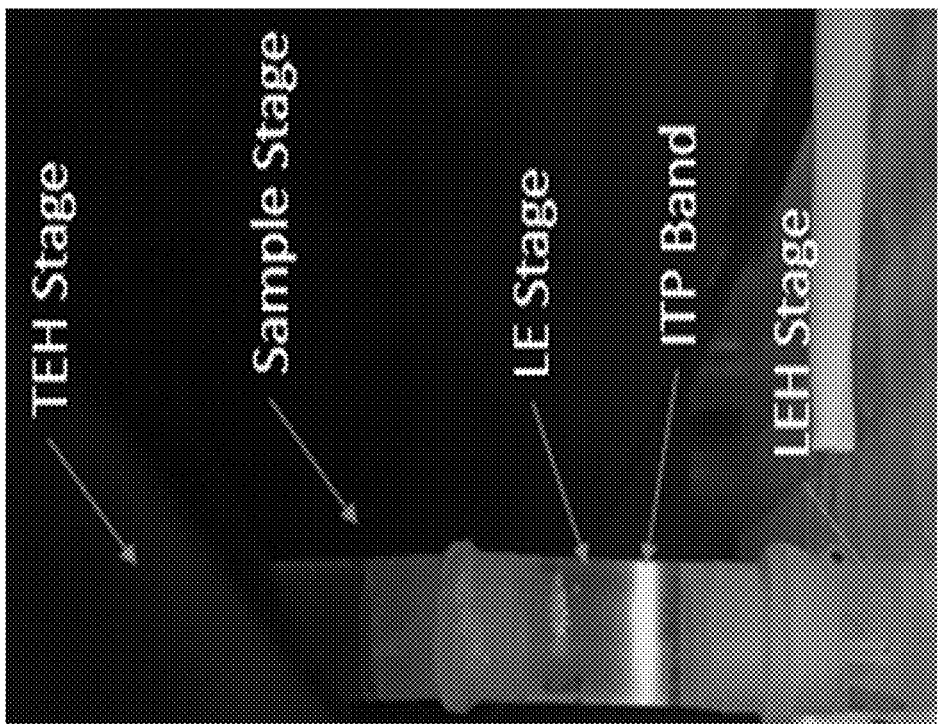
FIG. 22B shows an exemplary image of a vertical ITP set up with an DNA ITP band.
Figure 22A:
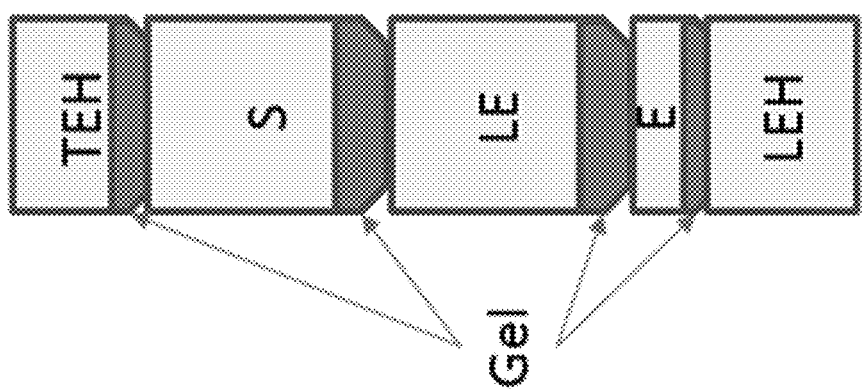
FIG. 22A shows an exemplary schematic of a vertical (or column) ITP setup.

FIG. 22A shows an exemplary schematic of a vertical (or column) ITP setup. The gels in each stage can support the weight of the water (e.g., aqueous electrolyte solution) above. The cross sectional area of the column can be approximately 9 mm×9 mm. Such a system can process a sample with an approximate cross sectional column area of 9 mm×9 mm. The design can be scaled, for example to 96 samples (columns), with overall device dimensions conforming to a standard microtiter plate. FIG. 22B shows an exemplary image of a vertical ITP set up with an DNA ITP band. The stages are: Trailing Electrolyte High (TEH), Sample, Leading Electrolyte (LE) and Leading Electrolyte High (LEH). The ITP zone is moving downward through the system. This image does not show the elution stage (E, shown in FIG. 22A) which is the final destination of the analyte.

Computer Control Systems

Figure 13B:
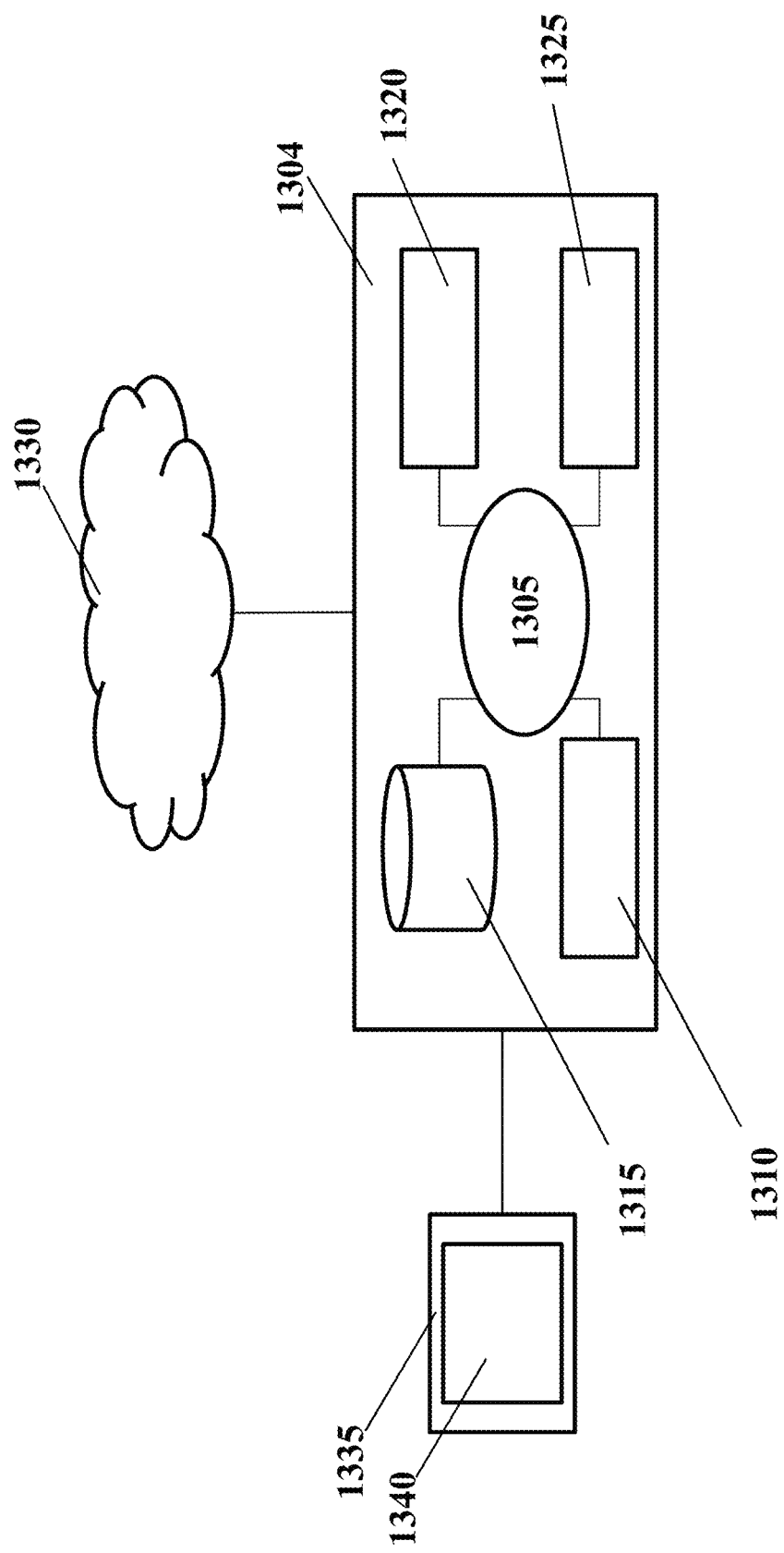
FIG. 13B shows an exemplary computer control system that is programmed or otherwise configured to implement methods provided herein.

The present disclosure provides computer control systems that are programmed to implement methods of the disclosure. FIG. 13B shows a computer system 1304 that is programmed or otherwise configured to control sample preparation, sample extraction or purification, or detection. The computer system 1304 can regulate various aspects of extraction, purification, and detection processes of the present disclosure, such as, for example, application of pressure or electric fields, thermal control, detection, quantitation, feedback, and beginning or ending a process. The computer system 1304 can be an electronic device of a user or a computer system that is remotely located with respect to the electronic device. The electronic device can be a mobile electronic device.

The computer system 1304 includes a central processing unit (CPU, also "processor" and "computer processor" herein) 1305, which can be a single core or multi core processor, or a plurality of processors for parallel processing. The computer system 1304 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The computer system 1304 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the computer system 1304, can implement a peer-to-peer network, which may enable devices coupled to the computer system 1304 to behave as a client or a server.

The CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and writeback.

The CPU 1305 can be part of a circuit, such as an integrated circuit. One or more other components of the system 1304 can be included in the circuit. In some cases, the circuit is an application specific integrated circuit (ASIC).

The storage unit 1315 can store files, such as drivers, libraries and saved programs. The storage unit 1315 can store user data, e.g., user preferences and user programs. The computer system 1304 in some cases can include one or more additional data storage units that are external to the computer system 1304, such as located on a remote server that is in communication with the computer system 1304 through an intranet or the Internet.

The computer system 1304 can communicate with one or more remote computer systems through the network 1330. For instance, the computer system 1304 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1304 via the network 1330.

Methods as described herein can be implemented by way of machine (e.g., computer processor) executable code stored on an electronic storage location of the computer system 1304, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1304, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1304 can include or be in communication with an electronic display 535 that comprises a user interface (UI) 1340 for providing, for example, operational parameters (e.g., processing time, temperature, field strength), nucleic acid quantitation information, or other information. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1305. The algorithm can, for example, regulate thermal controllers, calculate nucleic acid quantitation, control process functions, and begin or end a process.

Kits

This disclosure provides kits useful for conducting isotachophoresis processes. Generally, such kits comprise a microfluidic device provided herein and one or more buffers. The buffers may include one or more sample buffers, one or more leading electrolyte buffers, one or more trailing electrolyte buffers, one or more lysis buffers and/or one or more elution buffers, in any combination. In some cases, the kit may in include one or more enzymes (e.g., RNase, DNAs, nucleases, proteases, proteinases, polymerase). The buffers may be supplied in separate tubes. In some cases, the microfluidic device is pre-loaded with one or more buffers. The kits may include a set of instructions for operating the device and/or processing a sample.

EXAMPLES

Example 1—DNA Extraction from FFPE Samples

An FFPE sample from a human patient is obtained. A 1.1× aqueous alkaline buffer solution (Solution A1) is prepared with 80 mM NaOH, 11 mM DTT, and 0.5% v/v Igepal CA-630 in nuclease-free distilled or deionized water. A 10× quenching solution (Solution A2) is prepared with 776 mM HCl and 100 mM Tris base or Trizma base in nuclease-free distilled or deionized water. Commercially available Proteinase K solutions and RNases are also provided. Alternatively, a neutrally-buffered (e.g., pH from about 7.0 to about 8.0) 5-50 mM Tris-HCl solution with 0-80 mM NaCl, 5-10 mM DTT, and 0.1-0.5% v/v IGEPAL CA-630 can be prepared in nuclease-free distilled or deionized water.

An FFPE section or scroll is added to a 1.5-2.0 mL microcentrifuge tube. 175 μL of Solution A1 is added to the tube. The tube contents are incubated for 1-20 minutes at 50-99.9° C. (in some cases, the tube contents are incubated for 5-20 minutes at 95-99.9° C.) to deparaffinize the sample. 20 μL of Solution A2 are added to the tube to quench Solution A1 and achieve a buffered solution with pH of about 7-8.25. Alternatively, an FFPE section or scroll can be incubated in 195 μL of quenched or neutral buffer (e.g., pH from about 7.0 to about 8.0) for 1-30 minutes at 50-80° C. to deparaffinize the sample. Other deparaffinization protocols that can be used include (1) treating the sample with xylene, followed by one or more washes with 96%-100% ethanol at room temperature, followed by drying of the tissue; (2) incubating the sample at an elevated temperature (e.g., 50-100° C.) for 1-30 minutes in a buffered aqueous solution at about pH 7 to about pH 8.25; (3) incubating the sample at an elevated temperature (e.g., 50-100° C.) for 1-30 minutes in an alkaline aqueous solution followed by quenching to a buffered solution with pH of about 7 to about 8.25; or (4) incubating the sample at an elevated temperature (e.g., 50-100° C.) for 1-30 minutes in mineral oil.

5 μL of Proteinase K solution is added to the deparaffinized sample solution to a final concentration of 400-1000 μg/mL (typically 600-700 μg/mL) and a final volume of 200 μL. The solution is then incubated for 15-60 minutes at about 56° C. Optionally, the solution is further incubated for 2-60 minutes at 80-90° C. Optionally, 3 μL of RNase A (or about 50-200 μg/mL RNase A) is added to the solution. The solution is then cooled to room temperature, and the FFPE lysate is loaded onto a fluidic device for further processing, such as by isotachophoresis (ITP).

Example 2—Comparison of DNA Extraction Yields

DNA was extracted using a bench top controller device to automate isotachophoresis in a fluidic device from (i) qPCR buffer as a post-PCR clean-up (FIG. 3, triangle data points), and (ii) cell culture lysate (FIG. 3, square data points), with yield calculated using qPCR. Published DNA yield data using a traditional solid-phase extraction column (SPE; FIG. 3, diamond data points) are provided for comparison. FIG. 3 shows DNA yield versus input DNA mass. The leading electrolyte buffer used for isotachophoresis comprised 88 mM Tris with 44 mM HCl. Trailing electrolyte was loaded into the trailing electrolyte reservoir and comprised 1.2M Tris with 0.3 M Caproic Acid and 0.6 M MOPS. The cellular lysate sample was prepared in a second leading electrolyte buffer (sample buffer) comprising 10 mM Tris with 5.6 mM HCl. Extraction of DNA from human Jurkat cell culture lysate was performed at yields from about 60% to about 90% for input DNA masses from about $10^{-2}$ nanograms (ng) to about $10^3$ ng. Cells were lysed in an aqueous solution comprising 40 mM NaOH for 1 minute and subsequently quenched at a 1:1 volume ratio with a buffered acidic solution to bring the final cell lysate sample to 10 mM Tris with 5.6 mM HCl and 20 mM NaCl at pH 8. Proteinase K was added to a final concentration of 400 μg/ml within the cell lysate sample volume and incubated for 10 minutes and 56° C. The lysed sample was then brought to room temperature and loaded onto the fluidic device for isotachophoresis. Extraction of genomic DNA (pre-purified from human Jurkat cells using a commercial SPE kit) spiked into a buffer comprising 10 mM Tris-HCl pH 8 was performed at yields from about 90% to about 100% for input DNA masses from about $10^{-1}$ ng to about $10^3$ ng.

Compared to traditional SPE column kits, the isotachophoresis method and device used here allowed for higher yields. This may have been due to a higher off-chip lysis efficiency with the indicated lysis chemistry followed by a more efficient recovery of nucleic acids using isotachophoresis. The isotachophoresis methods and devices described herein may provide lower adsorption of nucleic acids samples to the surfaces of the chip compared to a standard column and/or lower dead volumes within the fluidic device than a column. The isotachophoresis methods and devices described herein may enable less biased or unbiased recovery of nucleic acids based on length and/or sequence, which may also provide for higher efficiency recovery. The spiked-in genomic DNA sample performed had a very high recovery (yield) which may indicate that isotachophoresis has very little systematic loss of sample due to the isotachophoresis process itself (whereas the cell lysate sample may have other factors which contribute to loss of efficiency such as the lysis chemistries used which may be improved for higher yields).

Example 3—Separation of Crosslinked and Non-Crosslinked Nucleic Acids

Figure 23:
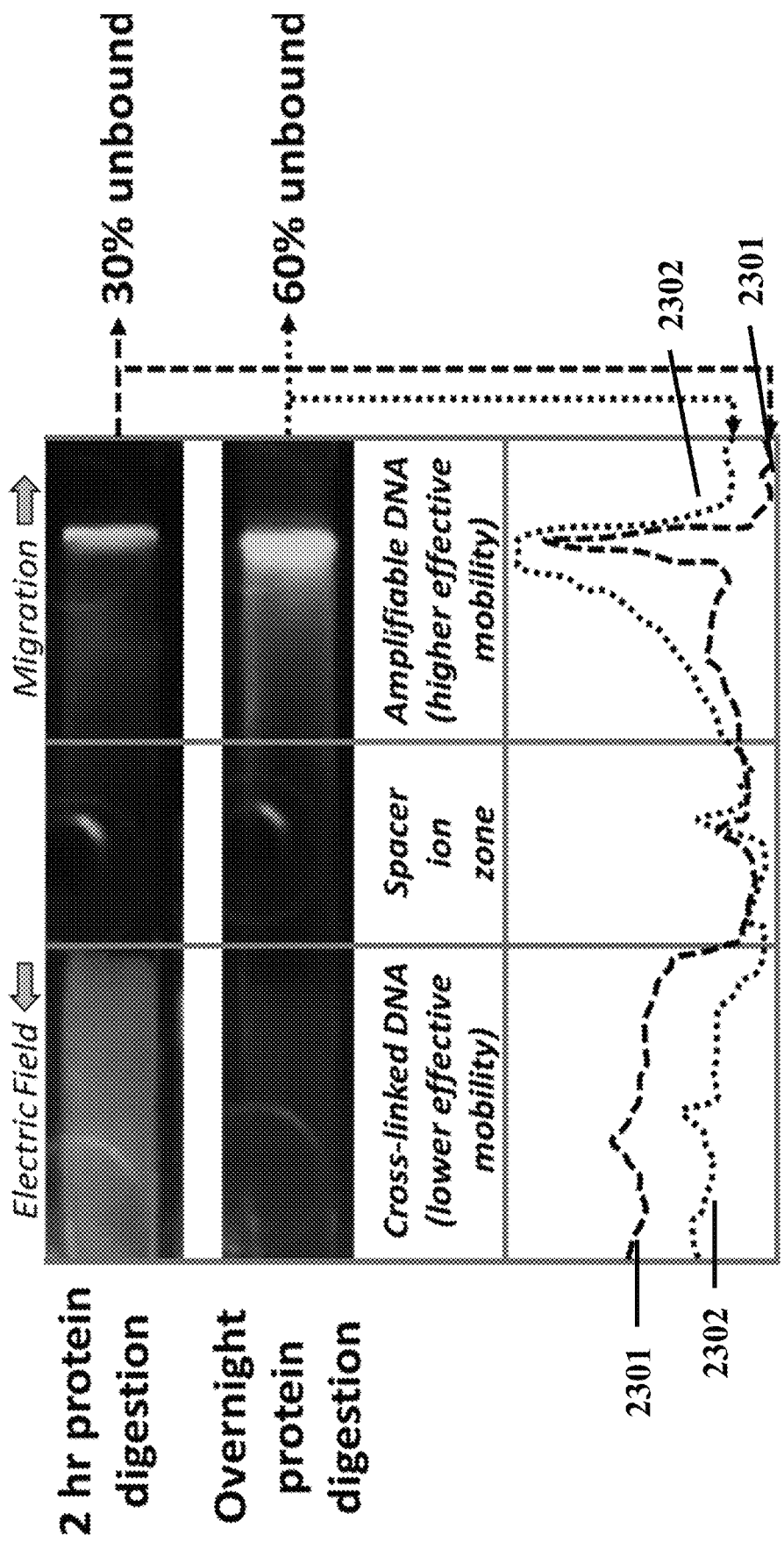
FIG. 23 shows exemplary images and corresponding fluorescence intensity traces of extraction and separation of amplifiable (e.g., decrosslinked) DNA from crosslinked DNA from an FFPE sample using isotachophoresis.

A deparaffinized and lysed mouse FFPE tissue sample (processed as described in Example 1) comprising crosslinked and non-crosslinked nucleic acids was loaded onto a fluidic device for isotachophoresis with leading electrolyte and trailing electrolyte. The sample was lysed as described in Example 1 and prepared in a leading electrolyte solution to a final concentration of 10 mM Tris with 5.6 mM HCl. The leading electrolyte comprised 140 mM Tris with 70 mM HCl. The trailing electrolyte comprised a mixture of 2.1 M Tris with 0.5 M caproic acid as a spacer ion with a higher effective mobility magnitude than HEPES and 0.7 M HEPES as an ion with a lower effective mobility magnitude. During isotachophoresis, non-crosslinked nucleic acids, having a higher effective mobility magnitude, focus ahead of the caproic acid zone and behind the leading electrolyte zone. Crosslinked nucleic acids and sample contaminants focus behind the caproic acid zone, and either ahead of or within the HEPES zone depending on the degree of crosslinking and their effective mobility magnitude. FIG. 23 shows two images of DNA separation in an isotachophoresis channel subsequent to a two hour (upper) or an overnight (lower) digestion to remove crosslinking proteins from the DNA. Proteinase K was added to the deparaffinized lysed tissue (quenched to pH 8.2) at final concentration of 700 µg/ml for digestion. Crosslinked DNA appears at the left end of the channel, separated by spacer ions from the amplifiable non-crosslinked DNA at the right end of the channel. The graph in FIG. 23 shows intensity of DNA signal versus position in the channel for the two hour 2301 and overnight 2302 digestions.

Example 4—Extraction and Purification of DNA from Lung and Liver FFPE Samples

Figure 24B:
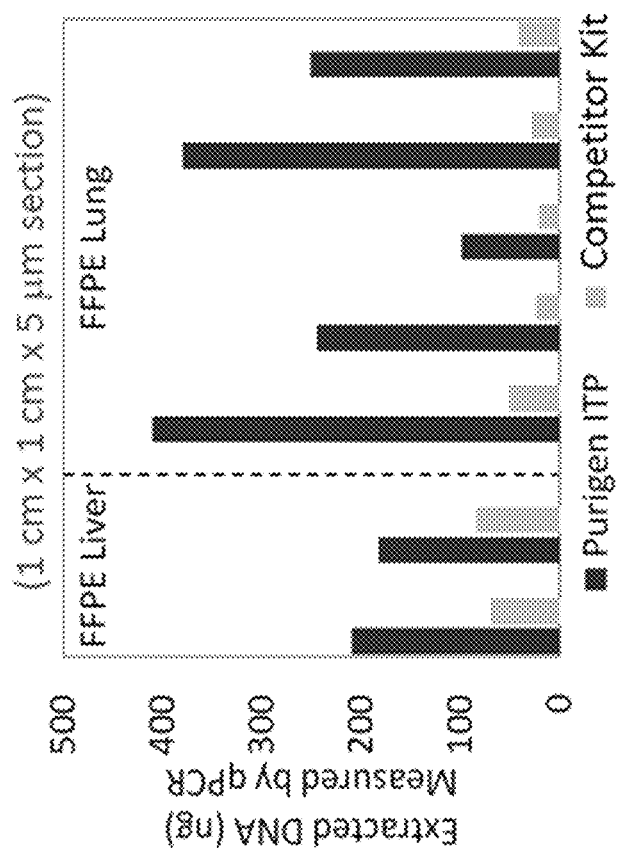
FIG. 24B shows exemplary DNA yields measured by quantitative PCR for extraction and purification of DNA from FFPE samples using isotachophoresis compared to exemplary results from a typical solid phase column extraction kit.
Figure 24A:
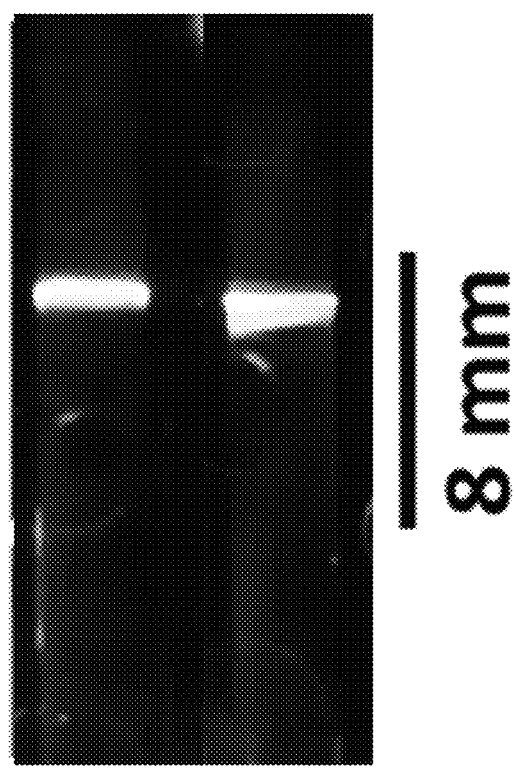
FIG. 24A shows an exemplary image of DNA extraction and purification from FFPE samples using isotachophoresis.

Formalin-fixed paraffin-embedded (FFPE) mouse lung and liver samples were obtained (e.g., Zyagen). Seven pairs of FFPE sections (1 cm by 1 cm by 5-10 µm) were processed, with one section from each pair processed by on-device isotachophoresis and one section processed by a different method (Promega ReliaPrep FFPE DNA kit) for comparison. The leading electrolyte buffer used for isotachophoresis comprised 88 mM Tris with 44 mM HCl. Trailing electrolyte was loaded into the trailing electrolyte reservoir and comprised 1.2M Tris with 0.3 M Caproic Acid and 0.6 M MOPS. Samples were deparaffinized by incubation in a 10 mM Tris-HCl buffer with 10 mM DTT, 72 mM NaCl and 0.5% IGEPAL CA-630 at pH 8.0 for approximately 1 minute at 80° C., and subsequently treated with proteinase K in the same solution for 60 minutes at 56° C. The digested sample was then incubated for 15 minutes at 90° C. ITP was conducted on one sample from each pair of sections by dispensing 200 µL of pre-processed sample mixture, including embedding and FFPE tissue debris, into the sample inlet of a fluidic device. The other section from each pair was extracted using Promega's ReliaPrep FFPE gDNA kit according to manufacturer's protocol. FIG. 24A shows an image of two neighboring ITP channels on a fluidic device with DNA from FFPE samples, labeled with intercalating dye for visualization. Extracted DNA from the samples was quantified with qPCR. FIG. 24B shows the quantified extracted DNA in nanograms (ng) for each of the seven sample pairs. For each pair, the darker left-hand bar shows results for ITP and the lighter right-hand bar shows results for the ReliaPrep kit. The leftmost two sample pairs are human liver samples, and the remaining five sample pairs are human lung samples. For all seven sample pairs, the amount of amplifiable nucleic acids extracted via ITP is significantly higher (typically about 1.5 to 8 times higher amplifiable yields) than the amount of nucleic acids extracted by the ReliaPrep kit.

Example 5—ITP-Based Quantitation of Nucleic Acids

Quantitation of nucleic acids using ITP was tested and compared to qPCR. The comparison was performed over the full range of sample amounts using an RNaseP human reference gene assay (ABI). Standard or calibration curves were generated from 50 qPCR runs (10 replicates each at 5 orders of magnitude concentrations) and were used to quantify qPCR measurement uncertainty for this range of DNA amounts.

DNA was extracted from 4 million Jurkat cells using a standard kit (e.g., Invitrogen PureLink Genomic DNA kit). For on-device ITP, Jurkat cells were lysed off-chip using a pH 12.7 NaOH solution for 2 minutes, quenched to buffered solution at pH 7.5-8 using a solution of hydrochloric acid and Tris base, and then treated with Proteinase K for at pH 8 and 56° C. for 10 minutes.

Figure 14:
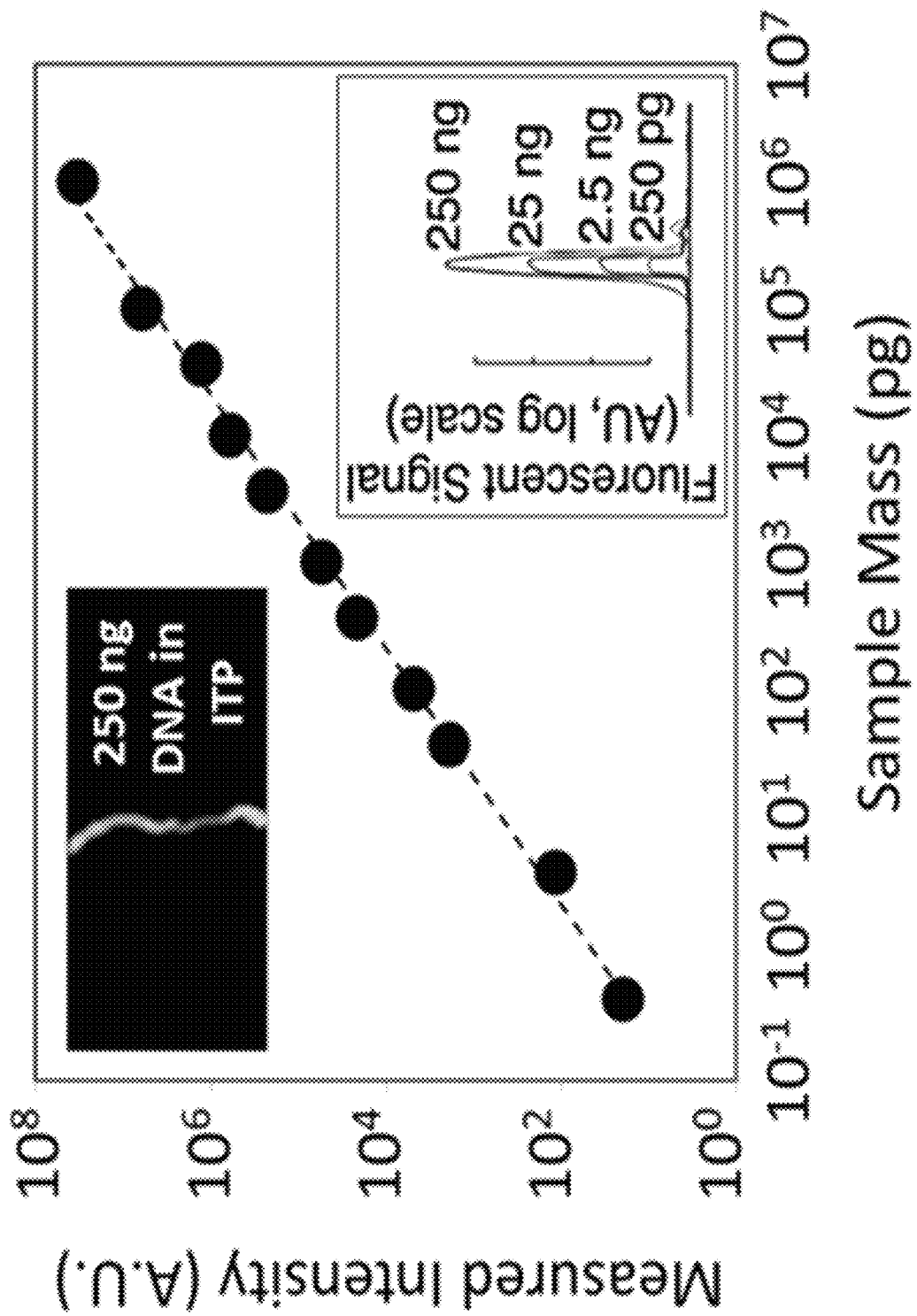
FIG. 14 shows exemplary results of fluorescence-based measurements and quantitation for a titration series of nucleic acids using isotachophoresis.

Pre-purified DNA was processed via ITP and quantified in the ITP channel via fluorescent intensity. The leading electrolyte buffer used for isotachophoresis comprised 88 mM Tris with 44 mM HCl. Trailing electrolyte was loaded into the trailing electrolyte reservoir and comprised 1.2M Tris with 0.3 M Caproic Acid and 0.6 M MOPS. The sample was prepared in a leading electrolyte buffer (sample buffer) comprising 10 mM Tris with 5.6 mM HCl. FIG. 14 shows a titration curve of measured fluorescent intensity from DNA compared to known DNA sample mass, and is linear over seven orders of magnitude, from 0.4 picograms (pg) to about $10^6$ pg. The upper left inset of FIG. 14 shows an image of 250 ng of DNA in an ITP channel. The lower right inset of FIG. 14 shows point detector fluorescent signal intensity on a logarithmic scale for ITP-extracted DNA in an ITP channel, at 250 pg, 2.5 ng, 25 ng, and 250 ng of DNA.

Example 6—Lack of Bias in ITP Extraction and Purification

Figure 4B:
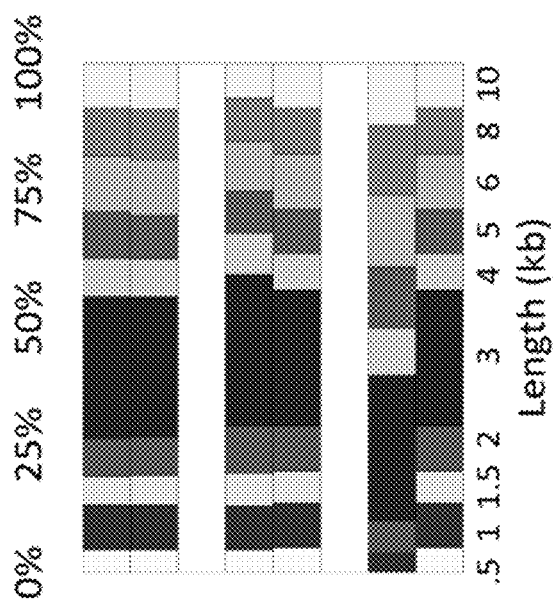
FIG. 4B shows exemplary results for unbiased (e.g., with respect to size or molecular weight), pre- and post-purification, of a DNA molecular weight ladder using isotachophoresis; comparisons to two solid phase column based nucleic acid purification methods are shown.
Figure 4A:
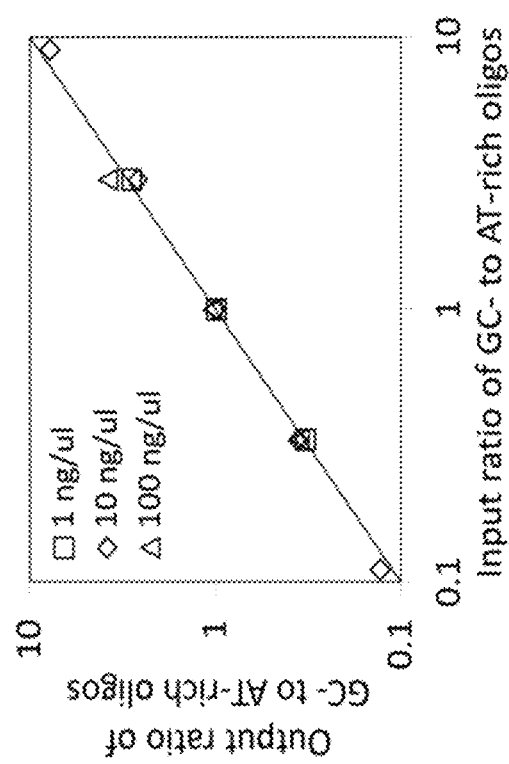
FIG. 4A shows exemplary results for unbiased (e.g., with respect to sequence) extractions of GC-rich and AT-rich synthetic DNA oligonucleotides mixed at sample concentration ratios using isotachophoresis.

Mixtures of synthetic 100 base labeled DNA oligonucleotides with 63% A-T content (37% G-C content, HEX label) and DNA oligonucleotides with 68% G-C content (FAM label) were prepared at three concentrations (1 ng/µL, square data points; 10 ng/µL, diamond data points; 100 ng/µL, triangle data points) and five concentration ratios (overall GC- to AT-rich ratio from 0.1 to 10). Ratios were calculated from fluorescence plate reader measurements obtained pre- and post-processing. FIG. 4A shows a comparison of the output GC- to AT-rich ratio versus the input GC- to AT-rich ratio for ITP processing, demonstrating a lack of bias in the ITP process.

A mixture of oligonucleotides from a 1 kb DNA ladder (New England Biosciences) was measured for length before and after processing, using integrated signals of electropherogram peaks from the Experion 12 k DNA analysis kit (BioRad). Size distribution within the sample before and after processing was compared for on-device ITP (FIG. 4B, top), Qiagen QiaAmp column kit (FIG. 4B, middle), and Invitrogen PureLink column kit (FIG. 4B, bottom). The leading electrolyte buffer used for isotachophoresis comprised 88 mM Tris with 44 mM HCl. Trailing electrolyte was loaded into the trailing electrolyte reservoir and comprised 1.2M Tris with 0.3 M Caproic Acid and 0.6 M MOPS. The sample was prepared in a leading electrolyte buffer (sample buffer) comprising 10 mM Tris with 5.6 mM HCl. For each comparison, the top row shows the size distribution in the recovered output fraction and the bottom row shows the initial size distribution in the sample.

Example 7—Off- or On-Chip Proteinase K Digestion of Cell Lysate Nucleic Acids

Figure 25B:
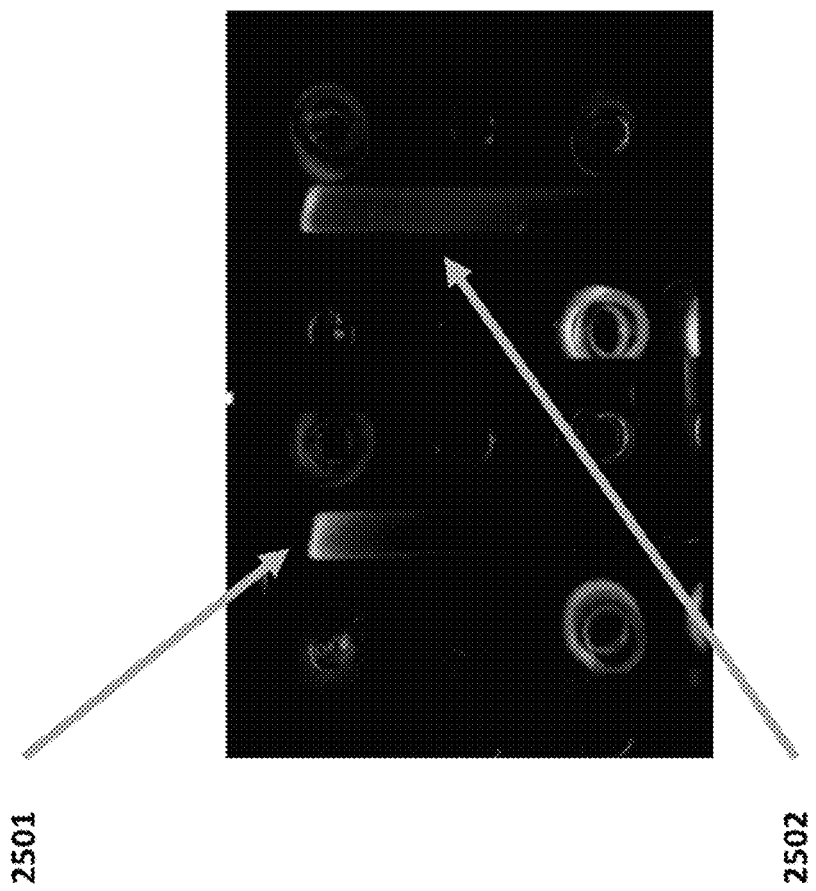
FIG. 25B shows an image of a single channel ITP chip loaded with nucleic acid (RNA extraction and digest from human cells) stained with dye for visualization.
Figure 25A:
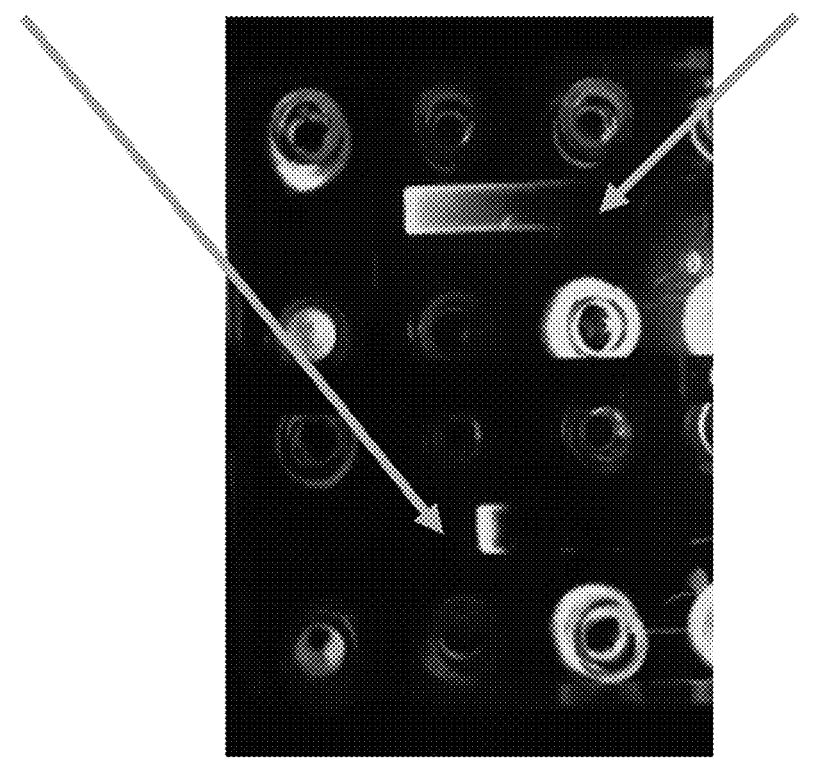
FIG. 25A shows an image of a single channel ITP chip loaded with nucleic acid (RNA extraction and digest from human cells) stained with dye for visualization.

FIG. 25A shows an image of a single channel ITP chip loaded with nucleic acid (RNA extraction and proteolytic digest from human cells) stained with dye for visualization. On the left 2501 is an ITP band from sample processed off-chip prior to loading with 200 μg/mL proteinase K in sample buffer, while on the right 2502 is a sample not processed with proteinase K. The leading electrolyte buffer used for isotachophoresis comprised 100 mM Tris with 50 mM HCl. Trailing electrolyte was loaded into the trailing electrolyte reservoir and comprised 1.8M Tris with 1 M Caproic Acid and 1 M MOPS. The sample was prepared in a leading electrolyte buffer (sample buffer) comprising 10 mM Tris with 5.6 mM HCl. FIG. 25B shows an image of a single channel ITP chip loaded with nucleic acid (RNA extraction and proteolytic digest from human cells) stained with dye for visualization. On the left 2501 is an ITP band from sample processed on-chip 200 μg/mL proteinase K in leading electrolyte, while on the right 2502 is a sample not processed with proteinase K. In both cases, the sample processed with proteinase K exhibits a tighter ITP band, representing nucleic acids not associated with protein (higher effective mobility magnitude), while the sample not processed with proteinase K exhibits a smeared band, representing nucleic acid associated with variable amounts of protein (lower effective mobility magnitude).

Figure 26B:
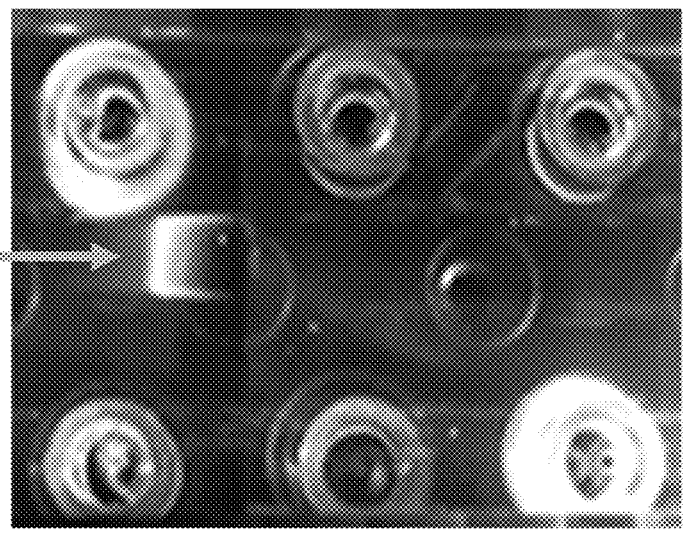
FIG. 26B shows an image of a total nucleic acid ITP band in a chip channel during purification.
Figure 26A:
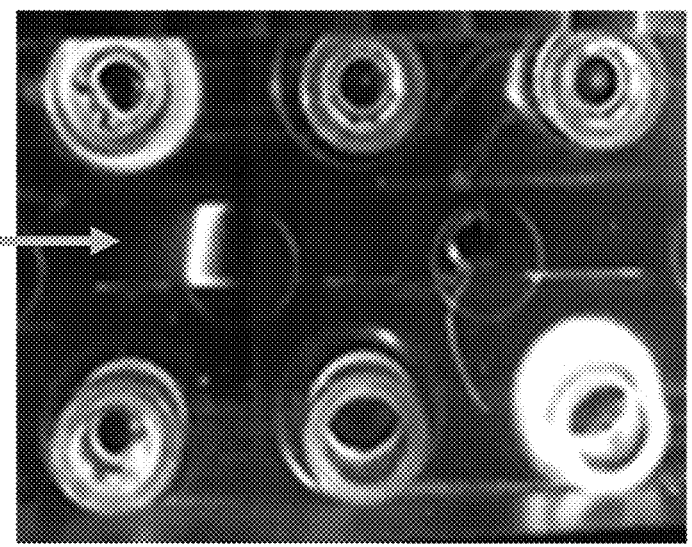
FIG. 26A shows an image of an RNA ITP band in a chip channel during purification.
Figure 26C:
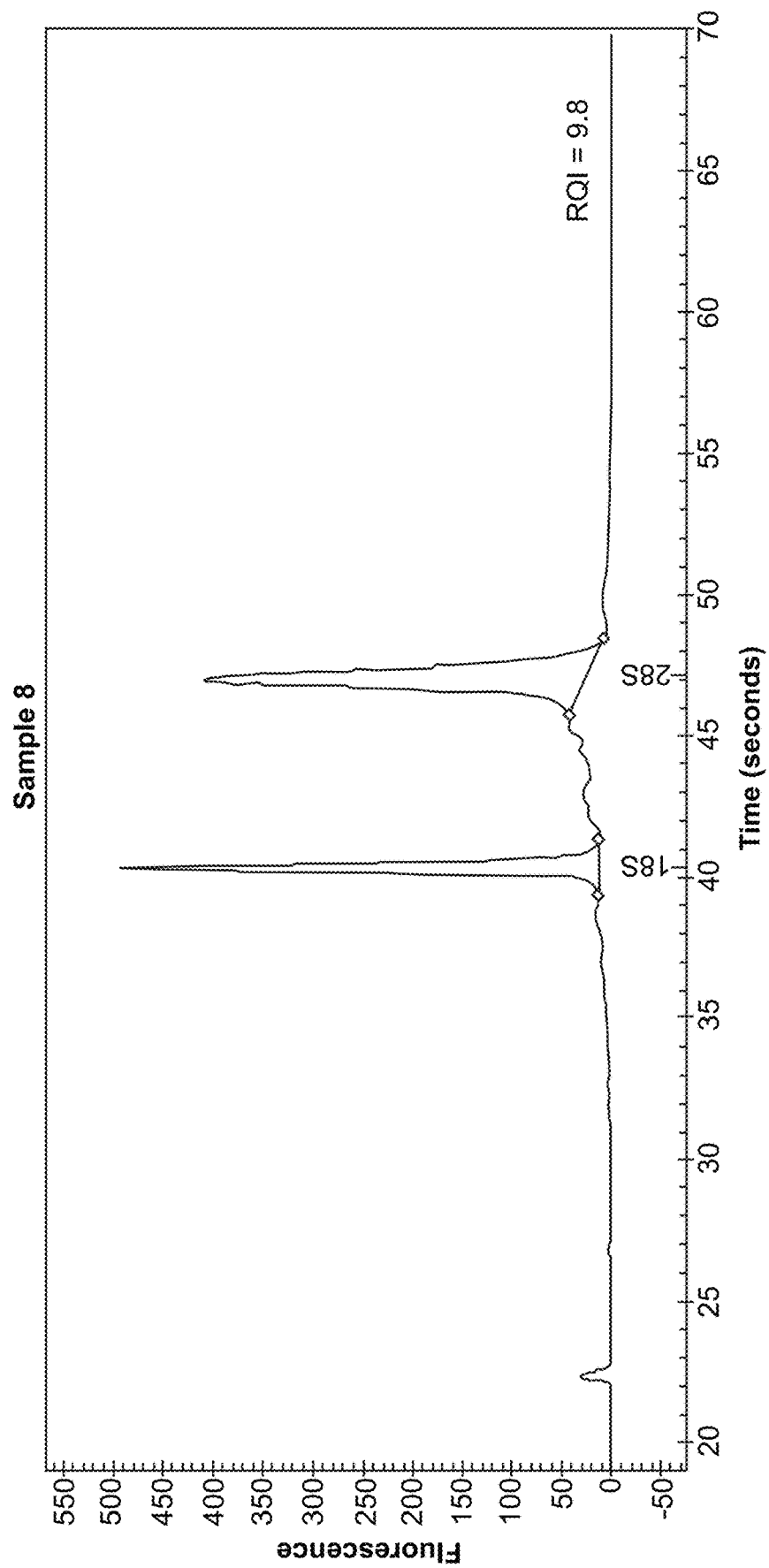
FIG. 26C shows a graph of an RNA quality electropherogram for the sample shown in FIG. 26A.
Figure 26D:
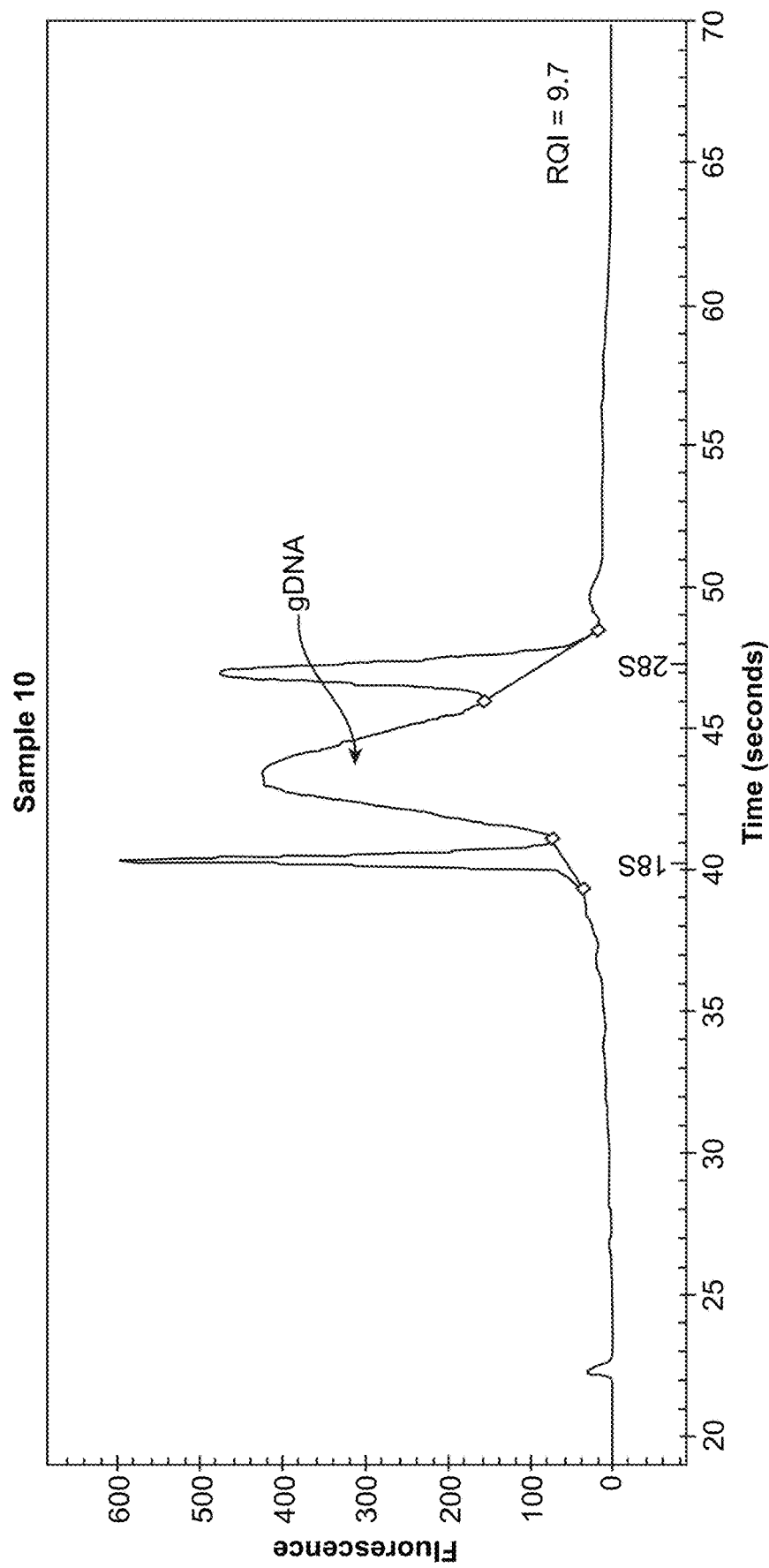
FIG. 26D shows a graph of an RNA quality electropherogram for the sample shown in FIG. 26B.

Example 8—RNA Extraction from Human Cells Using Off-Chip Lysis and On-Chip ITP Purification FIG. 26A shows an image of an RNA ITP band 2601 in a chip channel during extraction and purification of RNA from cell lysate (Jurkat cells) with DNA digested. FIG. 26B shows an image of a total nucleic acid ITP band 2602 in a chip channel during extraction and purification of RNA from cell lysate (Jurkat cells) without DNA digested. The leading electrolyte buffer used for isotachophoresis comprised 100 mM Tris with 50 mM HCl. Trailing electrolyte was loaded into the trailing electrolyte reservoir and comprised 1.8M Tris with 1 M Caproic Acid and 1 M MOPS. The sample was prepared in a leading electrolyte buffer (sample buffer) comprising 10 mM Tris with 5.6 mM HCl. FIG. 26C and FIG. 26D show graphs of RNA quality electropherograms (measured using the BioRad Experion) for the samples shown in FIG. 26A and FIG. 26B, respectively. Cell lysis and DNase digestion were performed in a buffered solution at pH 8 containing 7M urea, 2M thiourea, and a non-ionic surfactant as discussed herein. These results demonstrate the preparation of high quality RNA with or without DNA digestion.

Example 9—Extraction of Whole Lysed Blood Using ITP and 200 μl Chip Device

Figure 27A:
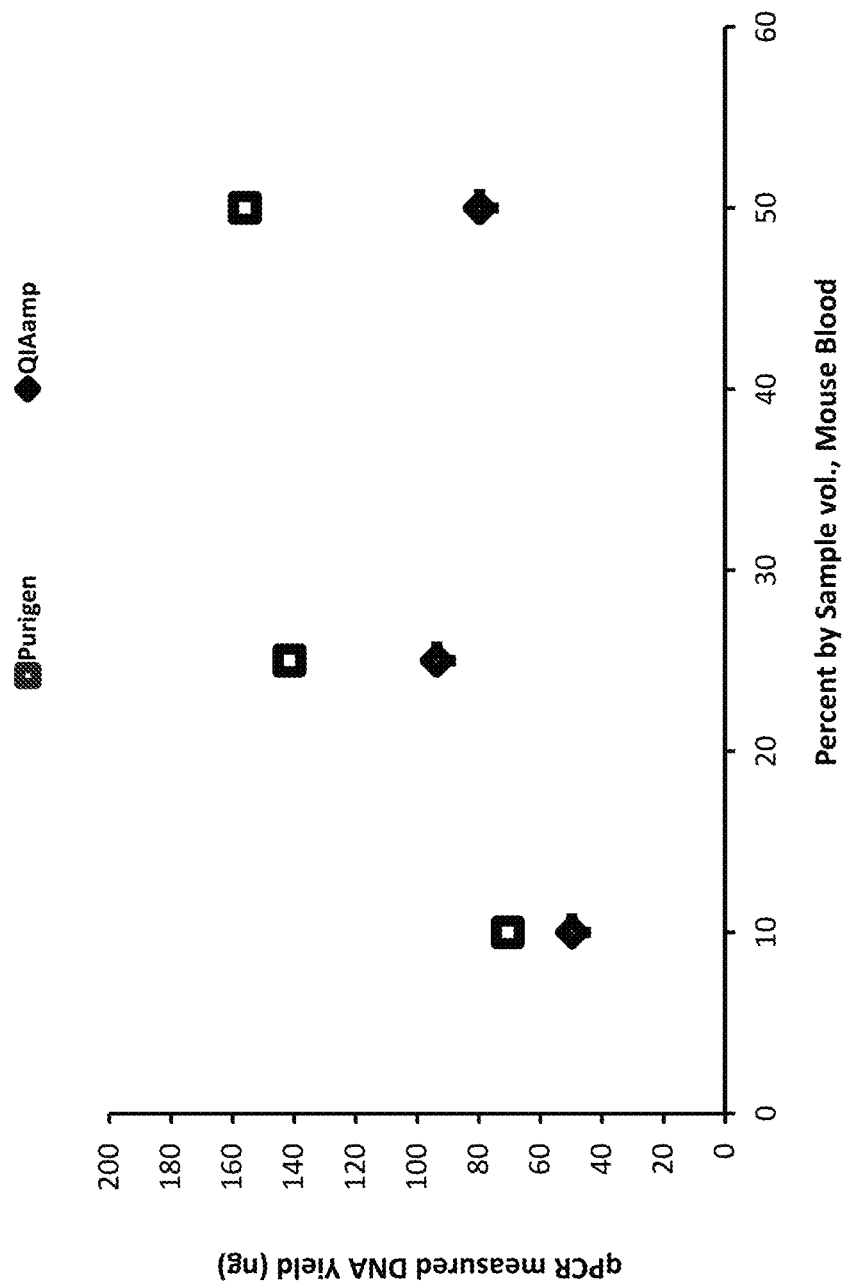
FIG. 27A shows results of DNA yield (ng) for ITP (square) compared to column (diamond, Qiagen QiaAmp) extraction of whole mouse blood as a function of percent by volume of whole blood in starting sample.
Figure 27B:
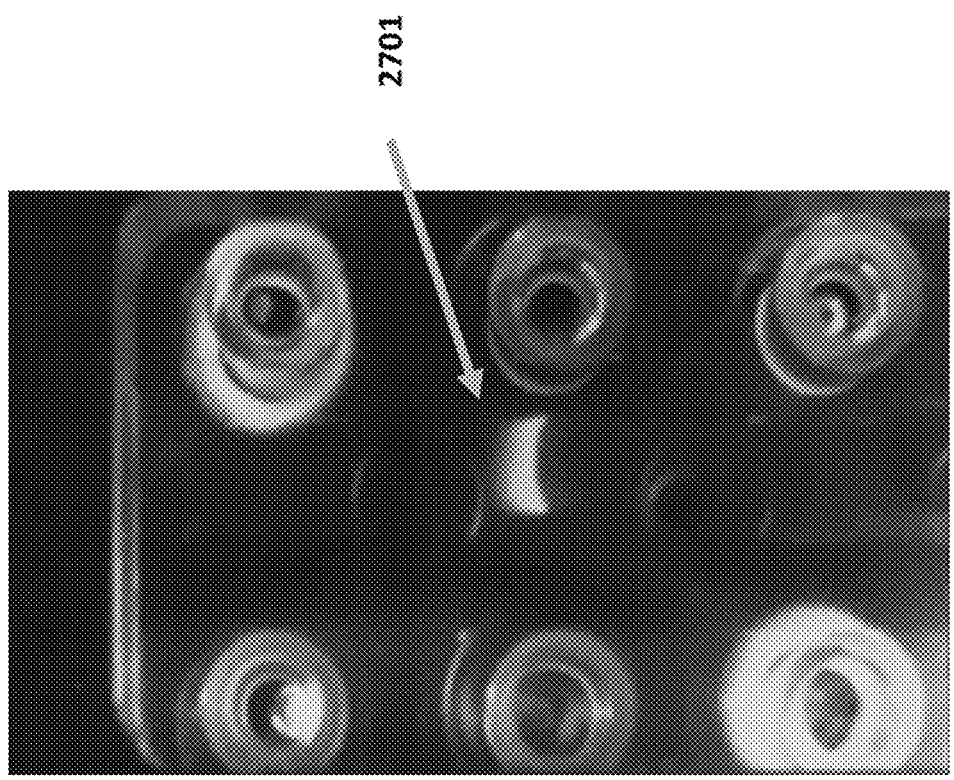
FIG. 27B shows an image of total nucleic acid in an ITP band during ITP purification of lysed whole mouse blood on a chip.

FIG. 27A shows results of DNA yield (ng) for ITP (square) compared to column (diamond, Qiagen QiaAmp) extraction of whole mouse blood as a function of percent by volume of whole blood in starting sample. FIG. 27B shows an image of total nucleic acid in an ITP band 2401 during ITP purification of lysed whole mouse blood on a chip. The leading electrolyte buffer used for isotachophoresis comprised 260 mM Tris with 130 mM HCl. Trailing electrolyte was loaded into the trailing electrolyte reservoir and comprised 2.1 M Tris with 0.5 M Caproic Acid and 0.7 M MOPS. The sample was prepared in a leading electrolyte buffer (sample buffer) comprising 10 mM Tris with 5.6 mM HCl.

Figure 27C:
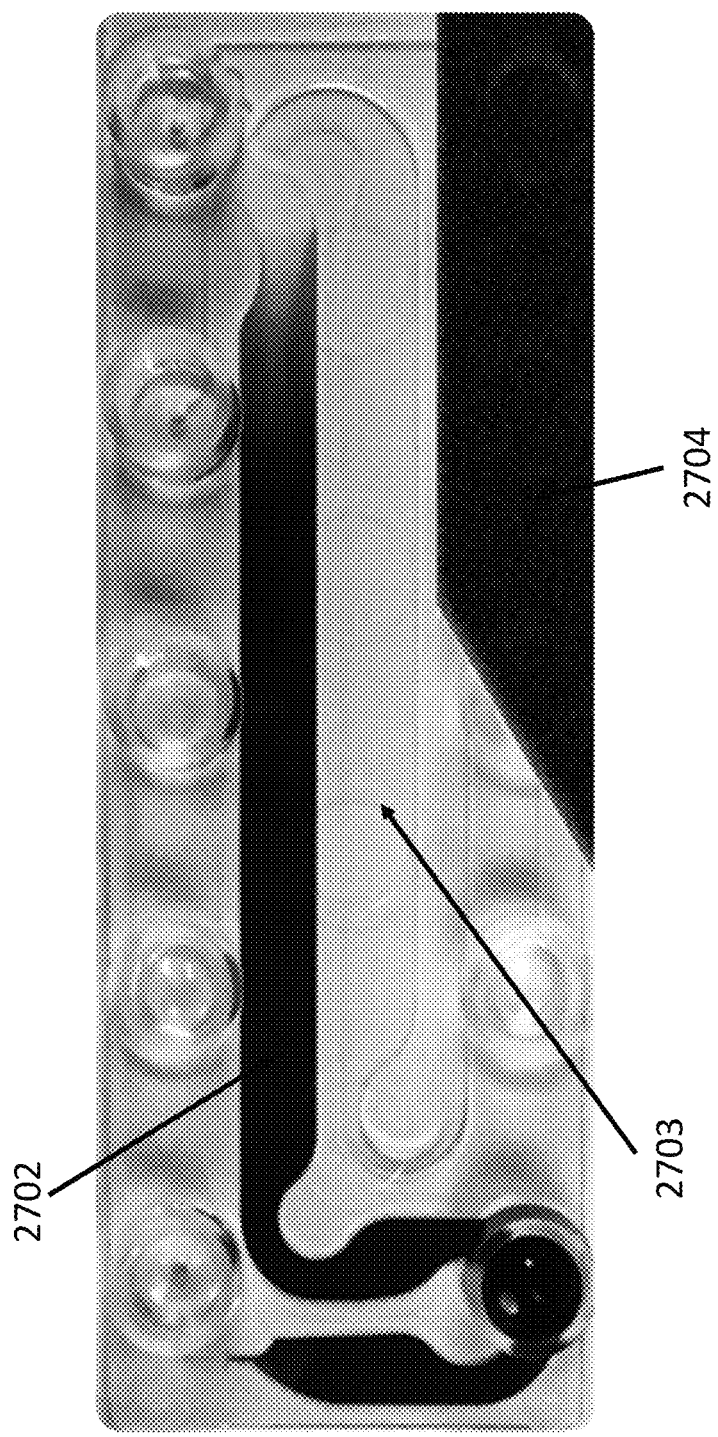
FIG. 27C and FIG. 27D show white light and fluorescence overlay images of ITP chip channels showing physical separation of heme in the sample/leading electrolyte channel from the elution channel and reservoir, before and after ITP purification of 50% by volume whole blood lysate. Nucleic acid is stained with green dye for visualization in elution well.
Figure 27D:
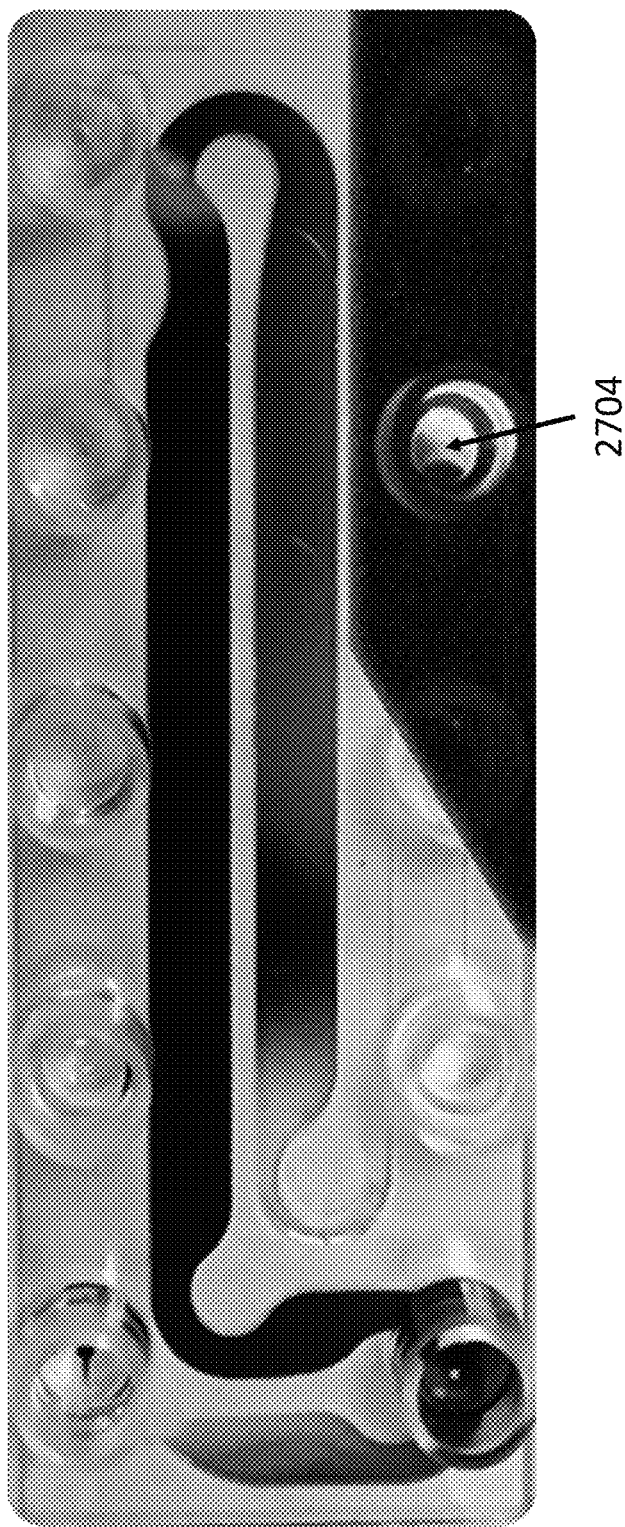
Figure 27E:
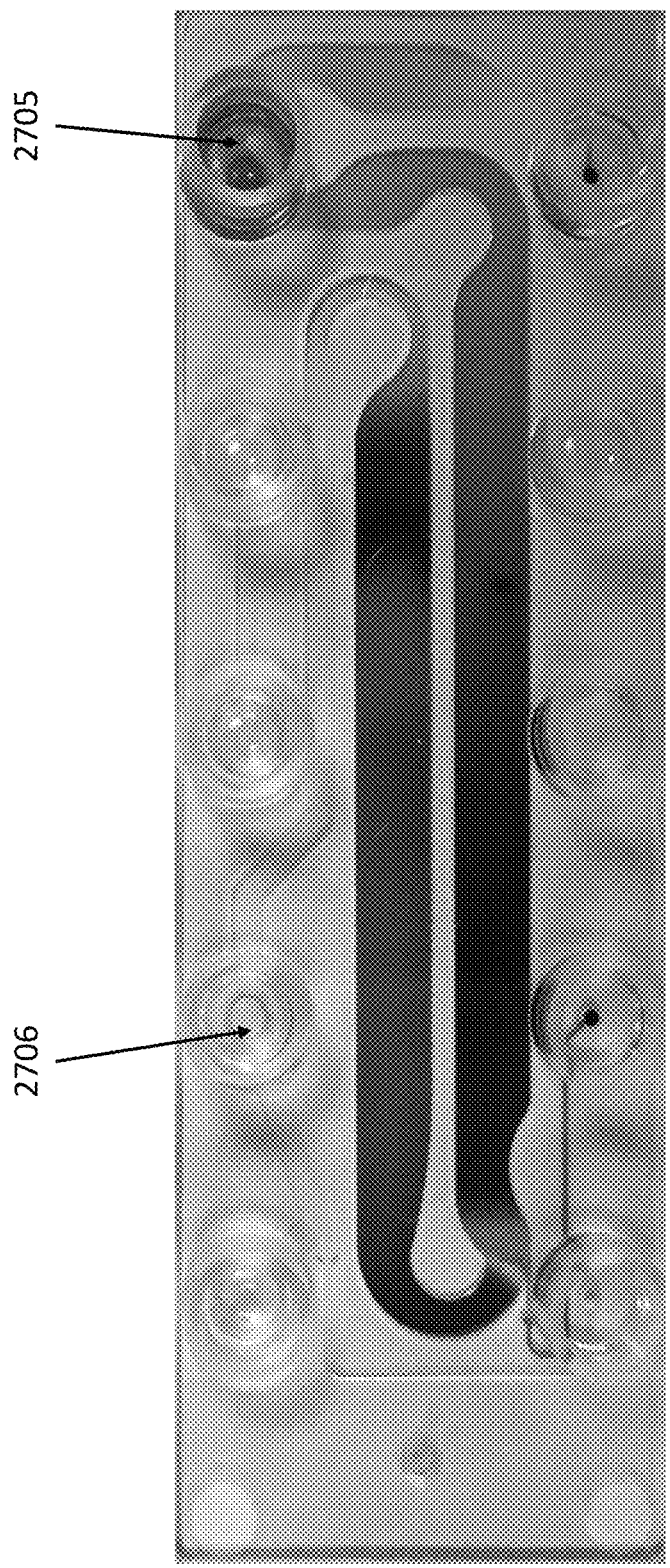
FIG. 27E shows an chip post ITP purification (50% by volume blood).
Figure 27F:
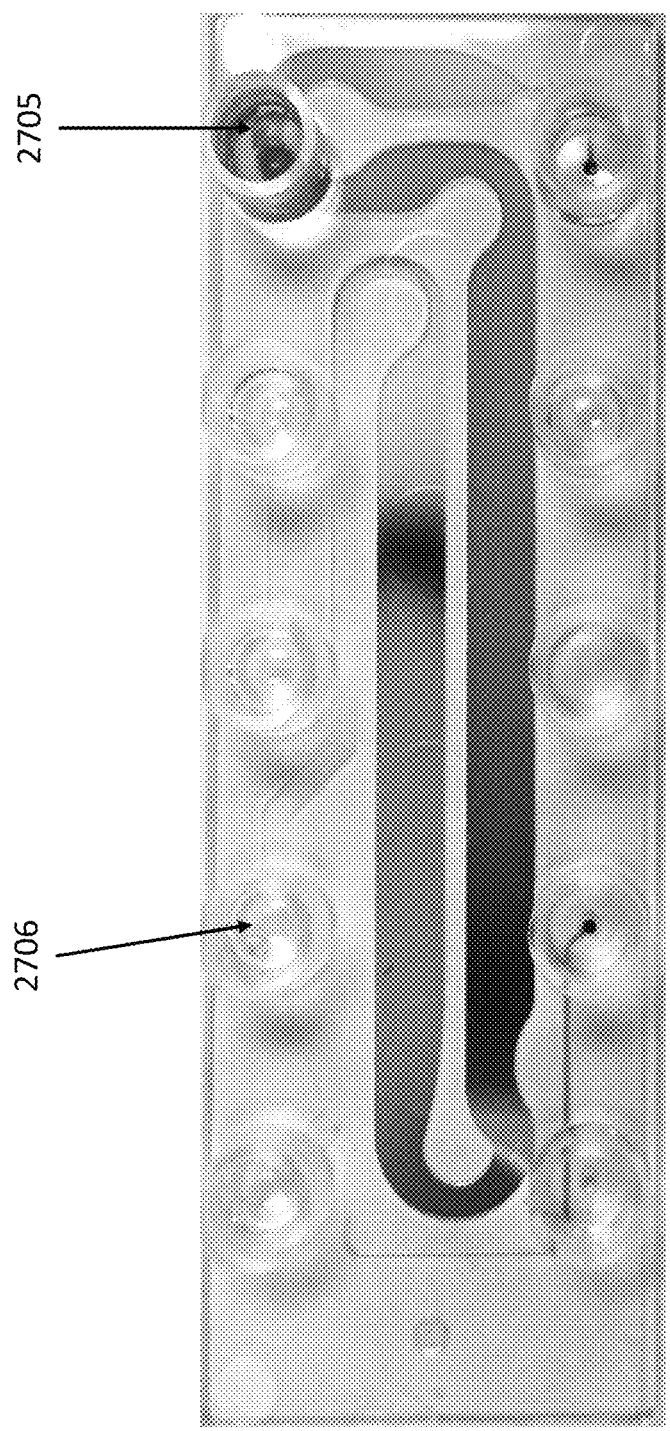
FIG. 27F shows an chip post ITP purification (25% by volume blood).

FIG. 27C and FIG. 27D show white light and fluorescence overlay images of ITP chip channels showing physical separation of heme from the blood sample in the sample channel and leading electrolyte (or separation) channel 2703 from the elution channel and reservoir 2704, before and after ITP purification of 50% by volume whole blood lysate 2702. The purified nucleic acid is stained with green dye for visualization in elution well. FIG. 27C shows the chip before ITP (blood lysate and ITP buffers loaded in chip; pure buffer and no DNA in elution well). FIG. 27D shows the chip after ITP (blood lysate and ITP buffers loaded in chip; pure buffer and DNA in elution well). FIG. 27E shows the chip post ITP purification, with a white light image of the chip channel showing physical separation of heme from the blood sample in the sample well 2705 and leading electrolyte (or separation) channel from the elution channel and reservoir 2706 in single channel chip device (50% by volume blood). FIG. 27F shows the chip post ITP purification, with a white light image of the chip channel showing physical separation of heme from the blood sample in the sample well 2705 and leading electrolyte (or separation) channel from the elution channel and reservoir 2706 in single channel chip device (25% by volume blood).

Figure 28:
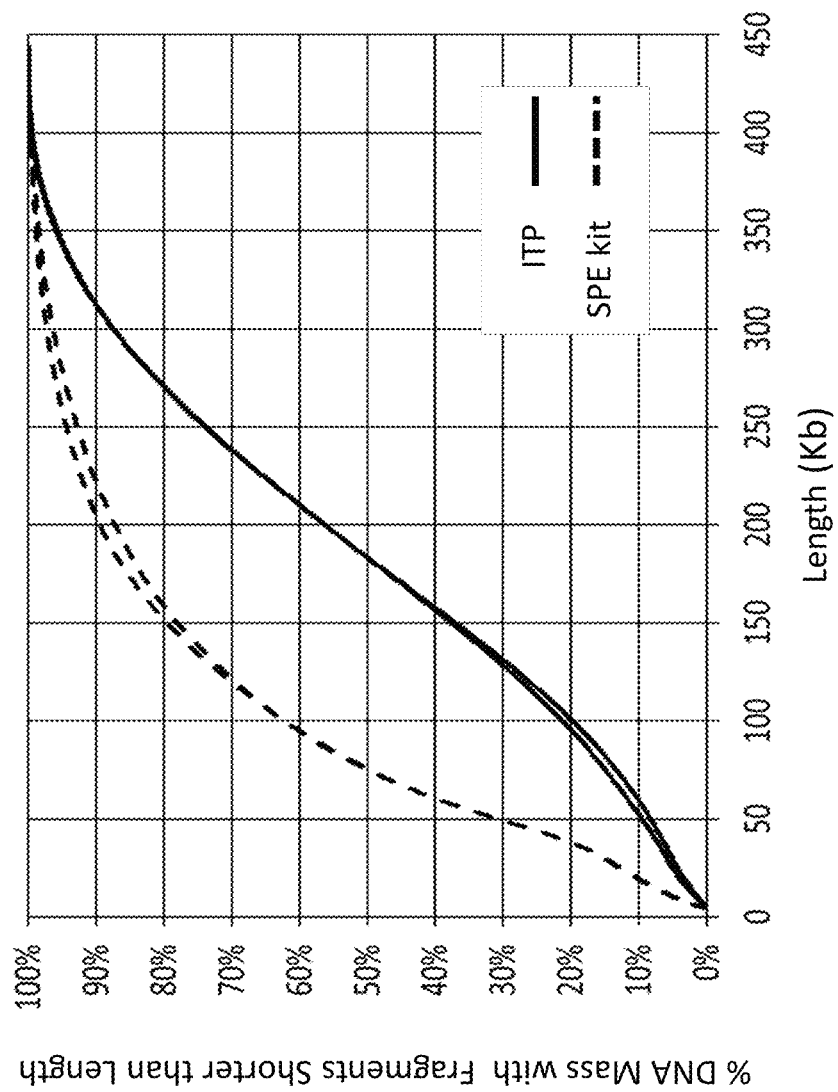
FIG. 28 shows results of high molecular weight DNA purification for ITP compared to solid phase extraction.

Example 10—Extraction of High Molecular Weight DNA from Cultured Human Cancer Cells Using Off-Chip Lysis and On-Chip ITP Purification FIG. 28 shows results of high molecular weight DNA purification for ITP (solid line) compared to solid phase extraction (SPE; dashed line, Qiagen MagAttract) of cultured human Jurkat cells as the percentage of DNA mass in the purified sample having fragments shorter than a given length (Kb). Cell lysis was performed off-chip in a buffered lysis solution containing 10 mM Tris with 5.6 mM HCl and 0.2% v/v IGEPAL CA-630. The buffered solution was configured to lyse the cells and reduce mechanical disruption of the DNA during lysis. Cell pellets were lysed in the lysis solution and mixed gently with inversion and slow-speed (automated pipettor), wide-bore tip pipetting (e.g. Rainin 200 μl wide bore tip) to aid in homogenization of the lysate. A final concentration of 500 μg/ml Proteinase K was added to the lysate and incubated for 20 min at 60° C. ITP was performed on the lysate with 88 mM Tris with 44 mM HCl as the leading electrolyte and 1.2 M Tris with 0.3 M caproic acid and 0.6 M MOPS as the trailing electrolyte. ITP-based purification led to 2 to 3 times greater mean DNA fragment lengths as compared to the bead-based PSE kit, in part due to reduced mechanical shearing of the DNA during isotachophoresis compared to SPE due to the lack of a solid phase component or high shear forces (e.g. from centrifugation) during the extraction process. The ITP purified DNA had an average DNA length of about 175 Kb (i.e. 50% of the DNA mass contained DNA fragments greater than about 175 Kb) compared to SPE purification which yielded DNA with an average length of about 75 Kb. More than 60% of the mass of the DNA extracted by ITP contained an average fragment length greater than 150 kB. ITP produced at least about three times as many DNA fragments with a size of at least 150 kB than the SPE method.

Example 11—Closing of Channels Using Mechanical Member

Figure 29A:
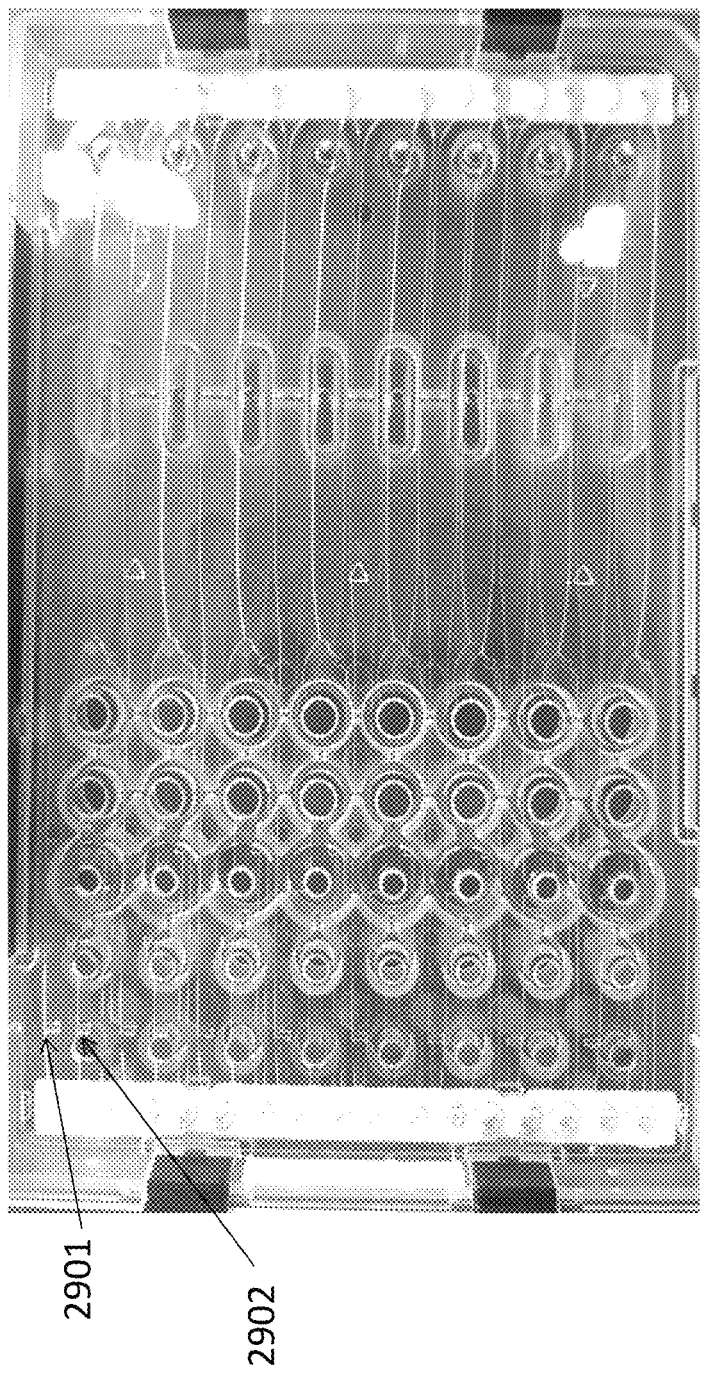
FIG. 29A shows a fluidic device comprising 8 closed channels.
Figure 29B:
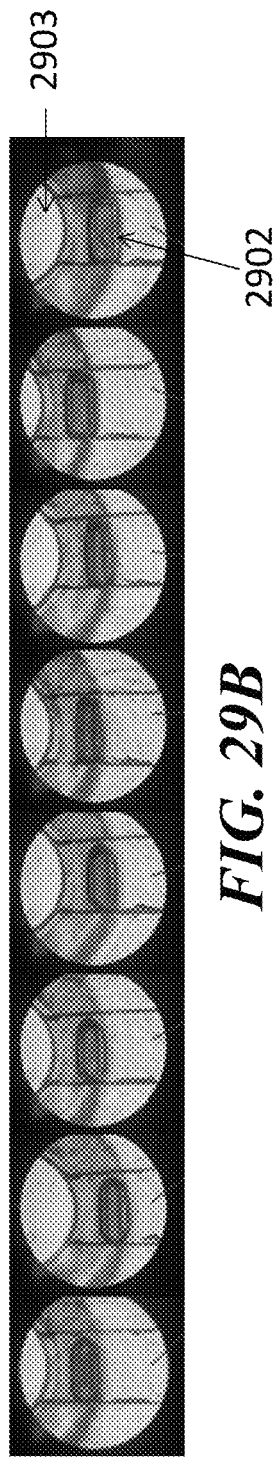
FIG. 29B shows a zoomed in microscopic view the second channel closure location adjacent the elution reservoir of each of the channels.
Figures 29C, 29D:
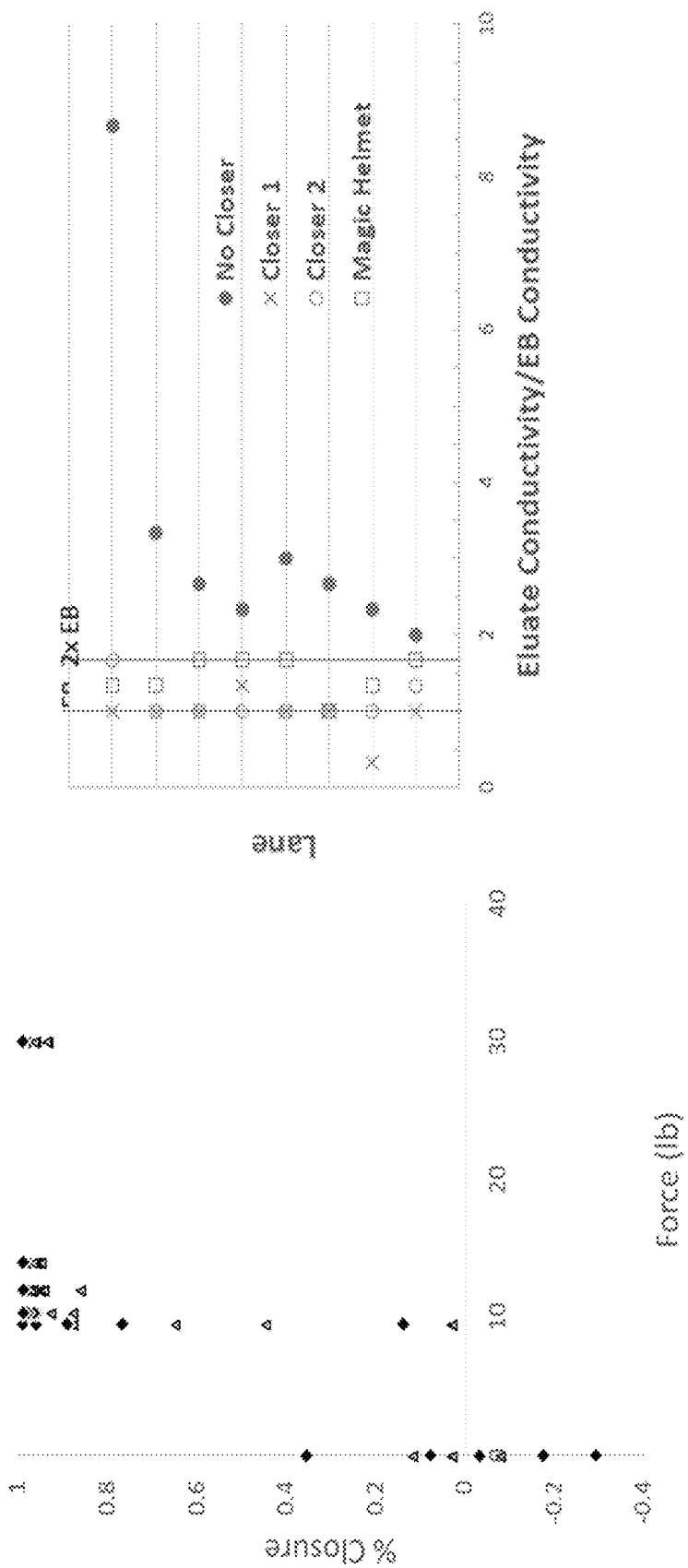
FIG. 29C shows the percent closure calculated as a function of force applied to the fluidic device.
FIG. 29D shows the results of conductivity measurements of channel closure.

FIG. 29A shows a fluidic device comprising 8 closed channels. Each channel was permanently closed at two locations 2902, 2902 as shown in FIG. 12B by applying a temperature of 150° C. and a pressure of 30 pounds (across all 16 locations; i.e. 1.875 pounds per tooth) to the device for 1 second with the comb-like mechanical member of FIG. 12A. FIG. 29B shows a zoomed in microscopic view the second channel closure location 2902 adjacent the elution reservoir 2903 of each of the channels. FIG. 29C shows the percent closure calculated as a function of force applied to the chips. The extent of channel closure was assessed without fluid loaded into the channel. Closure was measured by applying a constant pressure and measuring air flow rate through the channel. Five chips were assessed. Diamonds indicate closure data obtained from the first close location 2901 and triangles indicate closure data obtained from the second close location 2902. Without a force applied, the channels were open or mostly open. A force of 10 pounds across the device was sufficient close most of the channels while a force of 30 pounds across the device closed all or nearly all of the channels repeatedly. FIG. 29D shows the results of conductivity measurements with a conductivity meter to determine if channels are closed. The chip reservoirs and channels were loaded with ITP buffers as described in FIGS. 12A-12D or FIG. 15 (leading electrolyte, a high concentration of leading electrolyte for buffering, trailing electrolyte, elution buffer, a high concentration of elution buffer for buffering, and sample buffer without a biological sample). The channels were closed using the mechanical member and then the fluid in the elution reservoir 2903 was pipetted out of the reservoir and collected. The conductivity of the elution fluid was measured and compared to measurement of the conductivity of original (pre-loaded) elution buffer (same buffer initially loaded in the chip). It was expected that the conductivity of measured fluid would be the same as the original elution buffer if channel closure was sufficient to provide fluidic resistance at the first channel close location 2901 between the elution reservoir 2903 and the channel and at the second channel close location 2902 within the channel connecting the elution reservoir 2903 to the elution buffering reservoir (via the elution buffering channel; not shown). For a fully closed channel, the conductivity of the eluted volume (without performing ITP) can be equal to the conductivity of the elution buffer alone, indicating no transfer of fluids or ions during collection. Four situations were tested—without a closer (fully open channels), with the first close location 2901 closed (partially closed), with both locations 2901, 2902 closed (fully closed), or with every reservoir but the elution reservoir sealed with a film ("Magic Helmet"). In the Magic Helmet situation, the channels were not physically deformed by the mechanical member but were instead sealed with a film applied by the operator in order to increase resistance to fluid flow. Elution volumes from partially closed channels showed increased conductivity compared to fully closed channels. Sealing of the non-elution reservoirs with the Magic Helmet were increased compared to fully closed channels as well but remained generally less than the conductivity of a 2× elution buffer. These conductivity levels were, however, much lower than those obtained from eluates without channel closure.

Example 12—Voltage Measurement and End-of-Run Triggering

Figure 30:
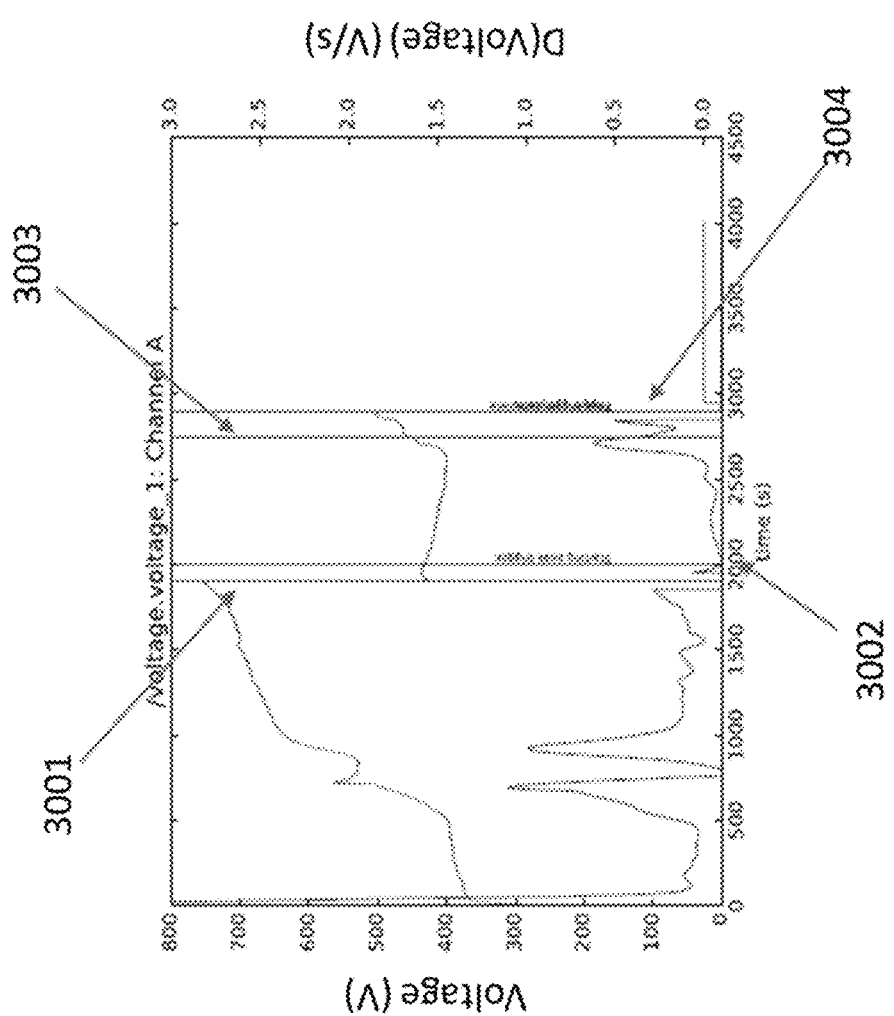
FIG. 30 a graph of voltage measurement and voltage derivative over time during an ITP run.

FIG. 30 shows an exemplary example using measurement of the driving voltage to trigger a reduction or removal of an electric current in one of the channels. A fluidic device comprising 8 channels was loaded with ITP buffers (leading electrolyte buffer comprising 88 mM Tris with 44 mM HCl, a high concentration of leading electrolyte for buffering, trailing electrolyte buffer comprising 1.2 M Tris with 0.3 M caproic acid and 0.6 M MOPS, an elution buffer comprising 10 mM Tris with 5.6 mM HCl, a high concentration of elution buffer for buffering) in each of the channels. A sample comprising 50,000 immortalized human cells lysed using the methods described herein was prepared and loaded into each of the channels. A pre-elution isotachophoresis separation was performed by driving 900 µA per channel through the channel for 1900 seconds. After 1900 seconds 3001, the current was reduced and 250 µA was applied to each channel to drive the nucleic acids into the elution reservoir. 100 seconds after starting isotachophoresis, signal processing using the voltage on the driving electrode as the data source was started 3002. The top line shown represents the voltage and the bottom line represents the derivative of the voltage. Two triggers were used to change the driving current (corresponding to triggers 1 and 4 described in FIG. 16, at locations C and D, respectively). Low-conductivity ions (e.g. sample ions or trailing electrolytes) entering the elution reservoir or channel can be detected by monitoring for peaks or maximums in the derivative of the voltage. The current was turned on at a first trigger point (trigger 1) 3001 to direct nucleic acids into the channel comprising elution buffer and signal processing 3002 was started shortly thereafter. A first increase was detected at trigger point 3 3003 as the nucleic acids entered the elution reservoir and a second increase was detected at trigger point 4 3004 as the trailing electrolytes began to enter the elution reservoir. The current was removed following detection of the second increase at trigger point 4 3004 so as to position or isolate the sample nucleic acids in the elution well.

Example 13—Temperature Sensing and End-of-Run Triggering

FIG. 21 shows exemplary temperature measurement results using an infra-red thermal sensor to trigger a reduction or elimination of an electric current in one of the channels. A fluidic device comprising 8 channels was loaded with ITP buffers (leading electrolyte buffer comprising 88 mM Tris with 44 mM HCl, a high concentration of leading electrolyte for buffering, trailing electrolyte buffer comprising 1.2 M Tris with 0.3 M caproic acid and 0.6 M MOPS, an elution buffer comprising 10 mM Tris with 5.6 mM HCl, a high concentration of elution buffer for buffering) in each of the channels. A sample comprising 50,000 immortalized human cells lysed using the methods described herein was prepared and loaded into each of the channels. A pre-elution isotachophoresis separation was performed by driving 900 µA per channel through the channel for 1900 seconds. After 1900 seconds, the current was reduced and 250 µA was applied to each channel to drive the nucleic acids into the elution reservoir. 100 seconds after starting isotachophoresis, signal processing using temperature data collected by a TMP007 infrared temperature sensor. The temperature was detected at location 2105 in the elution channel near the elution reservoir 2106, centered approximately 4.5 mm from the elution well 2106. The temperature sensor was place approximately 1 mm to 3 mm below the bottom surface of the fluidic channel. The temperature sensor may be centered approximately 4.5 mm from the elution reservoir 2106 (with edges at about 3.55 mm to about 5.45 mm from the elution reservoir). The temperature sensor was configured to detect temperature changes due to electrophoretic Joule heating in the channel. Electrophoretic joule heat dissipation per channel volume may be inversely proportional to conductivity at a constant current. During isotachophoresis, lower-conductivity ions (trailing electrolytes) may displace higher conductivity ions (leading electrolytes) as the ITP zone moves through the channel. The temperature sensor may sense the ITP zone moving past the detection location 2105, and the displacement of ions as the ITP zone moves, as a rise in temperature within the channel at the detection location.

The top line shows the temperature at the detection location 2105 and the bottom line shows the derivative of the temperature. The temperature was monitored in real-time for high derivatives in order to detect lower-conductivity buffer zones. The vertical lines indicate when key events occurred during monitoring. From left to right, the first line 2101 indicates the time at which the current was turned on and the second line 2102 indicates the start of signal processing shortly thereafter. The third line 2103 indicates the first detection of an increase in the derivative of the temperature, and the fourth line 2104 indicates the second detection of an increase in the derivative of the temperature, at which point the current was stopped and the voltage was disabled so as to land the voltage in the reservoir and position or isolate the nucleic acids in the elution reservoir.

Example 14—Simultaneous ITP in an 8-Channel Fluidic Device

Figure 31A:
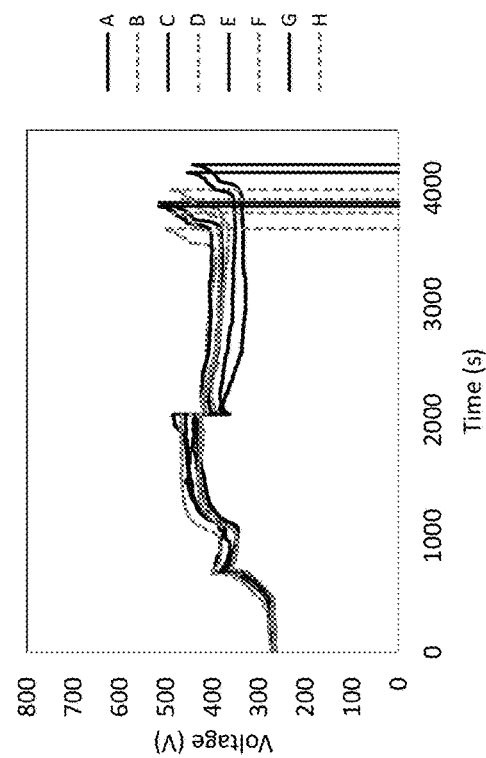
FIG. 31A shows a micrograph of ITP bands with focused DNA in each of 8 samples in the sample channel region of the device.
Figure 31B:
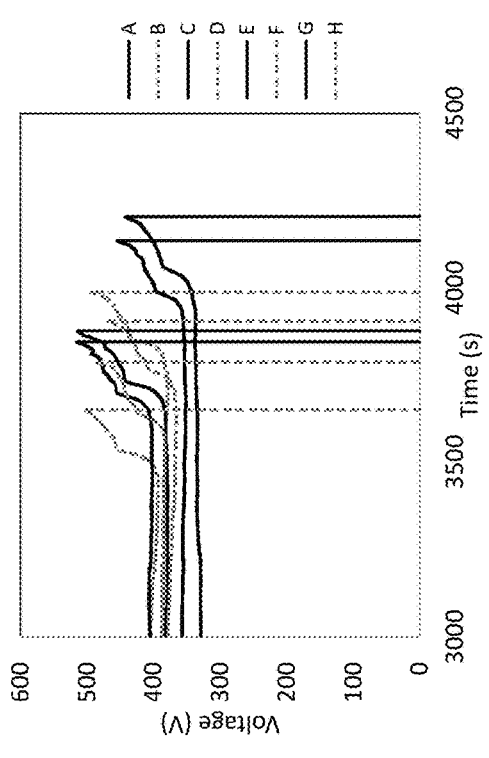
FIG. 31B shows independent voltage signal data at fixed currents for each of the 8 channels over time.
Figure 31C:
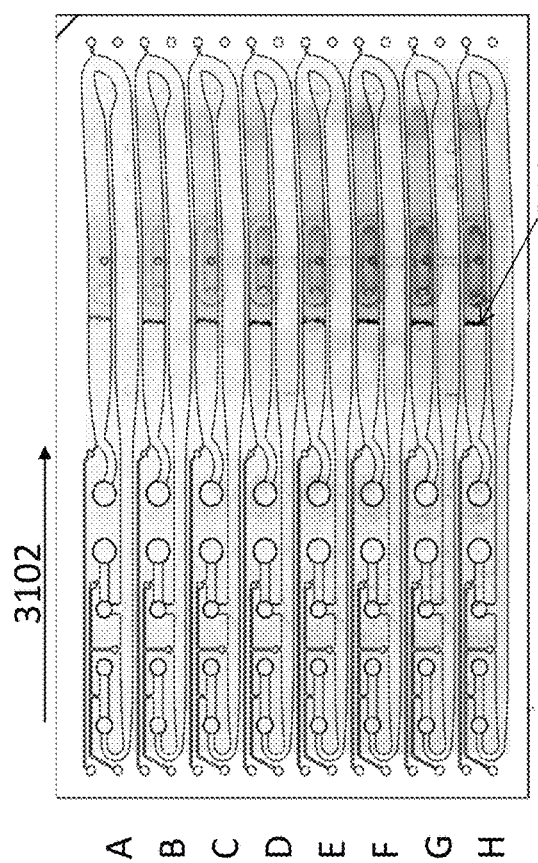
FIG. 31C shows a micrograph of the same 8 ITP bands with focused DNA from the samples eluted in the elution reservoir.
Figure 31D:
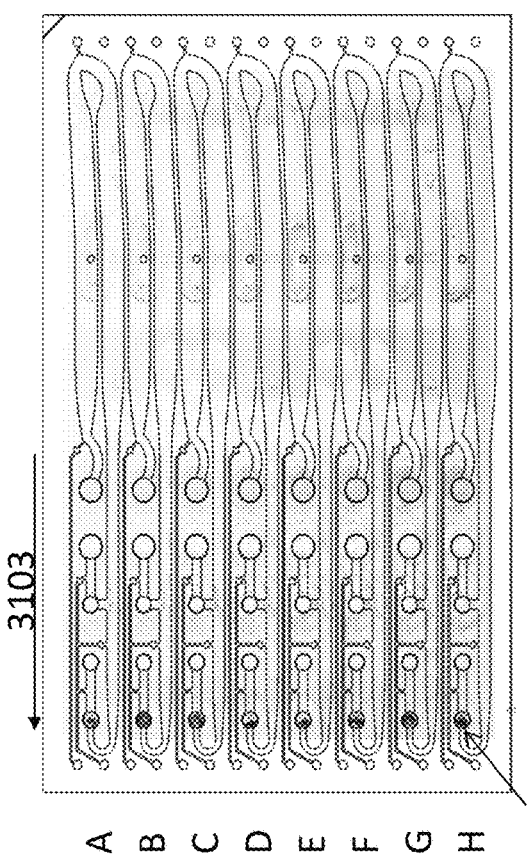
FIG. 31D is a magnified section of the voltage tracing (monitoring) used for triggering shown in FIG. 31B.

FIG. 31A, FIG. 31B, FIG. 31C, and FIG. 31D show the results of simultaneously performing isotachophoresis in 8 channels of a fluidic device. DNA was extracted from cell culture lysate using a bench top controller device to automate isotachophoresis in a monolithic, 8-channel fluidic device. Leading electrolyte buffer containing 88 mM Tris with 44 mM HCl and 0.002% Tween 20 was loaded into the leading electrolyte reservoir of each channel. Trailing electrolyte comprising 1.2M Tris with 0.3 M Caproic Acid and 0.6 M MOPS with 0.002% Tween 20 was loaded into the trailing electrolyte reservoir of each channel. The sample for each channel was prepared in a second leading electrolyte buffer (e.g. sample buffer) comprising 10 mM Tris with 5.6 mM HCl with 0.002% Tween 20. Each sample comprised a cell lysate. The total number of human COLO 320 cells per sample represented 100,000 diploid genome equivalents. Cells were pelleted and lysed off-chip in a lysis solution comprising 40 mM NaOH for 2 minutes and subsequently quenched at a 1:1 volume ratio with a buffered acidic solution to bring the final cell lysate sample to 10 mM Tris with 5.6 mM HCl and 20 mM NaCl at pH 8. Proteinase K was added to a final concentration of 400 µg/ml within the cell lysate sample volume. Four of the eight samples were treated with RNase A at a final concentration of 200 µg/ml and allowed to stand at room temperature for 2 minutes. All eight samples were then incubated for 10 minutes at 56° C. The lysed samples were then brought to room temperature and loaded into the separate eight sample reservoirs/channels on the microfluidic device, denoted by channels A through H, in preparation for isotachophoresis. The four samples that were not treated with RNase A were loaded into channels B, D, F and H. The four samples treated with RNase A were loaded into channels A, C, E, and G. Samples treated with RNase A contained additional buffering ions to enable optimal RNase activity, and therefore represented higher ionic strength or higher conductivity samples that, under fixed current (ITP conditions), resulted in different voltage data traces than the samples not treated with RNase. The independent electrical circuit control of channels A through H enabled voltage signal and feedback control for automated control and end-run triggering for each of the different channels of the device. FIG. 31A shows a micrograph of ITP bands with focused DNA 3101 in each of the 8 samples in the sample channel region of the device. The ITP band of DNA 3101 migrates within the channel in response to an applied electric field. The ITP band first travels away from the trailing electrolyte reservoir in the direction indicated by arrow 3102. The ITP band 3101 then traverses the 180° low-dispersion turn and continues through the channel towards the elution reservoir in the opposite direction (with respect to the chip) 3103 in response to the applied electric field. FIG. 31B shows independent voltage signal data at fixed currents for each of the 8 channels over time. FIG. 31C shows a micrograph of the same 8 ITP bands with focused DNA 3101 from the samples eluted in the elution reservoir by independently controlled end-of-run voltage based triggering (this image represents the end of the run with the electrical field automatically shut off). FIG. 31D is a magnified section of the voltage tracing (monitoring) used for triggering shown in FIG. 31B. The electric current of each channel was independently applied to the channel and the voltage of each channel was independently monitored in order to trigger a change (in this case cessation) in the electric field applied to each channel independently of every other channel.

As used herein, the term "or" means "and/or" unless stated otherwise.

The term "about" as used herein, unless otherwise indicated, refers to a value that is no more than 10% above or below the value being modified by the term. For example, the term "about −20° C." means a range of from −22° C. to −18° C. As another example, "about 1 hour" means a range of from 54 minutes to 66 minutes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It can be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A microfluidic device comprising one or more fluidic paths, wherein at least one of the fluidic paths comprises:
   a branched fluidic channel comprising a loading section and an isotachophoresis ("ITP") section wherein the ITP section comprises a leading electrolyte branch and an elution branch, meeting at a branch point;
   wherein:
   (a) the loading section comprises:
      (1) a trailing electrolyte well fluidically connected to a sample input region of the fluidic channel; and (2) a sample input well fluidically connected to the sample input region of the fluidic channel;

(b) a first capillary barrier is positioned between the sample input region of the fluidic channel and the ITP section; and (c) in the ITP section, (i) the leading electrolyte branch comprises a leading electrolyte well fluidically connected to the fluidic channel; and (ii) the elution branch comprises a sample elution well fluidically connected to the fluidic channel.

2. The microfluidic device of claim 1, wherein the loading section further comprises a trailing capillary barrier positioned between the trailing electrolyte well and the sample input well, and a gas channel connected to the trailing capillary barrier and to a pneumatic pressure port.

3. The microfluidic device of claim 1, wherein the ITP section further comprises a leading electrolyte buffering well fluidically connected to the leading electrolyte well through a leading electrolyte buffering channel.

4. The microfluidic device of claim 3, wherein the leading electrolyte buffering channel comprises a leading capillary barrier and a gas channel connected to the leading capillary barrier and to a pneumatic pressure port.

5. The microfluidic device of claim 1, wherein the elution branch further comprises an elution buffering well fluidically connected to the elution well through an elution buffering channel.

6. The microfluidic device of claim 5, wherein the elution buffering channel comprises an elution capillary barrier, and a gas channel connected to the elution capillary barrier and to a pneumatic pressure port.

7. The microfluidic device of claim 5, wherein the elution buffering channel comprises an elution capillary barrier, and a gas channel connected to the elution capillary barrier and to a pneumatic pressure port.

8. The microfluidic device of claim 1, wherein:

(A) the loading section further comprises a trailing capillary barrier positioned between the trailing electrolyte well and the sample input well, and a gas channel connected to the trailing capillary barrier and to a pneumatic pressure port;

(B) the ITP section further comprises a leading electrolyte buffering well fluidically connected to the leading electrolyte well through a leading electrolyte buffering channel; and (C) the elution branch further comprises an elution buffering well fluidically connected to the elution well through an elution buffering channel.

9. The microfluidic device of claim 8, wherein:

the leading electrolyte buffering channel comprises a leading capillary barrier and a gas channel connected to the leading capillary barrier and to a pneumatic pressure port; and the elution branch further comprises an elution buffering well fluidically connected to the sample elution well through an elution buffering channel.

10. The microfluidic device of claim 8, further comprising:

an electrode positioned in the elution buffering well;

an electrode positioned in the leading electrolyte buffering well; and an electrode positioned in the trailing electrolyte well.

11. The microfluidic device of claim 1, comprising a plurality of the at least one of the fluidic paths.

12. The microfluidic device of claim 1, comprising, in two interlocking parts:

(A) an insert comprising the fluidic channel, the sample input well, the trailing electrolyte well, and the leading electrolyte well; and (B) an outer ring comprising mating features to interlock with the insert.

13. The microfluidic device of claim 12, wherein the outer ring is sized and dimensioned to conform to a microtiter plate standard.

14. The microfluidic device of claim 1, wherein the loading section further comprises a gas channel connected to the first capillary barrier and to a pneumatic pressure port.

* * * * *

UNITED STATES PATENT AND TRADEMARK OFFICE
CERTIFICATE OF CORRECTION

PATENT NO. : 11,674,132 B2
APPLICATION NO. : 16/997614
DATED : June 13, 2023
INVENTOR(S) : Lewis A. Marshall et al.

It is certified that error appears in the above-identified patent and that said Letters Patent is hereby corrected as shown below:

In the Specification

Please replace "add)." with -- acid). -- (Column 13, Line 46).

Please replace "thourea)," with -- thiourea), -- (Column 26, Line 22).

Please replace "thourea)" with -- thiourea) -- (Column 26, Line 34).

Please replace "750 $s^{-1}$ 1000 $s^{-1}$ 2000 $s^{-1}$ 3000 $s^{-1}$ 4000 $s^{-1}$ 5000 $s^{-1}$ 6000 $s^{-1}$ 7000 $s^{-1}$ 8000 $s^{-1}$" with -- 750 $s^{-1}$, 1000 $s^{-1}$, 2000 $s^{-1}$, 3000 $s^{-1}$, 4000 $s^{-1}$, 5000 $s^{-1}$, 6000 $s^{-1}$, 7000 $s^{-1}$, 8000 $s^{-1}$, -- (Column 30, Lines 23-25).

Please replace "2-naphtalenesulfonic" with -- 2-naphthalenesulfonic -- (Column 32, Line 34).

Please replace "trimetylpyruvic" with -- trimethylpyruvic -- (Column 32, Line 37).

Please replace "benzylasparatic" with -- benzylaspartic -- (Column 32, Line 44).

Please replace "1200V" with -- 1200 V -- (Column 33, Line 2).

Please replace "1200V" with -- 1200 V -- (Column 33, Line 5).

Please replace "surfacts" with -- surfactants -- (Column 39, Line 11).

Please replace "electrolyes" with -- electrolytes -- (Column 42, Line 31).

Please replace "electrolyes" with -- electrolytes -- (Column 42, Line 33).

Please replace "isotachoporesis" with -- isotachophoresis -- (Column 49, Line 35).

Signed and Sealed this
Nineteenth Day of September, 2023

*Katherine Kelly Vidal*
Director of the United States Patent and Trademark Office Please replace "10 m" with -- 10 μm -- (Column 58, Line 60).

Please replace "Lanzcos" with -- Lanczos -- (Column 63, Line 7).